(12) United States Patent
Borcherding et al.

(10) Patent No.: US 7,429,595 B2
(45) Date of Patent: Sep. 30, 2008

(54) ACYL AND SULFONYL DERIVATIVES OF 6,9-DISUBSTITUTED 2-(TRANS-1,4-DIAMINOCYCLOHEXYL)-PURINES AND THEIR USE AS ANTIPROLIFERATIVE AGENTS

(75) Inventors: David Borcherding, Bangor, PA (US); Jennifer A. Dumont, Groton, MA (US); Norton P. Peet, North Andover, MA (US); Paul S. Wright, New Hope, PA (US)

(73) Assignee: Aventis Pharmaceuticals Inc., Bridgewater, NJ (US)

( * ) Notice: Subject to any disclaimer, the term of this patent is extended or adjusted under 35 U.S.C. 154(b) by 42 days.

(21) Appl. No.: 10/677,683

(22) Filed: Oct. 2, 2003

(65) Prior Publication Data

US 2004/0248908 A1 Dec. 9, 2004

Related U.S. Application Data

(63) Continuation of application No. 09/998,976, filed on Oct. 31, 2001, now Pat. No. 6,861,524.

(60) Provisional application No. 60/244,567, filed on Oct. 31, 2000.

(30) Foreign Application Priority Data

Jul. 13, 2001 (GB) .................. 0117075.2

(51) Int. Cl.
C07D 473/16 (2006.01)
A61K 31/52 (2006.01)
A61P 35/00 (2006.01)
A61P 35/02 (2006.01)

(52) U.S. Cl. .................. 514/263.22; 544/277
(58) Field of Classification Search .............. 544/277; 514/263.22
See application file for complete search history.

(56) References Cited

U.S. PATENT DOCUMENTS

| | | | | |
|---|---|---|---|---|
| 4,232,155 | A * | 11/1980 | Naito et al. .................. | 544/277 |
| 6,413,974 | B1 * | 7/2002 | Dumont et al. ............. | 514/234.5 |
| 6,479,487 | B1 * | 11/2002 | Dumont et al. ............. | 514/234.2 |
| 6,794,390 | B2 * | 9/2004 | Lum et al. .................. | 514/263.2 |
| 6,861,524 | B2 * | 3/2005 | Borcherding et al. ....... | 544/277 |
| 7,041,824 | B2 * | 5/2006 | Bordon-Pallier et al. .... | 544/277 |
| 7,122,669 | B1 * | 10/2006 | Haesslein ................... | 544/277 |
| 2002/0035252 | A1 * | 3/2002 | Lum et al. .................. | 544/277 |
| 2003/0018038 | A1 * | 1/2003 | Thompson et al. ........ | 514/263.21 |
| 2003/0092909 | A1 * | 5/2003 | Trova ......................... | 544/276 |
| 2003/0105098 | A1 * | 6/2003 | Dumont et al. ............. | 514/234.5 |
| 2005/0187228 | A1 * | 8/2005 | Haesslein ................... | 514/263.37 |

FOREIGN PATENT DOCUMENTS

| | | |
|---|---|---|
| EP | 545413 A1 * | 6/1993 |
| EP | 0545413 | 7/2000 |
| WO | WO 94/17090 | 8/1994 |
| WO | WO 9417090 A1 * | 8/1994 |
| WO | WO 96/02543 | 2/1996 |
| WO | WO 9602543 A1 * | 2/1996 |
| WO | WO 97/16452 | 5/1997 |
| WO | WO 9716452 A1 * | 5/1997 |
| WO | WO 98/05335 | 2/1998 |
| WO | WO 9805335 A1 * | 2/1998 |
| WO | WO 99/07705 | 2/1999 |
| WO | WO 9907705 A1 * | 2/1999 |
| WO | WO 00/44750 | 8/2000 |
| WO | WO 0044750 A1 * | 8/2000 |

OTHER PUBLICATIONS

Kath John C. Patent Focus: Inhibitors of Tumour Cell Growth, J.C., Oncologic, Endocrine & Metabolic, Exp. Opin. Ther. Patents (2000), 10(6):803-818.*

Myers Michael R et al., Inhibitors of Tyrosine Kinases Involved in Inflammation and Autoimmune Disease, Current Pharmaceuticals Design, 1997, vol. 3, No. 5, pp. 473-502.*

Park David S et al., G1/S Cell Cyclic Blockers and Inhibitors of Cyclin-Dependent Kinases Suppress Camptothecin-Induced Neuronal Apoptosis, J.*

Park David S et al., Inhibitors of Cyclin-Dependent Kinases Promote Survival of post-mitotic Neuronally Differentiated PC12 Cells and Sympathetic Neurons, J. of Biological Chemistry, vol. 271, No. 14:8161-8169 (1996).*

Janet R. Maurer, Lesson 23, vol. 14-Lymphangioleiomyomatosis <http://www.chestnet.org/education/online/pccu/vol14/lesson23.php> downloaded from the internet Mar. 5, 2003.*

Peckham, ed., Oxford Textbook of Oncology vol. 1 (Oxford University Press, 1995), p. 452.*

Kath John C, Patent Focus: Inhibitors of Tumour Cell Growth, J.C., Oncologic, Endocrine & Metabolic, Exp. Opin. Ther. Patents (2000), 10(6):803:818.

(Continued)

*Primary Examiner*—Mark L Berch

(57) ABSTRACT

The present invention is directed to acyl and sulfonyl derivatives of 6,9-disubstituted 2-(trans-1,4 -diaminocyclohexyl)-purines of the formula

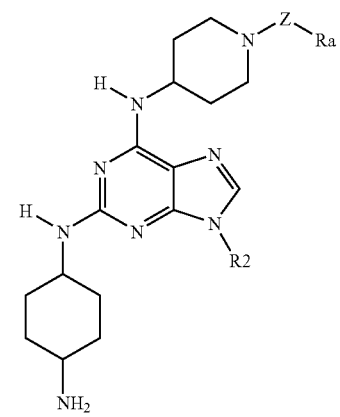

where Z is selected from the group consisting of —S(O)$_2$—, and —C(O)—.

16 Claims, No Drawings

OTHER PUBLICATIONS

Myers Michael R et al., Inhibitors of Tyrosine Kinases Involved In Inflammation and Autoimmune Disease, Current Pharmaceuticals Design, 1997, vol. 3, No. 5, pp. 473-502.

Park David S et al., G1/S Cell Cycle Blockers and Inhibitors of Cyclin-Dependent Kinases Suppress Camptothecin-Induced Neuronal Apoptosis, J. of Neuroscience, 17(4):1256-1270 (1997).

Park David S et al., Inhibitors of Cyclin-Dependent Kinases Promote Survival of Post-mitotic Neuronally Differentiated PC12 Cells and Sympathetic Neurons, J. of Biological Chemistry, vol. 271, No. 14:8161-8169 (1996).

Rosania gustavo R et al., Targeting Hyperproliferative Disorders with Cyclin Dependent Kianse Inhibitors, Publication Exp. Opin. Ther. Patents (2000) 10(2):215-230.

Knockaert et al., Pharmacological inhibitors of cyclin-dependent kinases, Trends in Pharmacological Sciences, vol. 23, No. 9, Sep. 2002, pp. 417-425.

Sherr et al., CDK inhibitors: positive and negative regulators of G1-phase progression, Genes & Dev. 1999, vol. 13, pp. 1501-1512.

* cited by examiner

SEQUENCE LISTING

<160> NUMBER OF SEQ ID NOS: 12

<210> SEQ ID NO 1
<211> LENGTH: 40
<212> TYPE: DNA
<213> ORGANISM: Artificial
<220> FEATURE:
<223> OTHER INFORMATION: artificially generated PCR oligionucleotide
      primer

<400> SEQUENCE: 1
gtcaggatcc tattcgaaac gatggcgctc cgagtcacca                          40

<210> SEQ ID NO 2
<211> LENGTH: 41
<212> TYPE: DNA
<213> ORGANISM: Artificial
<220> FEATURE:
<223> OTHER INFORMATION: pcr primer

<400> SEQUENCE: 2

-continued tgacgtcgac gaattcacta catcttctta atctgattgt c    41

<210> SEQ ID NO 3
<211> LENGTH: 40
<212> TYPE: DNA
<213> ORGANISM: Artificial
<220> FEATURE:
<223> OTHER INFORMATION: pcr primer

<400> SEQUENCE: 3
gtcaggatcc tattcgaaac gatggcgctc cgagtcacca    40

<210> SEQ ID NO 4
<211> LENGTH: 38
<212> TYPE: DNA
<213> ORGANISM: Artificial
<220> FEATURE:
<223> OTHER INFORMATION: pcr primer

<400> SEQUENCE: 4
tgacgtcgac gaattcatta cacctttgcc acagcctt    38

<210> SEQ ID NO 5
<211> LENGTH: 24
<212> TYPE: DNA
<213> ORGANISM: artificial
<220> FEATURE:
<223> OTHER INFORMATION: pcr primer

<400> SEQUENCE: 5
actagttggc gcttcatgga gaac    24

<210> SEQ ID NO 6
<211> LENGTH: 26
<212> TYPE: DNA
<213> ORGANISM: Artificial
<220> FEATURE:
<223> OTHER INFORMATION: pcr primer

<400> SEQUENCE: 6
ctcgagggag gagagggtga gattag    26

<210> SEQ ID NO 7
<211> LENGTH: 39
<212> TYPE: DNA
<213> ORGANISM: Artificial
<220> FEATURE:
<223> OTHER INFORMATION: pcr primer

<400> SEQUENCE: 7
gtcatctaga ttcgaaacga tgaaggagga cggcggcgc    39

<210> SEQ ID NO 8
<211> LENGTH: 33
<212> TYPE: DNA
<213> ORGANISM: Artificial
<220> FEATURE:
<223> OTHER INFORMATION: pcr primer

<400> SEQUENCE: 8
tgacctcgag gaattcatca cgccatttcc ggc    33

<210> SEQ ID NO 9
<211> LENGTH: 30

```
<212> TYPE: DNA
<213> ORGANISM: Artificial
<220> FEATURE:
<223> OTHER INFORMATION: pcr primer

<400> SEQUENCE: 9
gccggatcca tggctacctc tcgatatgaa                               30

<210> SEQ ID NO 10
<211> LENGTH: 54
<212> TYPE: DNA
<213> ORGANISM: Artificial
<220> FEATURE:
<223> OTHER INFORMATION: pcr primer

<400> SEQUENCE: 10
gccgaattca cgatgcatag tcaggtacat cgtactccgg gttaccttcg tcct   54

<210> SEQ ID NO 11
<211> LENGTH: 30
<212> TYPE: DNA
<213> ORGANISM: Artificial
<220> FEATURE:
<223> OTHER INFORMATION: pcr primer

<400> SEQUENCE: 11
cgcggatcca tggaacacca gctcctgtgc                               30

<210> SEQ ID NO 12
<211> LENGTH: 48
<212> TYPE: DNA
<213> ORGANISM: Artificial
<220> FEATURE:
<223> OTHER INFORMATION: pcr primer

<400> SEQUENCE: 12
gccgaattca gtgatggtga tggtgatgga tgtccacgtc ccgcacgt           48
```

ACYL AND SULFONYL DERIVATIVES OF 6,9-DISUBSTITUTED 2-(TRANS-1,4-DIAMINOCYCLOHEXYL)-PURINES AND THEIR USE AS ANTIPROLIFERATIVE AGENTS

RELATED APPLICATIONS

This application is a continuation of U.S. patent application Ser. No. 09/998,976, filed Oct. 31, 2001, which claims the benefit of U.S. Provisional Application No. 60/244,567 filed Oct. 31, 2000

The present invention relates to acyl and sulfonyl derivatives of 6,9-disubstituted 2-(trans-1,4-diaminocyclohexyl)-purines and methods of using the same as antiproliferative agents or to prevent apoptosis.

BACKGROUND

Cell division, in both normal and neoplastic cells, is a tightly controlled event which occurs by defined stages. Quiescent cells which are not actively dividing, are in the $G_0$ phase, as are those terminally differentiated or in a state of temporary arrest. The first phase is the first gap ($G_1$) phase during which the cell prepares to synthesize DNA. In late $G_1$ phase at what is termed a restriction point or R point, the cell commits to entering S phase during which DNA synthesis occurs. Upon completion of S phase, the cell enters the second gap ($G_2$) phase during which the cell prepares to divide, which is followed by mitosis, or M phase.

Initial experiments in cell cycle regulation revealed the existence of a protein called "Maturation Promoting Factor" (MPF), a heterodimer with kinase activity. Later, comparison of subsequently identified proteins and their underlying genes revealed a family of yeast genes known as cell division control (cdc) genes are identified. Further experiments demonstrated that some of the cdc genes encode kinases, and are later called cyclin-dependent kinases (cdks). As the result of this reclassification, some cell cycle proteins have dual designations, such as cdk1 which is also known as cdc2. The kinase component of the MPF is now identified as $p34^{cdc2}$ and the regulatory subunit of MPF is now called cyclin B. Cyclins are first identified as proteins whose levels oscillated during the cell cycle and are specifically degraded at mitosis. To date, animal cyclins A-I and cdks 1-8 have been identified. To further complicate nomenclature, subtypes of cyclins and cdks have been identified, such as cyclins B1 and B2. (For a review on cdks, see D. O. Morgan, Annu. Rev. Cell Dev. Biol. 13, 261-291, 1997).

Subsequent research on cell regulation has demonstrated that the stages of cellular division are achieved in part by modulation cyclins and cyclin-dependent kinases (cdks). Cyclins sequentially regulate cdks and are characterized by a 100 amino acid homology region termed the "cyclin box" which is involved in binding a protein kinase partner. Cdks are closely related in sequence and size (35-40 kDa) and are defined as protein kinases activated by bound cyclin regulatory subunits. Cdks contain a conserved active-site cleft of approximately 300 amino acids that is characteristic of all eukaryotic protein kinases. Thus, both the cyclins and cdks appear to be highly conserved protein families.

Isolation of individual cyclins and cdks has enabled further identification of the roles and interactions of each component in cell cycle phase transitions. Excess levels of cdks persist throughout the cell cycle. Activation of cdks occurs upon cyclin synthesis and binding to the catalytic cdk subunit, the result of which is stimulation of the cdk serine/threonine kinase activity. Complete cdk activation requires phosphorylation on a conserved threonine residue located in the T-loop by a cyclin-dependent kinase activating kinase (CAK).

Since their initial discover, cyclins and cdks also interact with other transcription factors and proteins involved in a broad range of cellular pathways. Cdk7 has been identified as a component in transcription factor IIH (TFIIH), which contains the RNA polymerase II C-terminal domain (CTD) kinase activity. More recently, cdk8, which partners with cyclin C, has also been discovered to phosphorylate the CTD of RNA polymerase II, but does not appear to possess CAK activity. Thus, it is clear that cdks participate in a broad range of cellular functions in addition to cell cycle regulation.

Inactivation of the cdk-cyclin complex can result from the phosphorylation of a threonine and/or tyrosine residue in the ATP-binding site of the cdk or from binding of one of a number of endogenous inhibitor proteins.

In $G_1$ phase, D-type cyclins bind to several different cdks, including cdk2, cdk4, cdk5 and cdk6, but are most commonly associated with cdk4 and cdk6. D-type cyclins are thought to act as growth factor sensors, which link cell cycle progression to external cues. Cyclin E-cdk2 complexes appear in the mammalian cell cycle after the D-type cyclin-cdk complexes. Cyclin E synthesis is tightly regulated and occurs in late $G_1$ and early S phase. The cyclin E-cdk2 complex is essential for the cell to begin DNA replication.

The $G_1$ cyclins, cyclin-D and cyclin-E, are transiently produced proteins, with a half-life of about 20 minutes. The short half-life is thought to result from a PEST sequence in the C-terminal regions of these proteins, the degradation of which appears to be mediated by the ubiquitination pathway.

The $G_2$ cyclins, cyclin-A and cyclin-B, are stable throughout interphase and specifically destroyed at mitosis through an ubiquitination pathway. Both cyclin A and cyclin B2 appear to be degraded only when complexed with their cdk partner [cyclinA-cdk2 and cyclin A/B-cdk1 (cdc2)]. However, cyclin BI destruction is connected with the integrity of the mitotic apparatus at the end of metaphase. If the spindle is incorrectly assembled, or chromosomes incorrectly aligned, then cyclin B1 destruction is prevented.

Retinoblastoma protein (Rb), a 105 kDa nuclear phosphoprotein, is a substrate of cyclin-cdk complexes of cdks-2, -4 and -6 in $G_1$ phase and functions as one of the major checkpoint controls in the cell cycle via carefully orchestrated phosphorylation and dephosphorylation. In $G_0/G_1$, Rb exists in a hypophosphorylated state. As the cell progresses into late $G_1$, Rb becomes hyperphosphorylated by D-cyclin complexes, which inactivates Rb and drives the cell into S phase resulting in cell cycle progression and cell division. This state of hyperphosphorylation of Rb remains in $G_2$. During late M phase, Rb is dephosphorylated, thus returning to the hypophosphorylated state. A high cellular level of p16 results in inactivation of cdk4 because p16 binds cyclinD/cdk4 and cyclin D/cdk6 complexes. Phosphorylation of the Rb protein alters its binding characteristics; in the hypophosphorylated state, Rb binds to and sequesters specific transcription factors, such as E2F, the binding of which prevents the exit from the $G_1$ phase. Once cdks hyperphosphorylate Rb, the transcription factors are released which can then activate transcription of genes necessary for S phase progression, for example, thymdine kinase, myc, myb, dihydrofolate reductase, and DNA polymerase-α.

Localization of cyclin-CDK complexes is also very suggestive about the role each complex plays in the pathway. Nuclear cyclins A and E bind to p107 and p130, possibly because they are in the nucleus. Mammalian cyclin B1 accumulates in the cytoplasm in $G_2$ phase and translocates into the nucleus at the beginning of mitosis. Cyclin B associates with the spindle apparatus, in particular with the spindle caps, and it is thought that the cyclin B-cdc2 kinase may be involved in the formation of the spindle through phosphorylating components of the mitotic apparatus. In addition, cyclin B1 is part of a feedback mechanism ensuring correct assembly of the metaphase mitotic apparatus. Human cyclin B2 is almost exclusively associated with the membrane compartment, and in particular the Golgi apparatus. Cyclin B2-cdc2 is involved in the disassembly of the Golgi apparatus when cells enter mitosis.

The $p34^{cdc2}$/cyclin B kinase is a key mitotic factor that is highly conserved and is thought to be involved in cell cycle transitions in all eukaryotic cells. Histone H1 is a substrate for $p34^{cdc2}$/CyClin B; histone H1 is selectively phosphorylated on specific sites in mitosis, which is thought to be important for chromatin condensation. $p34^{cdc2}$/CyClin B complex also phosphorylates lamin, which is responsible for nuclear lamina breakdown. Nuclear lamina is made up of a polymer of lamin subunits that are hyperphosphorylated at mitosis, and this phosphorylation is responsible for their disassembly. Lamins are part of the intermediate filament family of proteins, and $p34^{cdc2}$/cyclin B phosphorylates a subset of the sites phosphorylated at mitosis on the cytoplasmic intermediate filament subunits, vimentin and desmin. Thus, $p34^{cdc2}$/CyClin B complex is involved in the re-organization of the cell architecture at mitosis.

In addition, $p34^{cdc2}$/CyClin B is involved in the re-organization of microfilaments, through phosphorylation of non-muscle caldesmon, an 83 kDa protein that binds to actin and calmodulin, and inhibits actomyosin ATPase activity. At mitosis, caldesmon is phosphorylated by $p34^{cdc2}$/CyClin B, which weakens its affinity for actin and causes it to dissociate from microfilaments.

$p34^{cdc2}$/CyClin B is implicated in actomyosin filament regulation, by phosphorylating the myosin in the contractile ring, which divides the cell into two (cytokinesis). In metaphase, the myosin II regulatory light chain (MLC) is phosphorylated on two main sites at the N-terminus. Once phosphorylated, the myosin is prevented from interacting with actin. At anaphase, these two sites are dephosphorylated.

The $p34^{cdc2}$/CyClin B kinase also plays a role in reorganization of the membrane compartment at mitosis. For example, $p34^{cdc2}$/CyClin B phosphorylates rab1Ap and rab4p. When rab4p is phosphorylated by $p34^{cdc2}$/CyClin B, it dissociates from the membrane compartment.

At mitosis, most forms of transcription are inhibited. Again, $p34^{cdc2}$/CyClin B plays a role by inhibiting pol III-mediated transcription by phosphorylating TFIIIB. Given that pol I, pol II and pol III-mediated transcription share several common factors, such as TATA-binding protein (TBA), it is likely that $p34^{cdc2}$/CyClin B is involved in down-regulating all forms of transcription at mitosis.

Given the importance of cyclin/cdk complexes in triggering cell cycle division, they are under tight feedback mechanisms. CDK-inhibitor proteins (CDIs) are small proteins that bind and inactivate specific cyclin-CDK complexes, or monomeric CDKs. These inhibitors can be grouped into two families based on sequence and functional similarities. The INK4 family includes $p15^{INK4B}$, $p16^{INK4}$, p18 and p19 that specifically bind cdk4 and cdk6. Both $p16^{INK4}$ and $p15^{INK4}$B contain four ankyrin repeats and, in addition to sharing significant homology, are encoded by adjacent genes on the 9p12 locus.

The gene for $p16^{INK4}$ (MTS1) is recognized as a potential tumor suppressor gene, as it is rearranged, deleted or mutated in a large number of tumor cell lines, and in some primary tumors. In one study of hereditary melanoma, about half the families had germline mutations in the $p16^{INK4}$ gene. Rb is a repressor of $p16^{INK4}$. Inactivation of cellular Rb, either by mutation or viral antigens, correlates with increased levels of $p16^{INK4}$. $p16^{INK4}$, $p15^{INK4}$, $p15^{INK4}$B, and p18 inhibit binding of cyclin D and cdk4 and cdk6 complexes to bind to the Rb protein.

The second family of CDIs is the Kip/Cip family that includes $p21^{CiP1,\ WAF-1}$, $p27^{Kip1}$ and $p57^{Kip2}$. $P27^{KIP1}$ is present in proliferating cells in a latent or masked form. Upon stimulation, $p27^{KIP1}$ is unmasked binds to and inhibits cyclin-CDK4/6 complexes. The Kip/Cip family proteins have strong homology in the N-terminus, the region that binds the cyclin-cdk complexes. The Kip/Cip family proteins preferentially bind to and inhibit cyclin-cdk complexes involved in the $G_1$ and S phase complexes over those involved in the M phase.

p21 (also known as WAF1, Cip1 and Sdi1) is induced by p53 and forms a ternary complex with proliferating cell nuclear antigen (PCNA), a subunit of DNA polymerase δ in several cyclin-CDK2 complexes, including cyclins A, D1 and E. $p21^{WAF-1}$ expression in growing, quiescent and senescent cells correlates with a role as a negative regulator of S phase entry. $p21^{WAF-1}$ mRNA is upregulated as cells become senescent or quiescent, and after serum stimulation of quiescent cells, and decreases as cells enter S phase. P21 inactivates cyclin E-cdk2, cyclin-A-cdk2, and cyclins D1-, D2- and D3 cdk4 complexes.

Genetic analysis of numerous human tumors reveals a disproportionate number of altered cell cycle proteins, and it is this aberration that is thought to cause abnormal cell cycle. For example, cyclin D1 is the bcl-1/PRAD1 proto-oncogene that is either overexpressed or deregulated in a variety of human tumors. The cyclin D1/CCND1 gene, located at chromosome 11q13, is amplified in a number of cancers, mainly breast and non-small cell lung carcinomas. This correlates with the observation that overexpression of cyclin D1 is a common feature in the tumors with this specific 11q13 amplicon. The gene for p16 is rearranged, deleted or mutated in a large number of tumor cell lines, and in some primary tumors. Mutations in cdk4, specifically an Arg24Cys mutation, have been identified in two unrelated hereditary melanoma families. This mutation was found in 11/11 of the melanoma patients, 2/17 unaffecteds and 0/5 spouses. Zuo, L., et al., Nature Genetics 12 (1996):97-99. This mutation has a specific effect on the $p16^{INK4a}$ binding domain of cdk4, but has no affect on the ability to bind to cyclin D and form a functional kinase. As a result of this mutation, the resulting cyclin D/cdk4 complex is resistant to normal physiological inhibition by $p16^{INK4a}$. Other studies have demonstrated that about half the familial melanoma kindreds show evidence of linkage to the region of chromosome 9p21 that contains the $p16^{INK4a}$ gene. The types of $p16^{INK4a}$ mutations identified include a nonsense mutation, splice donor mutation, an unidentified mutation that prevents $p16^{INK4a}$ transcription, and 3 missense mutants that are unable to bind to cdk4 or cdk6. Overexpression of cdk4 as result of gene amplification has been identified in a study of 32 glioma cell lines. He, J., et al., Cancer Res. 54, 5804-5807 (1994). This alteration was observed among the ten cases having intact p16 genes. Genetic analysis of glioma cell lines revealed that 24 of 32 glioma cell lines had one of two alternative genetic alterations, each of which indicates that increased cdk4 kinase activity is important to glial tumor development. Cdk4 maps to the long arm of chromosome 12 and is found overexpressed in certain tumors because of its amplification as a component of an amplicon that includes other relevant genes, such as SAS and MDM2. All of the above conditions lead to activation of cdk4. Overexpression of cyclins B1 and E in leukemic and solid tumor cell lines, as well as altered patterns of cyclin E expression in breast cancer has also been reported.

Cellular hyperproliferation occurs in a number of disease states. The most common hyperproliferative diseases are neoplasms, which are typically named according to the original source of the hyperproliferative tissue. Neoplasms are defined as new growths of animal or plant tissue that resemble more or less the tissue from which it arises, but serve no physiologic function, and are benign, potentially malignant or malignant in character. Neoplasms arise as the result of loss of normal controls, leading to unregulated growth. Neoplastic cells may lack differentiation and acquire the ability to invade local tissues, that is metastasize. Neoplasms may develop in any type of tissue of any organ at any age. The incidence, and mortality rate, of neoplasms generally increases with age, with certain neoplasms having peak incidence between the ages of 60 and 80 (e.g. prostate, stomach and colon). However, other neoplasms have a peak incidence from birth to 10 years of age (e.g. acute lymphoblastic leukemia). Diet, exposure to carcinogens, particularly use of tobacco, and familial predisposition also affect incidence of particular neoplasms.

Neoplastic cells differ from normal cells in a number of important aspects, including loss of differentiation, increased invasiveness and decreased drug sensitivity. Another important difference is the unchecked growth of cells, which is thought to result from loss of normal cellular control mechanisms of these cells are either deactivated, bypassed or otherwise disregarded, leaving the neoplastic cells to proliferate without regard to the normal controlling mechanisms.

Neoplasm is an abnormal mass of tissue, the growth of which exceeds and is uncoordinated with that of the normal tissue, and persists in the same excessive manner after cessation of the stimuli that evoked the change.

Neoplasms are classified as either benign or malignant. Benign neoplasms exhibit slow, localized growth that is usually circumscribed due to their encapsulation by a fibrous connective tissue capsule. Whereas benign neoplasms rarely cause the death of the organism, untreated malignant neoplasms have a high probability of killing the organism. Malignant neoplasms are generally nonencapsulated, and usually exhibit more rapid growth rate. Malignant neoplasms often invade surrounding tissues and vessels and spread to distant body sites. Malignant neoplasms are generically described as "cancer" or as "tumors", the later term which denotes swelling.

Myeloproliferative disorders are a group of disorders characterized by abnormal proliferation by one or more hematopoietic cell lines or connective tissue elements. Four disorders are normally included as myeloproliferative disorders: polycythemia vera (primary polycythemia; Vaquez' Disease), myelofibrosis (agnogenic myeloid metaplasia), chronic myelogenous leukemia and primary (essential) thrombocythemia. Acute leukemia, especially erythroleukemia, and paroxysmal nocternal hemoglobinuria are also classified as myeloproliferative disorders. Each of these disorders is identified according to its predominant feature or site of proliferation. Although each results from proliferation of different cells, each has been shown to be caused by a clonal proliferation arising at the level of a pluripotent stem cell, which causes varying degrees of abnormal proliferation of erythroid, myeloid, and megakaryocytic precursors in the bone marrow. All myeloproliferative disorders have a tendency to terminate in acute leukemia.

Leukemias are malignant neoplasms of the blood-forming tissues. At least two viruses are associated with causing leukemias in humans, the Epstein-Barr virus is associated with Burkitt's lymphoma and the human T-cell lymphotropic virus, also called human acute leukemia/lymphoma virus (HTLV-1) has been linked to some T cell leukemias and lymphomas. Exposure, especially prolonged exposure to chemical agents, such as benzene and some antineoplastics, or to ionizing radiation, genetic predisposition (e.g. Down's syndrome) and some familial disorders (e.g. Fanconi's anemia) result in predispositions to leukemias.

Development of leukemias appears to occur through a single cell cycle through two or more steps with subsequent proliferation and clonal expansion. Leukemias are currently classified according to their cellular maturity; acute leukemias are predominantly undifferentiated cell populations and chronic leukemias are more mature cell forms. Acute leukemias are further divided into lymphoblastic (ALL, also known as acute lymphocytic leukemia) and myeloid (AML, also known as acute myelocytic, myelogenous, myeloblastic, myelomonoblastic) types. They may be further classified by morphologic and cytochemical appearance according to the French-American-British (FAB) classification or according to type and degree of differentiation. Chronic leukemias are classified as either lymphocytic (CLL) or myelocytic (CML). CLL is characterized by the appearance of mature lymphocytes in the blood, bone marrow and lymphoid organs. CML is characterized by the predominance of granulocytic cells of all stages of differentiation in blood, bone marrow, liver, spleen and other organs.

Myelodysplastic Syndrome (MDS) is characterized as a clonal proliferative disorder in which a normal or hypercellular bone marrow is associated with an ineffective and dysmyelopoiesis. Hemapoietic cells which may proliferate include erythroid, myeloid and megakaryocytic forms. MDS is a relative new designation of group of disorders known as Preleukemia, Refractory Anemias, Ph-Chromosome-Negative Chronic Myelocytic Leukemia, Chronic Myelomonocytic Leukemia and Agnogenic Myeloid Metaplasia. The FAB system provides further classification of Myelofibrosis.

Lymphomas are a heterogeneous group of neoplasms arising in the reticuloendothelial and lymphatic systems. The major types of lymphomas are Hodgkin's disease and non-Hodgkin's lymphoma, as well as the rarer Burkitt's lymphoma and mycosis fungoides. Hodgkin's disease is a chronic disease with lymphoreticular proliferation of unknown cause that may present in localized or disseminated form, and is further classified according to four histopathologic profiles. Non-Hodgkin's lymphomas are a heterogeneous group of diseases consisting of neoplastic proliferation of lymphoid cells that usually disseminate throughout the body. The former terms, lymphosarcoma and reticulum cell sarcoma, are now being replaced with terms that reflect that cell of origin and biology of the disease. The Rappaport classification is based on the histopathology; on the degree of the differentiation of the tumor and on whether the growth pattern is diffuse or nodular. The Lukes and Collins classification is based upon the cell of origin, specifically whether it is T cell or B cell derived, histiocytic (or monocytic) origin or unclassifiable. The International Panel Working Formulation of the National Cancer Institute categorizes non-Hodgkin's lymphomas using the above classifications.

Burkitt's lymphoma is a highly undifferentiated B cell lymphoma that tends to involve sites other than the lymph nodes and reticulendoethlial system. Burkitt's lymphoma, unlike other lymphomas, has a specific geographic distribution, which suggests an unidentified insect vector and an infectious agent. Evidence points to the herpes like Epstein-Barr virus.

Mycosis fungoides is an uncommon chronic T cell lymphoma primarily affecting the skin and occasionally internal organs.

Plasma cell dyscrasias (PCDs), or monoclonal gammopathy, are disorders characterized by the disproportionate proliferation of one clone of cells normally engaged in immunoglobulin (Ig) synthesis, and the presence of a structurally and electrophoretically homogeneous IG or polypeptide subunit in serum or urine. The disorders may be primarily asymptomatic to progressive, overt neoplasms (e.g., multiple myeloma). The disorder results from disproportionate proliferation of one clone producing a specific Ig: IgG, IgM, IgA, IgD or IgE.

Multiple myeloma, also known as plasma cell myeloma or myelomatosis, is a progressive neoplastic disease characterized by marrow plasma cell tumors and overproduction of an intact monoclonal Ig (IgG, IgA, IgD or IgE) or Bence Jones protein, which is free monoclonal $\kappa$ or $\lambda$ light chains. Diffuse osteoporosis or discrete osteolytic lesions arise due to replacement by expanding plasma cell tumors or an osteoclast-activating factor secreted by malignant plasma cells.

Macroglobulinemia, or primary or Waldenstrom's macroglobulinemia, is a plasma cell dyscrasia involving B cells that normally synthesize and secrete IgM. Macrogolbulinemia is distinct from myeloma and other PCDs, and resembles a lymphomatous disease. Many patients have symptoms of hyperviscosity; fatigue, weakness, skin and mucosal bleeding and so forth.

Heavy chain diseases are neoplastic plasma cell dyscrasias characterized by the overproduction of homogenous $\gamma$, $\alpha$, $\mu$, and $\delta$ Ig heavy chains. These disorders result in incomplete monoclonal Igs. The clinical picture is more like lymphoma than multiple myeloma.

Hypersplenism is a syndrome in which circulating cytopenia is associated with splenomegaly. Treatment of patients with hypersplenism requires therapy for the underlying disease, not splenectomy. Lymphoproliferative and myeloproliferative diseases are some, but not the sole, causes of hypersplenism. Myeloproliferative disorders causing hypersplenism include polycythemia vera, myelofibrosis with myeloid metaplasia, chronic myelogenous leukemia and essential thrombocythemia. Chronic lymphocytic leukemia and the lymphomas (including Hodkin's disease) are specific lymphoproliferative disorders that may cause hypersplenism.

Lung tissue is the site for both benign and malignant primary tumors, as well as the site of metastasis from cancers of many other organs and tissues. Cigarette smoking causes an overwhelming percentage of lung cancers, estimated at over ninety percent of the cases in men and about seventy percent of the cases in women, exposure to occupational agents such as asbestos, radiation, arsenic, chromates, nickel, chloromethyl ethers, poison gas, and coke oven emissions is also associated with lung cancer. The most common types of lung cancer are squamous cell, small and large cell and adenocarcinoma.

About ninety-five percent of the stomach cancers are carcinoma; less common are lymphomas and leiomyosarcomas. Gastric carcinomas are classified according to gross appearance; protruding, penetrating (the tumor has a sharp, well-circumscribed border and may be ulcerated) spreading or miscellaneous, which has characteristics of two of the other types.

Pancreatic cancers may be exocrine tumors, which are mostly adenocarcinomas arising from duct cells rather than the acinar cells, or endocrine tumors, which include insulinoama, Gastrin-producing pancreatic tumors involving cells of the non-$\beta$-type or in the duodenal wall can cause Zollinger-Ellison Syndrome, a syndrome marked by hypergastrinemeia. Sometimes other endocrine abnormalities, particularly with the parathyroids, or pituitary and adrenal glands cause polyglandular disorder known as multiple endocrine neoplasia (MEN). Non-$\beta$ islet cell tumors may cause a syndrome known as Vipoma Syndrome, which is characterized by prolonged massive watery diarrhea.

Neoplasms of the bowel include tumors of the small intestine, tumors of the large intestine, cancer of the colon and rectum. Benign small intestine tumors include may arise from jejunal and ileal neoplasms, including leiomyomas, lipomas, neurofibromas, and fibromas. Malignant small intestine tumors, such as adenocarcinomas, are uncommon, and typically arise in the proximal jejunum. Patients with Crohn's disease of the small intestine are more prone to such adenocarcinomas rather than patients with Crohn's disease of the colon. In patients with Crohn's disease, the tumors tend to occur distally in the bypassed or inflamed loops of the bowel. Carcinoid tumors typically arise in the small bowel, especially the ileum, and in about half the cases, multiple tumors exist. Kaposi's sarcoma, which occurs frequently in transplant recipients and AIDS patients, have gastrointestinal involvement in about half the cases. Lesions may occur anywhere in the GI tract, but are usually found in the stomach, small intestine, or distal colon.

Tumors of the large bowel include polyps of the colon and rectum. Polyps are a mass of tissue that arises from the bowel wall and protrudes into the lumen. Polyps are classified on the basis of their histology, as tubular adenomas, tubulovillous adenomas, villous adenomas, hyperplastic polyps, hamartomas, juvenile polyps, polypoid carcinomas, pseudopolyps, lipomas, leiomyomas and even rarer tumors.

Malignant tumors may also arise in the anorectum. These are epidermoid (squamous cells) carcinoma of the anorectum which comprise about three to five percent of rectal and anal cancers.

In Western countries, cancer of the colon and rectum are second to lung cancer in accounting for more new cases each year. In the USA, about 75,000 people died of these cancers in 1989; about 70% occurred in the rectum and sigmoid colon, and 95% are adenocarcinomas.

Neoplasms of the liver include benign neoplasms, which are relatively common but often undetected, and malignant neoplasms. Hepatocellular adenoma is the most important benign liver neoplasm. Asymptomatic small hemangiomas occur in one to five percent of adults. Bile duct adenomas and other mesenchymal neoplasms also occur, but are relatively rare. Malignant neoplasms of the liver are the most common form of hepatic tumor, and the liver is a frequent site of bloodborne metastases, usually from lung, breast, colon, pancreas and stomach primary tumors. The incidence of hepatocellular carcinoma is linked with chronic hepatitis B virus in certain parts of Africa and Southeast Asia. In North America, Europe and other areas of low prevalence, most of the patients have underlying cirrhosis. Fibrolamellar carcinoma is a distant variant of hepatocellular carcinoma with characteristic morphology of malignant hepatocytes enmeshed in lamellar fibrous tissue. Fibrolamellar carcinoma usually affects relatively young adults, and has no association with preexisting cirrhosis, chronic hepatitis B virus infection or other known risk factors. Other primary malignancies of the liver include cholangiocarcinoma (a tumor arising from intrahepatic biliary epithelium), hepatoblastoma (which is one of the most common cancers in infants) and angiosarcoma (which is associated with industrial exposure to vinyl chloride). Leukemia and related disorders may involve hepatic tissues, thought the result of infiltration with abnormal cells.

Multiple Endocrine Neoplasia (MEN) Syndromes are a group of genetically distinct familial diseases involving adenomatous hyperplasia and malignant tumor formation in several endocrine glands. Three distinct syndromes have been identified. Type I (MEN-I) is characterized by tumors of the parathyroid glands, pancreatic islets, and the pituitary. Type II (MEN-II) is characterized by medullary carcinoma of the thyroid, pheochromocytoma and hperparthyroidism. Type III (MEN-III) is characterized by multiple mucosal neuromas, medullary carcinoma of the thyroid, and pheochromocytoma.

Carcinoid syndrome is usually caused by metastatic intestinal carcinoid tumors that secrete excessive amount of vasoactive substances, including serotonin, bradykinin, histamine, prostaglandins and polypeptide hormones. Abnormal levels of these substances cause a variety of symptoms, often episodic cutaneous flushing, cyanosis, abdominal cramps, diarrhea, and valvular heart disease.

Neoplasms of the bone and joints may be benign or malignant. Benign tumors of the bone include osteochondromas (osteocartilaginous exostoses), which are the most common benign bone tumors in children between ages 10 to 20, benign chondromas (which are located within the bone), which occur most commonly in children and young adults between the ages 10 to 30, chondroblastoma (which arises in an epiphysis), which is rare, but most common in children between the ages of 10 to 20, chondromyxofibromas, osteoid osteoma, giant cell tumors and fibromatous lesions. Primary malignant tumors of the bone include osteogenic sarcoma (osteosarcoma), which is the second most common primary bone tumor, fibrosarcomas, malignant fibrous histiocytoma, chondrosarcomas, mesenchymal chondrosarcoma, Ewing's tumor (Ewing's sarcoma), malignant lymphoma of bone, multiple myeloma, malignant giant cell tumor.

Primary cancers of other tissues may metastasize to bone tissue. The most common are carcinomas arising in the breast, lung, prostate, kidney, and thyroid.

Central nervous system (CNS) neoplasms are generally classified according to the organ. Primary intracranial neoplasms are subdivided into six classes: tumors of (1) the skull; (2) the meninges; (3) the cranial nerves; (4) the neuroglia and ependyma; (5) pituitary or pineal gland; (6) congenital origin. Skull neoplasms include osteoma, hemangioma, granuloma, xanthoma, and osteitis deformans. The meninges neoplasms include meningioma, sarcoma, and glomatosis. The cranial nerve neoplasms include glioma of the optic nerve, and schwannoma of the 8th and 5th cranial nerves. The neuroglia neoplasms include gliomas and ependymomas. The pituitary or pineal body neoplasms include pituitary adenoma and pinealoma. The congenital origin neoplams include craniopharyngioma, chordoma, germinoma, teratoma, dermoid cyst, agioma and hemangioblastoma.

Spinal cord neoplasms are lesions that compress the spinal cord or its roots, arising from the cord parenchyma, roots, meninges, or vertebrae. Primary spinal cord neoplasms are much less common than intracranial tumors. Metastatic lesions are common and may arise from carcinomas of the lung, breast, prostate, kidney, thyroid or lymphoma.

Genitourinary neoplasms occur at any age and in both sexes; however, they account for about 30% of cancer in the male and 4% in the female. Adenocarcinoma of the prostate accounts for a significant number of malignancies in men over 50. Prostate adenocarcinoma is thought to be hormone related and its pathology is typically glandular. Carcinoma of the kidney, adenocarcinoma, is only about one to two percent of adult cancers, but most solid kidney tumors are malignant. Wilms' tumors, an embryonal adnomyosarcoma of the kidneys, occurs fetally and is often not diagnosed for several years. Renal pelvis and ureter neoplasms are histologically similar. Urinary bladder neoplasms may be induced by known urinary carcinogens such as aniline dyes, and the most common is transitional cell carcinoma, less common is squamous cell carcinoma. Rarer genitourinary neoplasms include carcinoma of the urethra, and penis. Neoplasms of the testis account for the majority of solid malignancies in males under 30. Most malignant testicular tumors arise from the primordial germ cell and are classified according the cell type involved.

Breast cancer is the most common cancer in women. In the USA, the cumulative risk for women of all ages of developing breast cancer is about 10%, but that of dying from the disease is only about 3.6%. However, the risk increases with age, a family history of breast cancer, exposure to radiation, and even diet is implicated in higher risk.

Breast cancers are routinely typed for estrogen- and progesterone-receptor analysis. About two thirds of the patients have estrogen-receptor positive (ER+) breast tumors. Tumors which are progesterone positive are thought to have functional estrogen receptor and the presence of both receptors gives a greater likelihood of favorable response to endocrine treatment than the presence of just one receptor. Endocrine therapy, usually tamoxifen, is preferred in estrogen receptor-positive tumors. Estrogens and androgens are also effective, but less favored due to undesirable side effects induced by higher levels of these hormones than other forms of endocrine treatment. Breast cancer may metastasize to almost any organ in the body, but most common sites of metastasis are the lung, liver, bone, lymph nodes and skin.

Lobular carcinoma in situ (LCIS) or lobular neoplasia, is most frequently found in premenopausal women. Ductal carcinoma in situ (DCIS) occurs in both pre- and postmenopausal women. DCIS forms a palpable mass. LCIS and DCIS account for about 90% of all breast cancers. The rarer forms, medullary and tubular lesions, have a somewhat better prognosis.

The most common gynecologic neoplasms are endometrial carcinomas, which ranks fourth in frequency after breast, colorectal and lung cancers in women. Endometrial carcinomas are characterized by their clinical staging, ranging from in situ at stage 0, to metastasis to distant organs at stage IVB. Endometrial carcinomas typically produce estrogen and the current treatment approaches are surgery and progesterone therapy.

Ovarian cancers account for about 18% of all gynecologic neoplasms. About 80% of malignant ovarian cancers arise from the ovarian epithelium and are classified according to their histology. Tumors may also arise from germ cells or stroma.

Vulvar carcinoma accounts for about 3-4% of all gynecologic neoplasms. Vulvar carcinoma usually occurs after menopause, and about 90% are squamous cell carcinomas. About 4% are basal cell carcinomas and the rest include intraepithelial carcinomas, adenocarcinoma of Bartholin's gland, fibrosarcoma and melanoma.

Vaginal carcinoma accounts for about 1% of gynecologic malignancies, with a peak incidence from about ages 45 to 65. About 95% of vaginal carcinomas are squamous cell carcinoma. Primary carcinoma of the oviduct is rare and typically spread directly or by the lymphatics.

Trophoblastic disease or neoplams of trophoblastic origin, can follow intra- or extrauterine pregnancy. A degenerating pregnancy results in a hydatidiform mole of which about 80% are benign.

Neoplasms may arise in the ear canal and affect hearing. Ceruminomas also arise, are typically malignant despite appearing benign histologically and are treated by surgical removal. Basal cell and squamous cell carcinomas frequently develop on the external ear as the result from regular sun exposure, and are also typically treated by surgical removal. The middle ear may be the site of squamous cell carcinomas. Nonchromaffin paragangliomas may arise in the temporal bone.

The most common malignant tumor in the nose and paranasal sinuses is squamous cell carcinoma; less common are adenoid cystic and mucoepidermod carcinomas, malignant mixed tumors, adenocarcinomas, lymphomas, fibrosarcomas, osteosarcomas, chondrosarcomas, and melanomas.

Squamous cell carcinoma of the nasopharynx is more commonly observed in children and young adults.

The most common malignancies of the upper respiratory tract are squamous cell carcinomas of the tonsil and of the larynx. Both are more common in males and are associated with tobacco smoking and ethanol ingestion; about 85% of patients with cancer of the head or neck have a history of ethanol and tobacco consumption In the head and neck, about 90% of the cancers are squamous cell (epidermoid) carcinoma. Melanomas, lymphomas and sarcomas are relatively rare forms of primary head and neck cancers. Cancers of the head and neck are classified according to the size and site of involvement of the primary neoplasm; number and size of metastases to the cervical lymph nodes and evidence of distant metastases.

Opthalmologic cancers may arise in the skin of the eyelids and may be benign or neoplastic. Common benign growths are xanthelasmas, which form yellow-white flat plaques of lipid material subcutaneously. Basal cell carcinomas are more common; treatment is typically surgical removal or radiation therapy. Other less common malignant tumors are squamous cell or meibomian gland carcinomas and other types of melanomas. The most common primary ocular malignancy is malignant melanoma of the choroid.

Tumors also arise in the skin tissue, and include benign tumors such as moles, lipomas and the like, as well as malignant tumors. About 40-50% of malignant melanomas arise from melanocytes in moles. Malignant skin cancers are either basal cell or squamous cell carcinomas and frequently arise in sun-exposed areas of skin. They are the most common malignancies, and the incidence is rising. Less common malignancies include malignant melanoma, Paget's disease of the nipple or estramammary Patent's, Kaposi's sarcoma (KS) and cutaneous T cell lymphoma (mycosis fungiodes). The incidence of KS is increasing as the result of the increased incidence of AIDS. KS arises in about one third of patients with AIDS.

Oral cancers account for about 5% of cancers in men and 2% of cancers in women. The most common form of oral cancer is squamous cell carcinoma. Incidence increases with age and risk factors, particularly tobacco and alcohol consumption.

Surgery is oldest effective form of treatment of neoplasms. Success is largely achieved if the neoplasm is detected in its early stages and has not metastasized. Radiation is also important therapy, and is the favored therapy of many neoplasms such as Hodgkin's disease, early stage non-Hodgkin's lymphomas, squamous cell carcinoma of the head and neck. Radiation has proven very successful as an adjunct to surgery and antineoplastic drugs.

Antineoplastic drugs are also useful in the treatment of neoplasms, and are classified according to their mechanism of action. Antineoplastic drugs frequently target fundamental biological processes necessary for cell replication or growth. Numerous combinations, typically of antineoplastic drugs with differing mechanisms of action, have proven to be particularly effective therapy, permit lower doses and frequently minimize negative side effects. The combinations of drugs with different mechansisms of action need to be evaluated for optimal doses and schedules of administration. For instance, the sequence of administration of the cyclin-dependent kinase inhibitor, flavopiridol, with a number of different chemotherapeutic agents determines whether the combination will have a synergistic or an antagonistic effect on tumor cell proliferation (Bible, K. C. and Kaufmann, S. H., Cancer Res. 57, 3375-3380, 1997).

Alkylating agents, such as mechlorethamin and cyclophosphamide, alkylate DNA, and restrict DNA replication.

Antimetabolites that are directed to disrupting necessary cell division pathways include:

Folate antagonists bind to dehydrofolate reductase and interfer with pyrimidine synthesis. Folate antagonists are S-phase specific. Methotrexate is a very commonly used antineoplastic folate antagonist.

Purine antagonists block de novo purine synthesis and are S-phase specific. 6-mercaptopurine is an example of a purine antagonist.

Pyrimidine antagonists interfere with thymidylate synthase to reduce thymidine production and are S-phase specific. A frequently used pyrimidine antagonist is 5-fluorouracil.

Cytarabine inhibits DNA polymerase and is S-phase specific.

Plant alkyloids include vincas, such as vinblastine and vincristine, and podophyllotoxins, such as etoposide. Plant alkyloids are effective in the metaphase and inhibit mitosis by a variety of mechanisms including altering microtubular proteins.

Antibiotics include doxorubicin and daunomycin, which intercalate between DNA strands to inhibit the uncoiling of DNA, bleomycin, which causes incisions in DNA strands, and mitomycin, which inhibits DNA synthesis by acting as bifunctional alkylator.

Nitrosureas include carmustine and lomustine and alkylate DNA or cause carbamoylate amino acids in proteins.

Inorganic ions, such as cisplatin, cause inter- and intracalation of DNA strands to inhibit the uncoiling of DNA.

Taxanes, such as taxol and taxotere, prevent cells from dividing by promoting the assembly and preventing the disassembly of microtubules.

DNA topoisomerase I inhibitors, including campothecin analogs like irinotecan, inhibit cell growth by interfering with DNA sysnthesis.

Biologic Response Modifiers, such as the interferons, have antiproliferative effects, but their specific role is not known. Interferons include α (leukocyte) interferon, β (fibroblast) interferon and γ lymphocyte) interferon.

Enzymes, such as asparaginase, are also used alter metabolic pathways important in cancerous cells. Asparaginase depletes the cell of asparagine, on which leukemic cells depend.

Hormones and their analogs, such as tamoxifen, flutamide and progesterone, have non-specific effects but are useful to treat certain neoplams which are known to be hormone responsive, especially breast, ovarian and prostate neoplasms. Tamoxifen, frequently used in the treatment of breast neoplasms, places cells at rest, and binds to the estrogen receptor. Flutamide, frequently used in the treatment of prostate neoplasms, binds the androgen receptor.

Cytokinins are naturally occurring and artificial plant growth regulators. Natural cytokinins tend to be non-specific inhibitors of various protein kinases. The molecular mechanisms by which cytokinins regulate cell growth and division are still being determined. Studies have indicated that cytokinins may increase accessibility of the DNA template, activate RNA polymerases, affect polyadenylation and secondary structure of mRNA and stimulate formation and activity of polyribosomes. Cytokinins are thought to affect cell division by interacting with regulatory proteins of the cell cycle. Both cytokinins and cyclin-dependent kinases (cdks) act at multiple and similar control points of cell cycle, for example, at the $G_1/S$ and $G_2/M$ transitions and S and M phases.

Olomoucine, [6-(benzylamino)-2-[(2-hydroxyethyl) amino]-9-methylpurine], was first discovered as an herbicide. More recently, it has been discovered that Olomoucine is an artificial cytokinin, which specifically inhibit some cdks, including $p34^{cdc2}$/CyClin B kinases, at micromolar concentration, but has no effect on other major protein kinases such as cAMP- and cGMP-dependent kinases, and protein kinase C. Olomoucine has recently been shown to have good selectivity for the CDK/cyclin protein kinases, but only has moderate inhibitory activity, with an $IC_{50}$ of about 7 μM for CDK2. Vesely, J., et al., *Eur. J. Biochem.*, 1994, 224, 771-786. A 2.4 Å crystal structure of olomucine revealed that the purine portion of olomoucine binds in the conserved ATP binding pocket, while the benzylamino group extends into a region of the active site unique to the cdk2 kinases.

Roscovitine, 2-(1-ethyl-2-hydroxyethylamino)-6-benzylamino-9-isopropylpurine, is a recently synthesized purine that has been shown to have selectivity towards some cyclin-dependent kinases and to have 10-fold more active on cdk than olomoucine. Meijer, L., et al., *Eur. J. Biochem.*, 243:527-536 (1997) and PCT/FR96/01905. Meijer et al report that most kinases are not significantly inhibited by roscovitine. However, cdc 2/cyclin B, cdk 2/cyclin A, cdk 2/cyclin E and cdk 5/p35 are substantially inhibited with $IC_{50}$ values of 0.65, 0.7, 0.7 and 0.2 μM, respectively. In contrast, cdk 4/cyclin D1 and cdk 6/cyclin D2 had $IC_{50}$ values of greater than 100 μM.

Havlicek, L., et al., *J. Med. Chem.* (1997)40:408-412 report that Roscovitine, and related analogs substituted in the 2, 6 and/or 9 positions, inhibit $p34^{cdc2}$/CyClin B kinases. None of the analogs had superior $IC_{50}$ values over the (R) enantiomer of Roscovitine, which had an $IC_{50}$ value of 0.2 μM. The (S) enantiomer had an $IC_{50}$ value of 0.8 μM; the racemic mixture (R/S) had an $IC_{50}$ value of 0.65 μM. These authors conclude that the $N^6$-benzyl substituent of Roscovitine was superior over the isopentenyl or cyclohexylmethyl substituents.

The National Cancer Institute (NCI) is a US Government-run organization directed at the discovery and development of novel therapuetic oncology products. In 1985, the NCI established a new cancer screening strategy involving human tumor cell lines in an in vitro assay as the primary cancer screen. A total of sixty human tumor cell lines, derived from seven cancer types (lung, colon, melanoma, renal, ovarian, brain and leukemia) are selected for inclusion in the NCI panel. Grever, M. R., et al., *Seminars in Oncology*, 19:1992: 622-638. The protocols used in the assays have also been reported in the literature. American Type Tissue Collection (ATCC) acts as a depository for these and other tumor cell lines. Useful human tumor cell lines include the following:

MCF7: human breast adenocarcinoma, hormone-dependent;

MDA-MB-231: human breast adenocarcinoma, hormone-independent;

MDA-MB-435: human breast adenocarcinoma, hormone-independent

HT-29: human colon adenocarcinoma, moderately well differentiated grade II;

HCT-15: human colon adenocarcinoma;

Colo-205: human colon adenocarcinoma;

A549: human non-small cell lung carcinoma;

DMS-114: human small cell lung carcinoma;

NCI-H460: human non-small cell lung carcinoma;

PC-3: human prostate adenocarcinoma, hormone-independent;

DU 145: human prostate carcinoma, hormone-independent;

HL-60: human acute promyelocytic leukemia;

Jurkat: human acute T-cell leukemia; and

Molt-4: human acute lymphoblastic leukemia.

Skehan, P., et al., *J. Natl. Cancer Inst.* 82: 1107-1112, 1990 sets forth useful protocol for using such tumor cell lines for screening antineoplastic drugs.

Meijer, et al., supra, report that roscovitine inhibits the proliferation of the NCI disease-oriented in vitro screen, i.e., 60 human tumour cell lines comprising nine tumour types (leukemia, non-small cell lung cancer, colon cancer, central nervous system cancer, melanoma, ovarian cancer, renal cancer, prostate cancer, breast cancer) mammalian cell lines with an average $IC_{50}$ value of 16 μM. The results of individual tumour lines are not reported.

Two distinct cdk inhibitors, flavopiridol and olomoucine, suppress the death of neuronal PC12 cells and sympathetic neurons in two model systems of neuronal survival. Park et al., *J. Biol. Chem.* 271(14):8161-8169 (1996). The concentration of each required to promote survival correlated with the amount required to inhibit proliferation. Neuronal apoptosis is an important aspect of both nervous system development and a component of neuronal injury and disease.

The PC12 cell line was initially derived from a rat adrenal medullary pheochromocytoma. When grown in serum-containing medium, PC12 cells divide and resemble precursors of adrenal chromaffin cells and sympathetic neurons. Upon addition of nerve growth factor (NGF), PC12 cells attain the phenotypic properties of sympathetic neurons. Upon removal of either serum or serum and NGF, both naive and neuronally differentiated PC12 cells undergo apoptosis, which is also analogous of sympathetic neurons.

The role of cell cycle regulation in apoptosis may be explained that withdrawal of NGF or serum results in uncoordinated cell cycle progression of naive PC12 cells. Differentiated or sympathetic neurons are hypothesized to attempt inappropriate re-entry of the cell cycle.

Changes in the activity of cdks and cyclins are observed during apoptosis of many different cell types. Camptothecin- or araC-induced apoptosis of HL60 cells is associated with elevated cdc2 activity and cyclin E-associated kinase activity. Camptothecin-induced apoptosis of RKO cells is associated with an increase in expression of cyclin D1.

Camptothecin causes apoptotic death of rat cerebral cortical neurons. Morris and Geller, *J. Cell Biol.* 134:757-770 (1996). Camptothecin-treated nonproliferating neuronally differentiated PC12 cells die within 6 days after treatment, and cultured rat sympathetic neurons die within 5 days after treatment, even in the presence of NGF. Park et al., *J. Neurosci.* 17(4):1256-1270 (1997). However, administration of either both, or individual olomoucine or flavopiridol, resulted in approximately 30% cell death at day 6. Maximal protection of PC12 cells, or rat sympathetic neurons, from death was observed at 1 µM flavopiridol and 200 µM olomoucine, which are the minimum concentrations that fully inhibit DNA synthesis by proliferating PC12 cells. Administration of iso-olomoucine, an inactive analog of olomoucine, failed to prevent the cell death of camptothecin-treated neuronal cells.

Olomoucine and flavopiridol appear to partially suppress neurite generation. Park et al. *J. Biol. Chem.* 271(14):8161-8169 (1996).

Flavopiridol and olomoucine were also shown to protect against camptothecin-induced cortical neuronal death. Park et al., *J. Neurosci.* 17(4):1256-1270 (1997). The $IC_{50}$ values of flavopiridol and olomoucine were 0.1 µM and 100 µM, respectively. Administration of iso-olomoucine failed to prevent the cell death of camptothecin-treated neuronal cells.

There are several implications of the above observations. It is well recognized that patients treated with radiation or antineoplastic agents experience undesirable side effects, including developing new neoplasms or undesirable cellular apoptosis. For example, some patients treated with high-dose araC for refractory leukemia develop a cerebellar toxicity syndrome, characterized by loss of Purkinje neurons. Winkelman and Hinges, *Ann Neurol.* 14:520-527 (1983) and Vogel and Horouipian, *Cancer* 71:1303-1308 (1993). Patients treated with cis-platinum have been reported to develop periperal neuropathies. Wallach, et al., *J. Fla. Med. Assoc.* 79:821-822 (1992) and Mansfield and Castillo, *AJNR Am. J. Neuroradiol.* 15:1178-1180 (1994). In view of these observations, either co-administration or sole administration of the present compounds in the treatment of neoplasms would reduce or preclude cellular apoptosis, in particular, neuronal damage caused by treatment with antineoplastic agents or radiation.

Cerebrovascular disease is the most common cause of neuologic disability in Western countries. The major specific types of cerebrovascular disease are cerebral insufficiency due to transient disturbances of blood flow, infarction, hemmorrhage, and arteriovenous malformation. Stroke generally denotes ischemic lesions. Undesirable neuronal apoptosis occurs in cerebrovascular disease.

Inhibition of cyclin-dependent kinases would also have therapeutic value in treating additional hyperproliferative disorders (see Meijer, et al., *Pharmacol. Ther.* 82, 279-284, 1999 for a review). Neointimal formation in vascular injury, such as occurs in angioplasty procedures, represents a hyperproliferative disorder (non-neoplastic) in which cell cycle inhibitors would have a therapeutic benefit. Flavopiridol has been shown to inhibit SMC growth in vitro and in vivo, suggesting potential for other CDK inhibitors in this area (Ruef et al., *Circulation* 100, 659-665, 1999). Atherosclerosis represents another widespread form of vascular injury. It has been shown that the CDK inhibitor, p27Kip1, and cyclin E are upregulated in human atherosclerotic tissue (Ihling et al., *Atherosclerosis* 144, 7-14, 1999). One of the implications of this study is that cell cycle control is altered in the regions of chronic inflammation associated with atherosclerosis.

Autoimmune disorders such as rheumatoid arthritis, Type I diabetes, inflammatory bowel disorder and allograft rejection may represent additional areas where reducing rapid cell proliferation by CDK inhibition would have therapeutic benefit. Lesion cellularity is a common component associated with these chronic inflammatory disorders. For instance, jejunal hyperplasia is associated with Type I diabetes, and is present in Streptozoticin treated rats (an animal model for Type I diabetes). Diabetic crypt enterocytes exhibited increased tyrosine kinase, ornithine decarboxylase (ODC), and cdk1 activities when compared with control rats. Treatment with an ODC inhibitor, difluoromethylornithine, prevented jejunal hyperplasia, and reduced the proliferation associated activities mentioned above (Parekh et al., J. Invest. Med. 47, 397-404, 1999).

Inhibitors of CDKs may also have utility as antivirals. For instance, the CDK inhibitors olomoucine and roscovitine inhibited the replication of herpes simplex virus (Schang et al., J. Virol. 72, 5626-5637, 1998).

SUMMARY OF THE INVENTION

The present invention provides a method of inhibiting cell cycle progression by administration of an antiproliferative compound for Formula (I). More specifically, the present invention provides a method of inhibiting the activity of cyclin-dependent kinase complexes, including cdk1/cyclin B, cdk2/cyclin E, and cdk4/cyclin D1.

The present invention also provides a method of preventing apoptosis in cells by administration of a compound for Formula (I). A preferred method of the invention is preventing apoptosis of neuronal cells by administration of a compound for Formula (I). A particularly preferred method of the present invention is preventing apoptosis of neuronal cells induced by antineoplastic agents or resulting from cerebrovascular disease. Another preferred embodiment of the present invention is the method of preventing apoptosis induced by oxygen depletion. A more preferred invention provides a method of preventing apoptosis induced cerebrovascular disease. Another preferred invention provides a method of preventing apoptosis induced by stroke or infarction.

The present invention provides a method of inhibiting the development of neoplasms by administration of a compound for Formula (I). The present invention provides a method for treating a patient afflicted with a neoplastic disease state comprising administering a compound of the Formula (I). It is preferred that the amount administered is a therapeutically effective amount of a compound of the formula. A preferred method of the present invention administers a single compound of the formula provided. Alternatively, a preferred method of the present invention administers an amount of a compound of the formula in conjunction with other antineoplastic agents.

A "hyperproliferative disorder" refers to a disease condition characterized by rapid, or uncontrolled cell division. Hyperproliferative disorders include neoplastic diseases and non-neoplastic diseases.

"Neoplastic disease" refers to an abnormal state or condition characterized by rapid or uncontrolled proliferation of a cells or tissue that serves no useful biologic purpose, but grows at the expense of the healthy organism. Neoplastic diseases include leukemias, carcinomas and adenocarcinomas, sarcomas, melanomas, and mixed types of neoplasms.

Leukemias include, but are not limited to, acute lymphoblastic, chronic lymphocytic, acute myeloblastic and chronic myelocytic leukemias.

Carcinomas and adenocarcinomas include, but are not limited to, those of the cervis, breast, prostate, esophagus, stomach, small intestines, colon, ovary and lungs.

Sarcomas include, but are not limited to, oesteromas, osteosarcoma, lipoma, lipsarcoma, hemangiomas and hemangiosarcoma.

Melanomas include, but are not limited to, amelanotic and melanotic melanomas.

Mixed types of neoplasms include, but are not limited to, carcinosarcoma, lymphoid tissue type, folicullar reticulum, cell sarcoma and Hodgkins Disease.

"Non-neoplastic diseases" refer to an abnormal state or condition characterized by rapid or uncontrolled proliferation of cells or tissue that otherwise serve a useful biologic purpose. Non-neoplastic diseases include restenosis and autoimmune diseases. Autoimmune diseases include, but are not limited to, atherosclerosis, rheumatoid arthritis, Type I diabetes, inflammatory bowel disorder and allograft rejection.

The term "therapeutically effective amount" of a compound of the formula refers to an amount that is effective, upon single or multiple dose administration to the patient, in controlling, slowing, reducing, or preventing cellular division or cellular proliferation, or the growth of the neoplasm or metastases of the neoplasm or preventing apoptosis. A therapeutically effective amount of a compound of the formula will vary according to the age and weight of the patient, renal function of the patient, bioavailability of the compound administered, type of neoplasm to be treated, the combination of other antineoplastic agents, and other criteria well known to those skilled in the art using standard clinical and laboratory tests and procedures. A therapeutically effective amount of a compound of the formula will vary according to the type of cell susceptible to apoptosis, the location of the neoplasm or site of hyperproliferation, or infarct.

"Controlling the growth" of the neoplasm refers to slowing, interrupting, arresting or stopping the growth of the neoplasm or metastases of the neoplasm. The term "controlling the growth" of the neoplasm also refers to killing the neoplasia or metastases of the neoplasm, as well as prophylatic treatment of a patient who is at risk of developing a hyperproliferative disease, or is at risk of undergoing, developing neuroal apoptosis.

An effective amount of a compound of the formula is that amount which is effective, upon single or multiple dose administration to a patient in providing a reduction of cellular proliferation, or in preventing apoptosis. An "antineoplastic effect" refers to the slowing, interrupting, preventing or destruction of further growth of neoplastic cells. An "antiapoptotic effect" refers to the slowing, interrupting, preventing of apoptosis of neuronal cells.

An effective antineoplastic amount of a compound of the formula can be readily determined by an attending diagnostician, as one skilled in the art, by the use of known techniques and by observing results obtained under analogous circumstances. In determining the effective amount, a number of factors are considered by the attending diagnostician, including but not limited to, the species of mammal; its size, age and general health; the specific disease involved; the degree of or involvement or the severity of the disease; the response of the individual patient; the particular compound of the formula administered; the mode of administration; the bioavailability characteristics of the preparation administered; the dose regimen selected; the use of concomitant medication; and other relevant circumstances.

A further embodiment of the present invention includes a method for the prophylactic treatment of a patient at risk of developing a hyperproliferative disease, such as a neoplastic or non-neoplastic, disease comprising administering a prophylactically effective antineoplastic amount of a compound of the formula. A patient at risk of developing a neoplastic disease refers to a patient who, because of an identified genetic predisposition to neoplasms, had or currently have neoplasms, exposure of carcinogenic agents, diet, age or has other risk factors associated with the development of neoplastic disease states. Preferred patients at risk of developing a neoplastic disease state include patients who are positive for oncogenic viruses, are in remission from prior treatment of neoplasm(s), use tobacco products or have previously been exposed to carcinogens such as asbestos, or are positive for various neoplastic genetic markers.

Oncogenic viruses are those viruses associated with cancers. For example, Rous sarcoma of chickens, Shope rabbit papilloma, murine leukemia viruses are animal viruses recognized as having a role in development of various cancers. Human papillomavirus is associated with genital cancer. Molluscum contagiosum virus is associated with molluscum contagiosum tumors. The JC virus, a human papovirus, is associated with disorders of reticulendothelial system such as leukemia and lymphoma. Human retroviruses such as human T-cell lymphotropic viruses (HTLV) types 1 and 2 are associated with some human leukemias and lymphomas. Human immunodeficiency viruses (HIV) types 1 and 2 are the causes of AIDS. Epstein-Barr virus has been associated with various malignancies, including nasopharyngeal carcinoma, African Burkitt's lymphoma and lymphomas in immunosuppressed organ transplant recipients.

Genetic markers such as mutations, rearrangements and the like in BRCA 1, bcl-1/PRAD1, cyclin D1/CCND1, p16, cdk4, especially an Arg24Cys mutation, $p16^{INK4a}$. Genetic markers are associated with predispositions to various neoplasms. For example, alterations in the BRCA 1 gene are associated with a higher risk for breast and ovarian cancer. Other genetic markers include alterations in the MMSC1 gene, which interacts with the MMCA1 brain and prostate cancer gene, in the CtIP gene, which is linked to the BRACA1 gene in breast and ovarian cancer, binds to the BRCA1 gene and is linked to the E1A oncogene pathway, and in the MKK3 gene, which is a cell cycle control gene that acts as a tumor suppressor in lung cancer by activating apoptosis. Patients at risk of developing a neoplastic disease state also include patients who overexpress various cell cycle proteins, including cdk4, cyclins B1 and E. Patients at risk of developing a neoplastic disease state include those with elevated levels of tumor markers. Known tumor markers include prostate specific antigen (PSA) and plasma insulin-like growth factor-1 (IGF-1), which are markers for prostate cancer. Nuclear matrix proteins (NMPs) are associated with the presence of cancer, particularly bladder and colon cancers.

DETAILED DESCRIPTION OF THE INVENTION

The present invention provides compounds according to the formula (I),

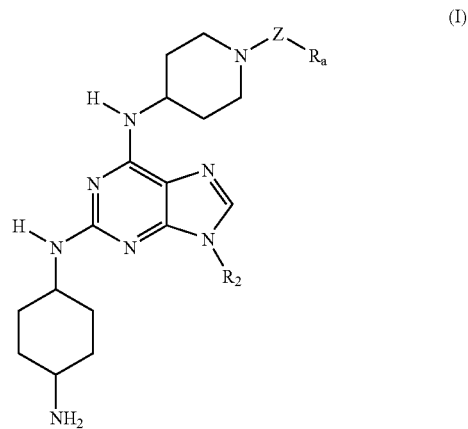

wherein

Z is selected from the group consisting of —S(O)$_2$— and —C(O)—;

when Z is —S(O)$_2$—, R$_a$ is selected from the group consisting of —R1 and —N(R1)(R3), or when Z is —C(O)—, R$_a$ is selected from the group consisting of —R1, —OR1, —N(R1)(R3) and —SR1, where R1 is selected from the group consisting of
- —C$_1$-C$_{11}$ alkyl, wherein each carbon may be optionally substituted with one, two or three X substituents,
- —C$_3$-C$_{10}$ cycloalkyl, wherein each carbon may be optionally substituted with one or two X substituents,
- —(CH$_2$)$_n$Q$_p$(CH$_2$)$_n$W, wherein each carbon of (CH$_2$)$_n$— may be optionally substituted with one or two X substituents,
- Q is O, S, or NR3,
- n is independently an integer 0-6,
- p is independently an integer 0 or 1,
- W is independently selected from the group consisting of hydrogen, C$_3$-C$_{10}$ cycloalkyl, —(C$_3$-C$_{10}$ cycloalkyl)-aromatic, and one of the following aromatic or heteroaromatic rings:

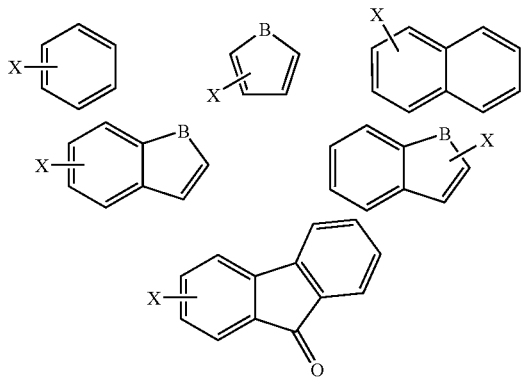

where B is —O—, —S—, —NR6-, where each carbon of the aromatic or heteroaromatic ring may be independently substituted by a nitrogen atom, and each carbon of the aromatic ring may be independently substituted with an X substituent;

and —(CH$_2$)$_n$CHW$_2$, where each X substituent is independently selected from the group consisting of hydrogen, halogen, methylenedioxy, —C$_1$-C$_8$ alkyl, —C$_3$-C$_{10}$ cycloalkyl, substituted or unsubstituted phenyl, —C$_1$-C$_8$ alkoxy, —SR3, —OH, =O, —CY$_3$, —OCY$_3$, —CO$_2$R3, —CN, —CO—NR4R5, —NO$_2$, —COR3, —NR4R5, —NH—C(O)—R3, —NH—C(O)—(C$_1$-C$_6$ alkyl)-aromatic, and —NH—C(O)—(C$_1$-C$_6$ alkyl)-heteroaromatic;

where each Y is independently selected from the group consisting of hydrogen and halogen;

where each R3 is independently selected from the group consisting of hydrogen, and C$_1$-C$_8$ alkyl, where C$_1$-C$_8$ alkyl may be straight or branched, saturated or unsaturated;

where each R4 and R5 is independently selected from the group consisting of hydrogen, and C$_1$-C$_6$ alkyl, where C$_1$-C$_6$ alkyl may be straight or branched, saturated or unsaturated, where which each carbon of C$_1$-C$_6$ alkyl is optionally substituted with an X substituent, or where R4 and R5 taken together with the nitrogen to which they are attached, form a heterocyclic ring of three to seven atoms including the nitrogen atom;

where —NR6- is selected from the group consisting of an unsubstituted N, an N substituted with -hydrogen, —(C$_1$-C$_6$ alkyl), —C$_3$-C$_{10}$ cycloalkyl, —S(O)$_2$—(C$_1$-C$_6$ alkyl), —S(O)$_2$—(C$_3$-C$_{10}$ cycloalkyl), —C(O)R3, —C(O)—(C$_0$-C$_6$ alkyl)-aromatic, and —S(O)$_2$—(C$_0$-C$_6$ alkyl)-aromatic, wherein each carbon of the aromatic ring may be optionally substituted with an X substituent; and where phenyl is substituted with one to five substituents independently selected from the group consisting of hydrogen, halogen, methylenedioxy, —C$_1$-C$_8$ alkyl, —C$_3$-C$_{10}$ cycloalkyl, —C$_1$-C$_8$ alkoxy, —OH, —CY$_3$, —OCY$_3$, —CO$_2$R3, —CN, —NO$_2$, —COR3, —NR4R5, —SR3, —CO—NR4R5, and —NH—C(O)—R3; and R2 is selected from the group consisting of cyclopentyl, cyclopentenyl, and isopropyl; and the pharmaceutically acceptable salts, optical isomers, solvates and hydrates thereof.

A preferred aspect of the present invention provides compounds of formula (Ia)

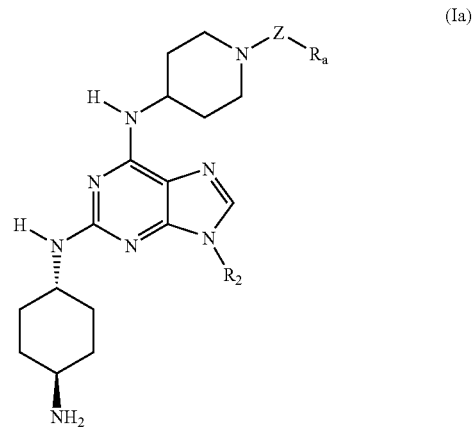

(Ia)

where Z, R$_a$, and R$_2$ are as defined hereinabove.

Another preferred aspect of the present invention provides compounds of formula (I) or formula (Ia) wherein R$_2$ is cyclopentyl.

Another preferred aspect of the present invention provides compounds of formula (Ia) wherein Z is —C(O)—.

Another preferred aspect of the present invention provides compounds of formula (Ia) wherein Z is —S(O)$_2$—.

A more preferred aspect of the present invention provides compounds of formula (Ia) wherein Z is —C(O)— and R$_a$ is —OR1 or —N(R1)(R3).

Another more preferred aspect of the present invention provides compounds of formula (Ia) wherein Z is —C(O)— and R$_a$ is —SR1.

Another more preferred aspect of the present invention provides compounds of formula (Ia) wherein Z is —C(O)— and R$_a$ is —OR1.

Still another more preferred aspect of the present invention provides compounds of formula (Ia) wherein Z is —C(O)— and R$_a$ is —N(R1)(R3).

A special embodiment of the present invention provides compounds of formula (I) or formula (Ia) wherein R1 is —(CH$_2$)$_n$Q$_p$(CH$_2$)$_n$W.

Another special embodiment of the present invention provides compounds of formula (Ia) wherein Z is —C(O)—, R$_a$ is —N(R1)(R3) and R1 is —(CH$_2$)$_n$Q$_p$(CH$_2$)$_n$W.

A preferred special embodiment of the present invention provides compounds of formula (Ia) wherein Z is —C(O)—, R$_a$ is —N(R1)(R3), R1 is —(CH$_2$)$_n$Q$_p$(CH$_2$)$_n$W and W is

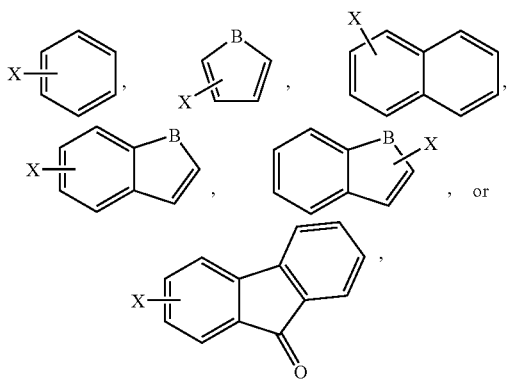

where B is —O—, —S—, —NR6-, where each carbon of the aromatic or heteroaromatic ring may be independently substituted by a nitrogen atom, and each carbon of the aromatic ring may be independently substituted with an X substituent.

Another preferred special embodiment of the present invention provides compounds of formula (Ia) wherein Z is —C(O)—, R$_a$ is —N(R1)(R3), R1 is —(CH$_2$)$_n$Q$_p$(CH$_2$)$_n$W and W is phenyl, each carbon of which may be independently substituted with an X substituent.

Preferred compounds of the present invention include:

trans-4-[2-(4-Amino-cyclohexylamino)-9-cyclopentyl-9H-purin-6-ylamino]-piperidine-1-carboxylic acid (4-fluoro-phenyl)-amide;

trans-4-[2-(4-Amino-cyclohexylamino)-9-cyclopentyl-9H-purin-6-ylamino]-piperidine-1-carboxylic acid (3-trifluoromethyl-phenyl)-amide;

trans-4-[2-(4-Amino-cyclohexylamino)-9-cyclopentyl-9H-purin-6-ylamino]-piperidine-1-carboxylic acid (2-methoxy-phenyl)-amide;

trans-4-[2-(4-Amino-cyclohexylamino)-9-cyclopentyl-9H-purin-6-ylamino]-piperidine-1-carboxylic acid (3-chloro-phenyl)-amide;

trans-4-[2-(4-Amino-cyclohexylamino)-9-cyclopentyl-9H-purin-6-ylamino]-piperidine-1-carboxylic acid (2-bromo-phenyl)-amide;

trans-4-[2-(4-Amino-cyclohexylamino)-9-cyclopentyl-9H-purin-6-ylamino]-piperidine-1-carboxylic acid (2-chloro-phenyl)-amide;

trans-4-[2-(4-Amino-cyclohexylamino)-9-cyclopentyl-9H-purin-6-ylamino]-piperidine-1-carboxylic acid (4-trifluoromethoxy-phenyl)-amide;

trans-4-[2-(4-Amino-cyclohexylamino)-9-cyclopentyl-9H-purin-6-ylamino]-piperidine-1-carboxylic acid (4-chloro-2-trifluoromethyl-phenyl)-amide;

trans-4-[2-(4-Amino-cyclohexylamino)-9-cyclopentyl-9H-purin-6-ylamino]-piperidine-1-carboxylic acid (4-chloro-3-trifluoromethyl-phenyl)-amide;

trans-4-[2-(4-Amino-cyclohexylamino)-9-cyclopentyl-9H-purin-6-ylamino]-piperidine-1-carboxylic acid (4-methyl-phenyl)-amide;

trans-4-[2-(4-Amino-cyclohexylamino)-9-cyclopentyl-9H-purin-6-ylamino]-piperidine-1-carboxylic acid (4-methylsulfanyl-phenyl)-amide;

trans-4-[2-(4-Amino-cyclohexylamino)-9-cyclopentyl-9H-purin-6-ylamino]-piperidine-1-carboxylic acid biphenyl-2-yl-amide;

trans-4-[2-(4-Amino-cyclohexylamino)-9-cyclopentyl-9H-purin-6-ylamino]-piperidine-1-carboxylic acid (4-isopropyl-phenyl)-amide;

trans-4-[2-(4-Amino-cyclohexylamino)-9-cyclopentyl-9H-purin-6-ylamino]-piperidine-1-carboxylic acid (4-ethoxy-phenyl)-amide;

trans-4-[2-(4-Amino-cyclohexylamino)-9-cyclopentyl-9H-purin-6-ylamino]-piperidine-1-carboxylic acid (2-fluoro-5-trifluoromethyl-phenyl)-amide;

trans-4-[2-(4-Amino-cyclohexylamino)-9-cyclopentyl-9H-purin-6-ylamino]-piperidine-1-carboxylic acid (4-fluoro-2-trifluoromethyl-phenyl)-amide; and trans-4-[2-(4-Amino-cyclohexylamino)-9-cyclopentyl-9H-purin-6-ylamino]-piperidine-1-carboxylic acid (4-fluoro-3-trifluoromethyl-phenyl)-amide and pharmaceutically acceptable salts, optical isomers, solvates and hydrates thereof.

Other preferred compounds of the present invention include:

trans-4-[2-(4-Amino-cyclohexylamino)-9-cyclopentyl-9H-purin-6-ylamino]-piperidine-1-carboxylic acid butyl ester;

trans-4-[2-(4-Amino-cyclohexylamino)-9-cyclopentyl-9H-purin-6-ylamino]-piperidine-1-carboxylic acid ethyl ester;

trans-4-[2-(4-Amino-cyclohexylamino)-9-cyclopentyl-9H-purin-6-ylamino]-piperidine-1-carboxylic acid 4-nitro-benzyl ester;

trans-4-[2-(4-Amino-cyclohexylamino)-9-cyclopentyl-9H-purin-6-ylamino]-piperidine-1-carboxylic acid allyl ester;

trans-4-[2-(4-Amino-cyclohexylamino)-9-cyclopentyl-9H-purin-6-ylamino]-piperidine-1-carboxylic acid 2-nitro-phenyl ester;

trans-4-[2-(4-Amino-cyclohexylamino)-9-cyclopentyl-9H-purin-6-ylamino]-piperidine-1-carboxylic acid 4,5-dimethoxy-2-nitro-benzyl ester;

trans-4-[2-(4-Amino-cyclohexylamino)-9-cyclopentyl-9H-purin-6-ylamino]-piperidine-1-carboxylic acid prop-2-ynyl ester; and trans-4-[2-(4-Amino-cyclohexylamino)-9-cyclopentyl-9H-purin-6-ylamino]-piperidine-1-carboxylic acid 4-methoxycarbonyl-phenyl ester; and pharmaceutically acceptable salts, optical isomers, solvates and hydrates thereof.

Still other preferred compounds of the present invention include:

trans-1-{4-[2-(4-Amino-cyclohexylamino)-9-cyclopentyl-9H-purin-6-ylamino]-piperidin-1-yl}-2-phenoxy-ethanone;

trans-1-{4-[2-(4-Amino-cyclohexylamino)-9-cyclopentyl-9H-purin-6-ylamino-piperidin-1-yl}-2-phenylsulfanyl-ethanone;

trans-1-{4-[2-(4-Amino-cyclohexylamino)-9-cyclopentyl-9H-purin-6-ylamino]-piperidin-1-yl}-2-(4-chloro-phenoxy)-ethanone;

trans-1-{4-[2-(4-Amino-cyclohexylamino)-9-cyclopentyl-9H-purin-6-ylamino]-piperidin-1-yl}-2-benzyloxy-ethanone;

trans-1-{4-[2-(4-Amino-cyclohexylamino)-9-cyclopentyl-9H-purin-6-ylamino]-piperidin-1-yl}-2-phenyl-butan-1-one;

trans-(E)-1-{4-[2-(4-Amino-cyclohexylamino)-9-cyclopentyl-9H-purin-6-ylamino]-piperidin-1-yl}-3-(3-trifluoromethyl-phenyl)-propenone; and trans-1-{4-[2-(4-Amino-cyclohexylamino)-9-cyclopentyl-9H-purin-6-ylamino]-piperidin-1-yl}-1-cyclobutyl-methanone; and pharmaceutically acceptable salts, optical isomers, solvates or hydrates thereof.

Most preferred compounds of the present invention include:

trans-1-{4-[2-(4-Amino-cyclohexylamino)-9-cyclopentyl-9H-purin-6-ylamino]-piperidin-1-yl}-2-phenoxy-ethanone;

trans-1-{4-[2-(4-Amino-cyclohexylamino)-9-cyclopentyl-9H-purin-6-ylamino]-piperidin-1-yl}-2-phenylsulfanyl-ethanone;

trans-1-{4-[2-(4-Amino-cyclohexylamino)-9-cyclopentyl-9H-purin-6-ylamino]-piperidin-1-yl}-2-(4-chloro-phenoxy)-ethanone; and trans-1-{4-[2-(4-Amino-cyclohexylamino)-9-cyclopentyl-9H-purin-6-ylamino]-piperidin-1-yl}-2-benzyloxy-ethanone; and pharmaceutically acceptable salts, optical isomers, solvates and hydrates thereof.

Other most preferred compounds of the present invention include:

trans-4-[2-(4-Amino-cyclohexylamino)-9-cyclopentyl-9H-purin-6-ylamino]-piperidine-1-carboxylic acid 4-methoxycarbonyl-phenyl ester; and trans-4-[2-(4-Amino-cyclohexylamino)-9-cyclopentyl-9H-purin-6-ylamino]-piperidine-1-carboxylic acid 2-nitrophenyl ester; and a pharmaceutically acceptable salts, optical isomers, solvates and hydrates thereof.

The term "$C_0$-$C_6$ alkyl" refers to a single bond, or a $C_1$-$C_6$ alkyl.

The term "$C_1$-$C_6$ alkyl" refers to a saturated or unsaturated, straight or branched chain hydrocarbyl radical of from one to six carbon atoms. An unsaturated $C_1$-$C_6$ alkyl may contain one or more double or triple bond between two adjacent carbon atoms, and requires at least two carbon atoms in the alkyl chain. A $C_1$-$C_6$ alkyl includes, but is not limited to, the following: methyl, ethyl, propyl, isopropyl, 1-propenyl, propynyl, 2-propenyl, n-butyl, isobutyl, 2-methyl-2-propenyl, 2-butynyl, 3-butynyl, tertiary butyl, sec-butyl, 1-butenyl, 2-butenyl, and 3-butenyl, pentyl, 2-pentenyl, 3-pentenyl, 4-pentenyl, 2-pentynyl, 3-pentynyl, 4-pentynyl, prenyl, neopentyl, hexyl, 2-hexenyl, 3-hexenyl, 4-hexenyl, 5-hexenyl, 2-hexynyl, 3-hexynyl, 4-hexynyl, 5-hexynyl. A $C_1$-$C_6$ alkyl includes smaller subsets of alkyl radicals, such as a $C_1$-$C_4$ alkyl, a $C_1$-$C_3$ alkyl, and a $C_1$-$C_2$ alkyl, as well as a $C_5$-$C_6$ alkyl.

The term "$C_1$-$C_8$ alkyl" refers to a saturated or unsaturated, straight or branched chain hydrocarbyl radical of from one to eight carbon atoms. A $C_1$-$C_8$ alkyl may be saturated or unsaturated. An unsaturated $C_1$-$C_8$ alkyl may contain one or more double or triple bond between two adjacent carbon atoms. A $C_1$-$C_8$ alkyl includes, but is not limited to, the following: methyl, ethyl, propyl, isopropyl, 1-propenyl, propynyl, 2-propenyl, n-butyl, isobutyl, 2-methyl-2-propenyl, 2-butynyl, 3-butynyl, tertiary butyl, sec-butyl, 1-butenyl, 2-butenyl, and 3-butenyl, pentyl, 2-pentenyl, 3-pentenyl, 4-pentenyl, 2-pentynyl, 3-pentynyl, 4-pentynyl, prenyl, neopentyl, hexyl, 2-hexenyl, 3-hexenyl, 4-hexenyl, 5-hexenyl, 2-hexynyl, 3-hexynyl, 4-hexynyl, 5-hexynyl, heptyl, heptenyl, heptynyl, octyl, octenyl and octynyl. A $C_1$-$C_8$ alkyl includes smaller subsets of alkyl radicals, such as a $C_1$-$C_4$ alkyl, a $C_1$-$C_3$ alkyl, a $C_1$-$C_2$ alkyl, as well as a $C_5$-$C_8$ alkyl, a $C_5$-$C_7$ alkyl, and a $C_6$-$C_8$ alkyl.

The term "$C_1$-$C_{11}$ alkyl" refers to a saturated or unsaturated, straight or branched chain hydrocarbyl radical of from one to eleven carbon atoms. A $C_1$-$C_{11}$ alkyl may be saturated or unsaturated. An unsaturated $C_1$-$C_{11}$ alkyl may contain one or more double or triple bond between two adjacent carbon atoms. A $C_1$-$C_{11}$ alkyl includes, but is not limited to, the following: methyl, ethyl, propyl, isopropyl, 1-propenyl, propynyl, 2-propenyl, n-butyl, isobutyl, 2-methyl-2-propenyl, 2-butynyl, 3-butynyl, tertiary butyl, sec-butyl, 1-butenyl, 2-butenyl, 3-butenyl, pentyl, 2-pentenyl, 3-pentenyl, 4-pentenyl, 2-pentynyl, 3-pentynyl, 4-pentynyl, prenyl, neopentyl, hexyl, 2-hexenyl, 3-hexenyl, 4-hexenyl, 5-hexenyl, 2-hexynyl, 3-hexynyl, 4-hexynyl, 5-hexynyl, heptyl, heptenyl, heptynyl, octyl, octenyl, octynyl, nanyl, nanenyl, nanynyl, decyl, decenyl, decynyl, n-decyl, and undecyl. A $C_1$-$C_{11}$ alkyl includes smaller subsets of alkyl radicals, such as a $C_1$-$C_6$ alkyl, a $C_1$-$C_5$ alkyl, a $C_1$-$C_4$ alkyl, a $C_1$-$C_3$ alkyl, a $C_1$-$C_2$ alkyl as well as a $C_7$-$C_{11}$, alkyl, a $C_7$-$C_{10}$ alkyl, a $C_6$-$C_8$ alkyl, a $C_8$-$C_{10}$ alkyl, and a $C_8$-$C_{11}$ alkyl. In addition, each carbon of the $C_1$-$C_{11}$ alkyl may be optionally substituted with one, two or three X substituents.

The term "$C_3$-$C_{10}$ cycloalkyl" refers to a saturated or unsaturated $C_3$-$C_{10}$ cyclic chain hydrocarbyl radical of from three to ten carbon atoms. A $C_3$-$C_{10}$ cycloalkyl may be saturated or unsaturated. An unsaturated $C_3$-$C_{10}$ cycloalkyl may contain one or more double bonds between two adjacent carbon atoms. A $C_3$-$C_{10}$ cycloalkyl includes, but is not limited to, the following: cyclopropyl, cyclobutyl, cyclopentyl, cyclopentenyl, cyclohexenyl, cyclohexyl, cycloheptyl, cyclooctyl, and the like, bicyclic ring structures, including, but not limited to a fused five-and-five membered cycloalkyl rings, a fused five-and-six membered cycloalkyl rings, a fused six-and-six membered cycloalkyl rings, and polycyclic ring structures, including, but is not limited to, adamantane. In addition, any single bond in the cycloalkyl may be a double or triple bond. In addition, each carbon of the $C_3$-$C_{10}$ cycloalkyl may be optionally substituted with one, two or three X substituents.

The term "—$(CH_2)_n Q_p (CH_2)_n W$" refers to a moiety where each n is independently an integer 0 to 6, p is independently an integer 0 or 1, Q is a oxygen, sulfur or —NR3, W is independently selected from the group consisting of hydrogen, $C_3$-$C_{10}$ cycloalkyl, —($C_3$-$C_{10}$ cycloalkyl)-aromatic, and the following aromatic or heteroaromatic rings:

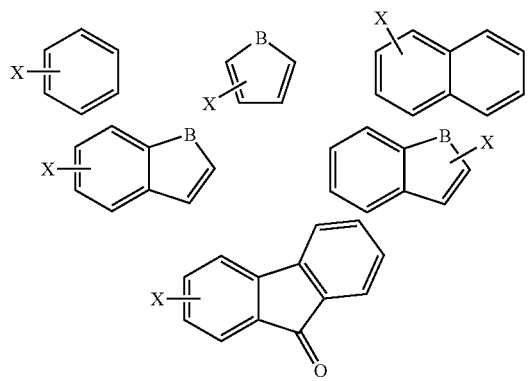

where B is —O—, —S—, —NR6-, where each carbon of the aromatic or heteroaromatic ring may be independently substituted by a nitrogen atom, and each carbon of the aromatic ring may be optionally substituted an X substituent. Each carbon of —(CH$_2$), alkyl chain is optionally substituted with one to two X substituents. R3 is independently selected from the group consisting of hydrogen, and C$_1$-C$_8$ alkyl, where C$_1$-C$_8$ alkyl may be straight or branched, saturated or unsaturated.

When R1 is —(CH$_2$)$_n$Q$_p$(CH$_2$)$_n$W and Q is NR3, the moiety includes —NR3W, —CH$_2$NR3W, —CH$_2$NR3CH$_2$W, —(CH$_2$)$_2$NR3W, —CH$_2$NR3CH$_2$CH$_2$W, —(CH$_2$)$_2$NR3CH$_2$W, —(CH$_2$)$_3$NR3W, —CH$_2$NR3(CH$_2$)$_2$CH$_2$W, —(CH$_2$)$_2$NR3CH$_2$CH$_2$W, —(CH$_2$)$_2$NR3(CH$_2$)$_2$CH$_2$W, —CH$_2$NR3(CH$_2$)$_3$CH$_2$W, —(CH$_2$)$_2$NR3(CH$_2$)$_2$CH$_2$W, —(CH$_2$)$_3$NR3CH$_2$CH$_2$W, —(CH$_2$)$_4$NR3CH$_2$W, —(CH$_2$)$_5$NR3W, —CH$_2$NR3(CH$_2$)$_4$CH$_2$W, —(CH$_2$)$_2$NR3CH$_2$)$_3$CH$_2$W, —(CH$_2$)$_3$NR3(CH$_2$)$_2$CH$_2$W, —(CH$_2$)$_4$NR3CH$_2$CH$_2$W, —(CH$_2$)$_5$NR3CH$_2$W, —(CH$_2$)$_6$NR3W, —CH$_2$NR3 (CH$_2$)$_5$CH$_2$W, —(CH$_2$)$_2$NR3 (CH$_2$)$_4$CH$_2$W, —(CH$_2$)$_3$NR3(CH$_2$)$_3$CH$_2$W, —(CH$_2$)$_4$NR3(CH$_2$)$_2$CH$_2$W, —(CH$_2$)$_5$NR3CH$_2$CH$_2$W, and —(CH$_2$)$_6$NR3CH$_2$W, where the terms n, p, W and R3 are previously defined.

When R1 is —(CH$_2$)$_n$Q$_p$(CH$_2$)$_n$W and Q is a sulfur, the moiety includes —SW, —CH$_2$SW, —CH$_2$SCH$_2$W, —(CH$_2$)$_2$SW, —CH$_2$SCH$_2$CH$_2$W, —(CH$_2$)$_2$SCH$_2$W, —(CH$_2$)$_3$SW, —CH$_2$SH(CH$_2$)$_2$CH$_2$W, —(CH$_2$)$_2$SCH$_2$CH$_2$W, —(CH$_2$)$_2$S(CH$_2$)$_2$CH$_2$W, —CH$_2$S(CH$_2$)$_3$CH$_2$W, —(CH$_2$)$_2$S(CH$_2$)$_2$CH$_2$W, —(CH$_2$)$_3$SCH$_2$CH$_2$W, —(CH$_2$)$_4$SCH$_2$W, —(CH$_2$)$_5$SW, —CH$_2$S(CH$_2$)$_4$CH$_2$W, —(CH$_2$)$_2$S(CH$_2$)$_3$CH$_2$W, —(CH$_2$)$_3$S(CH$_2$)$_2$CH$_2$W, —(CH$_2$)$_4$SCH$_2$CH$_2$W, —(CH$_2$)$_5$SCH$_2$W, —(CH$_2$)$_6$SW, —CH$_2$S(CH$_2$)$_5$CH$_2$W, —(CH$_2$)$_2$S(CH$_2$)$_4$CH$_2$W, —(CH$_2$)$_3$S(CH$_2$)$_3$CH$_2$W, —(CH$_2$)$_4$S(CH$_2$)$_2$CH$_2$W, —(CH$_2$)$_5$SCH$_2$CH$_2$W, and —(CH$_2$)$_6$SCH$_2$W, where the terms n, p and W are previously defined.

When R1 is —(CH$_2$)$_n$Q$_p$(CH$_2$)$_n$W and Q is an oxygen, the moiety includes —OW, —CH$_2$OW, —CH$_2$OCH$_2$W, —(CH$_2$)$_2$OW, —CH$_2$OCH$_2$CH$_2$W, —(CH$_2$)$_2$OCH$_2$W, —(CH$_2$)$_3$OW, —CH$_2$O(CH$_2$)$_2$CH$_2$W, —(CH$_2$)$_2$OCH$_2$CH$_2$W, —(CH$_2$)$_2$O(CH$_2$)$_2$CH$_2$W, —CH$_2$O(CH$_2$)$_3$CH$_2$W, —(CH$_2$)$_2$O(CH$_2$)$_2$CH$_2$W, —(CH$_2$)$_3$OCH$_2$CH$_2$W, —(CH$_2$)$_4$OCH$_2$W, —(CH$_2$)$_5$OW, —CH$_2$O(CH$_2$)$_4$CH$_2$W, —(CH$_2$)$_2$O(CH$_2$)$_3$CH$_2$W, —(CH$_2$)$_3$O(CH$_2$)$_2$CH$_2$W, —(CH$_2$)$_4$OCH$_2$CH$_2$W, —(CH$_2$)$_5$OCH$_2$W, —(CH$_2$)$_6$OW, —CH$_2$O(CH$_2$)$_5$CH$_2$W, —(CH$_2$)$_2$O(CH$_2$)$_4$CH2W, —(CH$_2$)$_3$O(CH$_2$)$_3$CH$_2$W, —(CH$_2$)$_4$O(CH$_2$)$_2$CH$_2$W, —(CH$_2$)$_5$OCH$_2$CH$_2$W, and —(CH$_2$)$_6$OCH$_2$W, where the terms n, p and W are previously defined.

The term "—(CH$_2$)$_n$CHW$_2$" refers to a moiety where n is independently an integer 0 to 6, and W is independently selected from the group consisting of hydrogen, C$_3$-C$_{10}$ cycloalkyl, —(C$_3$-C$_{10}$ cycloalkyl)-aromatic, and the following aromatic or heteroaromatic rings:

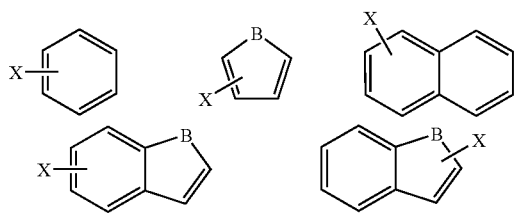

-continued

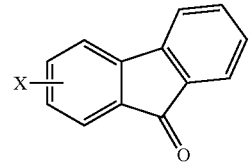

where B is —O—, —S—, —NR6-, where each carbon of the aromatic or heteroaromatic ring may be independently substituted by a nitrogen atom, and each carbon of the aromatic ring may be optionally substituted an X substituent. Each carbon of —(CH$_2$)$_n$ alkyl chain is optionally substituted with one to two X substituents.

The term "phenyl" refers to an aromatic phenyl ring of six carbons. The phenyl ring may be unsubstituted or substituted. An "unsubstituted phenyl" refers to a —C$_6$H$_5$ moiety. A "substituted phenyl" means that one or more of carbon atoms of the phenyl ring are substituted with one to five substitutuents independently selected from the group consisting of hydrogen, halogen, methylenedioxy, —C$_1$-C$_8$ alkyl, —C$_3$-C$_{10}$ cycloalkyl, —C$_1$-C$_8$ alkoxy, —OH, —CY$_3$, —OCY$_3$, —CO$_2$R3, —CN, —NO$_2$, —COR3, —NR4R5, —SR3, —CONR4R5, and —NH—C(O)—R3, where R3, R4 and R5 are independently selected from the group consisting of hydrogen, and C$_1$-C$_6$ alkyl, and if R4 or R5, in which each carbon of C$_1$-C$_6$ alkyl is optionally substituted with an X substituent or R4 and R5 can be connected to give a heterocycle. The substitutuents may be meta, para or ortho to the attachment site. A substituted phenyl includes subsets of substituted phenyls, and includes a phenyl substituted with one or more substituents selected from the group consisting of —C$_1$-C$_4$ alkyl, —C$_3$-C$_6$ cycloalkyl, —C$_1$-C$_4$ alkoxy, —OH, —CY$_3$, —OCY$_3$, —CO$_2$R3, —CN, —NO$_2$, —COR3, —NR4R5 and —SR3, where R3 is selected from the group consisting of hydrogen, and C$_1$-C$_8$ alkyl, and R4 and R5 are independently selected from the group consisting of hydrogen, and C$_1$-C$_6$ alkyl, and if R4 or R5, in which each carbon of C$_1$-C$_6$ alkyl is optionally substituted with an X substituent or R4 and R5 can be connected to give a heterocycle;

a phenyl substituted with one or more substituents selected from the group consisting of —C$_1$-C$_3$ alkyl, —C$_3$-C$_6$ cycloalkyl, —C$_1$-C$_3$ alkoxy, —OH, —CY$_3$, —OCY$_3$, —CO$_2$R3, —CN, —NO$_2$, —COR3, —NR4R5 and —SR3, where R3 is selected from the group consisting of hydrogen, and C$_1$-C$_8$ alkyl, and, R4 and R5 are independently selected from the group consisting of hydrogen, and C$_1$-C$_6$ alkyl, and if R4 or R5, in which each carbon of C$_1$-C$_6$ alkyl is optionally substituted with an X substituent or R4 and R5 can be connected to give a heterocycle;

a phenyl substituted with one or more substituents selected from the group consisting of —C$_1$-C$_3$ alkyl, —C$_3$ cycloalkyl, —C$_1$-C$_3$ alkoxy, —OH, —CY$_3$, —OCY$_3$, —CO$_2$R3, —CN, —NO$_2$, —COR3, —NR4R5 and —SR3, where R3 is selected from the group consisting of hydrogen, and C$_1$-C$_8$ alkyl, and, R4 and R5 are independently selected from the group consisting of hydrogen, and C$_1$-C$_6$ alkyl, and if R4 or R5, in which each carbon of C$_1$-C$_6$ alkyl is optionally substituted with an X substituent or R4 and R5 can be connected to give a heterocycle;

a phenyl substituted with one or more substituents selected from the group consisting of —$C_1$-$C_4$ alkyl, —$C_1$-$C_4$ alkoxy, —OH, —$CY_3$, —$OCY_3$, —$CO_2R3$, —CN, —$NO_2$, —COR3, —NR4R5 and —SR3, where R3 is selected from the group consisting of hydrogen, and $C_1$-$C_8$ alkyl, and, R4 and R5 are independently selected from the group consisting of hydrogen, and $C_1$-$C_6$ alkyl, and if R4 or R5, in which each carbon of $C_1$-$C_6$ alkyl is optionally substituted with an X substituent or R4 and R5 can be connected to give a heterocycle;

a phenyl substituted with one or more substituents selected from the group consisting of —$C_1$-$C_3$ alkyl, —$C_3$-$C_6$ cycloalkyl, —$C_1$-$C_3$ alkoxy, —OH, —$CY_3$, —$OCY_3$, —CN, —$NO_2$, —NR4R5 and —SR3, where R3 is selected from the group consisting of hydrogen, and $C_1$-$C_8$ alkyl, and, R4 and R5 are independently selected from the group consisting of hydrogen, and $C_1$-$C_6$ alkyl, and if R4 or R5, in which each carbon of $C_1$-$C_6$ alkyl is optionally substituted with an X substituent or R4 and R5 can be connected to give a heterocycle;

a phenyl substituted with one or more substituents selected from the group consisting of —$C_1$-$C_3$ alkyl, —$C_1$-$C_3$ alkoxy, —OH, —$CY_3$, —$OCY_3$, —CN, —$NO_2$, —NR4R5 and —SR3, where R3 is selected from the group consisting of hydrogen, and $C_1$-$C_8$ alkyl, and, R4 and R5 are independently selected from the group consisting of hydrogen, and $C_1$-$C_6$ alkyl, and if R4 or R5, in which each carbon of $C_1$-$C_6$ alkyl is optionally substituted with an X substituent or R4 and R5 can be connected to give a heterocycle;

a phenyl substituted with one or more substituents selected from the group consisting of —$CY_3$, and —$OCY_3$;

a phenyl substituted with one or more substituents selected from the group consisting of —$C_1$-$C_3$ alkyl, —$C_1$-$C_3$ alkoxy, —CN, and —SR3, where R3 is selected from the group consisting of hydrogen, and $C_1$-$C_8$ alkyl;

a phenyl substituted with one or more substituents selected from the group consisting of —OH, —$CY_3$, —$OCY_3$, —CN, —$NO_2$, —NR4R5 and —SR3, where R3 is selected from the group consisting of hydrogen, and $C_1$-$C_8$ alkyl, and R4 and R5 are independently selected from the group consisting of hydrogen, and $C_1$-$C_4$ alkyl, and if R4 or R5, in which each carbon of $C_1$-$C_4$ alkyl is optionally substituted with an X substituent or R4 and R5 can be connected to give a heterocycle;

a phenyl substituted with one or more substituents selected from the group consisting of —$C_4$-$C_6$ alkyl, —$C_4$-$C_6$ alkoxy, —OH, —$CY_3$, —$OCY_3$, —CN, —$NO_2$, —NR4R5 and —SR3, where R3 is selected from the group consisting of hydrogen, and $C_1$-$C_8$ alkyl, and, R4 and R5 are independently selected from the group consisting of hydrogen, and $C_1$-$C_6$ alkyl, and if R4 or R5, in which each carbon of $C_1$-$C_6$ alkyl is optionally substituted with an X substituent or R4 and R5 can be connected to give a heterocycle.

The term "heterocycle" refers to any $C_5$-$C_{12}$ closed-ring substituent wherein at least one or more carbon atoms of the ring is independently substituted with nitrogen, and optionally one or more carbon atoms of the ring may be substituted with nitrogen, sulfur or oxygen. In addition, any single bond of the heterocycle may be optionally substituted with a double bond. Heterocycle includes, but is not limited to the following: piperidinyl, pyrrolidinyl, morpholinyl, piperazinyl, pyrrolyl, imidazolidinyl, pyrazolidinyl, pyrazolinyl, thiomorpholinyl, and indolinyl.

The term "—$C_1$-$C_8$ alkoxy" refers to a oxygen connected to a ($C_1$-$C_8$ alkyl), which includes straight or branched, saturated or unsaturated alkyl of one to eight carbon atoms. A saturated —$C_1$-$C_8$ alkoxy includes, but is not limited to, a methoxy, ethoxy, propoxy, isopropoxy, butoxy, isobutoxy, pentoxy, hexoxy, heptoxy, and octoxy, and their corresponding branched chains. An unsaturated —$C_1$-$C_8$ alkoxy includes straight and branched alkoxy moieties and includes, but is not limited to, a —$OCHCH_2$, —OCCH, —$OCH_2CHCH_2$, —$OCCCH_2$, —$OCHCH_2CH_3$, —$OCH(CH_3)CHCH_2$, —$OC(CH_3)_2CHCH_2$, —$OCHCHCH_2CH_3$, —$OCH_2CHCHCH_3$, —$OCH_2CH_2CHCH_2$, —$OC(CH_3)CHCH_3$, —$OCHC(CH_3)CH_3$, —$OCH_2C(CH_3)CH_2$, —$OCHCH(CH_2)_2CH_3$, —$OCHCH(CH_2)_3CH_3$, —$OCH_2CHCH(CH_2)_2CH_3$, —$O(CH_2)_2CHCHCH_2CH_3$, —$OCHCH(CH_2)_4CH_3$, —$OCHCH(CH_2)_5CH_3$, and the like. Preferred —$C_1$-$C_8$ alkoxy moieties include a straight, saturated —$C_1$-$C_8$ alkoxy. Preferred straight, unsaturated —$C_2$-$C_8$ alkoxy moieties include a —$C_2$-$C_8$ alkoxy with a single double bond. Preferred straight, unsaturated —$C_2$-$C_8$ alkoxy moieties include a —$C_2$-$C_8$ alkoxy with a single triple bond.

The term "—SR3" refers to a thiol or thioalkyl moiety attached to a $C_1$-$C_8$ alkyl, which is an alkyl radical of one to eight carbon atoms. When R3 is hydrogen, the "—SR3" is a thiol, —SH. When R3 is a $C_1$-$C_8$ alkyl, the "—SR3" is a thioalkyl of one to eight carbon atoms, where the alkyl chain may be a straight or branched alkyl chain, or saturated or unsaturated alkyl. A —$SC_1$-$C_8$ alkyl includes saturated or unsaturated bonds, where one or more single bond between two adjacent carbon atoms is replaced with a double or triple bond. —SR3 includes —SH, —SCH3, —$SCH_2CH_3$, —$S(CH_2)_2CH_3$, —$S(CH_2)_3CH_3$, —$S(CH_2)_4CH_3$, —$S(CH_2)_5CH_3$, —$SCH(CH_3)_2$, —$SC(CH_3)_3$, —$SCH_2CH(CH_3)_2$, —$SCH_2C(CH_3)_3$, —$S(CH_2)_2CH(CH_3)_2$, —$S(CH_2)_2C(CH_3)_3$, —$SCH(CH_3)(CH_2)_3CH_3$, —$SCH_2CH(CH_3)_3(CH_2)_2CH_3$, —$S(CH_2)_2CH(CH_3)_3CH_2CH_3$ and the like, and includes their unsaturated counterparts. An unsaturated —SR3 includes straight or branched, unsaturated thioalkyl moieties and includes, but is not limited to, —$SCHCH_2$, —SCCH, —$SCH_2CHCH_2$, —$SCCCH_3$, —$SCHCH_2CH_3$, —$SCH(CH_3)CHCH_2$, —$SC(CH_3)_2CHCH_2$, —$SCHCHCH_2CH_3$, —$SCH_2CHCHCH_3$, —$SCH_2CH_2CHCH_2$, —$SC(CH_3)CHCH_3$, —$SCHC(CH_3)CH_3$, —$SCH_2C(CH_3)CH_2$, —$SCHCH(CH_2)_2CH_3$, —$SCHCH(CH_2)_3CH_3$, —$SCH_2CHCH(CH_2)_2CH_3$, —$S(CH_2)_2CHCHCH_2CH_3$, —$SCHCH(CH_2)_4CH_3$, —$SCHCH(CH_2)_5CH_3$, and the like. Preferred —$C_1$-$C_8$ thioalkyl moieties include straight, saturated —$SC_1$-$C_8$ alkyl. Preferred straight, unsaturated —$SC_2$-$C_8$ thioalkyl moieties include a —$SC_2$-$C_8$ thioalkyl with a single double bond. Preferred straight, unsaturated —$SC_2$-$C_8$ thioalkyl moieties include a —$SC_2$-$C_8$ thioalkyl with a single triple bond.

The term "aromatic" refers to a $C_6$-$C_{13}$ aromatic ring(s) of six to thirteen carbon atoms which contain at least three double bonds. An aromatic ring may be a single or polycyclic ring structure, including, but not limited to benzene, indene, naphthalene and fluorenone. In addition, each carbon of the aromatic ring may be independently substituted with one X substituent.

The term "heteroaromatic" refers to a $C_5$-$C_{10}$ heteroaromatic rings of five to ten carbon atoms which contain at least two double bonds. Heteroaromatic includes five and six membered rings, five- and six-membered bicyclic rings, and six- and six-membered bicyclic rings. Heteroaromatic includes, but is not limited to, benzene, indene and naphthalene rings wherein at least one of the carbon atoms is replaced with a sulfur, oxygen or nitrogen atom. Heteroaromatics include, but are not limited to, pyridinyl, isoxazolyl, benzimidazolyl, thiazolyl, thienyl, furanyl, indolyl, 1,3-benzodioxolyl, imidazolyl, pyrimidinyl, pyrazinyl, triazinyl, oxazolyl, purinyl, quinolinyl, and isoquinolinyl, pyrrolyl, pyrazolyl, isothiazolyl, oxadiazolyl, triazolyl, thiadiazolyl, pyridazolyl, indolinyl, indolyl, isoindolyl, indazolyl, benzthiazolyl, purinyl, quinazolinyl, quinoxalinyl, phthalazinyl, cinnolinyl, benzothiopheneyl, and benzofuranyl. In addition, each carbon of the heteroaromatic ring may be independently substituted with one X substituent.

The term "methylenedioxy" refers to a oxygen-methylene-oxygen moiety, —O—(CH$_2$)—O—. The methylenedioxy substituent is attached to two adjacent carbon atoms.

The term "—CY$_3$" refers to a carbon with three substituents independently selected from the group consisting of hydrogen and halogen. The term "halogen" refers to a halogen moiety and includes fluoro, chloro, bromo, and iodo moieties. Thus, "—CY$_3$" includes fully and partially halogenated carbon, and includes but is not limited to, —CF$_3$, —CHF$_2$, —CH$_2$F —Cl$_3$, —CH$_2$, —CH$_2$I, —CBr$_3$, —CHBr$_2$, —CH$_2$Br, —CCl$_3$, —CHCl$_2$, —CH$_2$Cl, —CF$_2$Cl, —CFCl$_2$ and —CFClH.

The term "—OCY$_3$" refers to a methoxy moiety with three substituents independently selected from the group consisting of hydrogen and halogen. Thus, "—OCY$_3$" includes fully and partially halogenated methoxy moieties, and includes but is not limited to, —OCF$_3$, —OCHF$_2$, —OCH$_2$F, —OCl$_3$, —OCHI$_2$, —OCH$_2$I, —OCBr$_3$, —OCHBr$_2$, —OCH$_2$Br, —OCCl$_3$, —OCHCl$_2$, —OCH$_2$Cl, —OCF$_2$Cl, —OCFCl$_2$ and —OCFClH.

The term "—CO$_2$R3" refers to a carboxy moiety where R3 is selected from the group consisting of hydrogen and C$_1$-C$_8$ alkyl. When R3 is hydrogen, the "—CO$_2$R3" is a carboxyl moiety. When R3 is a C$_1$-C$_8$ alkyl, the "—CO$_2$R3" is an ester of one to eight carbon atoms, where the alkyl chain may be a straight or branched alkyl chain, or saturated or unsaturated alkyl. Thus, the term "—CO$_2$R3" includes —COOH, —COOCH3, —COOCH$_2$CH$_3$, —COO(CH$_2$)$_2$CH$_3$, —COO(CH$_2$)$_3$CH$_3$, —COO(CH$_2$)$_4$CH$_3$, —COO(CH$_2$)$_5$CH$_3$, —COOCH(CH$_3$)$_2$, —COOC(CH$_3$)$_3$, —COOCH$_2$CH(CH$_3$)$_2$—COOCH$_2$C(CH$_3$)$_3$, —COO(CH$_2$)$_2$CH(CH$_3$)$_2$, —COO(CH$_2$)$_2$C(CH$_3$)$_3$, —COOCH(CH$_3$)(CH$_2$)$_3$CH$_3$, —COOCH$_2$CH(CH$_3$)$_2$CH$_2$CH$_3$, —COO(CH$_2$)$_2$CH(CH$_3$)$_3$ and the like, and their unsaturated counterparts.

The term "—COR3" refers to an aldehye or ketone moiety where R3 is selected from the group consisting of hydrogen and C$_1$-C$_8$ alkyl. When R3 is hydrogen, the "—COR3" is an aldehyde —COH. When R3 is a C$_1$-C$_8$ alkyl, the "—COR3" is a ketone containing one to eight carbon atoms, where the alkyl chain may be a straight or branched alkyl chain, or saturated or unsaturated alkyl. Thus, the term "—COR3" includes —COH, —COCH3, —COCH$_2$CH$_3$, —CO(CH$_2$)$_2$CH$_3$, —CO(CH$_2$)$_3$CH$_3$, —CO(CH$_2$)$_4$CH$_3$, —CO(CH$_2$)$_5$CH$_3$, —COCH(CH$_3$)$_2$, —COC(CH$_3$)$_3$, —COCH$_2$CH(CH$_3$)$_2$, —COCH$_2$C(CH$_3$)$_3$, —CO(CH$_2$)$_2$CH(CH$_3$)$_2$, —CO(CH$_2$)$_2$C(CH$_3$)$_3$, —COCH(CH$_3$)(CH$_2$)$_3$CH$_3$, —COCH$_2$CH(CH$_3$)$_2$CH$_2$CH$_3$, —CO(CH$_2$)$_2$CH(CH$_3$)$_3$ and the like, and includes their unsaturated counterparts.

The term "—NR4R5" refers to an amino moiety where R4 and R5 are each independently selected from the group consisting of hydrogen and C$_1$-C$_6$ alkyl. When R4 and R5 are hydrogen, the —NR4R5 is a primary amino moiety, —NH$_2$. When only one of R4 and R5 are hydrogen, the —NR4R5 is a secondary amino moiety —NH(C$_1$-C$_6$). When R4 and R5 are C$_1$-C$_6$ alkyl, the —NR4R5 is a tertiary amino moiety —N(C$_1$-C$_6$)$_2$. The C$_1$-C$_6$ alkyl, each independently containing one to six carbon atoms, and where each alkyl chain is independently a straight or branched alkyl chain, saturated or unsaturated alkyl chain. Thus, the term —NR4R5 includes —NH$_2$, —NHCH$_3$, —NHCH$_2$CH$_3$, —NH(CH$_2$)$_2$CH$_3$, —NH(CH$_2$)$_3$CH$_3$, —NH(CH$_2$)$_4$CH$_3$, —NH(CH$_2$)$_5$CH$_3$, —N(CH$_3$)$_2$, —N(CH$_2$CH$_3$)$_2$, —N((CH$_2$)$_2$CH$_3$)$_2$—N((CH$_2$)$_3$CH$_3$)$_2$, —N((CH$_2$)$_4$CH$_3$)$_2$, —N((CH$_2$)$_5$CH$_3$)$_2$, —N(CH$_2$CH$_3$)(CH$_3$), —N((CH$_2$)$_2$CH$_3$)(CH$_3$), —N((CH$_2$)$_4$CH$_3$)(CH$_3$), —N((CH$_2$)$_5$CH$_3$)(CH$_3$), and the like, and includes their branched and/or unsaturated counterparts. The term "—NR4R5" includes moieties where R4 and R5 are connected to give a heterocycle.

The term "—CO—NR4R5" refers to an amide moiety where R4 and R5 are each independently selected from the group consisting of hydrogen and C$_1$-C$_6$ alkyl. When R4 and R5 are hydrogen, the "—CO—NR4R5" is a primary amide moiety, —CONH$_2$. When only one of R4 and R5 are hydrogen, the "—CO—NR4R5" is a secondary amide moiety "—CONH(C$_1$-C$_6$). When R4 and R5 are C$_1$-C$_6$ alkyl, the "—CO—NR4R5" is a tertiary amide moiety "—CON(C$_1$-C$_6$)$_2$. The C$_1$-C$_6$ alkyl, each independently containing one to six carbon atoms, and where each alkyl chain is independently a straight or branched alkyl chain, saturated or unsaturated alkyl chain. Thus, the term "—CO—NR4R5" includes —CONH$_2$, —CONHCH$_3$, —CONHCH$_2$CH$_3$, —CONH(CH$_2$)$_2$CH$_3$, —CONH(CH$_2$)$_3$CH$_3$, —CONH(CH$_2$)$_4$CH$_3$, —CONH(CH$_2$)$_5$CH$_3$, —CON(CH$_3$)$_2$, —CON(CH$_2$CH$_3$)$_2$, —CON((CH$_2$)$_2$CH$_3$)$_2$, —CON((CH$_2$)$_3$CH$_3$)$_2$, —CON((CH$_2$)$_4$CH$_3$)$_2$, —CON((CH$_2$)$_5$CH$_3$)$_2$, —CON(CH$_2$CH$_3$)(CH$_3$), —CON((CH$_2$)$_2$CH$_3$)(CH$_3$), —CON((CH$_2$)$_4$CH$_3$)(CH$_3$), —CON((CH$_2$)$_5$CH$_3$)(CH$_3$), and the like, and includes their branched and/or unsaturated counterparts. The term "—CO—NR4R5" includes moieties where R4 and R5 are connected to give a heterocycle.

The term "—NH—C(O)—R31" refers to an amide moiety where R3 is selected from the group consisting of hydrogen and C$_1$-C$_8$ alkyl. When R3 is hydrogen, the "—NH—C(O)—R3" is an formamide, —NH—C(O)H. When R3 is a C$_1$-C$_8$ alkyl, the "—NH—C(O)—R3" is an alkyl of one to eight carbon atoms, where the alkyl chain may be a straight or branched alkyl chain, or saturated or unsaturated alkyl. Thus, the term "—NH—C(O)—R3" includes —NHC(O)H, —NHC(O)CH$_3$, —NHC(O)CH$_2$CH$_3$, —NHC(O)(CH$_2$)$_2$CH$_3$, —NHC(O)(CH$_2$)$_3$CH$_3$, —NHC(O)(CH$_2$)$_4$CH$_3$, —NHC(O)(CH$_2$)$_5$CH$_3$, —NHC(O)CH(CH$_3$)$_2$, —NHC(O)C(CH$_3$)$_3$, —NHC(O)CH$_2$CH(CH$_3$)$_2$, —NHC(O)CH$_2$C(CH$_3$)$_3$, —NHC(O)(CH$_2$)$_2$CH(CH$_3$)$_2$, —NHC(O)(CH$_2$)$_2$C(CH$_3$)$_3$, —NHC(O)CH(CH$_3$)(CH$_2$)$_3$CH$_3$, —NHC(O)CH$_2$CH(CH$_3$)$_2$(CH$_2$)$_2$CH$_3$, —NHC(O)(CH$_2$)$_2$C(CH$_3$)$_2$CH$_3$ and the like, and includes their unsaturated counterparts.

The term "—NH—C(O)—(C$_1$-C$_6$ alkyl)-aromatic" refers to an amide alkylaryl moiety where a C$_1$-C$_6$ alkyl is attached to an aromatic ring. The C$_1$-C$_6$ is an alkyl chain of one to six carbon atoms, where the alkyl chain may be a straight or branched alkyl chain, or saturated or unsaturated alkyl. The term "aromatic" refers to a ring of C$_6$-C$_{13}$ carbon atoms. Thus, the term "—NH—C(O)—(C$_1$-C$_6$)-aromatic" includes —NHC(O)CH$_2$-aromatic, —NHC(O)(CH$_2$)$_2$-aromatic, —NHC(O)(CH$_2$)$_3$-aromatic, —NHC(O)(CH$_2$)$_4$-aromatic, —NHC(O)(CH$_2$)$_5$-aromatic, —NHC(O)(CH$_2$)$_6$-aromatic, —NHC(O)(CH)(CH$_3$)-aromatic, —NHC(O)C(CH$_3$)$_2$-aromatic, —NHC(O)CH$_2$CH(CH$_3$)-aromatic, —NHC(O)CH$_2$C(CH$_3$)$_2$-aromatic, —NHC(O)(CH$_2$)$_2$CH(CH$_3$), -aromatic —NHC(O)(CH$_2$)$_2$C(CH$_3$)$_2$-aromatic and the like, and includes their branched and unsaturated counterparts.

The term "—NH—C(O)—(C$_1$-C$_6$)-heteroaromatic" refers to an amide alkyl heteroaryl moiety where a C$_1$-C$_6$ alkyl is attached to an heteroaromatic ring. The C$_1$-C$_6$ is an alkyl chain of one to six carbon atoms, where the alkyl chain may be a straight or branched alkyl chain, or saturated or unsaturated alkyl. The term "heteroaromatic" refers to an aromatic ring of $C_5$-$C_{10}$ carbon atoms, where one or more carbon atoms is replaced with a nitrogen, oxygen or sulfur. Thus, the term "—NH—C(O)—($C_1$-$C_6$)-heteroaromatic" includes —NHC(O)$CH_2$-heteroaromatic, —NHC(O)$(CH_2)_2$-heteroaromatic, —NHC(O)$(CH_2)_3$-heteroaromatic, —NHC(O)$(CH_2)_4$-heteroaromatic, —NHC(O)$(CH_2)_5$-heteroaromatic, —NHC(O)$(CH_2)_6$-heteroaromatic, —NHC(O)(CH)($CH_3$)-heteroaromatic, —NHC(O)C$(CH_3)_2$-heteroaromatic, —NHC(O)$CH_2CH(CH_3)$-heteroaromatic, —NHC(O)$CH_2C(CH_3)_2$-heteroaromatic, —NHC(O)$(CH_2)_2CH(CH_3)$-heteroaromatic, —NHC(O)$(CH_2)_2C(CH_3)_2$-heteroaromatic and the like, and includes their branched and unsaturated counterparts.

The term "—S(O)$_2$—($C_1$-$C_6$ alkyl)" refers to a saturated or unsaturated, straight or branched chain hydrocarbyl radical of from one to six carbon atoms attached to a sulfonyl radical, —S(O)$_2$—. A $C_1$-$C_6$ alkyl may be saturated or unsaturated. An unsaturated $C_2$-$C_6$ alkyl may contain one or more double or triple bond between two adjacent carbon atoms, and requires at least two carbon atoms in the alkyl chain. A $C_1$-$C_6$ alkylsulfonyl includes, but is not limited to, the following: methylsulfonyl, ethylsulfonyl, propylsulfonyl, isopropylsulfonyl, 1-propenylsulfonyl, propynylsulfonyl, 2-propenylsulfonyl, n-butylsulfonyl, isobutylsulfonyl, 2-methylsulfonyl-2-propenylsulfonyl, 2-butynylsulfonyl, 3-butynylsulfonyl, tertiary butylsulfonyl, sec-butylsulfonyl, 1-butenylsulfonyl, 2-butenylsulfonyl, and 3-butenylsulfonyl, pentylsulfonyl, 2-pentenylsulfonyl, 3-pentenylsulfonyl, 4-pentenylsulfonyl, 2-pentynylsulfonyl, 3-pentynylsulfonyl, 4-pentynylsulfonyl, prenylsulfonyl, neopentylsulfonyl, hexylsulfonyl, 2-hexenylsulfonyl, 3-hexenylsulfonyl, 4-hexenylsulfonyl, 5-hexenylsulfonyl, 2-hexynylsulfonyl, 3-hexynylsulfonyl, 4-hexynylsulfonyl, 5-. A $C_1$-$C_6$ alkyl includes smaller subsets of alkyl radicals, such as a $C_1$-$C_4$ alkylsulfonyl, a $C_1$-$C_3$ alkylsulfonyl, and a $C_1$-$C_2$ alkylsulfonyl, as well as a $C_5$-$C_6$ alkylsulfonyl.

The term "—S(O)$_2$—($C_3$-$C_{10}$ cycloalkyl)" refers to a saturated or unsaturated, branched or straight $C_3$-$C_{10}$ cyclic chain hydrocarbylsulfonyl radical of from three to ten carbon atoms. A $C_3$-$C_{10}$ cycloalkylsulfonyl may be saturated or unsaturated. An unsaturated $C_3$-$C_{10}$ cycloalkylsulfonyl may contain one or more double bonds between two adjacent carbon atoms. A $C_3$-$C_{10}$ cycloalkylsulfonyl includes, but is not limited to, the following: cyclopropylsulfonyl, cyclobutylsulfonyl, cyclopentylsulfonyl, cyclopentenylsulfonyl, cyclohexylsulfonyl, cyclohexenylsulfonyl, cycloheptylsulfonyl, cyclooctylsulfonyl, and the like, bicyclic ring structures, including, but not limited to a fused five-and-five membered cycloalkylsulfonyl ring, a fused five-and-six membered cycloalkylsulfonyl ring, a fused six- and -six membered cycloalkylsulfonyl ring, and polycyclicsulfonyl ring.

The term "—C(O)—($C_0$-$C_6$ alkyl)-aromatic" refers to an aromatic ring attached to a carbonyl moiety via a $C_0$-$C_6$ alkyl. When the alkyl chain is $C_0$, then the aromatic ring is directly attached to the carbonyl moiety. When the alkyl chain is $C_1$-$C_6$, then the aromatic ring is attached to the carbonyl moiety via a $C_1$-$C_6$ alkyl. The $C_1$-$C_6$ alkyl is a saturated or unsaturated, straight or branched alkyl chain of one to six carbon atoms. An unsaturated $C_2$-$C_6$ alkyl may contain one or more double or triple bond between two adjacent carbon atoms, and requires at least two carbon atoms in the alkyl chain. In addition, each carbon of the aromatic ring may be independently substituted with one X substituent.

The term "—S(O)$_2$—($C_0$-$C_6$ alkyl)-aromatic" refers to an aromatic ring attached to a sulfonyl moiety via a $C_0$-$C_6$ alkyl. When the alkyl chain is $C_0$, then the aromatic ring is directly attached to the sulfonyl moiety. When the alkyl chain is $C_1$-$C_6$, then the aromatic ring is attached to the sulfonyl moiety via a $C_1$-$C_6$ alkyl. The $C_1$-$C_6$ alkyl is a saturated or unsaturated, straight or branched alkyl chain of one to six carbon atoms. An unsaturated $C_2$-$C_6$ alkyl may contain one or more double or triple bond between two adjacent carbon atoms, and requires at least two carbon atoms in the alkyl chain. In addition, each carbon of the aromatic ring may be independently substituted with one X substituent.

The term "—($C_3$-$C_{10}$ cycloalkyl)-aromatic" refers to an aromatic ring attached to a $C_3$-$C_{10}$ cycloalkyl. The $C_3$-$C_{10}$ cylcoalkyl is a saturated or unsaturated alkyl chain of three to ten carbon atoms. An unsaturated $C_3$-$C_{10}$ cylcoalkyl may contain one or more double or triple bonds between two adjacent carbon atoms. In addition, each carbon of the $C_3$-$C_{10}$ cycloalkyl may be independently substituted with one or two X substituents and each carbon of the aromatic ring may be independently substituted with one X substituent.

An optical isomer, refers to any of the various stereo isomeric configurations which may exist for a given compound of Formula (I), and includes geometric isomers. It is understood that a substituent may be attached at a chiral center of a carbon atom. Therefore, the invention includes enantiomers, diastereomers or racemates of the compound. If the compound contains a double bond, the substituent may be E or Z configuration. If the compound contains a disubstituted cycloalkyl, the cycloalkyl substituent may have a cis- or trans-configuration.

A solvate refers to a compound, or an intermediate thereof, which contains a fraction, one or more molecules of a solvent. Solvate includes hemisolvate, monosolvate and multisolvate. Solvates may be formed with solvents including, but not limited to, pharmaceutically acceptable solvates such as ethanol and water.

A hydrate refers to a compound, or an intermediate thereof, which contains a fraction, one or more molecules of water. Hydrate includes hemihydrate, monohydrate and multihydrate.

A pharmaceutically-acceptable salts refers to the reaction product of one or more molecules of any non-toxic, organic or inorganic pharmaceutically-acceptable acids with a compound of Formula (I). Illustrative inorganic acids which form pharmaceutically-acceptable salts include hydrochloric acid, hydrobromic acid, sulphuric acid and phosphoric acid and metal acids, such as sodium monohydrogen orthophosphate and potassium hydrogen sulfate. Illustrative organic acids which form suitable pharmaceutically-acceptable salts include mono-, di- and tricarboxylic acids. Illustrative organic acids are, for example, acetic acid, glycolic acid, lactic acid, pyruvic acid, malonic acid, succinic acid, glutaric acid, fumaric acid, malic acid acid, tartaric acid, citric acid, ascorbic acid, maleic acid, hydroxymaleic acid, benzoic acid, hydroxybenzoic acid, phenylacetic acid, cinnamic acid, salacylic acid, 2-phenoxybenzoic acid and sulfonic acids such as methane sulfonic acid, trifluoromethane sulfonic acid and 2-hydroxyethane sulfonic acid.

A patient at risk of neuronal apoptosis refers to a patient who, because of the existence of an identified risk factor associated with neuoronal apoptosis, such as having had a stroke, a genetic predisposition to such a condition, had or currently have neoplasms, exposure of carcinogenic agents, diet, age or has other risk factors associated with the development of neoplastic disease states. Preferred patients at risk of developing a neoplastic disease state include patients who are positive for oncogenic viruses, are in remission from prior treatment of neoplasm(s), use tobacco products or have previously been exposed to carcinogens such as asbestos, or are positive for various neoplastic genetic markers.

An effective amount of a compound of the formula is expected to vary from about 1 microgram per kilogram of body weight per day (μg/kg/day) to about 500 mg/kg/day. A preferred effective amount of a compound of the formula is from about 10 μg/kg/day to about 50 mg/kg/day. A more preferred amount of a compound of the formula is from about 20 μg/kg/day to about 1 mg/kg/day.

A compound of the formula may be administered in any form or mode that makes the compound bioavailable in effective amounts. Compounds of the formula may be administered by oral or parental routes. Compounds of the formula may be administered orally, subcutaneously, intramuscularly, intravenously, transdermally, intranasally, rectally, ocularly and the like. Oral administration is preferred. One skilled in the art of preparing pharmaceutical formulations may readily determine appropriate forms of a compound of the formula by determining particular characteristics of the compound, the disease to be treated, the stage of the disease, response of other patients and other relevant circumstances.

A compound of the formula may be combined with carriers, excipients or other compounds to prepare compositions of a compound of the formula. A composition of the formula comprise a compound of the formula in admixture or otherwise in association with one or more inert carriers. Compositions of the formula are useful, for example, as convenient means of making bulk shipments, or for storing, a compound of the formula. An inert carrier is a material which does not degrade or otherwise covalently react with a compound of the formula. An inert carrier may be a solid, semi-solid or liquid material. Preferred carriers are water, aqueous buffers, organic solvents and pharmaceutically acceptable carriers or excipients. Preferred aqueous buffers provide a buffering range at which a compound of the formula does not degrade. Preferred buffering ranges are about pH 4 to about pH 9. Preferred organic solvents are acetonitrile, ethyl acetate, and hexane.

A pharmaceutical composition of a compound of the formula comprises a compound of the formula in admixture or otherwise in association with one or more pharmaceutically acceptable carrier or excipient. A pharmaceutically acceptable carrier or excipient may be a solid, semi-solid or liquid material that can serve as a vehicle or medium for the compound of the formula. Suitable pharmaceutically acceptable carriers or excipients are well known to those skilled in the art.

A pharmaceutical composition of a compound of the formula may be adapted for the route of administration. A preferred pharmaceutical composition of a compound of the formula is a tablet, troche, capsule, elixir, syrup, wafer, chewing gum, suppository, solution or suspension if the route of administration is oral, parental or topical.

A preferred oral pharmaceutical composition of a compound of the formula comprises a compound of the formula with an inert diluent or with an edible carrier. Preferred forms of oral pharmaceutical compositions of a compound of the formula are tablets, troches, capsules, elixirs, syrups, wafers, chewing gum, solutions or suspensions.

Preferred pharmaceutical compositions of a compound of the formula contain from about 4% to about 80% of the compound. Preferred pharmaceutical compositions contain an amount of the compound of the formula from about 1 μg to about 500 μg; more preferred pharmaceutical composition contain an amount of the compound of the formula from about 10 μg to about 200 μg.

A compound of the formula may be administered alone or in the form of a pharmaceutical composition in combination with pharmaceutically acceptable carriers or excipients.

As used herein, the following terms have the indicated meanings: "g" refers to grams; "mg" refers to milligrams; "mmol" refers to millimoles; "M" refers to molar; "h" or "hr" refers to hours; "min" refers to minutes; "sec" refers to seconds; "L" refers to liters; "mL" refers to milliliters; "bp" refers to boiling point; "mp" refers to melting point; "°C." refers to degrees Celsius; "mm Hg" refers to millimeters of mercury; "psi" refers to pounds per square inch; "μL" refers to microliters; "μg" refers to micrograms; "μM" refers to micromolar; "TLC" refers to Thin Layer Chromatography; "$R_f$" refers to retention factor, "$R_t$" refers to retention time; "HPLC" refers to high performance liquid chromatography; "MS" refers to Mass Spectrum; "LC/MS" refers to Liquid Chromatography Mass Spectrometry; "APCI" refers to Atmospheric Pressure Chemical Ionization; "HTPMS" refers to high through-put mass spectrometry; "HTPMS RT" refers to high through-put mass spectrometry retention time; "ESI" refers to Electrospray Ionization; "CI" refers to Chemical Ionization; "TOF-ES" refers to Time of Flight Electrospray; "$M^+$" refers to a positively charged molecular ion; "$MH^+$" refers to a protonated molecular ion; "BOC anhydride" refers to di-tert-butyl dicarbonate; "BOC" refers to the t-butyloxycarbonyl moiety, "THF" refers to tetrahydrofuran; "$CH_2Cl_2$" or "DCM" refers to dichloromethane or methylene chloride; "DMSO" refers to dimethylsulfoxide; "TEA" refers to triethylamine; "SPE" refers to Solid Phase Extraction; "DEAD" refers to diethyl azodicarboxylate; "NMR" refers to Nuclear Magnetic Resonance; "TMS" refers to tetramethylsilane; "ppm" refers to parts per million; "Hz" refers to hertz; "MHz" refers to megahertz; "MeOH", methanol; "EtOH", ethanol; "N", Normal; "HCl", hydrogen chloride; "TFA", trifluoroacetic acid, "DIEA", diisopropylethylamine; "RT PCR", reverse transcription polymerase chain reaction; "HEPES", 4-(2-hydroxyethyl0-1-piperazine ethanesulfonic acid); "$MgCl_2$," Magnesium chloride; "EGTA", ethylene glycol-bis (β-aminoethyl ether) N,N,N',N'-tetraacetic acid; "EDTA", ethylenediaminetetraacetic acid; "DTT", dithiothreitol; "MOI", multiplicity of infectivity; "NaF", sodium flouride; "BSA", bovine serum albumin; "p.o.", oral(ly); "i.v.", intravenous(ly); "s.c.", subcutaneous(ly). Unless otherwise specified, all starting materials and reagents were available from commercial sources.

The compounds of Formula (I) may be prepared by utilizing procedures and techniques well known and appreciated by one of ordinary skill in the art. General synthetic schemes for preparing these compounds are set forth in Scheme A, Scheme B and Scheme C wherein all substituents, unless otherwise indicated, are as previously defined.

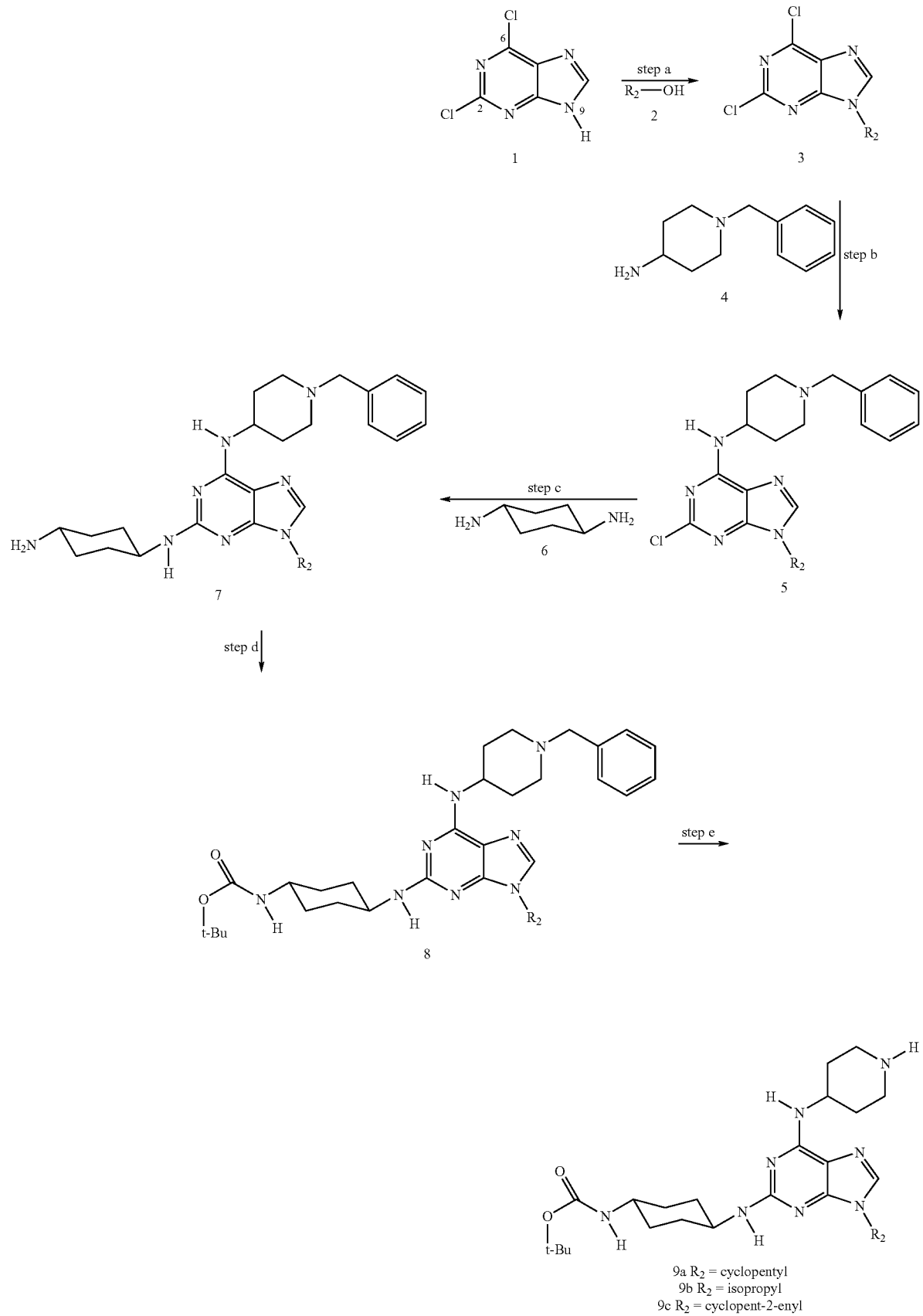

In Scheme A, step a, 2,6-dichloropurine (1) is reacted with an appropriate alcohol of structure 2 to give the corresponding 9-substituted-2,6-dichloropurine compound of structure 3 using techniques and procedures well known to one of ordinary skill in the art.

For example, 2,6-dichloropurine (1) can be reacted with an appropriate alcohol of structure 2 such as cyclopentanol, isopropanol, or 2-cyclopenten-1-ol in the presence of triphenylphosphine and diethyl azodicarboxylate in a suitable anhydrous aprotic solvent, such as tetrahydrofuran. The reactants are typically stirred together at room temperature for a period of time ranging from 5 hours to 5 days. The resulting 9-substituted-2,6-dichloropurine of structure 3 may be recovered from the reaction zone by extractive methods as are known in the art. More typically, the resulting 9-substituted-2,6-dichloropurine of structure 3 is recovered by removal of solvent followed by charging directly onto a silica gel column and eluting with a suitable solvent, such as methylene chloride, or mixture of solvents, such as a mixture of methylene chloride and methanol.

In step b, the 6-chloro functionality of the 9-substituted-2, 6-dichloropurine of structure 3 is displaced by reaction with 4-amino-1-benzylpiperidine (4) to give the corresponding 9-substituted-6-[4-(1-benzyl)piperidinylamino]-2-chloropurine of structure 5.

For example, the 9-substituted-2,6-dichloropurine of structure 3 can be reacted with 4-amino-1-benzylpiperidine (4) in a suitable anhydrous polar solvent such as ethanol. The reactants are typically stirred together at reflux temperature for a period of time ranging from 30 minutes to 3 days. The resulting 9-substituted-6-[4-(1-benzyl)piperidinylamino]-2-chloropurine (5) is recovered from the reaction zone by extractive methods as are known in the art or, if the 9-substituted-6-[4-(1-benzyl)piperidinylamino]-2-chloropurine of structure 5 precipitates out of solution, it may be recovered by filtration. More typically, the resulting 6-[4-(1-benzyl)piperidinyl-amino]-2-chloropurine (5) is recovered by removal of solvent followed by charging directly onto a silica gel column and eluting with a suitable solvent, such as methylene chloride, or mixture of solvents, such as a mixture of methylene chloride and methanol.

In step c, the 2-chloro functionality of the 9-substituted-6-[4-(1-benzyl)piperidinylamino]-2-chloropurine of structure 5 is displaced by reaction with trans-1,4-cyclohexanediamine (6) to give a 9-substituted-2-[trans-(4-aminocyclohexyl)amino]-6-[4-(1-benzyl)piperidinylamino]purine of structure 7.

For example, an appropriate 9-substituted-6-[4-(1-benzyl)piperidinylamino]-2-chloropurine of structure 5 can be reacted with a molar excess of trans-1,4-cyclohexandiamine (6). The reactants are typically placed in a pressure vessel, sealed, and heated at a temperature of from about 80° C. to about 150° C. for a period of time ranging from 30 minutes to 3 days. The resulting 9-substituted-2-[trans-(4-aminocyclohexyl)amino]-6-[4-(1-benzyl)piperidinylamino]purine of structure 7 is recovered from the reaction zone by extractive methods as are known in the art and may be purified by chromatography by charging directly onto a silica gel column and eluting with a suitable solvent, such as methylene chloride, or mixture of solvents, such as a mixture of methylene chloride and methanol. Concentration of the desired fractions provides the free base of 7 which may be dissolved in an alcoholic solvent, typically methanol, and converted to a mono-, di- or tri-acid addition salt by methods well known to those skilled in the art.

In step d, the primary amino functionality of a 9-substituted-2-[trans-(4-aminocyclohexyl)amino]-6-[4-(1-benzyl) piperidinylamino]purine of structure 7 is protected by reacting a compound of structure 7 with di-tert-butyl dicarbonate.

For example, a 9-substituted-2-[trans-(4-aminocyclohexyl)amino]-6-[4-(1-benzyl)piperidinylamino]purine of structure 7 is typically reacted with a molar excess of di-tert-butyl dicarbonate ("BOC anhydride") in the presence of an excess of a suitable base such as triethylamine at room temperature from about five hours to 24 hours. The resulting trans-{4-[6-(1-benzylpiperidin-4-ylamino)-9-substituted-9H-purin-2-ylamino]cyclohexyl}carbamic acid tert-butyl ester of structure 8 may be recovered from the reaction zone by diluting with water, and applying extractive methods as are known in the art. The crude product 8 may be purified by chromatography by charging directly onto a silica gel column and eluting with a suitable solvent, such as methylene chloride, or mixture of solvents, such as a mixture of methylene chloride and methanol.

In step e, the piperidine N-benzyl moiety is removed by catalytic or transfer hydrogenolysis from a trans-{4-[6-(1-benzylpiperidin-4-ylamino)-9-substituted-9H-purin-2-ylamino]cyclohexyl}carbamic acid tert-butyl ester of structure 8 to give a trans-{4-[6-(piperidin-4-ylamino)-9-substituted-9H-purin-2-ylamino]cyclohexyl}carbamic acid tert-butyl ester of structure 9.

For example, a methanol suspension of a trans-{4-[6-(1-benzylpiperidin-4-ylamino)-9-substituted-9H-purin-2-ylamino]cyclohexyl}carbamic acid tert-butyl ester of structure 8 and palladium black is typically treated with a methanol solution of ammonium formate and the mixture is stirred and heated at reflux from 6 to 48 hours. The resulting trans-{4-[6-(piperidin-4-ylamino)-9-substituted-9H-purin-2-ylamino]cyclohexyl}carbamic acid tert-butyl ester of structure 9 is recovered from the reaction by filtration and extractive methods as are known in the art and may be purified by chromatographic methods as are known in the art.

Starting materials for use in the general synthetic procedures outlined in Scheme A are readily available commercially.

In Scheme B, the secondary nitrogen atom in the piperidine ring of a trans-{4-[6-(piperidin-4-ylamino)-9-substituted-9H-purin-2-ylamino]cyclohexyl}carbamic acid tert-butyl ester of structure 9 may be acylated with various acylating reagents such as carboxylic acid halides; chloroformate esters; alkyl, aryl and aralkyl isocyanates or sulfonyl chlorides; and N-mono- or N,N-disubstituted sulfamoyl chlorides to provide amide, carbamate, urea, sulfonamide and sulfamide compounds of formula I, respectively.

For example, a methylene chloride solution of about equimolar amounts of a trans-{4-[6-(piperidin-4-ylamino)-9-substituted-9H-purin-2-ylamino]cyclohexyl}carbamic acid tert-butyl ester of structure 9, the desired acylating agent and triethylamine is stirred from 2 to 24 hours at room temperature. Triethylamine may be omitted when an isocyanate is the acylating agent. When an N-mono- or N,N-disubstituted sulfonyl chloride is used a polar aprotic solvent such as tetrahydrofuran is preferred. The reaction is then treated with an excess of dilute hydrochloric acid solution resulting in hydrolysis of the BOC protecting group and precipitation of the desired acylated compound of formula I. The precipitate is recovered by decanting the supernatant, and applying extractive methods and chromatographic purification methods as are known in the art.

In Scheme C, steps g and h, N-monosubstituted and N,N-disubstituted urea compounds I may also be prepared by protecting the primary amino group of trans-4-[2-(4-aminocyclohexylamino)-9-substituted-9H-purin-6-ylamino]-piperidine-1-carboxylic acid 4-nitro-phenyl ester 10 (step g), reaction of the N-protected 4-nitro-phenyl ester 11 with a primary or a secondary amine, and removal of the N-protecting group to afford N-monosubstituted or N,N'-disubstituted urea compounds I (step h).

For example, a 2-[trans-(4-aminocyclohexyl)amino)-9-substituted-9H-purin-6-ylamino]-piperidine-1-carboxylic acid 4-nitro-phenyl ester of structure 10 is typically reacted with a molar excess of di-tert-butyl dicarbonate ("BOC anhydride") in the presence of an excess of a suitable base such as triethylamine at room temperature from about five hours to 24 hours. The resulting trans-4-[2-(4-tert-butoxycarbonylamino-cyclohexylamino)-9-substituted-9H-purin-6-ylamino]-piperidine-1-carboxylic acid 4-nitro ester of structure 11 may be recovered from the reaction zone by diluting with water, and applying extractive methods as are known in the art. The crude N—BOC-protected ester 11 may be purified by chromatography by charging directly onto a silica gel column and eluting with a suitable solvent, such as methylene chloride, or mixture of solvents, such as a mixture of methylene chloride and methanol (step g).

In step h, a solution of the trans-4-[2-(4-tert-butoxycarbonylamino-cyclohexylamino)-9-substituted-9H-purin-6-ylamino]-piperidine-1-carboxylic acid 4-nitro ester of structure 11 and a suitable solvent such as tetrahydrdofuran may be treated with a primary or a secondary amine in the presence of a base such as triethylamine and stirred at a temperature of from about room temperature to about 90° C. for about two hours to about 24 hours. The reaction is

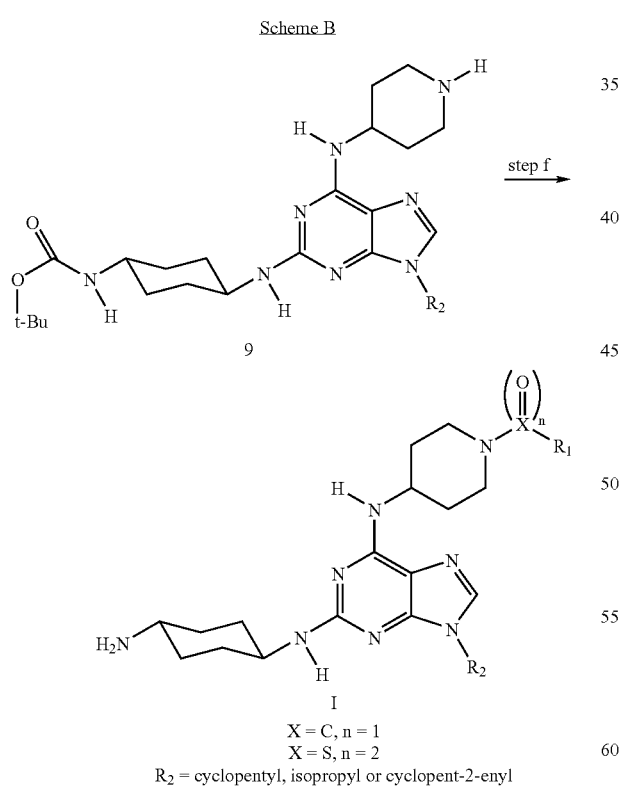

Scheme B step f

9

X = C, n = 1
X = S, n = 2
$R_2$ = cyclopentyl, isopropyl or cyclopent-2-enyl cooled to room temperature and stirred with an excess of dilute hydrochloric acid from about one to about 24 hours resulting in hydrolysis of the BOC protecting group. The solvent is removed under reduced pressure and the crude N-monosubstituted or N,N-disubstituted urea compound I may be purified by chromatographic methods as are well known in the art.

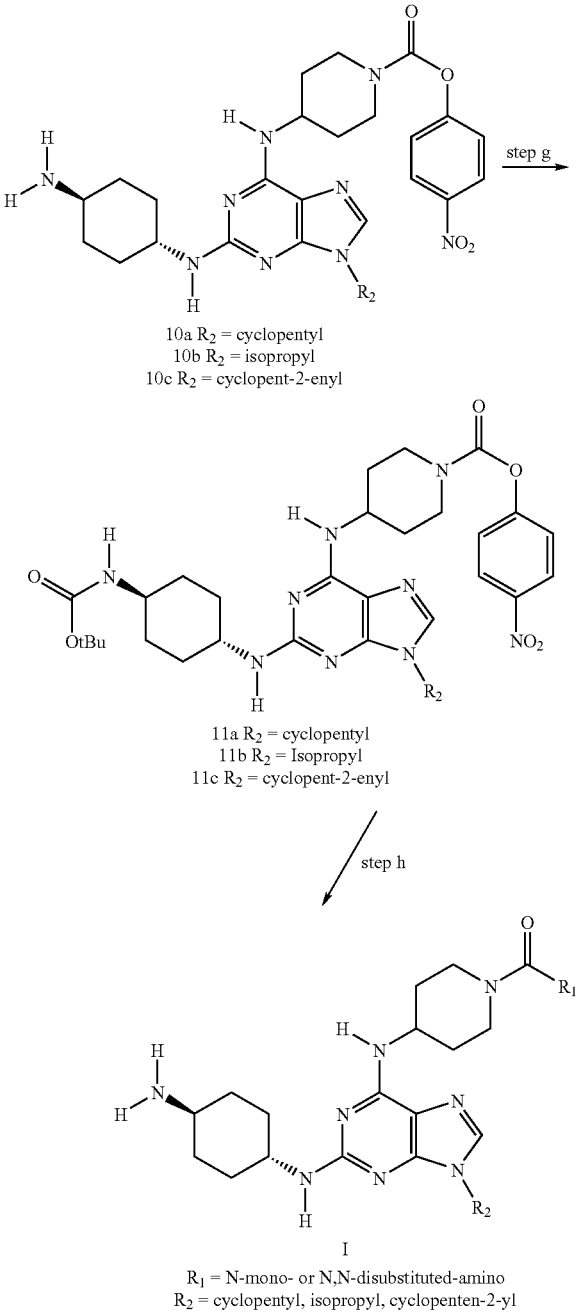

Scheme C step g

10a $R_2$ = cyclopentyl
10b $R_2$ = isopropyl
10c $R_2$ = cyclopent-2-enyl

11a $R_2$ = cyclopentyl
11b $R_2$ = Isopropyl
11c $R_2$ = cyclopent-2-enyl step h

I $R_1$ = N-mono- or N,N-disubstituted-amino
$R_2$ = cyclopentyl, isopropyl, cyclopenten-2-yl Example 1

Chemical Synthesis According to SCHEMES A, B and C

The following examples present typical syntheses as described in Schemes A, B and C. These examples are understood to be illustrative only and are not intended to limit the scope of the present invention in any way.

Synthesis of Intermediate trans-{4-[9-cyclopentyl-6-(piperidin-4-ylamino)-9H-purin-2-ylamino]-cyclohexyl}-carbamic acid tert-butyl ester (9a) According to Scheme A Scheme A step a: 2,6-dichloro-9-cyclopentyl-9H-purine (3a)

Dissolve 2,6-dichloropurine (1, 680 mg, 3.60 mmol), cyclopentanol (2a, 260 mg, 3.02 mmol), and triphenyl phosphine (950 mg, 3.60 mmol) in dry THF (20 mL) and cool to 0° C. Add diethyl azodicarboxylate (DEAD, 570 µL, 3.60 mmol) dropwise over a period of 15 minutes under a nitrogen atmosphere. Stir the resulting solution for 60 hours at room temperature. Evaporate the solvent in vacuo, charge directly onto a 500 g silica gel column, and elute with DCM and concentrate the desired fractions to give 2,6-dichloro-9-cyclopentyl-9H-purine (3a).

$^1$H-NMR (DMSO-d6): δ 8.82(s,1H), 4.95 (pentet, 1H), 2.3-1.6 (m, 8H); MS (ESI) 257 (MH$^+$); Anal. Calculated for $C_{10}H_{10}Cl_2N_4$: % C 46.71; % H 3.92; % N 21.79; Found % C 46.70; % H 3.90; % N 21.92.

Scheme A step b: 2-chloro-6-[4-(1-benzyl)piperidinylamino]-9-cyclopentyl-9H-purine (5a)

Add to a solution of 2,6-dichloro-9-cyclopentyl-9H-purine (3a 25 g, 97 mmol) and 4-amino-1-benzylpiperidine (4, 19 g, 100 mmol) in ethanol (200 mL), diisopropylethylamine (12.9 g, 100 mmol) and heat the reaction at reflux overnight. Concentrate the reaction, dissolve the residue in DCM, extract with water and brine, dry over sodium sulfate, filter and concentrate to dryness. Purify the material on a silica gel column (500 g) eluting with DCM:methanol (4:1) and concentrate the desired fractions to give 40 g of 2-chloro-6-[4-(1-benzyl)piperidinylamino]-9-cyclopentyl-9H-purine (5a).

$^1$H-MNR(CDCl$_3$): δ 7.75(s, 1H), 7.3 (m, 5H), 5.77 (brs, 1H), 4.9(p, 1H), 4.2 (brs, 1H), 3.56 (s, 2H), 2.85 (d, 2H), 2.25 (m, 4H), 2.1 (d, 2H), 1.85 (m, 6H), 1.6 (m, 2H); MS (APCI) 411 (MH$^+$).

Scheme A step c: 2-[trans-(4-aminocyclohexyl)amino]-6-[4-(1-benzyl)piperidinyl-amino]-9-cyclopentyl-9H-purine (7a)

Heat a mixture of 2-chloro-6-[4-(1-benzyl)piperidinylamino]-9-cyclopentyl-9H-purine (5a, 10 g, 24 mmol) and trans-1,4-diaminocyclohexane (6, 40 g, 6 wt. equivalents) at 140° C. for 16 hours in a sealed reaction bomb. Cool the reaction to room temperature, dissolve in DCM and wash with water. Extract the water layer with DCM and combine the organic layers. Extract the organic layer with brine, dry over sodium sulfate, filter and concentrate to dryness. Purify the material on a 200 g silica gel column eluting with DCM:methanol (4:1), and concentrate the desired fractions to give 2-[trans-(4-aminocyclohexyl)amino]-6-[4-(1-benzyl)piperidinyl-amino]-9-cyclopentyl-9H-purine (7a).

$^1$H-NMR (CDCl$_3$): δ 7.45(s, 1H), 7.3 (m, 5H), 5.48 (brs, 1H), 4.7(p, 1H), 4.6 (d, 1H), 4.1 (brs, 1H), 3.72 (m, 1H), 3.52 (s, 2H), 2.9 (d, 1H), 2.7 (m, 1H), 2.25-1.5 (m, 20H), 1.21 (m, 4H); MS (APCI) 489 (MH$^+$).

Convert 7a to the trihydrochloride by acidifying (pH=2) an ethanol solution of 7a with 6N HCL and concentrate the solution to give 8.59 g of 2-[trans-(4-aminocyclohexyl)amino]-6-[4-(1-benzyl)-piperidinyl-amino]-9-cyclopentyl-9H-purine trihydrochloride (7a trihydrochloride). MS (CI) 489 (MH$^+$); TLC (silica gel), DCM/methanol (4:1), R$_f$=0.1.

Scheme A step d: trans-{4-[6-(1-benzyl-piperidin-4-ylamino)-9-cyclopentyl-9H-purin-2-ylamino]-cyclohexyl}-carbamic acid tert-butyl ester (8a)

Stir a solution of 2-[trans-(4-aminocyclohexyl)amino]-6-[4-(1-benzyl)piperidinyl-amino]-9-cyclopentyl-9H-purine trihydrochloride (La trihydrochloride, 44 g, 90 mmol), BOC anhydride (39.4 g, 183 mmol), TEA (72.72 g, 72 mmol), and DCM (400 mL) overnight at room temperature. Mix the reaction with water, remove the resultant white participate by filtration through Celite®, wash the filtrate with brine, separate the phases and dry the organic phase over sodium sulfate. Filter and concentrate the organic phase to dryness, and purify the residue on a 500 g silica gel column using DCM:methanol (9:1) to give 40.2 grams of trans-{4-[6-(1-benzyl-piperidin-4-ylamino)-9-cyclopentyl-9H-purin-2-ylamino]-cyclohexyl}-carbamic acid tert-butyl ester (8a) as a white solid.

$^1$H-NMR (CDCl$_3$): δ 8.32 (s, 1H), 7.33 (d, 4H), 7.25 (m, 1H), 5.02 (m, 1H), 4.85 (m, 1H), 4.45 (m, 1H), 4.25 (m, 1H), 4.9 (m, 1H),3.6(m, 1H), 3.53 (s, 2H), 3.42 (m, 1H), 2.8 (m, 2H), 2.2-1.4 (m, 18H), 1.45 (s, 9H), 1.23 (m, 4H); MS (CI) 588 (M$^+$, base peak).

Scheme A step e: trans-{4-[9-cyclopentyl-6-(piperidin-4-ylamino)-9H-purin-2-ylamino]-cyclohexyl}-carbamic acid tert-butyl ester (9a)

Add to a solution of {4-[6-(1-benzyl-piperidin-4-ylamino)-9-cyclopentyl-9H-purin-2-ylamino]-cyclohexyl}-carbamic acid tert-butyl ester (8, 40.2 g, 68 mmol) in 400 mL of methanol, a suspension of Pd black (2 g) in a small amount of water. Then add a solution of ammonium formate (13.3 g, 215 mmol) in 100 mL of water, and heat at a gentle reflux overnight. TLC shows the presence of starting material (TLC, silica plates, 4:1 DCM:methanol; R$_f$: starting material 0.75, product 0.15). Add an additional 5 g of ammonium formate and reflux 24 hours. Remove the catalyst by filtration through Celite® and concentrate the filtrate. Dissolve the residue in DCM and extract with water. Remove the white precipitate by filtration through a pad of Celite®, wash the filtrate with brine, dry over sodium sulfate and filter. Concentrate the filtrate and purify the residue on silica gel (500 g) using DCM:methanol (4:1) to give 33.4 g of trans-{4-[9-cyclopentyl-6-(piperidin-4-ylamino)-9H-purin-2-ylamino]-cyclohexyl}-carbamic acid tert-butyl ester (9a) as a white solid.

$^1$H-NMR (CDCl$_3$/D$_2$0 exchange): δ 7.45 (s, 1H), 4.7 (pentet, 1H), 4.65 (d, 1H), 3.76 (brs, 1H), 3.45 (brs, 1H) 3.2 (d, 2H), 2.8 (t, 2H), 2.25-1.6 9 (m, 14H), 1.5 (m, 2H), 1.45 (s, 9H), 1.25 (m, 4H); $C_{26}H_{42}N_8O_2$ MW=498.6; MS (TOF-ES) 499.5 (M$^{+1}$).

Synthesis of Intermediate trans-{4-[9-Isopropyl-6-(piperidin-4-ylamino)-9H-purin-2-ylamino]-cyclohexyl}-carbamic acid tert-butyl ester (9b) According to Scheme A Scheme A step a: 2,6-dichloro-9-isopropyl-9H-purine (3b)

Add DEAD (4.7 g, 27.09 mmol) slowly to a solution of 2,6-dichloropurine (1, 5 g, 26.5 mmol), triphenylphosphine (11.75 g, 44.5 mmol) and isopropyl alcohol (2b, 10 ml) in THF (100 ml), and stir at room temperature for 24 hours. Concentrate the reaction mixture, dissolve the residue in DCM (20 ml) and filter to remove the unwanted solids. Load the filtrate onto a 90 gram silica gel column (Biotage), and elute with DCM/acetone (95:5). Concentrate the desired fractions to give 3.0 grams of 2,6-dichloro-9-isopropyl-9H-purine (3b). $^1$H-NMR (CDCl$_3$): δ 8.2(s, 1H), 4.95 (pentet, 1H), 1.63 (d, 6H)

Scheme A step b: 2-chloro-6-[4-(1-benzyl)piperidinylamino]-9-isopropyl-9H-purine (5b)

Reflux a solution of 2,6-dichloro-9-isopropyl-9H-purine (3b, 3.0 g, 13 mmol) and 4-amino-N-benzylpiperidine (4, 2.5 g, 13 mmol) in ethanol (100 mL) overnight. Concentrate the reaction to dryness and purify the residue on a 90 gram silica gel column (Biotage) eluting with DCM/methanol (95:5). Concentrate the desired fractions to give 3.1 g of 2-chloro-6-[4-(1-benzyl)piperidinylamino]-9-isopropyl-9H-purine (5b).

$^1$H-NMR (CDCl$_3$): δ 7.8(s, 1H), 7.3 (m, 5H), 4.92 (pentet, 1H), 3.58 (s, 2H), 2.9 (m, 2H), 2.4-1.9 (m, 5H), 1.6 (m, 8H).

Scheme A step c: 2-[trans-(4-aminocyclohexyl)amino]-6-[4-(1-benzyl)piperidinyl-amino]-9-isopropyl-9H-purine (7b)

Heat a mixture of 2-chloro-6-[4-(1-benzyl)piperidinylamino]-9-isopropyl-9H-purine (3.0 g, 7.1 mmol) and trans-1,4-diaminocyclohexane (6, 18 g) in a steel bomb at 140° C. for 60 hours. Cool the reaction and dissolve the mixture in DCM/water (3:1). Separate the layers, basify the aqueous layer with saturated sodium carbonate solution, and extract with DCM (2×50 ml). Combine the organic layers, wash with brine, dry over sodium sulfate, filter and concentrate to dryness. Purify the residue on a 40 gram silica gel column (Biotage) eluting with DCM/methanol (4:1 with 0.5% ammonium hydroxide and concentrate the desired fractions to give 3.71 grams of 2-[trans-(4-aminocyclohexyl)amino]-6-[4-(1-benzyl)piperidinyl-amino]-9-isopropyl-9H-purine (7b).

TLC (silica gel): R$_f$=0.13, CH$_2$Cl$_2$/EtOH (4:1).

Scheme A step d: trans-{4-[6-(1-benzyl-piperidin-4-ylamino)-9-isopropyl-9H-purin-2-ylamino]-cyclohexyl}-carbamic acid tert-butyl ester (8b)

Add TEA (4.14 g, 41.4 mmol) to a solution of 2-[trans-(4-aminocyclohexyl)amino]-6-[4-(1-benzyl)piperidinyl-amino]-9-isopropyl-9H-purine (7b, 3.7 g, 6.9 mmol) and di-tert-butyl dicarbonate (3.0 g, 13.9 mmol) in 50 ml of DCM. Stir the reaction for 45 minutes at room temperature, and then wash with water. Filter through Celite® to remove a milky white precipitate, wash the filtrate with brine, dry over sodium sulfate, filter and concentrate to dryness. Purify the residue on a 40 gram silica gel column (Biotage) using DCM/methanol (9:1) to give 2.7 grams of trans-{4-[6-(1-benzyl-piperidin-4-ylamino)-9-isopropyl-9H-purin-2-ylamino]-cyclohexyl}-carbamic acid tert-butyl ester (8b).

$^1$H-NMR (CDCl$_3$): δ 7.5(s, 1H), 7.4-7.2 (m, 5H), 5.45 (brs, 1H), 4.62 (m, 2H), 4.44 (brs, 1H), 4.1 (brs, 1H), 3.85 (brs, 1H), 3.55 (s, 2H), 3.5 (m, 1H), 2.9 (m, 2H), 2.25-2.0 (m, 9H), 1.7-1.4 (m,17H), 1.3 (M,3H).

Scheme A step e: trans-{4-[9-isopropyl-6-(piperidin-4-ylamino)-9H-purin-2-ylamino]-cyclohexyl}-carbamic acid tert-butyl ester (9b)

Add to a solution of trans-{4-[6-(1-benzyl-piperidin-4-ylamino)-9-isopropyl-9H-purin-2-ylamino]-cyclohexyl}-carbamic acid tert-butyl ester (8b, Ig, 1 mmol) and methanol (40 ml), a suspension of palladium black (0.25 g) in a little water. Then add a solution of ammonium formate (0.4 mg, 6.4 mmol) and 10 ml of water, and reflux overnight. Filter the reaction through Celite® and concentrate the filtrate to dryness. Dissolve the residue in methylene chloride (50 ml), extracted with water, and filter through Celite® to remove a milky white precipitate. Separate the organic layer, wash with brine, dry over sodium sulfate, filter and concentrate the filtrate to dryness. Purify the residue on a 40 gram silica gel column (Biotage) using DCM/methanol (4:1) to give 0.8 grams of trans-{4-[9-isopropyl-6-(piperidin-4-ylamino)-9H-purin-2-ylamino]-cyclohexyl}-carbamic acid tert-butyl ester (9b). H1-NMR (CDCl$_3$): δ 7.5 (s, 1H), 5.45 (brs, 1H), 4.64 (m, 2H), 4.45 (m, 1H), 4.2 (m, 1H), 3.75 (m, 1H), 3.5 (m, 1H), 3.2 (m, 1H), 3.0 (m, 1H), 2.8 (t, 1H), 2.5-2.0 (m, 9H), 1.6 (m, 2H), 1.53 (d, 6H), 1.45 (s, 9H), 1.25 (m, 3H).

Synthesis of Intermediate trans-{4-[9-Cyclopent-2-enyl-6-(piperidin-4-ylamino)-9H-purin-2-ylamino]-cyclohexyl}-carbamic acid tert-butyl ester (9c) According to Scheme A Scheme A step a 2,6-dichloro-9-cyclopent-2-enyl-9H-purine (3c)

Add to a stirred solution of 2-cyclopenten-1-ol (2c 2.60 g, 30.9 mmol), 2,6-dichloropurine (1, 7.00 g, 37.0 mmol) and triphenyl phosphine (9.70 g, 37.0 mmol) in dry THF (120 ml) at 0° C., diethyl azodicarboxylate (5.85 ml, 37.0 mmol) dropwise over a period of 15 min. under a nitrogen atmosphere. Stir the resulting solution for 60 hrs at room temperature. Concentrate the reaction mixture, charge the residue directly onto a silica gel column and elute with hexane:ethyl acetate (3:1) to give of 2,6-dichloro-9-cyclopent-2-enyl-9H-purine (3c) (3.20 g, 41%.)

$^1$H-NMR (CDCl$_3$): δ 8.05 (s, 1H,purine H-8), 6.37 (m, 1H,CH═C), 5.89 (m, 1H,CH═C), 5.77 (m, 1H), 2.49-2.78 (m, 3H), 1.95 (m, 1H).

Scheme A step b: 2-chloro-6-[4-(1-benzyl)piperidinylamino]-9-cyclopent-2-enyl-9H-purine (5c)

Add to a solution of 2,6-dichloro-9-cyclopent-2-enyl-9H-purine (3c, 1.0 mmol) and 4-amino-1-benzylpiperidine (4, 1.0 mmol) in ethanol (200 mL), diisopropylethylamine (1.0 mmol) and heat the reaction at reflux overnight. Concentrate the reaction, dissolve the residue in DCM, extract with water and brine, dry over sodium sulfate, filter and concentrate to dryness. Purify the material on a silica gel column (50 g) eluting with DCM:methanol (4:1) and concentrate the desired fractions to give 2-chloro-6-[4-(1-benzyl)piperidinylamino]-9-cyclopent-2-enyl-9H-purine (5c).

Scheme A step c: 2-[trans-(4-aminocyclohexyl)amino]-6-[4-(1-benzyl)piperidinyl-amino]-9-cyclopent-2-enyl-9H-purine (7c)

Heat a mixture of 2-chloro-6-[4-(1-benzyl)piperidinylamino]-9-cyclopent-2-enyl-9H-purine (5c, 1.0 mmol) and trans-1,4-diaminocyclohexane (6, 6 wt. equivalents) at 140° C. for 16 hours in a sealed reaction bomb. Cool the reaction to room temperature, dissolve in DCM and wash with water. Extract the water layer with DCM and combine the organic layers. Extract the organic layer with brine, dry over sodium sulfate, filter and concentrate to dryness. Purify the material on a 20 g silica gel column eluting with DCM:methanol (4:1), and concentrate the desired fractions to give 2-[trans-(4-aminocyclohexyl)amino]-6-[4-(1-benzyl)piperidinyl-amino]-9-cyclopent-2-enyl-9H-purine (7c).

Scheme A step d: trans-{4-[6-(1-benzyl-piperidin-4-ylamino)-9-cyclopent-2-enyl-9H-purin-2-ylamino]-cyclohexyl}-carbamic acid tert-butyl ester (8c)

Stir a solution of 2-[trans-(4-aminocyclohexyl)amino]-6-[4-(1-benzyl)piperidinyl-amino]-9-cyclopent-2-enyl-9H-purine (7c, 1.0 mmol), BOC anhydride (2.0 mmol), TEA (1 mmol), and DCM (40 mL) overnight at room temperature. Mix the reaction with water, filter through Celite®, wash the filtrate with brine, separate the phases and dry the organic phase over sodium sulfate. Filter and concentrate the organic phase to dryness, and purify the residue on a 500 g silica gel column using DCM:methanol (9:1) to give trans-{4-[6-(1-benzyl-piperidin-4-ylamino)-9-cyclopent-2-enyl-9H-purin-2-ylamino]-cyclohexyl}-carbamic acid tert-butyl ester (8c).

Scheme A step e: trans-{4-[9-cyclopent-2-enyl-6-(piperidin-4-ylamino)-9H-purin-2-ylamino]-cyclohexyl}-carbamic acid tert-butyl ester (29c)

Add to a solution of trans-{4-[6-(1-benzyl-piperidin-4-ylamino)-9-cyclopent-2-enyl-9H-purin-2-ylamino]-cyclohexyl}-carbamic acid tert-butyl ester (8c, 1.0-mmol) in 40 mL of methanol, a suspension of Pd black (0.5 wt %) in a small amount of water. Then add a solution of ammonium formate (2.2 mmol) in 10 mL of water, and heat at a gentle reflux overnight. Remove the catalyst by filtration through Celite® and concentrate the filtrate. Dissolve the residue in DCM and extract with water. Remove the white precipitate by filtration through a pad of Celite®, wash the filtrate with brine, dry over sodium sulfate and filter. Concentrate the filtrate and purify the residue on silica gel (50 g) using DCM:methanol (4:1) to give trans-{4-[9-cyclopent-2-enyl-6-(piperidin-4-ylamino)-9H-purin-2-ylamino]-cyclohexyl}-carbamic acid tert-butyl ester (9c.

General Method for Acylation of Intermediate 9-Cyclopentyl Analog 9a and Hydrolysis to Compound I According to Scheme B

Scheme B step f

Stir a mixture of trans-{4-[9-cyclopentyl-6-(piperidin-4-ylamino)-9H-purin-2-ylamino]-cyclohexyl}-carbamic acid tert-butyl ester (9a, 0.2 mmol), an acylating agent such as a carboxylic acid halide; a chloroformate ester; alkyl, aryl or aralkyl isocyanates; alkyl, aryl or aralkyl sulfonyl chlorides or alkyl, aryl or aralkyl sulfamoyl chlorides (0.2 mmol) and triethylamine (0.2 mmol, omitted when isocyanates used) in methylene chloride (2 ml) overnight at room temperature. Add 1.0 ml of 4N HCl in dioxane and a precipitate forms. Allow to stand for 3 hours, decant the solvent and dissolve the solid in DCM using a small amount of methanol as co-solvent if necessary. Purify the product by chromatography on a 2 g silica gel SPE cartridge pre-equilibrated with heptane. Elute the column in three fractions; first fraction 5 ml DCM; fractions 2 and 3 with 10-15 ml of DCM/methanol (4:1). Concentrate the desired fractions, dissolve the residue in ethanol and adjust to pH 2.0 with 10% HCl. Concentrate to dryness to give 9-cyclopentyl compound I, and analyze the product by LC/MS as summarized in Table 1.

General Method for Acylation of Intermediate 9-Isopropyl Analog 9b or Intermediate 9-cyclopent-2-enyl Analog 9c, and Hydrolysis to Compound I According to Scheme B

Scheme B step f

Add to a solution of 6-(piperidinyl-4-amino)-2-(trans-4-tert-butoxycarbonylamino-cyclohexylamino)-9-isopropylpurine (9b, 100 mg) or trans-{4-[9-cyclopent-2-enyl-6-(piperidin-4-ylamino)-9H-purin-2-ylamino]-cyclohexyl}-carbamic acid tert-butyl ester, and an acylating agent such as a carboxylic acid halide; a chloroformate ester; alkyl, aryl or aralkyl isocyanates; alkyl, aryl or aralkyl sulfonyl chlorides, or alkyl, aryl or aralkyl sulfamoyl chlorides (0.5 mmol) in DCM (2 ml), 200 □l of TEA and stir overnight at room temperature (when the acylating agent is an isocyanate TEA is omitted). Add 1 ml of 4N HCl in dioxane and allow the reaction to sit for 3 hours at room temperature to effect removal of the N—BOC protecting group. The product precipitates and the solvent is decanted. Dissolve the precipitate in a small amount of DCM/methanol (4:1) and load on a 5 gram silica gel SPE cartridge that is pre-equilibrated with heptane. Elute with 5 ml of DCM into the first fraction, followed by five 15 ml fractions using 4:1 DCM/methanol. Concentrate the desired fractions, dissolve the residue in ethanol and treat with 3 drops of 6 N aqueous HCl. Further concentrate to provide compound I as the HCl salt and analyze the product by LC/MS as summarized in Table 1.

General Method for Preparing BOC-Protected N-Monosubstituted and N,N-Disubstituted Urea Compounds I and Hydrolysis to N-Monosubstituted and N,N-Disubstituted Urea Compounds I According to Scheme C Scheme C step g: trans-9-Substituted-4-[2-(4-tert-butoxycarbonylamino-cyclohexylamino)-9H-purin-6-ylamino]piperidine-1-carboxylic acid 4-nitro-phenyl ester (11a, 11b and 11c)

Stir a solution of trans-4-[2-(4-amino-cyclohexylamino)-9-cyclopentyl-9H-purin-6-ylamino]piperidine-1-carboxylic acid 4-nitro-phenyl ester (10a 1 mmol), BOC anhydride (2 mmol), TEA (8 mmol), and DCM (40 mL) overnight at room temperature. Mix the reaction with water, remove the resultant white participate by filtration through Celite®, wash the filtrate with brine, separate the phases and dry the organic phase over sodium sulfate. Filter and concentrate the organic phase to dryness, and purify the residue on a 50 g silica gel column using DCM:methanol (9:1) to give trans-4-[2-(4-tert-butoxycarbonylamino-cyclohexylamino)-9-cyclopentyl-9H-purin-6-ylamino]piperidine-1-carboxylic acid 4-nitro-phenyl ester (11a).

trans-4-[2-(4-tert-Butoxycarbonylamino-cyclohexylamino)-9-isopropyl-9H-purin-6-ylamino]piperidine-1-carboxylic acid 4-nitro-phenyl ester 11b and trans-4-[2-(4-tert-butoxycarbonylamino-cyclohexylamino)-9-cyclopent-2-enyl-9H-purin-6-ylamino]piperidine-1-carboxylic acid 4-nitro-phenyl ester 11c may be prepared from trans-4-[2-(4-amino-cyclohexylamino)-9-isopropyl-9H-purin-6-ylamino]piperidine-1-carboxylic acid 4-nitro-phenyl ester (10b) and trans-4-[2-(4-amino-cyclohexylamino)-9-cyclopent-2-enyl-9H-purin-6-ylamino]piperidine-1-carboxylic acid 4-nitrophenyl ester (10c) under similar conditions, respectively.

Scheme C step h

To a solution of 11a (0.1 mmol) in THF (40 mL) was added a primary or secondary amine (0.1 mmol) in the presence of TEA (0.2 mmol). Stir the reaction at about room temperature to about 90° C. for 2 to 24 hours. Cool the reaction and add 4N HCl in dioxane (1 mL). Stir the mixture for about 3 hours and remove the solvent under reduced pressure. Purify the residue by chromatography on a 2 g silica gel SPE cartridge pre-equilibrated with heptane. Elute the column in three fractions; first fraction 5 ml DCM; fractions 2 and 3 with 10-15 ml of DCM/methanol (4:1). Collect and concentrate the fractions containing compound I where $R_2$ is cyclopentyl. N-Monosubstituted and N,N-disubstituted urea compounds I where $R_2$ is isopropyl or cyclopent-2-enyl may be prepared in a similar manner from 11b or 11c, respectively.

Preparation of N-Mono-Substituted Sulfamoyl Chlorides

The preparation of N-methyl sulfamoyl chloride was performed as described by G. Weiss and G. Schulze [Liebigs Ann. Chem. 729, 40-51 (1969)], herein incorporated by reference. A suspension of anhydrous methylamine hydrochloride (1 mole) and acetonitrile is treated with sulfuryl chloride (1 mole) and $SbCl_5$ (0.5 g), and then heated under reflux with vigorous stirring (HCl gas evolves from the reaction). After 4 hours sulfuryl chloride (1 mole) is added. After 24 hours the mixture is evaporated and the residue is distilled under high vacuum (70° C., 0.04 mmHg) to afford N-methyl sulfamoyl chloride (125 g). Other N-monosubstituted sulfamoyl chlorides may be prepared by this procedure including N-ethyl-, N-propyl, N-isopropyl, N-isobutyl, N-butyl, and N-cyclohexyl-sulfamoyl chlorides.

Preparation of N,N-Disubstituted Sulfamoyl Chlorides

N,N-Disubstituted sulfamoyl chlorides were prepared as described by Binkley and Degering [J. Am. Chem. Soc., 61, 3250-3251 (1939)], herein incorporated by reference. For example, diethylamine (0.33 mole) was added very slowly to sulfuryl chloride (0.33 mole) with vigorous stirring and ice water chilling. The mixture was warmed and heated under reflux for 24 hours. The cooled mixture was extracted with anhydrous ethyl ether, and the extract was concentrated and the residue distilled under reduced pressure to afford N,N-diethyl sulfamoyl chloride, b.p. 69° (10 mmHg). N,N-Dimethyl-sulfamoyl chloride was purchased commercially.

Preparation of Compound I Sulfonic Acid Amides

Scheme B, step f:

Treat a stirred, cooled (0° C.) solution of N-methyl sulfamoyl chloride (0.2 mmol) and anhydrous tetrahydrofuran (275 mL) with a solution of trans-{4-[9-cyclopentyl-6-(piperidin-4-ylamino)-9H-purin-2-ylamino]-cyclohexyl}-carbamic acid tert-butyl ester (9a, 0.2 mmol) triethylamine (9a 0.2 mmol) and tetrahydrofuran (4 mL) overnight at room temperature. Warm to 55° C., cool to room temperature and add 1.0 ml of 4N HCl in dioxane. Allow to stand for 3 hours, concentrate and dissolve the residue in DCM using a small amount of methanol as co-solvent if necessary. Purify the product by chromatography on a 2 g silica gel SPE cartridge pre-equilibrated with heptane. Elute the column in three fractions; first fraction 5 ml DCM; fractions 2 and 3 with 10-15 ml of DCM/methanol (4:1). Concentrate the desired fractions, dissolve the residue in ethanol and adjust to pH 2.0 with 10% HCl. Concentrate to dryness to give 4-[2-(4-amino-cyclohexylamino)-9-cyclopentyl-9H-purin-6-ylamino]-piperidine-1-sulfonic acid methylamide. Using N,N-dimethyl sulfamoyl chloride under similar conditions provides the corresponding trans-4-[2-(4-amino-cyclohexylamino)-9-cyclopentyl-9H-purin-6-ylamino]-piperidine-1-sulfonic acid dimethylamide. The corresponding 9-isopropyl and 9-cyclopent-2-enyl compound I sulfonic acid amides are prepared in a similar manner from 9b and 9c.

Preparation of 2-Cyclopenten-1-ol

Heat a mixture of cyclopentene (10 g, 147 mmol), N-bromosuccinimide (13 g, 178 mmol) and benzoyl peroxide (0.5 g, cat.) in carbon tetrachloride (25 ml) at reflux for 1 hour. Cool the reaction and concentrate under vacuum to give a dark oil. Stir the oil in sodium bicarbonate (saturated, 50 ml) overnight and then extract the mixture with DCM (2×100 ml). Combine the organic phases, dry over magnesium sulfate and concentrate to yield 5 grams of a reddish residue. Vacuum distill the crude residue to give 2-cyclopenten-1-ol (bp 71° C., 46 mmHg, 2.5 g, 41%).

$^1$H-NMR (CDCl$_3$): δ 6.02(m, 1H), 5.85 (m, 1H), 4.8 (m, 1H), 2.55 (m, 1H), 2.4 (m, 2H), 1.75 (m, 1H).

Preparation of Salts of Compounds I

Salts of compounds I may be prepared by methods well known to those skilled in the art. For example, one dissolves the purified compound I in a minimum volume of absolute EtOH, and adds 1 to 3 equivalents of the desired inorganic or organic acid to provide to provide the mono-, di-, or tri-salt of compound I, such as the mono-, di-, or tri-hydrochloride. One isolates the solid salt by filtration, or by removal of the EtOH in vacuo or by a stream of nitrogen under gentle heating. The isolated salt may be recrystallized and dried by methods well known to those skilled in the art. Selection of pharmaceutically acceptable salts may be based on but not limited to the salts discussed by Gould [International Journal of Pharmaceutics, 33, 201-217 (1986)] or Berge et al. [J. Pharm. Sci., 66, 1-19 (1977)], incorporated herein by reference. Pharmaceutically acceptable salts include but are not limited to salts of hydrochloric acid, hydrobromic acid, phosphoric acid, sulfuric acid, nitric acid, acetic acid, fumaric acid, maleic acid, gluconic acid, citric acid, or methanesulfonic acid. Other acids such a s oxalic acid and picric acid may be used to aid in purification of compounds I and those salts may be subsequently converted to a pharmaceutically acceptable salt of compound I by methods well known to those skilled in the art.

High Performance Liquid Chromatography (HPLC)

Atmospheric Pressure Chemical Ionisation Mass Spectrometry (APCI/MS) Analysis of Examples Conditions for product analysis are readily ascertainable by one skilled in the art. The following conditions represent typical analytic parameters. HPLC columns or cartridges were obtained from YMC Inc., 3233 Burnt Mill Drive, Wilmington, N.C. 28403, and Waters Corporation, 34 Maple Street, Milford, Mass. 01757. The conditions for the product analysis are summarized as follows, and the particular set of conditions used is indicated by reference in the table of examples to one of the following HPLC-APCI/MS conditions.

HPLC-APCI/MS Condition A:
A) 95/5/0.1% Water/Acetonitrile/Acetic acid
B) 5/95/0.1% Water/Acetonitrile/Acetic acid The above sample was analyzed using a HP1100 binary HPLC system and a Micromass LCT mass spectrometer equipped with an electrospray ionization source. The column was a YMC ODS-AQ (2 mm×50 mm) cartridge. The initial HPLC conditions consisted of 100% (A) flowing at 1 mL/minute. After 0.1 minute a linear gradient was performed so that at 2 minutes the HPLC conditions were 100% (B). These conditions were then held until 3.5 minutes at which time the system switched back to initial conditions and equilibrated for the next analysis.

HPLC-APCI/MS Condition B:
A) 95/5/0.1% Water/Acetonitrile/Formic acid
B) 5/95/0.1% Water/Acetonitrile/Formic acid The above sample was analyzed using a HP1100 binary HPLC system and a Micromass LCT mass spectrometer equipped with an electrospray ionization source. The column was a YMC ODS-AQ (2 mm×50 mm) cartridge. The initial HPLC conditions consisted of 100% (A) flowing at 1 mL/minute. After 0.1 minute a linear gradient was performed so that at 2 minutes the HPLC conditions were 100% (B). These conditions were then held until 3.5 minutes at which time the system switched back to initial conditions and equilibrated for the next analysis.

HPLC-APCI/MS Condition C:
A) 95/5/0.1% Water/Acetonitrile/Acetic acid
B) 5/95/0.1% Water/Acetonitrile/Acetic acid The above sample was analyzed using a Waters 600 HPLC system and a Finnigan SSQ-710 or TSQ-700 mass spectrometer equipped with an atmospheric pressure chemical ionization source. The column was a YMC ODS-AQ (4 mm×50 mm) cartridge. The initial HPLC conditions consisted of 100% (A) flowing at 1 mL/minute. After 0.1 minute a linear gradient was performed so that at 2 minutes the HPLC conditions were 100% (B). These conditions were then held until 6 minutes at which time the system switched back to initial conditions and equilibrated for the next analysis.

HPLC-APCI/MS Condition D:
A) 95/5/0.1% Water/Acetonitrile/Formic acid
B) 5/95/0.1% Water/Acetonitrile/Formic acid The above sample was analyzed using a Waters 600 HPLC system and a Finnigan SSQ-710 or TSQ-700 mass spectrometer equipped with an atmospheric pressure chemical ionization source. The column was a YMC ODS-A (4 mm×50 mm) cartridge. The initial HPLC conditions consisted of 100% (A) flowing at 2 mL/minute. After 0.1 minute a linear gradient was performed so that at 2 minutes the HPLC conditions were 100% (B). These conditions were then held until 3.4 minutes at which time the system switched back to initial conditions and equilibrated for the next analysis.

HPLC-APCI/MS Condition E:
A) 95/5/0.1% Water/Acetonitrile/Formic acid
B) 5/95/0.1% Water/Acetonitrile/Formic acid The above sample was analyzed using a Waters 600 HPLC system and a Finnigan SSQ-710 or TSQ-700 mass spectrometer equipped with an atmospheric pressure chemical ionization source. The column was a YMC ODS-AQ (4 mm×50 mm) cartridge. The initial HPLC conditions consisted of 100% (A) flowing at 2 mL/minute. After 0.1 minute a linear gradient was performed so that at 2 minutes the HPLC conditions were 100% (B). These conditions were then held until 5 minutes at which time the system switched back to initial conditions and equilibrated for the next analysis.

HPLC-APCI/MS Condition F:
A) 95/5/0.1% Water/Acetonitrile/Acetic acid
B) 5/95/0.1% Water/Acetonitrile/Acetic acid The above sample was analyzed using a Waters 600 HPLC system and a Finnigan SSQ-710 or TSQ-700 mass spectrometer equipped with an atmospheric pressure chemical ionization source. The column was a YMC ODS-A (4 mm×50 mm) cartridge. The initial HPLC conditions consisted of 100% (A) flowing at 2 mL/minute. After 0.1 minute a linear gradient was performed so that at 2 minutes the HPLC conditions were 100% (B). These conditions were then held until 3.4 minutes at which time the system switched back to initial conditions and equilibrated for the next analysis.

TABLE 1

PHYSICAL PROPERTIES AND ACYLATING AGENTS FOR SYNTHESIS OF COMPOUNDS

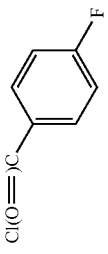

| Ex. No. | Name | Z | Ra | R2 | Salt | HPLC Conditions | LC/MS, HTPMS MH+ | LC/MS HTPMS RT (min or min:sec) | Acylating Agent R1•C(=O)Cl |
|---|---|---|---|---|---|---|---|---|---|
| 1 | trans-1-{4-[2-(4-Amino-cyclohexylamino)-9-cyclopentyl-9H-purin-6-ylamino]-piperidin-1-yl]}-1-(4-fluoro-phenyl)-methanone dihydrochloride | —C(O)— | 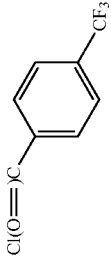 | 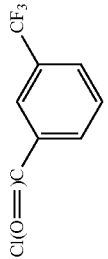 | 2HCl | C | 521 | 2.52 |  |
| 2 | trans-1-{4-[2-(4-Amino-cyclohexylamino)-9-cyclopentyl-9H-purin-6-ylamino]-piperidin-1-yl]}-1-(4-trifluoromethyl-phenyl)-methanone dihydrochloride | —C(O)— |  |  | 2HCl | C | 570(M+) | 2.52 | 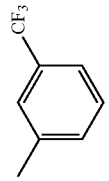 |
| 3 | trans-1-{4-[2-(4-Amino-cyclohexylamino)-9-cyclopentyl-9H-purin-6-ylamino]-piperidin-1-yl]}-1-(4-trifluoromethyl-phenyl)-methanone dihydrochloride | —C(O)— | 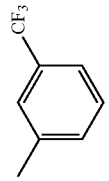 |  | 2HCl | C | 571 | 2.58 |  |

TABLE 1-continued

PHYSICAL PROPERTIES AND ACYLATING AGENTS FOR SYNTHESIS OF COMPOUNDS

| # | Name | | | | | | | |
|---|---|---|---|---|---|---|---|---|
| 4 | trans-1-{4-[2-(4-Amino-cyclohexylamino)-9-cyclopentyl-9H-purin-6-ylamino]-piperidin-1-yl}-1-quinoxalin-2-yl-methanone dihydrochloride | —C(O)— | 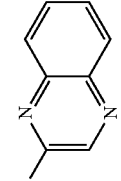 | 2HCl | 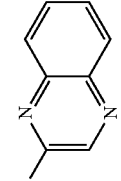 | C | 555 | 2.55 | Cl(O=)C— 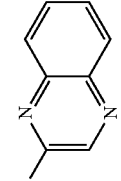 |
| 5 | trans-1-{4-[2-(4-Amino-cyclohexylamino)-9-cyclopentyl-9H-purin-6-ylamino]-piperidin-1-yl}-1-benzo[1,3]dioxol-5-yl-methanone dihydrochloride | —C(O)— | | 2HCl | | C | 547 | 2.52 | Cl(O=)C— |
| 6 | trans-1-{4-[2-(4-Amino-cyclohexylamino)-9-cyclopentyl-9H-purin-6-ylamino]-piperidin-1-yl}-1-(3-chloro-phenyl)-methanone dihydrochloride | —C(O)— | | 2HCl | | C | 537 | 2.55 | Cl(O=)C— |
| 7 | trans-1-{4-[2-(4-Amino-cyclohexylamino)-9-cyclopentyl-9H-purin-6-ylamino]-piperidin-1-yl}-1-(2-methoxy-phenyl)-methanone dihydrochloride | —C(O)— | | 2HCl | | C | 533 | 2.55 | Cl(O=)C— |
| 8 | trans-1-{4-[2-(4-Amino-cyclohexylamino)-9-cyclopentyl-9H-purin-6-ylamino]-piperidin-1-yl}-1-(4-methoxy-phenyl)-methanone dihydrochloride | —C(O)— | | 2HCl | | C | 532(M+) | 2.60 | Cl(O=)C— |
| 9 | trans-1-{4-[2-(4-Amino-cyclohexylamino)-9-cyclopentyl-9H-purin-6-ylamino]-piperidin-1-yl}-1-phenyl-methanone dihydrochloride | —C(O)— | | 2HCl | | C | 502(M+) | 2.50 | Cl(O=)C— |

TABLE 1-continued

PHYSICAL PROPERTIES AND ACYLATING AGENTS FOR SYNTHESIS OF COMPOUNDS

| # | Name | Linker | R | Salt | Form | MW | Ret. time | Acylating agent |
|---|---|---|---|---|---|---|---|---|
| 10 | trans-1-{4-[2-(4-Amino-cyclohexylamino)-9-cyclopentyl-9H-purin-6-ylamino]-piperidin-1-yl}-1-thiophen-2-yl-methanone dihydrochloride | —C(O)— | 2-thienyl | 2HCl | C | 509 | 2.48 | Cl(O=)C-thiophene |
| 11 | trans-4-(1-{4-[2-(4-Amino-cyclohexylamino)-9-cyclopentyl-9H-purin-6-ylamino]-piperidin-1-yl}-methanoyl)-benzoic acid methyl ester dihydrochloride | —C(O)— | 4-(CO2Me)phenyl | 2HCl | F | 561 | 1.53 | Cl(O=)C-C6H4-CO2CH3 |
| 12 | trans-1-{4-[2-(4-Amino-cyclohexylamino)-9-cyclopentyl-9H-purin-6-ylamino]-piperidin-1-yl}-1-(2-fluoro-3-trifluoromethyl-phenyl)-methanone dihydrochloride | —C(O)— | 2-F-3-CF3-phenyl | 2HCl | F | 589 | 1.58 | Cl(O=)C-C6H3(F)(CF3) |
| 13 | trans-1-{4-[2-(4-Amino-cyclohexylamino)-9-cyclopentyl-9H-purin-6-ylamino]-piperidin-1-yl}-1-(2-bromo-phenyl)-methanone | —C(O)— | 2-Br-phenyl | — | A | 581 | 1:09 | Cl(O=)C-C6H4-Br |
| 14 | trans-1-{4-[2-(4-Amino-cyclohexylamino)-9-cyclopentyl-9H-purin-6-ylamino]-piperidin-1-yl}-1-(2,6-dichloro-phenyl)-methanone | —C(O)— | 2,6-diCl-phenyl | — | A | 571 | 1:09 | Cl(O=)C-C6H3Cl2 |
| 15 | trans-1-{4-[2-(4-Amino-cyclohexylamino)-9-cyclopentyl-9H-purin-6-ylamino]-piperidin-1-yl}-1-(3,4-dichloro-phenyl)-methanone | —C(O)— | 3,4-diCl-phenyl | — | A | 571 | 1:06 | Cl(O=)C-C6H3Cl2 |

TABLE 1-continued

PHYSICAL PROPERTIES AND ACYLATING AGENTS FOR SYNTHESIS OF COMPOUNDS

| # | Name | | | | | | Acylating agent |
|---|---|---|---|---|---|---|---|
| 16 | trans-1-{4-[2-(4-Amino-cyclohexylamino)-9-cyclopentyl-9H-purin-6-ylamino]-piperidin-1-yl}-1-(3,4,5-trimethoxy-phenyl)-methanone | —C(O)— | 3,4,5-trimethoxyphenyl | — | A | 593 | 1:06 | 3,4,5-trimethoxybenzoyl chloride |
| 17 | trans-1-{4-[2-(4-Amino-cyclohexylamino)-9-cyclopentyl-9H-purin-6-ylamino]-piperidin-1-yl}-1-(3,5-dimethoxy-phenyl)-methanone | —C(O)— | 3,5-dimethoxyphenyl | — | A | 563 | 1:08 | 3,5-dimethoxybenzoyl chloride |
| 18 | trans-1-{4-[2-(4-Amino-cyclohexylamino)-9-cyclopentyl-9H-purin-6-ylamino]-piperidin-1-yl}-1-(4-butoxy-phenyl)-methanone | —C(O)— | 4-butoxyphenyl | — | A | 575 | 1:36 | 4-butoxybenzoyl chloride |
| 19 | trans-1-{4-[2-(4-Amino-cyclohexylamino)-9-cyclopentyl-9H-purin-6-ylamino]-piperidin-1-yl}-1-(4-heptoxy-phenyl)-methanone | —C(O)— | 4-heptoxyphenyl | — | A | 617 | 1:20 | 4-heptoxybenzoyl chloride |
| 20 | trans-1-{4-[2-(4-Amino-cyclohexylamino)-9-cyclopentyl-9H-purin-6-ylamino]-piperidin-1-yl}-1-(4-tert-butyl-phenyl)-methanone | —C(O)— | 4-tert-butylphenyl | — | A | 559 | 1:20 | 4-tert-butylbenzoyl chloride |
| 21 | trans-1-{4-[2-(4-Amino-cyclohexylamino)-9-cyclopentyl-9H-purin-6-ylamino]-piperidin-1-yl}-1-(4-butyl-phenyl)-methanone | —C(O)— | 4-butylphenyl | — | A | 559 | 1:22 | 4-butylbenzoyl chloride |

TABLE 1-continued

PHYSICAL PROPERTIES AND ACYLATING AGENTS FOR SYNTHESIS OF COMPOUNDS

| | | | | | | | |
|---|---|---|---|---|---|---|---|
| 22 | trans-1-{4-[2-(4-Amino-cyclohexylamino)-9-cyclopentyl-9H-purin-6-ylamino]-piperidin-1-yl}-1-(4-pentyl-phenyl)-methanone | —C(O)— | 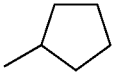 | — | A | 573 | 1:28 | 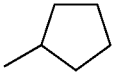 |
| 23 | trans-1-{4-[2-(4-Amino-cyclohexylamino)-9-cyclopentyl-9H-purin-6-ylamino]-piperidin-1-yl}-1-(4-hexyl-phenyl)-methanone | —C(O)— | 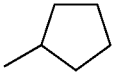 | — | A | 587 | 1:32 | 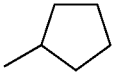 |
| 24 | trans-1-{4-[2-(4-Amino-cyclohexylamino)-9-cyclopentyl-9H-purin-6-ylamino]-piperidin-1-yl}-1-(4-heptyl-phenyl)-methanone | —C(O)— | 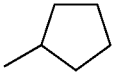 | — | A | 601 | 1:37 | 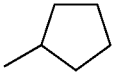 |
| 25 | trans-1-{4-[2-(4-Amino-cyclohexylamino)-9-cyclopentyl-9H-purin-6-ylamino]-piperidin-1-yl}-1-(4-cyano-phenyl)-methanone | —C(O)— | 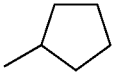 | — | A | 528 | 1:04 | 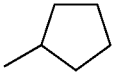 |
| 26 | trans-1-{4-[2-(4-Amino-cyclohexylamino)-9-cyclopentyl-9H-purin-6-ylamino]-piperidin-1-yl}-1-(3-nitro-phenyl)-methanone | —C(O)— | 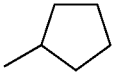 | — | A | 548 | 1:06 | 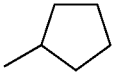 |
| 27 | trans-1-{4-[2-(4-Amino-cyclohexylamino)-9-cyclopentyl-9H-purin-6-ylamino]-piperidin-1-yl}-1-(4-nitro-phenyl)-methanone | —C(O)— | 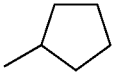 | — | A | 548 | 1:09 | 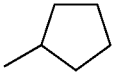 |
| 28 | trans-1-{4-[2-(4-Amino-cyclohexylamino)-9-cyclopentyl-9H-purin-6-ylamino]-piperidin-1-yl}-2-phenoxy-ethanone dihydrochloride | —C(O)— | 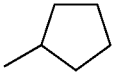 | 2HCl | A | 533 | 1.12 | 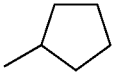 |

TABLE 1-continued

PHYSICAL PROPERTIES AND ACYLATING AGENTS FOR SYNTHESIS OF COMPOUNDS

| # | Name | Linker | Structure 1 | Salt | Method | MW | RT | Acylating Agent |
|---|------|--------|-------------|------|--------|-----|------|-----------------|
| 29 | trans-3-{4-[2-(4-Amino-cyclohexylamino)-9-cyclopentyl-9H-purin-6-ylamino]-piperidin-1-yl}-3-oxo-propionic acid ethyl ester dihydrochloride | —C(O)— | ethyl propanoate ester | 2HCl | A | 513 | 1.03 | Cl(O=)C-CH2-C(O)O-CH2CH3 |
| 30 | trans 1-{4-[2-(4-Amino-cyclohexylamino)-9-cyclopentyl-9H-purin-6-ylamino]-piperidin-1-yl}-3-methyl-but-2-en-1-one dihydrochloride | —C(O)— | 3-methyl-but-2-enyl | 2HCl | A | 481 | 1.05 | Cl(O=)C-CH=C(CH3)2 |
| 31 | trans-1-{4-[2-(4-Amino-cyclohexylamino)-9-cyclopentyl-9H-purin-6-ylamino]-piperidin-1-yl}-2-(4-chloro-phenoxy)-ethanone dihydrochloride | —C(O)— | 4-chlorophenoxy ethyl | 2HCl | A | 567 | 1.18 | Cl(O=)C-CH2-O-C6H4-Cl |
| 32 | trans 1-{4-[2-(4-Amino-cyclohexylamino)-9-cyclopentyl-9H-purin-6-ylamino]-piperidin-1-yl}-2-(3,4-dimethoxy-phenyl)-ethanone dihydrochloride | —C(O)— | 3,4-dimethoxyphenyl ethyl | 2HCl | A | 577 | 1.08 | Cl(O=)C-CH2-C6H3(OCH3)2 |
| 33 | trans 1-{4-[2-(4-Amino-cyclohexylamino)-9-cyclopentyl-9H-purin-6-ylamino]-piperidin-1-yl}-3-phenyl-propan-1-one dihydrochloride | —C(O)— | 3-phenylpropyl | 2HCl | A | 531 | 1.15 | Cl(O=)C-CH2CH2-C6H5 |

TABLE 1-continued

PHYSICAL PROPERTIES AND ACYLATING AGENTS FOR SYNTHESIS OF COMPOUNDS

| # | Name | | | | | | Acylating agent |
|---|---|---|---|---|---|---|---|
| 34 | trans 1-{4-[2-(4-Amino-cyclohexylamino)-9-cyclopentyl-9H-purin-6-ylamino]-piperidin-1-yl}-3-(2,5-dimethoxy-phenyl)-propan-1-one dihydrochloride | —C(O)— | (2,5-dimethoxyphenyl propyl) | (cyclopentyl) | 2HCl | A | 577 | 1.14 | (2,5-dimethoxyphenyl propanoyl chloride) |
| 35 | trans (E)-1-{4-[2-(4-Amino-cyclohexylamino)-9-cyclopentyl-9H-purin-6-ylamino]-piperidin-1-yl}-but-2-en-1-one dihydrochloride | —C(O)— | (but-2-enyl) | (cyclopentyl) | 2HCl | A | 467 | 1.02 | (but-2-enoyl chloride) |
| 36 | trans-1-{4-[2-(4-Amino-cyclohexylamino)-9-cyclopentyl-9H-purin-6-ylamino]-piperidin-1-yl}-3-cyclopentyl-propan-1-one dihydrochloride | —C(O)— | (cyclopentylpropyl) | (cyclopentyl) | 2HCl | A | 523 | 1.21 | (cyclopentylpropanoyl chloride) |
| 37 | trans-1-{4-[2-(4-Amino-cyclohexylamino)-9-cyclopentyl-9H-purin-6-ylamino]-piperidin-1-yl}-2-benzyloxy-ethanone dihydrochloride | —C(O)— | (benzyloxymethyl) | (cyclopentyl) | 2HCl | A | 547 | 1.13 | (benzyloxyacetyl chloride) |
| 38 | trans-1-{4-[2-(4-Amino-cyclohexylamino)-9-cyclopentyl-9H-purin-6-ylamino]-piperidin-1-yl}-2-(3-methoxy-phenyl)-ethanone dihydrochloride | —C(O)— | (3-methoxybenzyl) | (cyclopentyl) | 2HCl | A | 547 | 1.12 | (3-methoxyphenylacetyl chloride) |
| 39 | trans-1-{4-[2-(4-Amino-cyclohexylamino)-9-cyclopentyl-9H-purin-6-ylamino]-piperidin-1-yl}-1-cyclopentyl-methanone | —C(O)— | (cyclopentyl) | (cyclopentyl) | 2HCl | A | 495 | 1.1 | (cyclopentanecarbonyl chloride) |

TABLE 1-continued

PHYSICAL PROPERTIES AND ACYLATING AGENTS FOR SYNTHESIS OF COMPOUNDS

| | | | | | | | | |
|---|---|---|---|---|---|---|---|---|
| 40 | trans-1-{4-[2-(4-Amino-cyclohexylamino)-9-cyclopentyl-9H-purin-6-ylamino]-piperidin-1-yl}-2,2-diphenyl-ethanone dihydrochloride | —C(O)— | 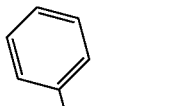 | | 2HCl | A | 593 | 1.23 | 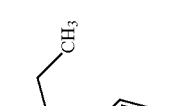 |
| 41 | trans-1-{4-[2-(4-Amino-cyclohexylamino)-9-cyclopentyl-9H-purin-6-ylamino]-piperidin-1-yl}-2-phenyl-butan-1-one dihydrochloride | —C(O)— | | | 2HCl | A | 545 | 1.19 | |
| 42 | trans-1-{4-[2-(4-Amino-cyclohexylamino)-9-cyclopentyl-9H-purin-6-ylamino]-piperidin-1-yl}-2-(4-methoxy-phenyl)-ethanone dihydrochloride | —C(O)— | | | 2HCl | A | 547 | 1.11 | |
| 43 | (±)-trans-1-{4-[2-(4-Amino-cyclohexylamino)-9-cyclopentyl-9H-purin-6-ylamino]-piperidin-1-yl}-1-(2-phenyl-cyclopropyl)-methanone dihydrochloride | —C(O)— | | | 2HCl | A | 543 | 1.17 | |
| 44 | trans-(E)-1-{4-[2-(4-Amino-cyclohexylamino)-9-cyclopentyl-9H-purin-6-ylamino]-piperidin-1-yl}-3-(3-trifluoromethyl-phenyl)-propenone dihydrochloride | —C(O)— | | | 2HCl | A | 597 | 1.25 | |
| 45 | (±)-trans-1-{4-[2-(4-Amino-cyclohexylamino)-9-cyclopentyl-9H-purin-6-ylamino]-piperidin-1-yl}-3,5,5-trimethyl-hexan-1-one dihydrochloride | —C(O)— | | | 2HCl | A | 539 | 1.24 | |

TABLE 1-continued

PHYSICAL PROPERTIES AND ACYLATING AGENTS FOR SYNTHESIS OF COMPOUNDS

| # | Compound | | | | | | Acylating Agent |
|---|---|---|---|---|---|---|---|
| 46 | trans-1-{4-[2-(4-Amino-cyclohexylamino)-9-cyclopentyl-9H-purin-6-ylamino]-piperidin-1-yl}-2-phenylsulfanyl-ethanone dihydrochloride | —C(O)— | [phenylsulfanylethyl] | [cyclopentyl] | 2HCl | A | 549 | 1.16 | Cl(O=)C—CH₂—S—Ph |
| 47 | trans-(S)-1-{4-[2-(4-Amino-cyclohexylamino)-9-cyclopentyl-9H-purin-6-ylamino]-piperidin-1-yl}-2-hydroxy-propan-1-one dihydrochloride | —C(O)— | [(S)-1-hydroxyethyl] | [cyclopentyl] | 2HCl | A | 471 | 0.97 | Cl(O=)C—CH(OC(O)CH₃)— |
| 48 | trans-1-{4-[2-(4-Amino-cyclohexylamino)-9-cyclopentyl-9H-purin-6-ylamino]-piperidin-1-yl]-2-(4-fluoro-phenyl)-ethanone dihydrochloride | —C(O)— | [4-fluorobenzyl] | [cyclopentyl] | 2HCl | A | 535 | 1.13 | Cl(O=)C—CH₂—(4-F-C₆H₄) |
| 49 | trans-1-{4-[2-(4-Amino-cyclohexylamino)-9-cyclopentyl-9H-purin-6-ylamino]-piperidin-1-yl]-pent-4-en-1-one dihydrochloride | —C(O)— | [but-3-enyl] | [cyclopentyl] | 2HCl | A | 481 | 1.26 | Cl(O=)C—CH₂CH₂CH=CH₂ |
| 50 | (±)-trans-1-{4-[2-(4-Amino-cyclohexylamino)-9-cyclopentyl-9H-purin-6-ylamino]-piperidin-1-yl]-2-hydroxy-2-phenyl-ethanone dihydrochloride | —C(O)— | [hydroxy(phenyl)methyl] | [cyclopentyl] | 2HCl | A | 533 | 1.07 | Cl(O=)C—CH(OC(O)CH₃)—Ph |
| 51 | trans-1-{4-[2-(4-Amino-cyclohexylamino)-9-cyclopentyl-9H-purin-6-ylamino]-piperidin-1-yl]-3,3-dimethyl-butan-1-one dihydrochloride | —C(O)— | [2,2-dimethylpropyl] | [cyclopentyl] | 2HCl | A | 497 | 1.11 | Cl(O=)C—CH₂—C(CH₃)₃ |

TABLE 1-continued

PHYSICAL PROPERTIES AND ACYLATING AGENTS FOR SYNTHESIS OF COMPOUNDS

| # | Compound | Linker | R group | Salt | Method | MS | RT | Acylating agent |
|---|---|---|---|---|---|---|---|---|
| 52 | trans-1-{4-[2-(4-Amino-cyclohexylamino)-9-cyclopentyl-9H-purin-6-ylamino]-piperidin-1-yl}-2-phenyl-ethanone dihydrochloride | —C(O)— | benzyl | 2HCl | A | 517 | 1.11 | Cl(O=)C-CH₂-phenyl |
| 53 | trans-1-{4-[2-(4-Amino-cyclohexylamino)-9-cyclopentyl-9H-purin-6-ylamino]-piperidin-1-yl}-propan-1-one dihydrochloride | —C(O)— | ethyl | 2HCl | A | 455 | 1.00 | Cl(O=)C-CH₂-CH₃ |
| 54 | trans-1-{4-[2-(4-Amino-cyclohexylamino)-9-cyclopentyl-9H-purin-6-ylamino]-piperidin-1-yl}-hexan-1-one dihydrochloride | —C(O)— | pentyl | 2HCl | A | 497 | 1.13 | Cl(O=)C-(CH₂)₄-CH₃ |
| 55 | trans-1-{4-[2-(4-Amino-cyclohexylamino)-9-cyclopentyl-9H-purin-6-ylamino]-piperidin-1-yl}-1-cyclohexyl-methanone dihydrochloride | —C(O)— | cyclohexyl | 2HCl | A | 509 | 1.13 | Cl(O=)C-cyclohexyl |
| 56 | trans-1-{4-[2-(4-Amino-cyclohexylamino)-9-cyclopentyl-9H-purin-6-ylamino]-piperidin-1-yl}-pentan-1-one dihydrochloride | —C(O)— | butyl | 2HCl | A | 483 | 1.55 | Cl(O=)C-(CH₂)₃-CH₃ |
| 57 | (±)-trans-1-{4-[2-(4-Amino-cyclohexylamino)-9-cyclopentyl-9H-purin-6-ylamino]-piperidin-1-yl}-2-ethyl-hexan-1-one dihydrochloride | —C(O)— | 2-ethyl-pentyl | 2HCl | A | 525 | 1.21 | Cl(O=)CH(CH₂CH₃)(CH₂CH₂CH₂CH₃) |
| 58 | trans-1-{4-[2-(4-Amino-cyclohexylamino)-9-cyclopentyl-9H-purin-6-ylamino]-piperidin-1-yl}-butan-1-one dihydrochloride | —C(O)— | propyl | 2HCl | A | 469 | 1.04 | Cl(O=)C-CH₂-CH₂-CH₃ |

TABLE 1-continued

PHYSICAL PROPERTIES AND ACYLATING AGENTS FOR SYNTHESIS OF COMPOUNDS

| # | Name | | | | | | |
|---|---|---|---|---|---|---|---|
| 59 | trans-1-{4-[2-(4-Amino-cyclohexylamino)-9-cyclopentyl-9H-purin-6-ylamino]-piperidin-1-yl}-2-methyl-propan-1-one dihydrochloride | —C(O)— | isopropyl | 2HCl | A | 469 | 1.04 | isopropyl via Cl(O=)C |
| 60 | trans-1-{4-[2-(4-Amino-cyclohexylamino)-9-cyclopentyl-9H-purin-6-ylamino]-piperidin-1-yl}-3-methyl-butan-1-one dihydrochloride | —C(O)— | sec-butyl | 2HCl | A | 483 | 1.55 | isobutyl via Cl(O=)C |
| 61 | trans-1-{4-[2-(4-Amino-cyclohexylamino)-9-cyclopentyl-9H-purin-6-ylamino]-piperidin-1-yl}-2-thiophen-2-yl-ethanone dihydrochloride | —C(O)— | 2-ethylthiophene | 2HCl | A | 523 | 2.09 | thiophen-2-ylmethyl via Cl(O=)C |
| 62 | trans-(E)-1-{4-[2-(4-Amino-cyclohexylamino)-9-cyclopentyl-9H-purin-6-ylamino]-piperidin-1-yl}-3-phenyl-propenone dihydrochloride | —C(O)— | styryl | 2HCl | A | 529 | 1.18 | cinnamyl via Cl(O=)C |
| 63 | trans-1-{4-[2-(4-Amino-cyclohexylamino)-9-cyclopentyl-9H-purin-6-ylamino]-piperidin-1-yl}-1-cyclobutyl-methanone dihydrochloride | —C(O)— | cyclobutyl | 2HCl | A | 481 | 1.09 | cyclobutyl via Cl(O=)C |
| 64 | trans-1-{4-[2-(4-Amino-cyclohexylamino)-9-cyclopentyl-9H-purin-6-ylamino]-piperidin-1-yl}-1-cyclopropyl-methanone dihydrochloride | —C(O)— | cyclopropyl | 2HCl | A | 467 | 1.26 | cyclopropyl via Cl(O=)C |

TABLE 1-continued

PHYSICAL PROPERTIES AND ACYLATING AGENTS FOR SYNTHESIS OF COMPOUNDS

| # | Name | | | | | | |
|---|---|---|---|---|---|---|---|
| 65 | trans-1-{4-[2-(4-Amino-cyclohexylamino)-9-cyclopentyl-9H-purin-6-ylamino]-piperidin-1-yl}-2-methoxy-ethanone dihydrochloride | —C(O)— | (ethoxymethyl) | 2HCl | A | 471 | 1.55 | Cl(O=)C—CH₂—O—CH₃ |
| 66 | trans-4-(1-{4-[2-(4-Amino-cyclohexylamino)-9-cyclopentyl-9H-purin-6-ylamino]-piperidin-1-yl}-methanoyl)-fluoren-9-one | —C(O)— | (fluorenone) | — | A | 605 | 1.13 | Cl(O=)C-(fluorenone) |
| 67 | trans-1-{4-[2-(4-Amino-cyclohexylamino)-9-cyclopentyl-9H-purin-6-ylamino]-piperidin-1-yl}-1-pyridin-3-yl-methanone | —C(O)— | (3-pyridyl) | — | A | 504 | 0.98 | Cl(O=)C-(3-pyridyl) |
| 68 | trans-1-{4-[2-(4-Amino-cyclohexylamino)-9-cyclopentyl-9H-purin-6-ylamino]-piperidin-1-yl}-1-pyridin-4-yl-methanone | —C(O)— | (4-pyridyl) | — | A | 504 | 0.96 | Cl(O=)C-(4-pyridyl) |
| 69 | trans-1-{4-[2-(4-Amino-cyclohexylamino)-9-cyclopentyl-9H-purin-6-ylamino]-piperidin-1-yl}-1-(2-fluoro-5-trifluoromethyl-phenyl)-methanone | —C(O)— | (2-F-5-CF₃-phenyl) | — | A | 589 | 1.14 | Cl(O=)C-(2-F-5-CF₃-phenyl) |
| 70 | trans-1-{4-[2-(4-Amino-cyclohexylamino)-9-cyclopentyl-9H-purin-6-ylamino]-piperidin-1-yl}-1-(2-methyl-phenyl)-methanone | —C(O)— | (2-methylphenyl) | — | A | 517 | 1.09 | Cl(O=)C-(2-methylphenyl) |

TABLE 1-continued

PHYSICAL PROPERTIES AND ACYLATING AGENTS FOR SYNTHESIS OF COMPOUNDS

| # | Name | | | | | | |
|---|---|---|---|---|---|---|---|
| 71 | trans-1-{4-[2-(4-Amino-cyclohexylamino)-9-cyclopentyl-9H-purin-6-ylamino]-piperidin-1-yl}-1-(3-bromo-phenyl)-methanone | —C(O)— | 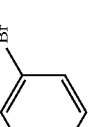 | — | A | 581 | 1.12 | 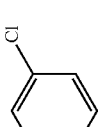 |
| 72 | trans-1-{4-[2-(4-Amino-cyclohexylamino)-9-cyclopentyl-9H-purin-6-ylamino]-piperidin-1-yl}-1-(3-chloro-phenyl)-methanone | —C(O)— | 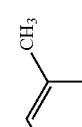 | — | A | 537 | 1.12 | 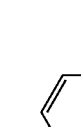 |
| 73 | trans-1-{4-[2-(4-Amino-cyclohexylamino)-9-cyclopentyl-9H-purin-6-ylamino]-piperidin-1-yl}-1-(3-methyl-phenyl)-methanone | —C(O)— | 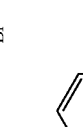 | — | A | 517 | 1.10 |  |
| 74 | trans-1-{4-[2-(4-Amino-cyclohexylamino)-9-cyclopentyl-9H-purin-6-ylamino]-piperidin-1-yl}-1-(4-bromo-phenyl)-methanone | —C(O)— | 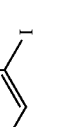 | — | A | 581 | 1.12 | 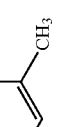 |
| 75 | trans-1-{4-[2-(4-Amino-cyclohexylamino)-9-cyclopentyl-9H-purin-6-ylamino]-piperidin-1-yl}-1-(4-chloro-phenyl)-methanone | —C(O)— | 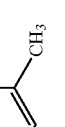 | — | A | 537 | 1.11 | 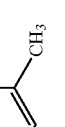 |
| 76 | trans-1-{4-[2-(4-Amino-cyclohexylamino)-9-cyclopentyl-9H-purin-6-ylamino]-piperidin-1-yl}-1-(4-iodo-phenyl)-methanone | —C(O)— | 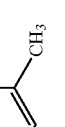 | — | A | 629 | 1.14 | 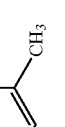 |
| 77 | trans-1-{4-[2-(4-Amino-cyclohexylamino)-9-cyclopentyl-9H-purin-6-ylamino]-piperidin-1-yl}-1-(4-methyl-phenyl)-methanone | —C(O)— | 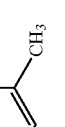 | — | A | 517 | 1.10 | |

TABLE 1-continued

PHYSICAL PROPERTIES AND ACYLATING AGENTS FOR SYNTHESIS OF COMPOUNDS

| # | Compound name | | | | | | MS | |
|---|---|---|---|---|---|---|---|---|
| 78 | trans-1-{4-[2-(4-Amino-cyclopentyl-amino)-9-cyclopentyl-9H-purin-6-ylamino]-piperidin-1-yl}-1-(2,4-dichloro-phenyl)-methanone | —C(O)— | 2,4-dichlorophenyl | cyclopentyl | — | A | 571 | 1.15 | 2,4-dichlorophenyl acyl chloride |
| 79 | trans-1-{4-[2-(4-Amino-cyclopentyl-amino)-9-cyclopentyl-9H-purin-6-ylamino]-piperidin-1-yl}-1-(3,5-dichloro-phenyl)-methanone | —C(O)— | 3,5-dichlorophenyl | cyclopentyl | — | A | 571 | 1.17 | 3,5-dichlorophenyl acyl chloride |
| 80 | trans-1-{4-[2-(4-Amino-cyclohexylamino)-9-isopropyl-9H-purin-6-ylamino]-piperidin-1-yl}-2-phenoxy-ethanone dihydrochloride | —C(O)— | phenoxyethyl | isopropyl | 2HCl | B | (ES+) 507* (TOF MS) | 1.16 | phenoxyacetyl chloride |
| 81 | trans-4-[2-(4-Amino-cyclohexylamino)-9-cyclopentyl-9H-purin-6-ylamino]-piperidine-1-carboxylic acid 4-bromo-phenyl ester dihydrochloride | —C(O)— | 4-bromophenoxy | cyclopentyl | 2HCl | F | 597 | 1.63 | 4-bromophenyl chloroformate |
| 82 | trans-4-[2-(4-Amino-cyclohexylamino)-9-cyclopentyl-9H-purin-6-ylamino]-piperidine-1-carboxylic acid p-tolyl ester dihydrochloride | —C(O)— | 4-methylphenoxy | cyclopentyl | 2HCl | F | 533 | 1.65 | p-tolyl chloroformate |
| 83 | trans-4-[2-(4-Amino-cyclohexylamino)-9-cyclopentyl-9H-purin-6-ylamino]-piperidine-1-carboxylic acid 4-methoxycarbonyl-phenyl ester dihydrochloride | —C(O)— | 4-carboxyphenoxy | cyclopentyl | 2HCl | F | 577 | 1.57 | 4-methoxycarbonylphenyl chloroformate |

TABLE 1-continued

PHYSICAL PROPERTIES AND ACYLATING AGENTS FOR SYNTHESIS OF COMPOUNDS

| | | | | | | | |
|---|---|---|---|---|---|---|---|
| 84 | trans-4-[2-(4-Amino-cyclohexylamino)-9-cyclopentyl-9H-purin-6-ylamino]-piperidine-1-carboxylic acid 4-methoxy-phenyl ester dihydrochloride | 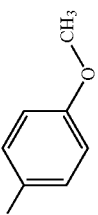 | 2HCl | F | 549 | 1.60 | |
| 85 | trans-4-[2-(4-Amino-cyclohexylamino)-9-cyclopentyl-9H-purin-6-ylamino]-piperidine-1-carboxylic acid phenyl ester dihydrochloride | 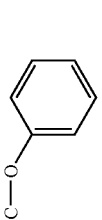 | 2HCl | F | 519 | 1.53 | |
| 86 | trans-4-[2-(4-Amino-cyclohexylamino)-9-cyclopentyl-9H-purin-6-ylamino]-piperidine-1-carboxylic acid (1R,2S,5R)-2-isopropyl-5-methyl-cyclohexyl ester dihydrochloride | 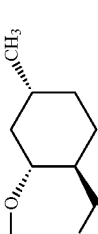 | 2HCl | F | 581 | 1.87 | |
| 87 | trans-4-[2-(4-Amino-cyclohexylamino)-9-cyclopentyl-9H-purin-6-ylamino]-piperidine-1-carboxylic acid 4-fluoro-phenyl ester dihydrochloride | 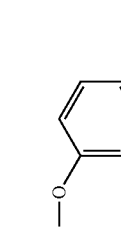 | 2HCl | F | 537 | 1.65 | |
| 88 | trans-4-[2-(4-Amino-cyclohexylamino)-9-cyclopentyl-9H-purin-6-ylamino]-piperidine-1-carboxylic acid 4-chloro-phenyl ester dihydrochloride | 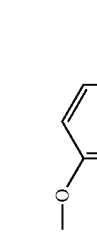 | 2HCl | F | 553 | 1.65 | |
| 89 | trans-4-[2-(4-Amino-cyclohexylamino)-9-cyclopentyl-9H-purin-6-ylamino]-piperidine-1-carboxylic acid 4-nitro-phenyl ester dihydrochloride | 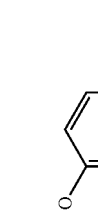 | 2HCl | F | 564 | 1.57 | |

TABLE 1-continued

PHYSICAL PROPERTIES AND ACYLATING AGENTS FOR SYNTHESIS OF COMPOUNDS

| # | Compound | Linker | R group | Salt | | MS | Rf | Acylating agent |
|---|---|---|---|---|---|---|---|---|
| 90 | trans-4-[2-(4-Amino-cyclohexylamino)-9-cyclopentyl-9H-purin-6-ylamino]-piperidine-1-carboxylic acid benzyl ester dihydrochloride | —C(O)— | —CH₂—O—CH₂—C₆H₅ | cyclopentyl | 2HCl | F | 533 | 1.53 | Cl(C=O)—O—CH₂—C₆H₅ |
| 91 | trans-4-[2-(4-Amino-cyclohexylamino)-9-cyclopentyl-9H-purin-6-ylamino]-piperidine-1-carboxylic acid isobutyl ester dihydrochloride | —C(O)— | isobutoxy | cyclopentyl | 2HCl | F | 499 | 1.52 | Cl(C=O)—O—CH₂—CH(CH₃)₂ |
| 92 | trans-4-[2-(4-Amino-cyclohexylamino)-9-cyclopentyl-9H-purin-6-ylamino]-piperidine-1-carboxylic acid butyl ester dihydrochloride | —C(O)— | butoxy | cyclopentyl | 2HCl | F | 499 | 1.50 | Cl(C=O)—O—(CH₂)₃—CH₃ |
| 93 | trans-4-[2-(4-Amino-cyclohexylamino)-9-cyclopentyl-9H-purin-6-ylamino]-piperidine-1-carboxylic acid ethyl ester dihydrochloride | —C(O)— | ethoxy | cyclopentyl | 2HCl | F | 471 | 1.43 | Cl(C=O)—O—CH₂—CH₃ |
| 94 | trans-4-[2-(4-Amino-cyclohexylamino)-9-cyclopentyl-9H-purin-6-ylamino]-piperidine-1-carboxylic acid 4-nitro-benzyl ester dihydrochloride | —C(O)— | 4-nitrobenzyloxy | cyclopentyl | 2HCl | F | 578 | 1.53 | Cl(C=O)—O—CH₂—C₆H₄—NO₂ |
| 95 | trans-4-[2-(4-Amino-cyclohexylamino)-9-cyclopentyl-9H-purin-6-ylamino]-piperidine-1-carboxylic acid allyl ester dihydrochloride | —C(O)— | allyloxy | cyclopentyl | 2HCl | F | 483 | 1.43 | Cl(C=O)—O—CH₂—CH=CH₂ |

TABLE 1-continued

PHYSICAL PROPERTIES AND ACYLATING AGENTS FOR SYNTHESIS OF COMPOUNDS

| # | Name | | | | | MS | RT | |
|---|---|---|---|---|---|---|---|---|
| 96 | trans-4-[2-(4-Amino-cyclohexylamino)-9-cyclopentyl-9H-purin-6-ylamino]-piperidine-1-carboxylic acid propyl ester dihydrochloride | —C(O)— |  |  | 2HCl | 485 | F | 1.45 | 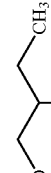 |
| 97 | (±)-trans-4-[2-(4-Amino-cyclohexylamino)-9-cyclopentyl-9H-purin-6-ylamino]-piperidine-1-carboxylic acid 2-ethyl-hexyl ester dihydrochloride | —C(O)— |  |  | 2HCl | 555 | F | 1.73 | 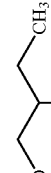 |
| 98 | trans-4-[2-(4-Amino-cyclohexylamino)-9-cyclopentyl-9H-purin-6-ylamino]-piperidine-1-carboxylic acid hexyl ester dihydrochloride | —C(O)— |  |  | 2HCl | 527 | F | 1.65 | 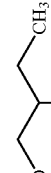 |
| 99 | trans-4-[2-(4-Amino-cyclohexylamino)-9-cyclopentyl-9H-purin-6-ylamino]-piperidine-1-carboxylic acid 2-nitro-phenyl ester dihydrochloride | —C(O)— |  |  | 2HCl | 564 | F | 1.53 | 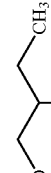 |
| 100 | trans-4-[2-(4-Amino-cyclohexylamino)-9-cyclopentyl-9H-purin-6-ylamino]-piperidine-1-carboxylic acid but-3-enyl ester dihydrochloride | —C(O)— |  |  | 2HCl | 497 | F | 1.48 | 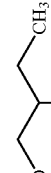 |
| 101 | trans-4-[2-(4-Amino-cyclohexylamino)-9-cyclopentyl-9H-purin-6-ylamino]-piperidine-1-carboxylic acid 4,5-dimethoxy-2-nitro-benzyl ester dihydrochloride | —C(O)— |  |  | 2HCl | 638 | F | 1.57 | 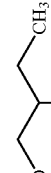 |

TABLE 1-continued

PHYSICAL PROPERTIES AND ACYLATING AGENTS FOR SYNTHESIS OF COMPOUNDS

| # | Name | Linker | R | Salt | Method | MS | RT | Acylating agent |
|---|---|---|---|---|---|---|---|---|
| 102 | trans-4-[2-(4-Amino-cyclohexylamino)-9-cyclopentyl-9H-purin-6-ylamino]-piperidine-1-carboxylic acid prop-2-ynyl ester dihydrochloride | —C(O)— | cyclopentyl | 2HCl | F | 481 | 1.43 | Cl(O=)C—O—CH₂C≡CH |
| 103 | trans-4-[2-(4-Amino-cyclohexylamino)-9-cyclopentyl-9H-purin-6-ylamino]-piperidine-1-carboxylic acid 2,2-dimethyl-propyl ester dihydrochloride | —C(O)— | cyclopentyl | 2HCl | F | 513 | 1.55 | Cl(O=)C—O—CH₂C(CH₃)₃ |
| 104 | trans-4-[2-(4-Amino-cyclohexylamino)-9-isopropyl-9H-purin-6-ylamino]-piperidine-1-carboxylic acid ethyl ester dihydrochloride | —C(O)— | isopropyl (CH₃)₂CH | 2HCl | B | (ES⁺) 445* (TOF MS) | 1.10 | Cl(O=)C—O—CH₂CH₃ |
| 105 | trans-N²-(4-Amino-cyclohexyl)-N⁶-(1-benzenesulfonyl-piperidin-4-yl)-9-cyclopentyl-9H-purine-2,6-diamine dihydrochloride | —S(O)₂— | cyclopentyl | 2HCl | F | 539 | 1.58 | ClO₂S—C₆H₅ |
| 106 | trans-N²-(4-Amino-cyclohexyl)-N⁶-[1-(4-fluoro-benzenesulfonyl)-piperidin-4-yl]-9H-purine-2,6-diamine dihydrochloride | —S(O)₂— | cyclopentyl | 2HCl | F | 557 | 1.53 | ClO₂S—C₆H₄—F |
| 107 | trans-1-{4-[2-(4-Amino-cyclohexylamino)-9-cyclopentyl-9H-purin-6-ylamino]-piperidine-1-sulfonylmethyl}-7,7-dimethyl-bicyclo[2.2.1]heptan-2-one dihydrochloride | —S(O)₂— | cyclopentyl | 2HCl | F | 613 | 1.60 | ClO₂S-camphor derivative |

TABLE 1-continued

PHYSICAL PROPERTIES AND ACYLATING AGENTS FOR SYNTHESIS OF COMPOUNDS

| # | Name | | | | | | |
|---|---|---|---|---|---|---|---|
| 108 | trans-N²-(4-Amino-cyclohexyl)-9-cyclopentyl-N⁶-[1-(4-chloro-benzenesulfonyl)-piperidin-4-yl]-9H-purine-2,6-diamine dihydrochloride | —S(O)₂— | 4-Cl-C₆H₄— | cyclopentyl | 2HCl | 573 | 1.62 | 4-Cl-C₆H₄-SO₂Cl |
| 109 | trans-N²-(4-Amino-cyclohexyl)-9-cyclopentyl-N⁶-[1-(4-cyano-benzenesulfonyl)-piperidin-4-yl]-9H-purine-2,6-diamine dihydrochloride | —S(O)₂— | 4-CN-C₆H₄— | cyclopentyl | 2HCl | 564 | 1.60 | 4-CN-C₆H₄-SO₂Cl |
| 110 | trans-N²-(4-Amino-cyclohexyl)-9-cyclopentyl-N⁶-[1-(3,5-dimethyl-isoxazole-4-sulfonyl)-piperidin-4-yl]-9H-purine-2,6-diamine dihydrochloride | —S(O)₂— | 3,5-dimethyl-isoxazol-4-yl | cyclopentyl | 2HCl | 558 | 1.53 | 3,5-dimethyl-isoxazole-4-SO₂Cl |
| 111 | trans-2-{4-[2-(4-Amino-cyclohexylamino)-9-cyclopentyl-9H-purin-6-ylamino]-piperidine-1-sulfonyl}-benzoic acid methyl ester dihydrochloride | —S(O)₂— | 2-(CO₂CH₃)-C₆H₄— | cyclopentyl | 2HCl | 597 | 1.58 | 2-(CO₂CH₃)-C₆H₄-SO₂Cl |
| 112 | trans-N²-(4-Amino-cyclohexyl)-9-cyclopentyl-N⁶-[1-(3-trifluoromethyl-benzenesulfonyl)-piperidin-4-yl]-9H-purine-2,6-diamine dihydrochloride | —S(O)₂— | 3-CF₃-C₆H₄— | cyclopentyl | 2HCl | 607 | 1.65 | 3-CF₃-C₆H₄-SO₂Cl |

TABLE 1-continued

PHYSICAL PROPERTIES AND ACYLATING AGENTS FOR SYNTHESIS OF COMPOUNDS

| # | Compound | Linker | Ring | Salt | Form | MW | Rt | Acylating Agent |
|---|---|---|---|---|---|---|---|---|
| 113 | trans-N-(5-{4-[2-(4-Amino-cyclohexylamino)-9-cyclopentyl-9H-purin-6-ylamino]-piperidine-1-sulfonyl}-4-methyl-thiazol-2-yl)-acetamide dihydrochloride | —S(O)₂— | cyclopentyl | 2HCl | F | 617 | 1.43 | 4-methyl-2-acetamido-thiazole-5-sulfonyl chloride |
| 114 | trans-N²-(4-Amino-cyclohexyl)-9-cyclopentyl-N⁶-[1-(4-bromo-benzenesulfonyl)-piperidin-4-yl]-9H-purine-2,6-diamine dihydrochloride | —S(O)₂— | cyclopentyl | 2HCl | F | 617 | 1.62 | 4-bromobenzenesulfonyl chloride |
| 115 | trans-N-(4-{4-[2-(4-Amino-cyclohexylamino)-9-cyclopentyl-9H-purin-6-ylamino]-piperidine-1-sulfonyl}-phenyl)-acetamide dihydrochloride | —S(O)₂— | cyclopentyl | 2HCl | F | 596 | 1.47 | 4-acetamidobenzenesulfonyl chloride |
| 116 | trans-N²-(4-Amino-cyclohexyl)-9-cyclopentyl-N⁶-[1-(naphthalene-2-sulfonyl)-piperidin-4-yl]-9H-purine-2,6-diamine dihydrochloride | —S(O)₂— | cyclopentyl | 2HCl | F | 589 | 1.63 | naphthalene-2-sulfonyl chloride |
| 117 | trans-2-{4-[2-(4-Amino-cyclohexylamino)-9-cyclopentyl-9H-purin-6-ylamino]-piperidine-1-sulfonyl}-4,6-dichloro-phenol dihydrochloride | —S(O)₂— | cyclopentyl | 2HCl | F | 623 | 1.63 | 3,5-dichloro-2-hydroxybenzenesulfonyl chloride |
| 118 | trans-N²-(4-Amino-cyclohexyl)-9-cyclopentyl-N⁶-[1-((E)-2-phenyl-ethenesulfonyl)-piperidin-4-yl]-9H-purine-2,6-diamine dihydrochloride | —S(O)₂— | cyclopentyl | 2HCl | F | 565 | 1.60 | (E)-2-phenylethenesulfonyl chloride |

TABLE 1-continued

PHYSICAL PROPERTIES AND ACYLATING AGENTS FOR SYNTHESIS OF COMPOUNDS

| # | Name | | | | | | Acylating agent |
|---|---|---|---|---|---|---|---|
| 119 | trans-$N^2$-(4-Amino-cyclohexyl)-9-cyclopentyl-$N^6$-(1-phenylmethanesulfonyl-piperidin-4-yl)-9H-purine-2,6-diamine dihydrochloride | —S(O)$_2$— | 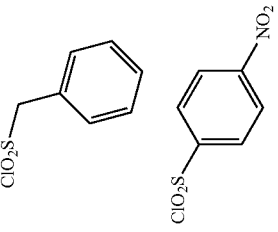 | 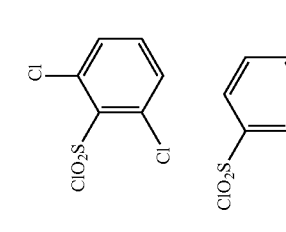 | 2HCl | 553 F 1.53 | 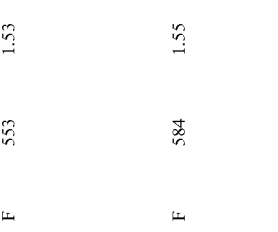 |
| 120 | trans-$N^2$-(4-Amino-cyclohexyl)-9-cyclopentyl-$N^6$-[1-(4-nitro-benzenesulfonyl)-piperidin-4-yl]-9H-purine-2,6-diamine dihydrochloride | —S(O)$_2$— | 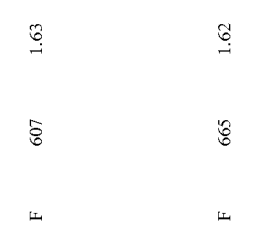 | 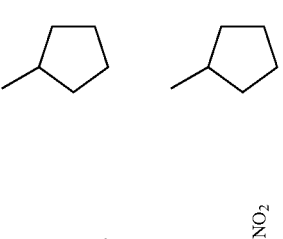 | 2HCl | 584 F 1.55 | 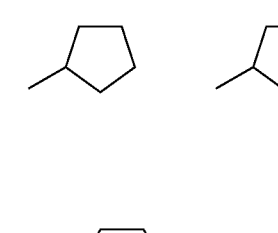 |
| 121 | trans-$N^2$-(4-Amino-cyclohexyl)-9-cyclopentyl-$N^6$-[1-(2,6-dichloro-benzenesulfonyl)-piperidin-4-yl]-9H-purine-2,6-diamine dihydrochloride | —S(O)$_2$— | 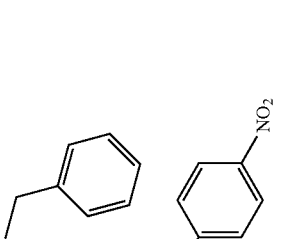 | | 2HCl | 607 F 1.63 | |
| 122 | trans-$N^2$-(4-Amino-cyclohexyl)-9-cyclopentyl-$N^6$-[1-(4-iodo-benzenesulfonyl)-piperidin-4-yl]-9H-purine-2,6-diamine dihydrochloride | —S(O)$_2$— | 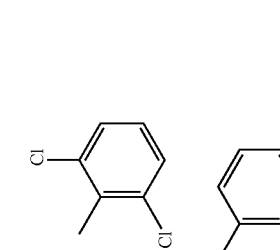 | | 2HCl | 665 F 1.62 | |
| 123 | trans-$N^2$-(4-Amino-cyclohexyl)-9-cyclopentyl-$N^6$-[1-(naphthalene-1-sulfonyl)-piperidin-4-yl]-9H-purine-2,6-diamine dihydrochloride | —S(O)$_2$— | 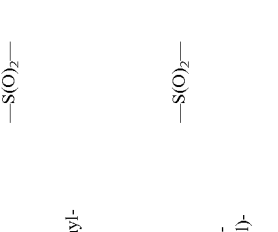 | | 2HCl | 589 F 1.63 | |
| 124 | trans-$N^2$-(4-Amino-cyclohexyl)-9-cyclopentyl-$N^6$-[1-(toluene-4-sulfonyl)-piperidin-4-yl]-9H-purine-2,6-diamine dihydrochloride | —S(O)$_2$— | 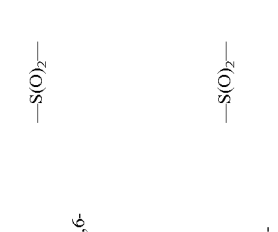 | 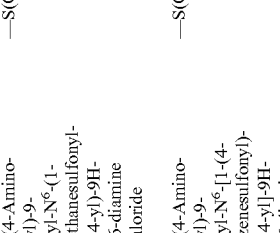 | 2HCl | 553 F 1.55 | 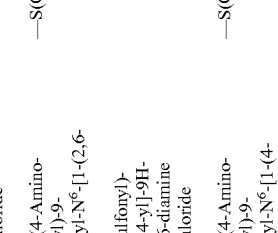 |

TABLE 1-continued

PHYSICAL PROPERTIES AND ACYLATING AGENTS FOR SYNTHESIS OF COMPOUNDS

| | | | | | | | | |
|---|---|---|---|---|---|---|---|---|
| 125 | trans-N²-(4-Amino-cyclohexyl)-9-cyclopentyl-N⁶-[1-(propane-2-sulfonyl)-piperidin-4-yl]-9H-purine-2,6-diamine dihydrochloride | —S(O)₂— |  |  | 2HCl | F | 505 | 1.42 |
| 126 | trans-4-[4-[2-(4-Amino-cyclohexylamino)-9-cyclopentyl-9H-purin-6-ylamino]-piperidine-1-sulfonyl]-benzoic acid dihydrochloride | —S(O)₂— |  |  | 2HCl | F | 583 | 2.20 |
| 127 | trans-N²-(4-Amino-cyclohexyl)-9-cyclopentyl-N⁶-[1-(3-nitro-benzenesulfonyl)-piperidin-4-yl]-9H-purine-2,6-diamine dihydrochloride | —S(O)₂— |  |  | 2HCl | F | 584 | 1.57 |
| 128 | trans-N²-(4-Amino-cyclohexyl)-9-cyclopentyl-N⁶-[1-(thiophene-2-sulfonyl)-piperidin-4-yl]-9H-purine-2,6-diamine dihydrochloride | —S(O)₂— |  |  | 2HCl | F | 545 | 1.50 |
| 129 | trans-N²-(4-Amino-cyclohexyl)-9-cyclopentyl-N⁶-[1-(butane-1-sulfonyl)-piperidin-4-yl]-9H-purine-2,6-diamine dihydrochloride | —S(O)₂— | 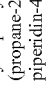 |  | 2HCl | F | 519 | 1.50 |
| 130 | trans-N²-(4-Amino-cyclohexyl)-N⁶-[1-(4-tert-butyl-benzenesulfonyl)-piperidin-4-yl]-9-cyclopentyl-9H-purine-2,6-diamine dihydrochloride | —S(O)₂— | | | 2HCl | F | 595 | 1.72 |

TABLE 1-continued

PHYSICAL PROPERTIES AND ACYLATING AGENTS FOR SYNTHESIS OF COMPOUNDS

| # | Compound name | linker | R group | salt | F | MS | RT |
|---|---|---|---|---|---|---|---|
| 131 | trans-N²-(4-Amino-cyclohexyl)-N⁶-[1-(propane-1-sulfonyl)-piperidin-4-yl]-9-cyclopentyl-9H-purine-2,6-diamine dihydrochloride | —S(O)₂— | propyl-CH₃ | 2HCl | F | 505 | 1.42 |
| 132 | trans-N²-(4-Amino-cyclohexyl)-9-cyclopentyl-N⁶-[1-(2-nitro-4-trifluoromethyl-benzenesulfonyl)-piperidin-4-yl]-9H-purine-2,6-diamine dihydrochloride | —S(O)₂— | 2-nitro-4-CF₃-phenyl | 2HCl | F | 652 | 1.68 |
| 133 | trans-N²-(4-Amino-cyclohexyl)-9-cyclopentyl-N⁶-[1-(2,2,2-trifluoro-ethanesulfonyl)-piperidin-4-yl]-9H-purine-2,6-diamine dihydrochloride | —S(O)₂— | CH₂CF₃ | 2HCl | F | 545 | 1.50 |
| 134 | trans-N²-(4-Amino-cyclohexyl)-9-cyclopentyl-N⁶-[1-(4-trifluoromethoxy-benzenesulfonyl)-piperidin-4-yl]-9H-purine-2,6-diamine dihydrochloride | —S(O)₂— | 4-OCF₃-phenyl | 2HCl | F | 623 | 1.65 |
| 135 | trans-3-[2-(4-Amino-cyclohexylamino)-9-cyclopentyl-9H-purin-6-ylamino]-piperidine-1-sulfonyl]-benzoic acid methyl ester dihydrochloride | —S(O)₂— | 3-COOH-phenyl | 2HCl | F | 583 | 1.50 |
| 136 | trans-N²-(4-Amino-cyclohexyl)-9-cyclopentyl-N⁶-[1-(2-bromo-benzenesulfonyl)-piperidin-4-yl]-9H-purine-2,6-diamine dihydrochloride | —S(O)₂— | 2-Br-phenyl | 2HCl | F | 617 | 1.55 |

TABLE 1-continued

PHYSICAL PROPERTIES AND ACYLATING AGENTS FOR SYNTHESIS OF COMPOUNDS

| | | | | | | | |
|---|---|---|---|---|---|---|---|
| 137 | trans-N$^2$-(4-Amino-cyclohexyl)-N$^6$-[1-(3,4-dimethoxy-benzenesulfonyl)-piperidin-4-yl]-9H-purine-2,6-diamine dihydrochloride | —S(O)$_2$— |  | 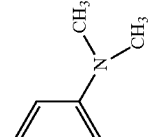 | 2HCl | F | 599 | 1.53 |
| 138 | trans-N$^2$-(4-Amino-cyclohexyl)-N$^6$-[1-(3,4-dichloro-benzenesulfonyl)-piperidin-4-yl]-9H-purine-2,6-diamine dihydrochloride | —S(O)$_2$— | | | 2HCl | F | 607 | 1.67 |
| 139 | trans-N$^2$-(4-Amino-cyclohexyl)-N$^6$-(1-ethanesulfonyl)-piperidin-4-yl]-9H-purine-2,6-diamine dihydrochloride | —S(O)$_2$— | | | 2HCl | F | 491 | 1.38 |
| 140 | trans-N$^2$-(4-Amino-cyclohexyl)-N$^6$-[1-(4-chloro-3-nitro-benzenesulfonyl)-piperidin-4-yl]-9H-purine-2,6-diamine dihydrochloride | —S(O)$_2$— | | | 2HCl | F | 618 | 1.63 |
| 141 | trans-N$^2$-(4-Amino-cyclopentyl)-N$^6$-[1-(5-dimethylamino-naphthalene-1-sulfonyl)-piperidin-4-yl]-9H-purine-2,6-diamine dihydrochloride | —S(O)$_2$— | | | 2HCl | F | 632 | 1.68 |

TABLE 1-continued

PHYSICAL PROPERTIES AND ACYLATING AGENTS FOR SYNTHESIS OF COMPOUNDS

| # | Name | Linker | Aryl/NH group | R | Salt | Class | MS | Rt | Acylating agent |
|---|---|---|---|---|---|---|---|---|---|
| 142 | trans-$N^2$-(4-Amino-cyclohexyl)-9-cyclopentyl-$N^6$-[1-(4-methoxy-benzenesulfonyl)-piperidin-4-yl]-9H-purine-2,6-diamine dihydrochloride | —S(O)$_2$— | 4-methoxyphenyl (—NH attached) | cyclopentyl | 2HCl | F | 569 | 1.53 | 4-methoxybenzenesulfonyl chloride (ClO$_2$S-C$_6$H$_4$-OCH$_3$) |
| 143 | trans-$N^2$-(4-Amino-cyclohexyl)-9-cyclopentyl-$N^6$-[1-(2-nitro-benzenesulfonyl)-piperidin-4-yl]-9H-purine-2,6-diamine dihydrochloride | —S(O)$_2$— | 2-nitrophenyl | cyclopentyl | 2HCl | F | 584 | 1.55 | 2-nitrobenzenesulfonyl chloride |
| 144 | trans-$N^2$-(4-Amino-cyclohexyl)-9-cyclopentyl-$N^6$-[1-(quinoline-8-sulfonyl)-piperidin-4-yl]-9H-purine-2,6-diamine dihydrochloride | —S(O)$_2$— | quinolin-8-yl | cyclopentyl | 2HCl | F | 590 | 1.50 | quinoline-8-sulfonyl chloride |
| 145 | trans-4-{4-[2-(4-Amino-cyclohexylamino)-9-isopropyl-9H-purin-6-ylamino]-piperidine-1-sulfonyl}-benzonitrile dihydrochloride | —S(O)$_2$— | 4-cyanophenyl | isopropyl | 2HCl | B | (ES$^+$) 538* (TOF MS) | 1.19 | 4-cyanobenzenesulfonyl chloride |
| 146 | trans-4-[2-(4-Amino-cyclohexylamino)-9-cyclopentyl-9H-purin-6-ylamino]-piperidine-1-carboxylic acid phenylamide dihydrochloride | —C(O)— | —NH-phenyl | cyclopentyl | 2HCl | F | 518 | 1.58 | phenyl isocyanate (O=C=N-C$_6$H$_5$) |
| 147 | trans-4-[2-(4-Amino-cyclohexylamino)-9-cyclopentyl-9H-purin-6-ylamino]-piperidine-1-carboxylic acid (4-fluoro-phenyl)-amide dihydrochloride | —C(O)— | —NH-(4-fluorophenyl) | cyclopentyl | 2HCl | F | 536 | 1.58 | 4-fluorophenyl isocyanate |

TABLE 1-continued

PHYSICAL PROPERTIES AND ACYLATING AGENTS FOR SYNTHESIS OF COMPOUNDS

| # | Name | R1 | R2 | R3 | Salt | Method | MW | RT | Acylating Agent |
|---|------|----|----|----|------|--------|----|----|-----------------|
| 148 | trans-4-[2-(4-Amino-cyclohexylamino)-9-cyclopentyl-9H-purin-6-ylamino]-piperidine-1-carboxylic acid ethylamide dihydrochloride | —C(O)— | —NH—CH₂—CH₃ | cyclopentyl | 2HCl | D | 470 | 1.32 | O=C=N—CH₂—CH₃ |
| 149 | trans-4-[2-(4-Amino-cyclohexylamino)-9-cyclopentyl-9H-purin-6-ylamino]-piperidine-1-carboxylic acid (4-trifluoromethyl-phenyl)-amide dihydrochloride | —C(O)— | —NH—(4-CF₃-phenyl) | cyclopentyl | 2HCl | F | 586 | 1.73 | O=C=N—(4-CF₃-phenyl) |
| 150 | trans-4-[2-(4-Amino-cyclohexylamino)-9-cyclopentyl-9H-purin-6-ylamino]-piperidine-1-carboxylic acid (4-chloro-phenyl)-amide dihydrochloride | —C(O)— | —NH—(4-Cl-phenyl) | cyclopentyl | 2HCl | F | 552 | 1.65 | O=C=N—(4-Cl-phenyl) |
| 151 | trans-4-[2-(4-Amino-cyclohexylamino)-9-cyclopentyl-9H-purin-6-ylamino]-piperidine-1-carboxylic acid (2,4-dimethoxy-phenyl)-amide dihydrochloride | —C(O)— | —NH—(2,4-diOMe-phenyl) | cyclopentyl | 2HCl | F | 578 | 1.63 | O=C=N—(2,4-diOMe-phenyl) |
| 152 | trans-4-[2-(4-Amino-cyclohexylamino)-9-cyclopentyl-9H-purin-6-ylamino]-piperidine-1-carboxylic acid (3-fluoro-phenyl)-amide dihydrochloride | —C(O)— | —NH—(3-F-phenyl) | cyclopentyl | 2HCl | F | 536 | 1.62 | O=C=N—(3-F-phenyl) |

TABLE 1-continued

PHYSICAL PROPERTIES AND ACYLATING AGENTS FOR SYNTHESIS OF COMPOUNDS

| # | Name | | | | | | |
|---|---|---|---|---|---|---|---|
| 153 | trans-4-[2-(4-Amino-cyclohexylamino)-9-cyclopentyl-9H-purin-6-ylamino]-piperidine-1-carboxylic acid (4-methoxy-phenyl)-amide dihydrochloride | —C(O)— | —NH— 4-methoxyphenyl | 2HCl | F | 548 | 1.58 | O=C=N-(4-methoxyphenyl) |
| 154 | trans-4-[(1-{4-[2-(4-Amino-cyclopentyl-9H-purin-6-ylamino]-piperidin-1-yl]-methanoyl)-amino]-benzoic acid ethyl ester dihydrochloride | —C(O)— | —NH— 4-(ethoxycarbonyl)phenyl | 2HCl | F | 590 | 1.65 | O=C=N-(4-ethoxycarbonylphenyl) |
| 155 | trans-4-[2-(4-Amino-cyclohexylamino)-9-cyclopentyl-9H-purin-6-ylamino]-piperidine-1-carboxylic acid (3-methoxy-phenyl)-amide dihydrochloride | —C(O)— | —NH— 3-methoxyphenyl | 2HCl | F | 548 | 1.57 | O=C=N-(3-methoxyphenyl) |
| 156 | (±)-trans-4-[2-(4-Amino-cyclohexylamino)-9-cyclopentyl-9H-purin-6-ylamino]-piperidine-1-carboxylic acid (2-phenyl-cyclopropyl)-amide dihydrochloride | —C(O)— | —NH—(2-phenylcyclopropyl) | 2HCl | F | 558 | 1.27 | O=C=N-(2-phenylcyclopropyl) |
| 157 | trans-4-[2-(4-Amino-cyclohexylamino)-9-cyclopentyl-9H-purin-6-ylamino]-piperidine-1-carboxylic acid isopropylamide dihydrochloride | —C(O)— | —NH—CH(CH₃)₂ | 2HCl | F | 484 | 1.03 | O=C=N-CH(CH₃)₂ |
| 158 | trans-4-[2-(4-Amino-cyclohexylamino)-9-cyclopentyl-9H-purin-6-ylamino]-piperidine-1-carboxylic acid (2-trifluoromethyl-phenyl)-amide dihydrochloride | —C(O)— | —NH— 2-(trifluoromethyl)phenyl | 2HCl | A | 586 | 1.15 | O=C=N-(2-trifluoromethylphenyl) |

TABLE 1-continued

PHYSICAL PROPERTIES AND ACYLATING AGENTS FOR SYNTHESIS OF COMPOUNDS

| # | Name | Linker | NH-group | Ring | Salt | Method | MW | RT | Acylating agent |
|---|------|--------|----------|------|------|--------|-----|------|-----------------|
| 159 | trans-4-[2-(4-Amino-cyclohexylamino)-9-cyclopentyl-9H-purin-6-ylamino]-piperidine-1-carboxylic acid (3-trifluoromethyl-phenyl)-amide dihydrochloride | —C(O)— | 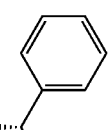 | 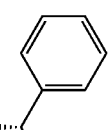 | 2HCl | A | 586 | 1.21 | 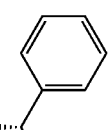 |
| 160 | trans-4-[2-(4-Amino-cyclohexylamino)-9-cyclopentyl-9H-purin-6-ylamino]-piperidine-1-carboxylic acid ((R)-1-phenyl-ethyl)-amide dihydrochloride | —C(O)— | 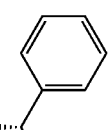 | 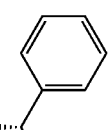 | 2HCl | A | 546 | 1.13 | 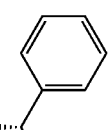 |
| 161 | trans-4-[2-(4-Amino-cyclohexylamino)-9-cyclopentyl-9H-purin-6-ylamino]-piperidine-1-carboxylic acid ((S)-1-phenyl-ethyl)-amide dihydrochloride | —C(O)— | | | 2HCl | A | 546 | 1.11 | |
| 162 | trans-4-[2-(4-Amino-cyclohexylamino)-9-cyclopentyl-9H-purin-6-ylamino]-piperidine-1-carboxylic acid (4-bromo-phenyl)-amide dihydrochloride | —C(O)— | | | 2HCl | A | 598 | 1.19 | |
| 163 | trans-4-[2-(4-Amino-cyclohexylamino)-9-cyclopentyl-9H-purin-6-ylamino]-piperidine-1-carboxylic acid (2-methoxy-phenyl)-amide dihydrochloride | —C(O)— | | | 2HCl | A | 548 | 1.12 | |
| 164 | trans-4-[2-(4-Amino-cyclohexylamino)-9-cyclopentyl-9H-purin-6-ylamino]-piperidine-1-carboxylic acid allylamide dihydrochloride | —C(O)— | | | 2HCl | A | 482 | 1 | |

TABLE 1-continued

PHYSICAL PROPERTIES AND ACYLATING AGENTS FOR SYNTHESIS OF COMPOUNDS

| # | Name | | | | | | | |
|---|---|---|---|---|---|---|---|---|
| 165 | trans-4-[2-(4-Amino-cyclohexylamino)-9-cyclopentyl-9H-purin-6-ylamino]-piperidine-1-carboxylic acid (3-chloro-phenyl)-amide dihydrochloride | —C(O)— | —NH—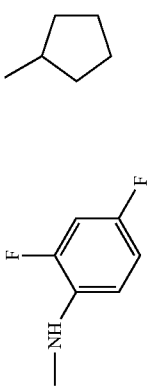 | 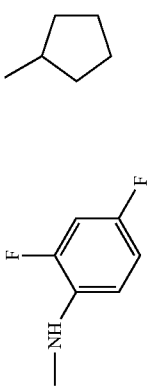 | 2HCl | A | 552 | 1.17 | O=C=N—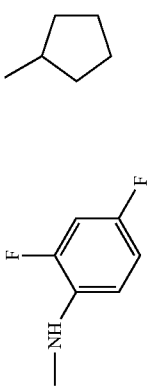 |
| 166 | trans-4-[2-(4-Amino-cyclohexylamino)-9-cyclopentyl-9H-purin-6-ylamino]-piperidine-1-carboxylic acid (2,4-difluoro-phenyl)-amide dihydrochloride | —C(O)— | —NH—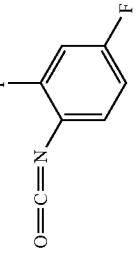 | 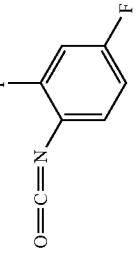 | 2HCl | A | 554 | 1.1 | O=C=N—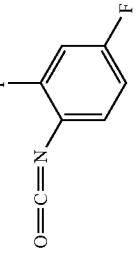 |
| 167 | trans-4-[2-(4-Amino-cyclohexylamino)-9-cyclopentyl-9H-purin-6-ylamino]-piperidine-1-carboxylic acid (2,4-dichloro-phenyl)-amide dihydrochloride | —C(O)— | —NH—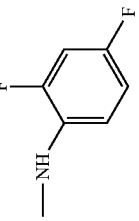 | 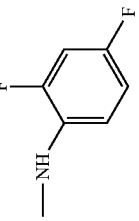 | 2HCl | A | 586 | 1.27 | O=C=N—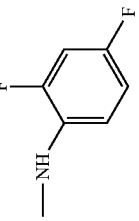 |
| 168 | trans-4-[2-(4-Amino-cyclohexylamino)-9-cyclopentyl-9H-purin-6-ylamino]-piperidine-1-carboxylic acid (2-bromo-phenyl)-amide dihydrochloride | —C(O)— | —NH—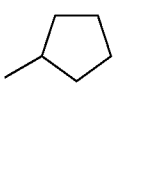 | 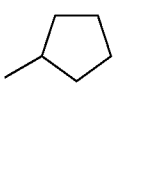 | 2HCl | A | 596 | 1.15 | O=C=N—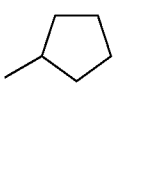 |
| 169 | trans-4-[2-(4-Amino-cyclohexylamino)-9-cyclopentyl-9H-purin-6-ylamino]-piperidine-1-carboxylic acid (2-chloro-phenyl)-amide dihydrochloride | —C(O)— | —NH— |  | 2HCl | A | 552 | 1.13 | O=C=N— |
| 170 | trans-4-[2-(4-Amino-cyclohexylamino)-9-cyclopentyl-9H-purin-6-ylamino]-piperidine-1-carboxylic acid (3-bromo-phenyl)-amide dihydrochloride | —C(O)— | —NH—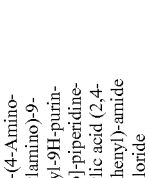 | 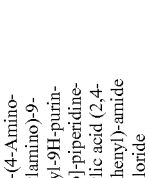 | 2HCl | A | 598 | 1.18 | O=C=N—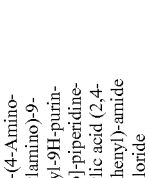 |

TABLE 1-continued

PHYSICAL PROPERTIES AND ACYLATING AGENTS FOR SYNTHESIS OF COMPOUNDS

| # | Name | | | | | | |
|---|---|---|---|---|---|---|---|
| 171 | trans-4-[2-(4-Amino-cyclopentyl-amino)-9-cyclopentyl-9H-purin-6-ylamino]-piperidine-1-carboxylic acid (2-ethoxy-phenyl)-amide dihydrochloride | —C(O)— |  | 2HCl | A | 562 | 1.16 |
| 172 | trans-N-(1-{2-[(4-Amino-cyclopentyl-amino)-9-cyclopentyl-9H-purin-6-ylamino]-piperidin-1-yl}-methanoyl)-benzamide dihydrochloride | —C(O)— | 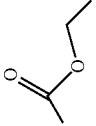 | 2HCl | A | 546 | 1.07 |
| 173 | trans-(1-{4-[2-(4-Amino-cyclopentyl-amino)-9-cyclopentyl-9H-purin-6-ylamino]-piperidin-1-yl}-methanoyl)-carbamic acid ethyl ester dihydrochloride | —C(O)— |  | 2HCl | A | 514 | 1 |
| 174 | trans-4-[2-(4-Amino-cyclopentyl-amino)-9-cyclopentyl-9H-purin-6-ylamino]-piperidine-1-carboxylic acid (2-trifluoromethoxy-phenyl)-amide dihydrochloride | —C(O)— | 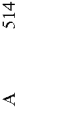 | 2HCl | A | 602 | 1.18 |
| 175 | trans-4-[2-(4-Amino-cyclopentyl-amino)-9-cyclopentyl-9H-purin-6-ylamino]-piperidine-1-carboxylic acid (4-trifluoromethoxy-phenyl)-amide dihydrochloride | —C(O)— | 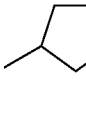 | 2HCl | A | 602 | 1.23 |
| 176 | trans-4-[2-(4-Amino-cyclopentyl-amino)-9-cyclopentyl-9H-purin-6-ylamino]-piperidine-1-carboxylic acid (3,5-bis-trifluoromethyl-phenyl)-amide dihydrochloride | —C(O)— | 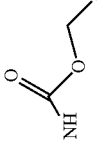 | 2HCl | A | 654 | 1.34 |

TABLE 1-continued

PHYSICAL PROPERTIES AND ACYLATING AGENTS FOR SYNTHESIS OF COMPOUNDS

| # | Name | | | | | | |
|---|---|---|---|---|---|---|---|
| 177 | trans-4-[2-(4-Amino-cyclohexylamino)-9-cyclopentyl-9H-purin-6-ylamino]-piperidine-1-carboxylic acid (2-chloro-5-trifluoromethyl-phenyl)-amide dihydrochloride | —C(O)— | (cyclopentyl) | 2HCl | A | 620 | 1.26 |
| 178 | trans-4-[2-(4-Amino-cyclohexylamino)-9-cyclopentyl-9H-purin-6-ylamino]-piperidine-1-carboxylic acid (4-chloro-2-trifluoromethyl-phenyl)-amide dihydrochloride | —C(O)— | (cyclopentyl) | 2HCl | A | 620 | 1.22 |
| 179 | trans-4-[2-(4-Amino-cyclohexylamino)-9-cyclopentyl-9H-purin-6-ylamino]-piperidine-1-carboxylic acid (4-chloro-3-trifluoromethyl-phenyl)-amide dihydrochloride | —C(O)— | (cyclopentyl) | 2HCl | A | 620 | 1.28 |
| 180 | trans-4-[2-(4-Amino-cyclohexylamino)-9-cyclopentyl-9H-purin-6-ylamino]-piperidine-1-carboxylic acid (2,5-difluoro-phenyl)-amide dihydrochloride | —C(O)— | (cyclopentyl) | 2HCl | A | 554 | 1.13 |
| 181 | trans-4-[2-(4-Amino-cyclohexylamino)-9-cyclopentyl-9H-purin-6-ylamino]-piperidine-1-carboxylic acid adamantan-1-ylamide dihydrochloride | —C(O)— | (cyclopentyl) | 2HCl | A | 576 | 1.24 |

TABLE 1-continued

PHYSICAL PROPERTIES AND ACYLATING AGENTS FOR SYNTHESIS OF COMPOUNDS

| | | | | | | | |
|---|---|---|---|---|---|---|---|
| 182 | trans-4-[2-(4-Amino-cyclohexylamino)-9-cyclopentyl-9H-purin-6-ylamino]-piperidine-1-carboxylic acid (3,5-dichloro-phenyl)-amide dihydrochloride | —C(O)— |  | 2HCl | A | 586 | 1.18 |  |
| 183 | trans-4-[2-(4-Amino-cyclohexylamino)-9-cyclopentyl-9H-purin-6-ylamino]-piperidine-1-carboxylic acid (4-methyl-phenyl)-amide dihydrochloride | —C(O)— |  | 2HCl | A | 532 | 1.13 |  |
| 184 | trans-4-[2-(4-Amino-cyclohexylamino)-9-cyclopentyl-9H-purin-6-ylamino]-piperidine-1-carboxylic acid pentylamide dihydrochloride | —C(O)— |  | 2HCl | A | 512 | 1.12 |  |
| 185 | trans-4-[2-(4-Amino-cyclohexylamino)-9-cyclopentyl-9H-purin-6-ylamino]-piperidine-1-carboxylic acid hexylamide dihydrochloride | —C(O)— |  | 2HCl | A | 526 | 1.18 |  |
| 186 | trans-4-[2-(4-Amino-cyclohexylamino)-9-cyclopentyl-9H-purin-6-ylamino]-piperidine-1-carboxylic acid (4-methylsulfanyl-phenyl)-amide dihydrochloride | —C(O)— |  | 2HCl | A | 564 | 1.12 |  |
| 187 | trans-4-[2-(4-Amino-cyclohexylamino)-9-cyclopentyl-9H-purin-6-ylamino]-piperidine-1-carboxylic acid biphenyl-2-yl-amide dihydrochloride | —C(O)— |  | 2HCl | A | 594 | 1.22 |  |

TABLE 1-continued

PHYSICAL PROPERTIES AND ACYLATING AGENTS FOR SYNTHESIS OF COMPOUNDS

| | | | | | | | | |
|---|---|---|---|---|---|---|---|---|
| 188 | trans-4-[2-(4-Amino-cyclopentyl-9H-purin-6-ylamino)-piperidine-1-carboxylic acid (4-acetyl-phenyl)-amide dihydrochloride | —C(O)— | —NH—4-acetylphenyl | cyclopentyl | 2HCl | A | 560 | 1.09 | 4-acetylphenyl isocyanate |
| 189 | trans-4-[2-(4-Amino-cyclopentyl-9H-purin-6-ylamino)-piperidine-1-carboxylic acid (3-acetyl-phenyl)-amide dihydrochloride | —C(O)— | —NH—3-acetylphenyl | cyclopentyl | 2HCl | A | 560 | 1.08 | 3-acetylphenyl isocyanate |
| 190 | trans-4-[2-(4-Amino-cyclopentyl-9H-purin-6-ylamino)-piperidine-1-carboxylic acid (4-isopropyl-phenyl)-amide dihydrochloride | —C(O)— | —NH—4-isopropylphenyl | cyclopentyl | 2HCl | A | 560 | 1.25 | 4-isopropylphenyl isocyanate |
| 191 | trans-4-[2-(4-Amino-cyclopentyl-9H-purin-6-ylamino)-piperidine-1-carboxylic acid (4-ethoxy-phenyl)-amide dihydrochloride | —C(O)— | —NH—4-ethoxyphenyl | cyclopentyl | 2HCl | A | 562 | 1.14 | 4-ethoxyphenyl isocyanate |
| 192 | trans-4-[2-(4-Amino-cyclopentyl-9H-purin-6-ylamino)-piperidine-1-carboxylic acid tert-butyl-amide dihydrochloride | —C(O)— | —NH—C(CH3)3 | cyclopentyl | 2HCl | A | 498 | 1.07 | tert-butyl isocyanate |
| 193 | trans-2-[({4-[2-(4-Amino-cyclopentyl-9H-purin-6-ylamino)-piperidin-1-yl]-methanoyl}-amino]-benzoic acid methyl ester dihydrochloride | —C(O)— | —NH—2-(methoxycarbonyl)phenyl | cyclopentyl | 2HCl | A | 576 | 1.21 | methyl 2-isocyanatobenzoate |

TABLE 1-continued

PHYSICAL PROPERTIES AND ACYLATING AGENTS FOR SYNTHESIS OF COMPOUNDS

| | | | | | | | | |
|---|---|---|---|---|---|---|---|---|
| 194 | trans-4-[2-(4-Amino-cyclohexylamino)-9-cyclopentyl-9H-purin-6-ylamino]-piperidine-1-carboxylic acid (3-cyano-phenyl)-amide dihydrochloride | —C(O)— | 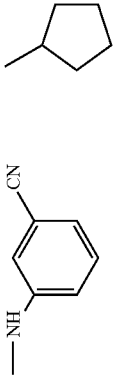 |  | 2HCl | A | 543 | 1.12 | 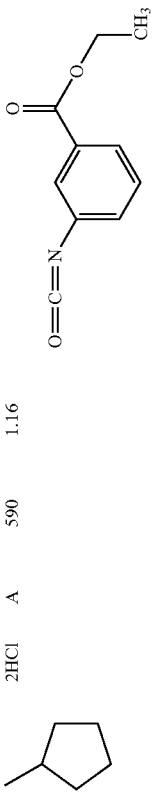 |
| 195 | trans-3-[(1-{4-[2-(4-Amino-cyclohexylamino)-9-cyclopentyl-9H-purin-6-ylamino]-piperidin-1-yl}-methanoyl)-amino]-benzoic acid ethyl ester dihydrochloride | —C(O)— |  | | 2HCl | A | 590 | 1.16 | |
| 196 | trans-4-[2-(4-Amino-cyclohexylamino)-9-cyclopentyl-9H-purin-6-ylamino]-piperidine-1-carboxylic acid (2-chloro-6-methyl-phenyl)-amide dihydrochloride | —C(O)— |  | | 2HCl | A | 566 | 1.12 |  |
| 197 | trans-4-[2-(4-Amino-cyclohexylamino)-9-cyclopentyl-9H-purin-6-ylamino]-piperidine-1-carboxylic acid phenethyl-amide dihydrochloride | —C(O)— |  | | 2HCl | A | 546 | 1.13 |  |
| 198 | trans-4-[2-(4-Amino-cyclohexylamino)-9-cyclopentyl-9H-purin-6-ylamino]-piperidine-1-carboxylic acid (3,4,5-trimethoxy-phenyl)-amide dihydrochloride | —C(O)— |  | | 2HCl | A | 608 | 1.09 |  |

TABLE 1-continued

PHYSICAL PROPERTIES AND ACYLATING AGENTS FOR SYNTHESIS OF COMPOUNDS

| # | Name | | | | | | | |
|---|---|---|---|---|---|---|---|---|
| 199 | trans-2-[(1-{4-[2-(4-Amino-cyclohexylamino)-9-cyclopentyl-9H-purin-6-ylamino]-piperidin-1-yl}-methanoyl)-amino]-benzoic acid ethyl ester dihydrochloride | —C(O)— | [2-ethoxycarbonyl-phenyl-NH—] | 2HCl | A | 590 | 1.26 | [2-ethoxycarbonyl-phenyl isocyanate] |
| 200 | trans-4-[2-(4-Amino-cyclohexylamino)-9-cyclopentyl-9H-purin-6-ylamino]-piperidine-1-carboxylic acid (2-fluoro-5-trifluoromethyl-phenyl)-amide dihydrochloride | —C(O)— | [2-F-5-CF₃-phenyl-NH—] | 2HCl | A | 604 | 1.21 | [2-F-5-CF₃-phenyl isocyanate] |
| 201 | trans-4-[2-(4-Amino-cyclohexylamino)-9-cyclopentyl-9H-purin-6-ylamino]-piperidine-1-carboxylic acid (2-fluoro-6-trifluoromethyl-phenyl)-amide dihydrochloride | —C(O)— | [2-CF₃-6-F-phenyl-NH—] | 2HCl | A | 604 | 1.13 | [2-CF₃-6-F-phenyl isocyanate] |
| 202 | trans-4-[2-(4-Amino-cyclohexylamino)-9-cyclopentyl-9H-purin-6-ylamino]-piperidine-1-carboxylic acid (4-fluoro-2-trifluoromethyl-phenyl)-amide dihydrochloride | —C(O)— | [4-F-2-CF₃-phenyl-NH—] | 2HCl | A | 604 | 1.15 | [4-F-2-CF₃-phenyl isocyanate] |
| 203 | trans-4-[2-(4-Amino-cyclohexylamino)-9-cyclopentyl-9H-purin-6-ylamino]-piperidine-1-carboxylic acid (4-fluoro-3-trifluoromethyl-phenyl)-amide dihydrochloride | —C(O)— | [4-F-3-CF₃-phenyl-NH—] | 2HCl | A | 604 | 1.24 | [4-F-3-CF₃-phenyl isocyanate] |

TABLE 1-continued

PHYSICAL PROPERTIES AND ACYLATING AGENTS FOR SYNTHESIS OF COMPOUNDS

| # | Name | | | | | | |
|---|---|---|---|---|---|---|---|
| 204 | trans-4-[2-(4-Amino-cyclohexylamino)-9-cyclopentyl-9H-purin-6-ylamino]-piperidine-1-carboxylic acid butylamide dihydrochloride | —C(O)— | —NH—(CH₂)₃—CH₃ | 2HCl | A | 498 | 1.07 | O=C=N—(CH₂)₃—CH₃ |
| 205 | trans-4-[2-(4-Amino-cyclohexylamino)-9-cyclopentyl-9H-purin-6-ylamino]-piperidine-1-carboxylic acid cyclohexylamide dihydrochloride | —C(O)— | —NH-cyclohexyl | 2HCl | A | 524 | 1.12 | O=C=N-cyclohexyl |
| 206 | trans-4-[2-(4-Amino-cyclohexylamino)-9-cyclopentyl-9H-purin-6-ylamino]-piperidine-1-carboxylic acid propylamide dihydrochloride | —C(O)— | —NH—CH₂CH₂—CH₃ | 2HCl | A | 484 | 1.03 | O=C=N—CH₂CH₂—CH₃ |
| 207 | trans-4-[2-(4-Amino-cyclohexylamino)-9-cyclopentyl-9H-purin-6-ylamino]-piperidine-1-carboxylic acid (2-fluoro-phenyl)-amide dihydrochloride | —C(O)— | —NH-(2-fluorophenyl) | 2HCl | A | 536 | 1.09 | O=C=N-(2-fluorophenyl) |

TABLE 1-continued

PHYSICAL PROPERTIES AND ACYLATING AGENTS FOR SYNTHESIS OF COMPOUNDS

| # | Name | | | | | | Acylating agent |
|---|---|---|---|---|---|---|---|
| 208 | trans-4-[2-(4-Amino-cyclohexylamino)-9-cyclopentyl-9H-purin-6-ylamino]-piperidine-1-carboxylic acid (2-methyl-phenyl)-amide dihydrochloride | —C(O)— | ![cyclopentyl] | ![NH-2-methylphenyl] | 2HCl | A | 532 | 1.11 | ![2-methylphenyl isocyanate] |
| 209 | trans-4-[2-(4-Amino-cyclohexylamino)-9-cyclopentyl-9H-purin-6-ylamino]-piperidine-1-carboxylic acid (3,4-dichloro-phenyl)-amide dihydrochloride | —C(O)— | ![cyclopentyl] | ![NH-3,4-dichlorophenyl] | 2HCl | A | 586 | 1.25 | ![3,4-dichlorophenyl isocyanate] |
| 210 | trans-4-[2-(4-Amino-cyclohexylamino)-9-cyclopentyl-9H-purin-6-ylamino]-piperidine-1-carboxylic acid (3-methyl-phenyl)-amide dihydrochloride | —C(O)— | ![cyclopentyl] | ![NH-3-methylphenyl] | 2HCl | A | 532 | 1.13 | ![3-methylphenyl isocyanate] |
| 211 | trans-4-[2-(4-Amino-cyclohexylamino)-9-isopropyl-9H-purin-6-ylamino]-piperidine-1-carboxylic acid (4-trifluoromethoxy-phenyl)-amide dihydrochloride | —C(O)— | ![isopropyl] | ![NH-4-trifluoromethoxyphenyl] | 2HCl | B | (ES+) 576* (TOF MS) | 1.24 | ![4-trifluoromethoxyphenyl isocyanate] |

Example 2

Cyclin-Dependent Kinase Assays

The $IC_{50}$ values for cdk1/cyclin B, cdk2/cyclin E, and cdk4/cyclin D1 inhibition are determined using the following methods:

The cdk1 sequence (accession number Y00272) is amplified by PCR and cloned into the BamHI and SalI sites of pFASTBAC1 (Life Technologies). The sense oligonucleotide primer, SEQ ID. NO. 1 5'-GTCAGGATCCTATTCGAAACG ATGGCGCTCCGAGTCACCA3', contains a BamHI and AsuII restriction enzyme sites for cloning and the translational initiation codon, ATG (the cdk1 sequence is underlined). The antisense oligonucleotide primer, SEQ ID. NO. 2 5'-TGACGTCGACGAATTCA CTACATCTTCTTAATCTGATTGTC-3', contains SalI and EcoRI restriction enzyme sites for cloning as well as the stop codon, TGA (the cdk1 sequence is underlined).

The cyclin B1 sequence (accession number M25753) is amplified by PCR and cloned into the BamHI and SalI sites of pFASTBAC1 (Life Technologies). The sense oligonucleotide primer, SEQ ID. NO. 3 5'-GTCAGGATCCTATTCGAAACG ATGGCGCTCCGAGTCACCA-3', contains a BamHI and AsuII restriction enzyme sites for cloning and the translational initiation codon, ATG (the Cyclin B1 sequence is underlined). The antisense oligonucleotide primer, SEQ ID. NO. 4 5'-TGACGTCGACGAATTCA TTACACCTTTGCCACAGCCTT-3', contains SalI and EcoRI restriction enzyme sites for cloning as well as the stop codon, TAA (the cyclin B1 sequence is underlined).

The cdk2 sequence (accession number X62071) is amplified by PCR and cloned into the SpeI and XhoI sites of pFASTBAC1 (Life Technologies). The sense oligonucleotide primer, SEQ ID. NO. 5 5'-ACTAGT TGGCGCTTCATGGAGAAC-3', contains a SpeI restriction enzyme site for cloning and the translational initiation codon, ATG (the cdk2 sequence is underlined). The antisense oligonucleotide primer, SEQ ID. NO. 6 5'-CTCGAG GGAGGAGAGGGTGAGATTAG-3', contains XhoI restriction enzyme site for cloning (the cdk2 sequence is underlined). This primer would anneal in the 3' untranslated sequence.

The cyclin E sequence (accession number M73812) is amplified by PCR and cloned into the XbaI and XhoI sites of pFASTBAC1 (Life Technologies). The sense oligonucleotide primer, SEQ ID. NO. 7 5'-GTCATCTAGATTCGAAACG ATGAAGGAGGACGGCGGCGC-3', contains a XbaI and AsuII restriction enzyme sites for cloning and the translational initiation codon, ATG (the Cyclin E sequence is underlined). The antisense oligonucleotide primer, SEQ ID. NO. 8 5'-TGACCTCGAGGAATTCA TCACGCCATTTCCGGC-3', contains XhoI and EcoRI restriction enzyme sites for cloning as well as the stop codon, TGA (the cyclin E sequence is underlined).

The cdk4 sequence (accession number U37022) is amplified by PCR and cloned into the BamHI and EcoRI sites of pFASTBAC1 (Life Technologies). The sense oligonucleotide primer, SEQ ID. NO. 9 5'-GCCGGATCC ATGGCTACCTCTCGATATGAA-3', contains a BamHI restriction enzyme site for cloning and the translational initiation codon, ATG (the cdk4 sequence is underlined). The antisense oligonucleotide primer, SEQ ID. NO. 10 5'-GC- CGAATTCACGATGCATAGTCAGGTACATCGTA CTCCGGGTTACCTTCGTCCT-3', contains and EcoRI restriction enzyme sites for cloning as well as the hemagglutinin (HA) sequence and the stop codon, TGA (the cdk4 sequence is underlined and the HA sequence is italics).

The cyclin D1 sequence (accession number M64349) is amplified by PCR and cloned into the BamHI and EcoRI sites of pFASTBAC1 (Life Technologies). The sense oligonucleotide primer, SEQ ID. NO. 11 5'-CGCGGATCC ATGGAACACCAGCTCCTGTGC-3', contains a BamHI restriction enzyme site for cloning, the translational initiation codon (the Cyclin D1 sequence is underlined). The antisense oligonucleotide primer, SEQ ID. NO. 12 5'-GCCGAAT- TCAGTGATGGTGATGGTGATG GATGTCCACGTCCCGCACGT-3', contains an EcoRI restriction enzyme site for cloning as well as the $His_6$ tag and a stop codon, TGA (the cyclin D1 sequence is underlined and the $His_6$ tag is italics).

The cDNA for each of the cyclin-dependent kinases (CDK) and the corresponding cyclins are cloned into the baculovirus expression vector, pFASTBAC1 (Life Technologies). The sequences of each of the constructs are confirmed by automated fluorescent DNA sequencing according to the manufacture's protocol (Perkin Elmer/Applied Biosystems Inc).

The insect cell (Sf9) expression is optimized for each of the CDK/cyclin pairs according to the manufacturer's protocols (Life Technologies). For cdk-4-HA/cyclin D1-$His_6$ an infection of 0.1 multiplicity of infection (MOI) for 48 hours gives the best expression levels of the complex as well as activity. For cdk2/cyclin E, the best expression is observed with an infection of 1.0 MOI for 72 hours, while for cdk1/cyclin B, the best expression is observed with 2.0 MOI for 48 hours.

The Sf9 cells are grown at 27° C. in 500 ml of SF900 II SFM medium (Life Technologies) until the cells reached a density of ~$2 \times 10^6$ cells/ml. The viruses are added to the cells and the culture is incubated at 27° C. for the desired time. The cells are harvested by centrifugation at 3000 rpm for 10 minutes. The cells are snap frozen on dry ice and stored at −80° C.

Cell extracts are made following a standard procedure. The cell pellet is resuspended in lysis buffer (50 mM HEPES, pH 8.0, 10 mM MgCl2, 1 mM DTT, 2.5 mM EGTA, 1 mM EDTA, 10 mM β-glycerophosphate, 1 mM sodium vanadate, 1 mM sodium fluoride, 1× Protease inhibitor cocktail). The cells are lysed using the microfluidizer (Microfluidics) for 20 minutes. Cell debris is removed by centrifugation at 100,000× g. The cell extracts are aliquoted in 1 ml aliquots, frozen on dry ice, and stored at −80° C.

The kinase reactions are performed following a standard procedure. The enzyme and inhibitor are diluted in kinase buffer (50 mM HEPES, pH 8.0, 10 mM $MgCl_2$, 2.5 mM EGTA, 10 mM β-glycerophosphate, 1 mM sodium vanadate, 1 mM sodium fluoride, and 1 mM DTT) and pre-incubated for 30 minutes. The cdk2 and cdk4 enzyme activities are assayed using 500 ng of the GST-pRb substrate (see description below) in the presence of 10 μM cold ATP and 1 μCi of [$\gamma$-$^{33}$P] ATP for 30 minutes at room temperature. The cdk1 enzyme activity is assayed using Histone H1 (Sigma) in the presence of 10 μM ATP for 30 min at room temperature. The reactions are terminated by the addition of 50 μL of 10 mM cold ATP to stop the reactions. The reactions are transferred to a pre-soaked 96-well multi-screen plate containing 30 μL of 100% TCA per well. After incubation for one hour at room temperature, the plates are washed twice with 200 μl of 20% TCA, followed by 200 μl of 10% TCA and finally with 200 μl of 5% TCA. After drying the plates at room temperature, the filter plates are placed in adapter plates (Packard) and 40 μl of Microscint-O® (Packard) is added to each well. Top Seal A film is used to cover the plates before counting in a Top Count Scintillation Counter.

Glutathione S-transferase—retinoblastoma fusion protein (GST-Rb) (Kaelin, W. G., Jr., et al., *Cell* 64: 521-532, 1991) is obtained from Dr. William Kaelin. GST-Rb is prepared by transformation of *E. coli* with the plasmid pGEX-Rb (379-928). The transformed bacteria are grown overnight to saturation, then diluted in YT broth and incubated at 37° C. for 2 h. The protein is induced by incubation with 0.1 mM isopropylthioglycoside for 3 h. Following sedimentation by centrifugation, the cells are lysed by sonication in STE buffer (0.1 mM NaCl, 10 mM Tris, pH 8.0, 1 mM EDTA) containing 10% sarkosyl. Particulate matter is removed by centrifugation and the lysate is incubated with glutathione-Sepharose at 4° C. The beads are washed with kinase buffer and then quantitated of Coomassie blue-stained proteins separated by SDS-PAGE using a protein standard of known concentration.

Determination of $IC_{50}$ Values:

The % remained activity of the indicated Cdk/cyclin kinase complex in the presence of inhibitor is calculated by the ratio of cpm in the presence of inhibitor to cpm in the absence of inhibitor (% Activity=vi/vo x 100%). The $IC_{50}$ values are defined as the concentration of inhibitor that results in a 50% inhibition of the indicated cdk/cyclin enzyme activity. Table 2 shows inhibition of activity for select compounds using this assay method.

The $IC_{50}$ values for the CDK inhibitor flavopiridol are presented for comparison.

TABLE 2

INHIBITION OF CYCLIN B/CDK 1, CYCLIN E/CDK 2, AND CYCLIN D1/CDK 4 ENZYME ACTIVITIES

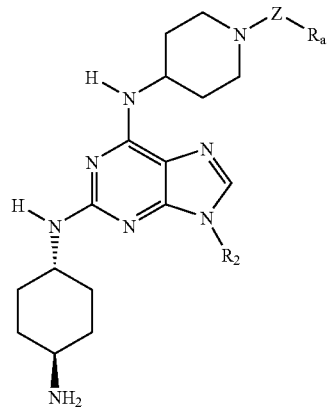

| Compound No. | Z | $R_a$ | $R_2$ | CDK1 $IC_{50}$, nM | CDK2 $IC_{50}$, nM | CDK4 $IC_{50}$, nM |
|---|---|---|---|---|---|---|
| 1 | —C(O)— | 4-F-phenyl | cyclopentyl | 64 | 98 | 555 |
| 2 | —C(O)— | 4-CF₃-phenyl | cyclopentyl | 48 | 92 | 427 |
| 3 | —C(O)— | 3-CF₃-phenyl | cyclopentyl | 55 | 48 | 1122 |
| 4 | —C(O)— | quinoxalinyl | cyclopentyl | 197 | 339 | 641 |
| 5 | —C(O)— | benzo[1,3]dioxolyl | cyclopentyl | | | |

TABLE 2-continued

INHIBITION OF CYCLIN B/CDK 1, CYCLIN E/CDK 2, AND
CYCLIN D1/CDK 4 ENZYME ACTIVITIES

| Compound No. | Z | $R_a$ | $R_2$ | CDK1 IC$_{50}$, nM | CDK2 IC$_{50}$, nM | CDK4 IC$_{50}$, nM |
|---|---|---|---|---|---|---|
| 6 | —C(O)— | 3-chlorophenyl | cyclopentyl | 160 | 201 | 87 |
| 7 | —C(O)— | 2-methoxyphenyl | cyclopentyl | 399 | 487 | 96 |
| 8 | —C(O)— | 4-methoxyphenyl | cyclopentyl | 74 | 137 | 711 |
| 9 | —C(O)— | phenyl | cyclopentyl | | | |
| 10 | —C(O)— | 2-thienyl | cyclopentyl | 49 | 57 | 761 |
| 11 | —C(O)— | 4-(methoxycarbonyl)phenyl | cyclopentyl | 46 | 78 | 620 |
| 12 | —C(O)— | 2-fluoro-3-(trifluoromethyl)phenyl | cyclopentyl | 88 | 5 | 614 |

TABLE 2-continued
INHIBITION OF CYCLIN B/CDK 1, CYCLIN E/CDK 2, AND
CYCLIN D1/CDK 4 ENZYME ACTIVITIES
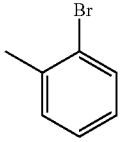
| Compound No. | Z | $R_a$ | $R_2$ | CDK1 $IC_{50}$, nM | CDK2 $IC_{50}$, nM | CDK4 $IC_{50}$, nM |
|---|---|---|---|---|---|---|
| 13 | —C(O)— | 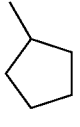 | 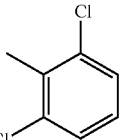 | 197 | 364 | 373 |
| 14 | —C(O)— |  | 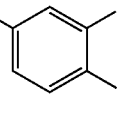 | 164 | 514 | 17 |
| 15 | —C(O)— | 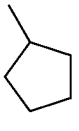 | 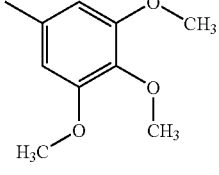 | 61 | 291 | 732 |
| 16 | —C(O)— |  | 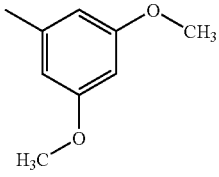 | 43 | 83 | 372 |
| 17 | —C(O)— |  | 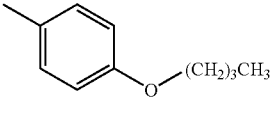 | 89 | 189 | 467 |
| 18 | —C(O)— | 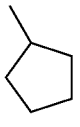 | 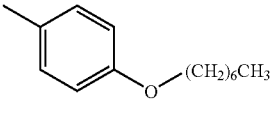 | 506 | 336 | 1490 |
| 19 | —C(O)— |  | | 62 | 567 | 883 |

TABLE 2-continued
INHIBITION OF CYCLIN B/CDK 1, CYCLIN E/CDK 2, AND
CYCLIN D1/CDK 4 ENZYME ACTIVITIES
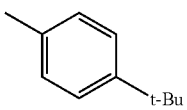
| Compound No. | Z | $R_a$ | $R_2$ | CDK1 $IC_{50}$, nM | CDK2 $IC_{50}$, nM | CDK4 $IC_{50}$, nM |
|---|---|---|---|---|---|---|
| 20 | —C(O)— | 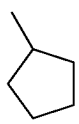 | 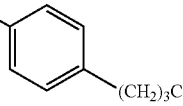 | 161 | 352 | 682 |
| 21 | —C(O)— | 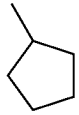 | 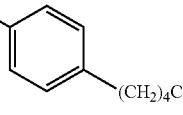 | 89 | 121 | 476 |
| 22 | —C(O)— | 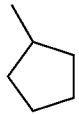 | 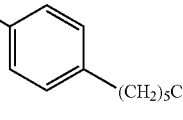 | 182 | 571 | 383 |
| 23 | —C(O)— | 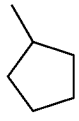 | 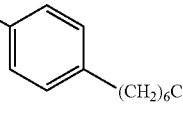 | 300 | 596 | 629 |
| 24 | —C(O)— | 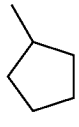 | 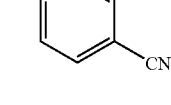 | | | |
| 25 | —C(O)— | 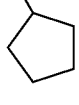 | 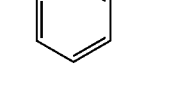 | 56 | 79 | 629 |
| 26 | —C(O)— | 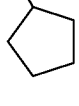 | 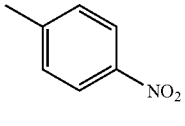 | 31 | 78 | 564 |
| 27 | —C(O)— | 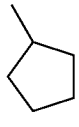 | | | | |

TABLE 2-continued
INHIBITION OF CYCLIN B/CDK 1, CYCLIN E/CDK 2, AND CYCLIN D1/CDK 4 ENZYME ACTIVITIES
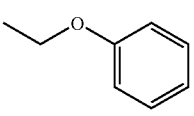
| Compound No. | Z | $R_a$ | $R_2$ | CDK1 IC$_{50}$, nM | CDK2 IC$_{50}$, nM | CDK4 IC$_{50}$, nM |
|---|---|---|---|---|---|---|
| 28 | —C(O)— | 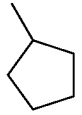 | 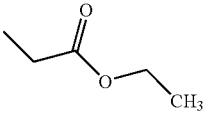 | 20 | 52 | 140 |
| 29 | —C(O)— | 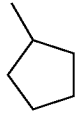 | 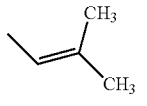 | 27 | 56 | 632 |
| 30 | —C(O)— | 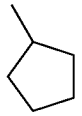 | 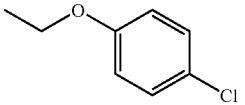 | 25 | 77 | 683 |
| 31 | —C(O)— | 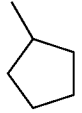 | 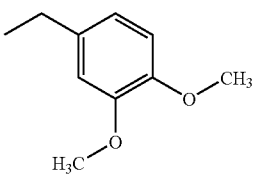 | 105 | 5 | 2041 |
| 32 | —C(O)— | 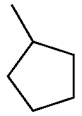 | 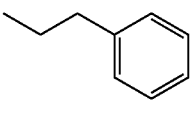 | 24 | 53 | 189 |
| 33 | —C(O)— | 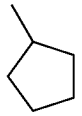 |  | 58 | 30 | 427 |

TABLE 2-continued
INHIBITION OF CYCLIN B/CDK 1, CYCLIN E/CDK 2, AND
CYCLIN D1/CDK 4 ENZYME ACTIVITIES
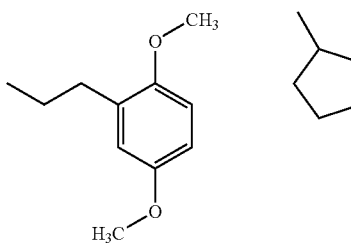
| Compound No. | Z | R$_a$ | R$_2$ | CDK1 IC$_{50}$, nM | CDK2 IC$_{50}$, nM | CDK4 IC$_{50}$, nM |
|---|---|---|---|---|---|---|
| 34 | —C(O)— | 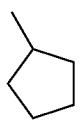 | 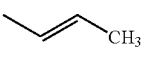 | 31 | 58 | 997 |
| 35 | —C(O)— | 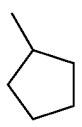 | 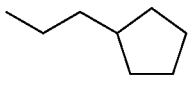 | 48 | 55 | 766 |
| 36 | —C(O)— | 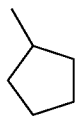 | 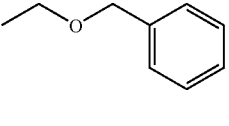 | 45 | 79 | 697 |
| 37 | —C(O)— | 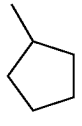 | 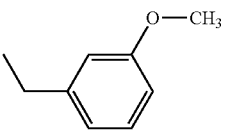 | 15 | 32 | 1697 |
| 38 | —C(O)— | 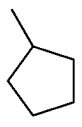 | 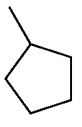 | 27 | 66 | 703 |
| 39 | —C(O)— | 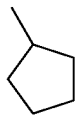 |  | 66 | 51 | 664 |

TABLE 2-continued
INHIBITION OF CYCLIN B/CDK 1, CYCLIN E/CDK 2, AND
CYCLIN D1/CDK 4 ENZYME ACTIVITIES
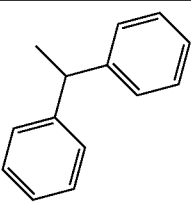
| Compound No. | Z | R$_a$ | R$_2$ | CDK1 IC$_{50}$, nM | CDK2 IC$_{50}$, nM | CDK4 IC$_{50}$, nM |
|---|---|---|---|---|---|---|
| 40 | —C(O)— | 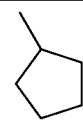 | 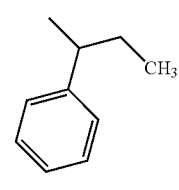 | 36 | 61 | 238 |
| 41 | —C(O)— | 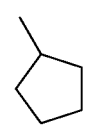 | 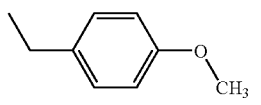 | 59 | 93 | 404 |
| 42 | —C(O)— | 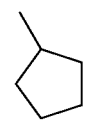 | 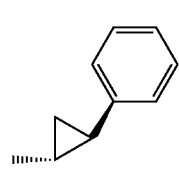 | 21 | 51 | 103 |
| 43 | —C(O)— | 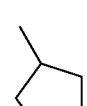 | 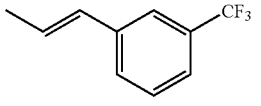 | 51 | 77 | 293 |
| 44 | —C(O)— |  | 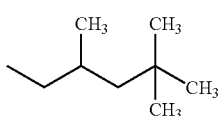 | 129 | 76 | 1495 |
| 45 | —C(O)— | 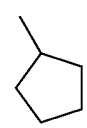 | 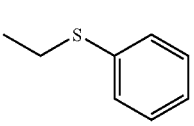 | 76 | 154 | 485 |
| 46 | —C(O)— | 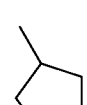 |  | 153 | 55 | 709 |

TABLE 2-continued

INHIBITION OF CYCLIN B/CDK 1, CYCLIN E/CDK 2, AND
CYCLIN D1/CDK 4 ENZYME ACTIVITIES

| Compound No. | Z | $R_a$ | $R_2$ | CDK1 $IC_{50}$, nM | CDK2 $IC_{50}$, nM | CDK4 $IC_{50}$, nM |
|---|---|---|---|---|---|---|
| 47 | —C(O)— | (S)-CH(CH₃)OH | cyclopentyl | 36 | 14 | 361 |
| 48 | —C(O)— | 4-fluorobenzyl | cyclopentyl | 48 | 61 | 503 |
| 49 | —C(O)— | but-3-enyl | cyclopentyl | 121 | 49 | 88 |
| 50 | —C(O)— | CH(OH)phenyl | cyclopentyl | 43 | 44 | 206 |
| 51 | —C(O)— | C(CH₃)₂CH₂CH₃ | cyclopentyl | 109 | 65 | 99 |
| 52 | —C(O)— | benzyl | cyclopentyl | 40 | 59 | 350 |
| 53 | —C(O)— | CH₂CH₃ | cyclopentyl | 40 | 80 | 934 |
| 54 | —C(O)— | n-pentyl | cyclopentyl | 45 | 49 | 315 |

TABLE 2-continued
INHIBITION OF CYCLIN B/CDK 1, CYCLIN E/CDK 2, AND CYCLIN D1/CDK 4 ENZYME ACTIVITIES
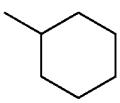
| Compound No. | Z | $R_a$ | $R_2$ | CDK1 IC$_{50}$, nM | CDK2 IC$_{50}$, nM | CDK4 IC$_{50}$, nM |
|---|---|---|---|---|---|---|
| 55 | —C(O)— |  | 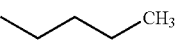 | 99 | 56 | 621 |
| 56 | —C(O)— |  | 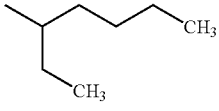 | 43 | 53 | 909 |
| 57 | —C(O)— | 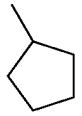 | 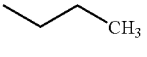 | 193 | 480 | 1305 |
| 58 | —C(O)— | 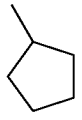 | 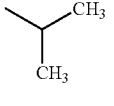 | 52 | 68 | 357 |
| 59 | —C(O)— | 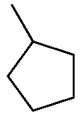 | 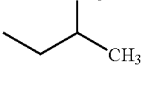 | 93 | 52 | 721 |
| 60 | —C(O)— |  | 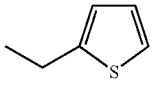 | 83 | 37 | 91 |
| 61 | —C(O)— |  | | 40 | 38 | 750 |
| 62 | —C(O)— | 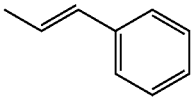 |  | 25 | 66 | 167 |

TABLE 2-continued
INHIBITION OF CYCLIN B/CDK 1, CYCLIN E/CDK 2, AND
CYCLIN D1/CDK 4 ENZYME ACTIVITIES
| Compound No. | Z | $R_a$ | $R_2$ | CDK1 $IC_{50}$, nM | CDK2 $IC_{50}$, nM | CDK4 $IC_{50}$, nM |
|---|---|---|---|---|---|---|
| 63 | —C(O)— | 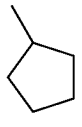 |  | 23 | 66 | 441 |
| 64 | —C(O)— | 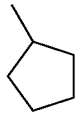 | 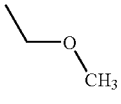 | 65 | 62 | 593 |
| 65 | —C(O)— |  | 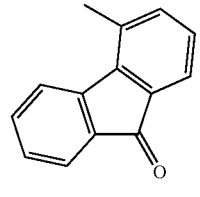 | 72 | 50 | 764 |
| 66 | —C(O)— | 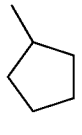 | 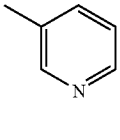 | 234 | 325 | 1721 |
| 67 | —C(O)— | 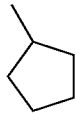 | 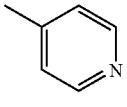 | 824 | 441 | 3155 |
| 68 | —C(O)— | 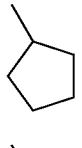 | 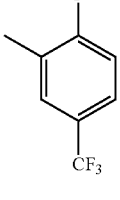 | 136 | 84 | 1442 |
| 69 | —C(O)— |  | | 48 | 84 | 852 |

TABLE 2-continued

INHIBITION OF CYCLIN B/CDK 1, CYCLIN E/CDK 2, AND
CYCLIN D1/CDK 4 ENZYME ACTIVITIES

| Compound No. | Z | $R_a$ | $R_2$ | CDK1 IC$_{50}$, nM | CDK2 IC$_{50}$, nM | CDK4 IC$_{50}$, nM |
|---|---|---|---|---|---|---|
| 70 | —C(O)— | 2-methylphenyl | cyclopentyl | 277 | 430 | 4506 |
| 71 | —C(O)— | 3-bromophenyl | cyclopentyl | 53 | 91 | 698 |
| 72 | —C(O)— | 3-chlorophenyl | cyclopentyl | 51 | 89 | 864 |
| 73 | —C(O)— | 3-methylphenyl | cyclopentyl | 100 | 73 | 410 |
| 74 | —C(O)— | 4-bromophenyl | cyclopentyl | 62 | 239 | 560 |
| 75 | —C(O)— | 4-chlorophenyl | cyclopentyl | 71 | 58 | 801 |
| 76 | —C(O)— | 4-iodophenyl | cyclopentyl | 57 | 179 | 787 |
| 77 | —C(O)— | 4-methylphenyl | cyclopentyl | 100 | 71 | 606 |

TABLE 2-continued
INHIBITION OF CYCLIN B/CDK 1, CYCLIN E/CDK 2, AND
CYCLIN D1/CDK 4 ENZYME ACTIVITIES
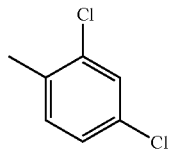
| Compound No. | Z | $R_a$ | $R_2$ | CDK1 $IC_{50}$, nM | CDK2 $IC_{50}$, nM | CDK4 $IC_{50}$, nM |
|---|---|---|---|---|---|---|
| 78 | —C(O)— | 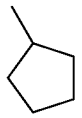 | 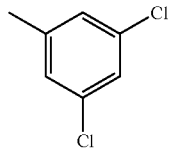 | 101 | 155 | 523 |
| 79 | —C(O)— | 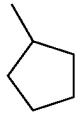 | 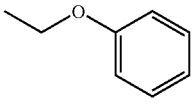 | 44 | 73 | 483 |
| 80 | —C(O)— | 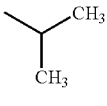 | 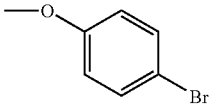 | 244 | 39 | 8100 |
| 81 | —C(O)— | 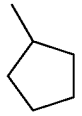 | 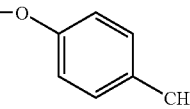 | 16 | 39 | 67 |
| 82 | —C(O)— | 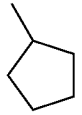 | 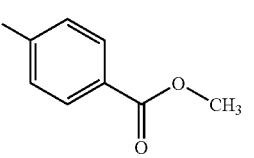 | 31 | 45 | 131 |
| 83 | —C(O)— |  | 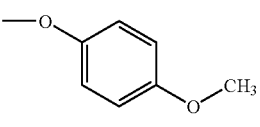 | 19 | 44 | 185 |
| 84 | —C(O)— | 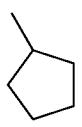 | | 19 | 9 | 69 |

TABLE 2-continued

INHIBITION OF CYCLIN B/CDK 1, CYCLIN E/CDK 2, AND
CYCLIN D1/CDK 4 ENZYME ACTIVITIES

| Compound No. | Z | $R_a$ | $R_2$ | CDK1 $IC_{50}$, nM | CDK2 $IC_{50}$, nM | CDK4 $IC_{50}$, nM |
|---|---|---|---|---|---|---|
| 85 | —C(O)— | —O-phenyl | cyclopentyl | 26 | 8 | 65 |
| 86 | —C(O)— | —O-menthyl | cyclopentyl | | | |
| 87 | —C(O)— | —O-(4-F-phenyl) | cyclopentyl | 15 | 42 | 27 |
| 88 | —C(O)— | —O-(4-Cl-phenyl) | cyclopentyl | 35 | 7 | 204 |
| 89 | —C(O)— | —O-(4-$NO_2$-phenyl) | cyclopentyl | 20 | 42 | 65 |
| 90 | —C(O)— | —OCH$_2$-phenyl | cyclopentyl | | | |
| 91 | —C(O)— | —OCH$_2$CH(CH$_3$)$_2$ | cyclopentyl | | | |
| 92 | —C(O)— | —OCH$_2$CH$_2$CH$_3$ | cyclopentyl | 45 | 18 | 2102 |

TABLE 2-continued
INHIBITION OF CYCLIN B/CDK 1, CYCLIN E/CDK 2, AND CYCLIN D1/CDK 4 ENZYME ACTIVITIES
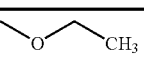
| Compound No. | Z | $R_a$ | $R_2$ | CDK1 $IC_{50}$, nM | CDK2 $IC_{50}$, nM | CDK4 $IC_{50}$, nM |
|---|---|---|---|---|---|---|
| 93 | —C(O)— | 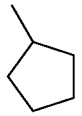 | 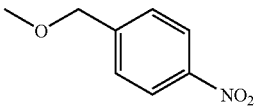 | 46 | 5 | 856 |
| 94 | —C(O)— | 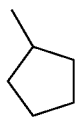 | 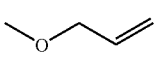 | 27 | 69 | 827 |
| 95 | —C(O)— | 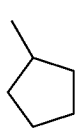 | 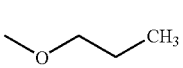 | 75 | 23 | 526 |
| 96 | —C(O)— | 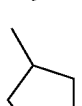 | 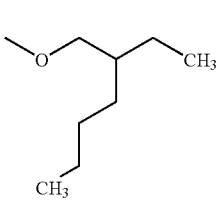 | | | |
| 97 | —C(O)— | 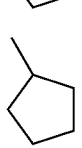 | 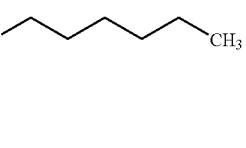 | | | |
| 98 | —C(O)— | 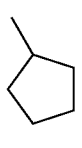 | 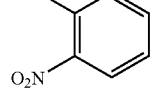 | | | |
| 99 | —C(O)— | 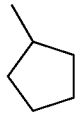 | 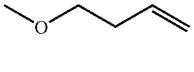 | 33 | 9 | 1515 |
| 100 | —C(O)— | 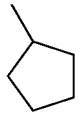 | | 60 | 50 | >10000 |

TABLE 2-continued
INHIBITION OF CYCLIN B/CDK 1, CYCLIN E/CDK 2, AND CYCLIN D1/CDK 4 ENZYME ACTIVITIES
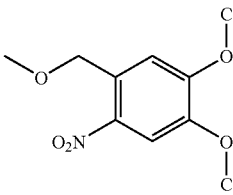
| Compound No. | Z | $R_a$ | $R_2$ | CDK1 $IC_{50}$, nM | CDK2 $IC_{50}$, nM | CDK4 $IC_{50}$, nM |
|---|---|---|---|---|---|---|
| 101 | —C(O)— | 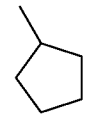 | 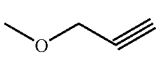 | 31 | 80 | >10000 |
| 102 | —C(O)— | 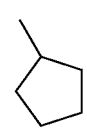 | 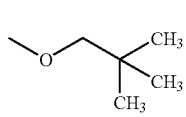 | 31 | 42 | 926 |
| 103 | —C(O)— | 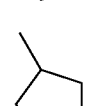 | 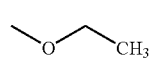 | | | |
| 104 | —C(O)— | 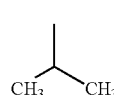 | 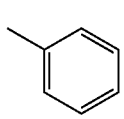 | 750 | 731 | 8000 |
| 105 | —S(O)$_2$— | 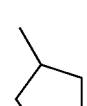 | 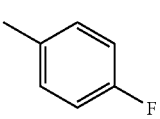 | 7 | 8 | 69 |
| 106 | —S(O)$_2$— | 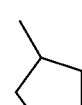 | 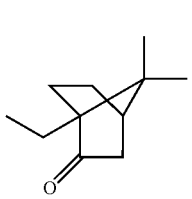 | 8 | 8 | 15 |
| 107 | —S(O)$_2$— | 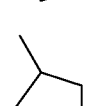 | 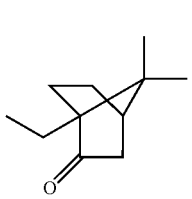 | 250 | 35 | 10 |

TABLE 2-continued

INHIBITION OF CYCLIN B/CDK 1, CYCLIN E/CDK 2, AND CYCLIN D1/CDK 4 ENZYME ACTIVITIES

| Compound No. | Z | $R_a$ | $R_2$ | CDK1 IC$_{50}$, nM | CDK2 IC$_{50}$, nM | CDK4 IC$_{50}$, nM |
|---|---|---|---|---|---|---|
| 108 | —S(O)$_2$— | 4-Cl-phenyl | cyclopentyl | 7 | 10 | 170 |
| 109 | —S(O)$_2$— | 4-CN-phenyl | cyclopentyl | 18 | 45 | 12 |
| 110 | —S(O)$_2$— | 3,5-dimethyl-4-methylisoxazole | cyclopentyl | 27 | 9 | 158 |
| 111 | —S(O)$_2$— | 2-(methoxycarbonyl)phenyl | cyclopentyl | 17 | 9 | 51 |
| 112 | —S(O)$_2$— | 3-CF$_3$-phenyl | cyclopentyl | 32 | 48 | 224 |
| 113 | —S(O)$_2$— | 2-(acetylamino)-4,5-dimethylthiazole | cyclopentyl | 18 | 7 | 39 |
| 114 | —S(O)$_2$— | 4-Br-phenyl | cyclopentyl | 5 | 15 | 80 |

TABLE 2-continued

INHIBITION OF CYCLIN B/CDK 1, CYCLIN E/CDK 2, AND CYCLIN D1/CDK 4 ENZYME ACTIVITIES

| Compound No. | Z | $R_a$ | $R_2$ | CDK1 IC$_{50}$, nM | CDK2 IC$_{50}$, nM | CDK4 IC$_{50}$, nM |
|---|---|---|---|---|---|---|
| 115 | —S(O)$_2$— | 4-(NHC(O)CH$_3$)-phenyl | cyclopentyl | 5 | 5 | 14 |
| 116 | —S(O)$_2$— | 2-naphthyl | cyclopentyl | 18 | 32 | 382 |
| 117 | —S(O)$_2$— | 2,4-dichloro-6-hydroxyphenyl | cyclopentyl | 290 | 31 | 558 |
| 118 | —S(O)$_2$— | styryl | cyclopentyl | 22 | 38 | 38 |
| 119 | —S(O)$_2$— | benzyl (CH$_2$-phenyl) | cyclopentyl | 25 | 31 | 65 |
| 120 | —S(O)$_2$— | 4-nitrophenyl | cyclopentyl | — | — | — |
| 121 | —S(O)$_2$— | 2,6-dichlorophenyl | cyclopentyl | 120 | 50 | 83 |

TABLE 2-continued

INHIBITION OF CYCLIN B/CDK 1, CYCLIN E/CDK 2, AND CYCLIN D1/CDK 4 ENZYME ACTIVITIES

| Compound No. | Z | R$_a$ | R$_2$ | CDK1 IC$_{50}$, nM | CDK2 IC$_{50}$, nM | CDK4 IC$_{50}$, nM |
|---|---|---|---|---|---|---|
| 122 | —S(O)$_2$— | 4-iodophenyl | cyclopentyl | 10 | 38 | 590 |
| 123 | —S(O)$_2$— | 1-naphthyl | cyclopentyl | 62 | 54 | 49 |
| 124 | —S(O)$_2$— | 4-methylphenyl | cyclopentyl | 10 | 26 | 77 |
| 125 | —S(O)$_2$— | isobutyl | cyclopentyl | 180 | 38 | 62 |
| 126 | —S(O)$_2$— | 4-carboxyphenyl | cyclopentyl | 20 | 6 | 55 |
| 127 | —S(O)$_2$— | 3-nitrophenyl | cyclopentyl | 14 | 17 | 48 |
| 128 | —S(O)$_2$— | 2-thienyl | cyclopentyl | 9 | 7 | 5 |

TABLE 2-continued

INHIBITION OF CYCLIN B/CDK 1, CYCLIN E/CDK 2, AND CYCLIN D1/CDK 4 ENZYME ACTIVITIES

| Compound No. | Z | $R_a$ | $R_2$ | CDK1 IC$_{50}$, nM | CDK2 IC$_{50}$, nM | CDK4 IC$_{50}$, nM |
|---|---|---|---|---|---|---|
| 129 | —S(O)$_2$— | pentyl | cyclopentyl | 60 | 9 | 60 |
| 130 | —S(O)$_2$— | 4-tert-butylphenyl | cyclopentyl | 8 | 53 | 159 |
| 131 | —S(O)$_2$— | butyl | cyclopentyl | 100 | 17 | 70 |
| 132 | —S(O)$_2$— | 2-methyl-3-nitro-5-(trifluoromethyl)phenyl | cyclopentyl | 74 | 35 | 590 |
| 133 | —S(O)$_2$— | 3,3,3-trifluoropropyl | cyclopentyl | 200 | 55 | 85 |
| 134 | —S(O)$_2$— | 4-(trifluoromethoxy)phenyl | cyclopentyl | 200 | 35 | 84 |
| 135 | —S(O)$_2$— | 3-carboxyphenyl | cyclopentyl | 80 | 4 | 62 |

TABLE 2-continued
INHIBITION OF CYCLIN B/CDK 1, CYCLIN E/CDK 2, AND
CYCLIN D1/CDK 4 ENZYME ACTIVITIES
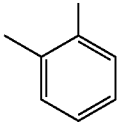
| Compound No. | Z | R$_a$ | R$_2$ | CDK1 IC$_{50}$, nM | CDK2 IC$_{50}$, nM | CDK4 IC$_{50}$, nM |
|---|---|---|---|---|---|---|
| 136 | —S(O)$_2$— | 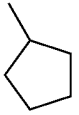 | 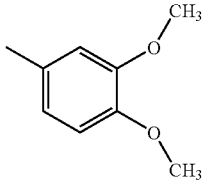 | 50 | 37 | 10 |
| 137 | —S(O)$_2$— | 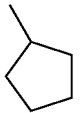 | 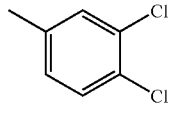 | 26 | 7 | 144 |
| 138 | —S(O)$_2$— | 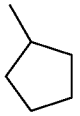 | 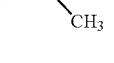 | 40 | 60 | 69 |
| 139 | —S(O)$_2$— | 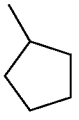 | 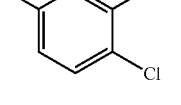 | 23 | 6 | 64 |
| 140 | —S(O)$_2$— | 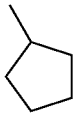 | 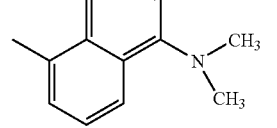 | 36 | 41 | 75 |
| 141 | —S(O)$_2$— |  | 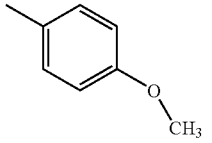 | 27 | 61 | 66 |
| 142 | —S(O)$_2$— | 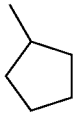 | | <5 | 9 | 47 |

TABLE 2-continued
INHIBITION OF CYCLIN B/CDK 1, CYCLIN E/CDK 2, AND
CYCLIN D1/CDK 4 ENZYME ACTIVITIES
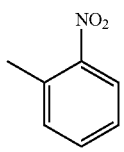
| Compound No. | Z | $R_a$ | $R_2$ | CDK1 $IC_{50}$, nM | CDK2 $IC_{50}$, nM | CDK4 $IC_{50}$, nM |
|---|---|---|---|---|---|---|
| 143 | —S(O)$_2$— | 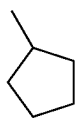 | 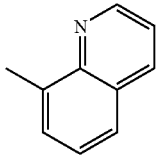 | 7.5 | 28 | 154 |
| 144 | —S(O)$_2$— | 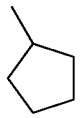 | 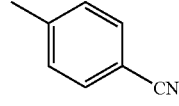 | 2 | 2 | 75 |
| 145 | —S(O)$_2$— | 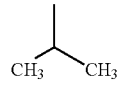 | 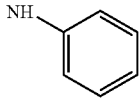 | 21 | 70 | 8800 |
| 146 | —C(O)— | 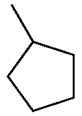 | 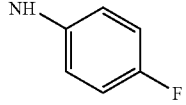 | 18 | 42 | 200 |
| 147 | —C(O)— | 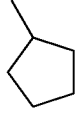 | 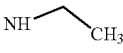 | 38 | 46 | 258 |
| 148 | —C(O)— | 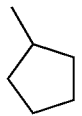 | 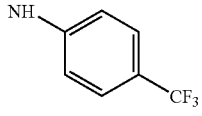 | 197 | 61 | 699 |
| 149 | —C(O)— | 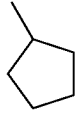 | | 30 | 51 | 91 |

TABLE 2-continued
INHIBITION OF CYCLIN B/CDK 1, CYCLIN E/CDK 2, AND
CYCLIN D1/CDK 4 ENZYME ACTIVITIES
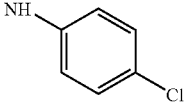
| Compound No. | Z | R$_a$ | R$_2$ | CDK1 IC$_{50}$, nM | CDK2 IC$_{50}$, nM | CDK4 IC$_{50}$, nM |
|---|---|---|---|---|---|---|
| 150 | —C(O)— | 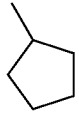 | 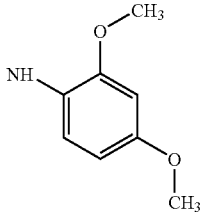 | 26 | 55 | 91 |
| 151 | —C(O)— | 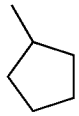 | 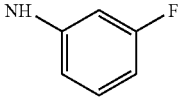 | 60 | 32 | 391 |
| 152 | —C(O)— | 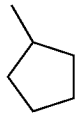 | 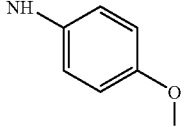 | 17 | 42 | 753 |
| 153 | —C(O)— | 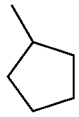 | 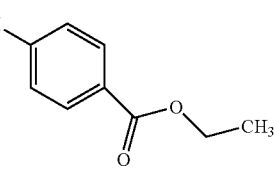 | 20 | 30 | 444 |
| 154 | —C(O)— | 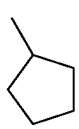 | 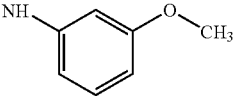 | 11 | 30 | 285 |
| 155 | —C(O)— | 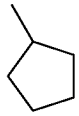 | | 20 | 43 | 482 |

TABLE 2-continued

INHIBITION OF CYCLIN B/CDK 1, CYCLIN E/CDK 2, AND CYCLIN D1/CDK 4 ENZYME ACTIVITIES

| Compound No. | Z | $R_a$ | $R_2$ | CDK1 $IC_{50}$, nM | CDK2 $IC_{50}$, nM | CDK4 $IC_{50}$, nM |
|---|---|---|---|---|---|---|
| 156 | —C(O)— | NH-cyclopropyl-phenyl | cyclopentyl | 75 | 79 | 1618 |
| 157 | —C(O)— | NH-CH(CH$_3$)$_2$ | cyclopentyl | 310 | 32 | 2038 |
| 158 | —C(O)— | NH-(2-CF$_3$-phenyl) | cyclopentyl | 82 | 87 | 825 |
| 159 | —C(O)— | NH-(3-CF$_3$-phenyl) | cyclopentyl | 4 | 16 | 702 |
| 160 | —C(O)— | NH-CH(CH$_3$)-phenyl | cyclopentyl | 85 | 94 | 357 |
| 161 | —C(O)— | NH-CH(CH$_3$)-phenyl | cyclopentyl | 56 | 78 | 601 |
| 162 | —C(O)— | NH-(4-Br-phenyl) | cyclopentyl | 15 | 72 | 603 |

TABLE 2-continued
INHIBITION OF CYCLIN B/CDK 1, CYCLIN E/CDK 2, AND
CYCLIN D1/CDK 4 ENZYME ACTIVITIES
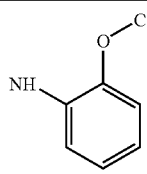
| Compound No. | Z | $R_a$ | $R_2$ | CDK1 $IC_{50}$, nM | CDK2 $IC_{50}$, nM | CDK4 $IC_{50}$, nM |
|---|---|---|---|---|---|---|
| 163 | —C(O)— | 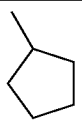 | 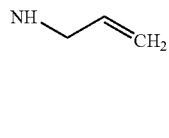 | 37 | 57 | 855 |
| 164 | —C(O)— | 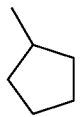 | 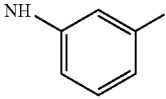 | 151 | 86 | 739 |
| 165 | —C(O)— | 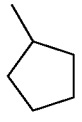 |  | 11 | 21 | 711 |
| 166 | —C(O)— | 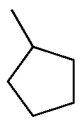 | 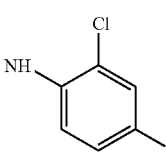 | | | |
| 167 | —C(O)— | 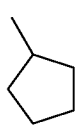 | 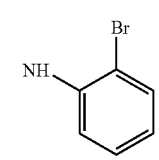 | 4 | 54 | 63 |
| 168 | —C(O)— | 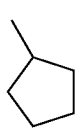 | 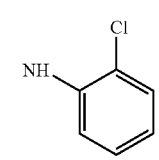 | 29 | 52 | 111 |
| 169 | —C(O)— | 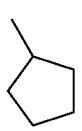 | | 28 | 45 | 130 |

TABLE 2-continued
INHIBITION OF CYCLIN B/CDK 1, CYCLIN E/CDK 2, AND
CYCLIN D1/CDK 4 ENZYME ACTIVITIES
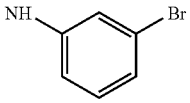
| Compound No. | Z | R$_a$ | R$_2$ | CDK1 IC$_{50}$, nM | CDK2 IC$_{50}$, nM | CDK4 IC$_{50}$, nM |
|---|---|---|---|---|---|---|
| 170 | —C(O)— | 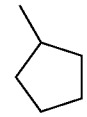 | 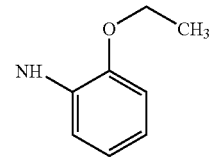 | 3 | 51 | 156 |
| 171 | —C(O)— | 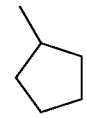 | 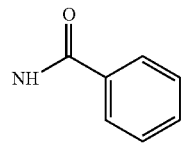 | 51 | 89 | 963 |
| 172 | —C(O)— |  | 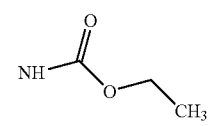 | 23 | 62 | 829 |
| 173 | —C(O)— | 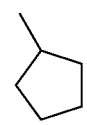 | 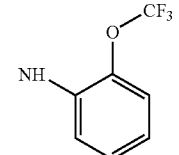 | 18 | 30 | 424 |
| 174 | —C(O)— | 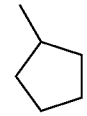 | 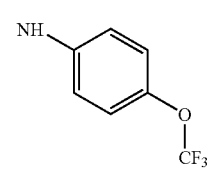 | 48 | 89 | 795 |
| 175 | —C(O)— | 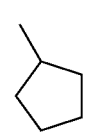 | | 12 | 114 | 682 |

TABLE 2-continued
INHIBITION OF CYCLIN B/CDK 1, CYCLIN E/CDK 2, AND CYCLIN D1/CDK 4 ENZYME ACTIVITIES
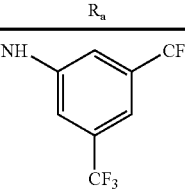
| Compound No. | Z | $R_a$ | $R_2$ | CDK1 $IC_{50}$, nM | CDK2 $IC_{50}$, nM | CDK4 $IC_{50}$, nM |
|---|---|---|---|---|---|---|
| 176 | —C(O)— | 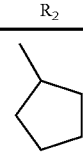 NH, 3,5-bis(CF$_3$)phenyl | 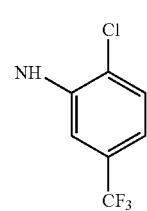 cyclopentyl | 7 | 378 | 898 |
| 177 | —C(O)— | 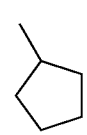 NH, 2-Cl-5-CF$_3$-phenyl | 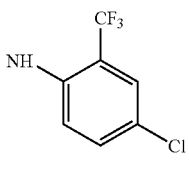 cyclopentyl | 7 | 60 | 432 |
| 178 | —C(O)— | 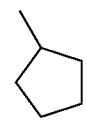 NH, 2-CF$_3$-4-Cl-phenyl | 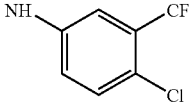 cyclopentyl | 49 | 100 | 879 |
| 179 | —C(O)— | 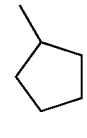 NH, 3-CF$_3$-4-Cl-phenyl | 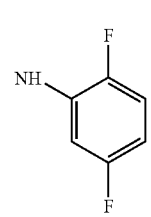 cyclopentyl | 8 | 261 | 497 |
| 180 | —C(O)— | 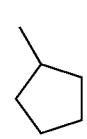 NH, 2,5-diF-phenyl | 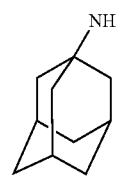 cyclopentyl | 12 | 44 | 431 |
| 181 | —C(O)— | 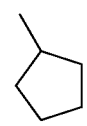 NH-adamantyl | cyclopentyl | 67 | 548 | 1303 |

TABLE 2-continued
INHIBITION OF CYCLIN B/CDK 1, CYCLIN E/CDK 2, AND CYCLIN D1/CDK 4 ENZYME ACTIVITIES
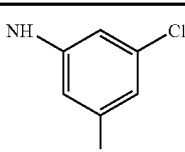
| Compound No. | Z | $R_a$ | $R_2$ | CDK1 IC$_{50}$, nM | CDK2 IC$_{50}$, nM | CDK4 IC$_{50}$, nM |
|---|---|---|---|---|---|---|
| 182 | —C(O)— | 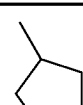 | 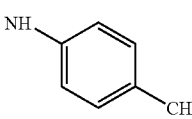 | 32 | 174 | 305 |
| 183 | —C(O)— | 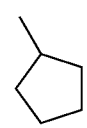 | 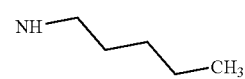 | 17 | 64 | 338 |
| 184 | —C(O)— | 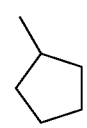 | 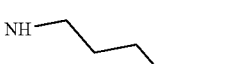 | 77 | 85 | 377 |
| 185 | —C(O)— |  | 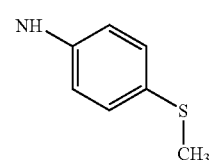 | 72 | 79 | 280 |
| 186 | —C(O)— | 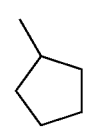 | 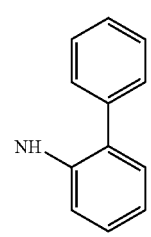 | 11 | 56 | 465 |
| 187 | —C(O)— | 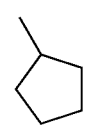 | | 280 | 61 | 831 |

TABLE 2-continued
INHIBITION OF CYCLIN B/CDK 1, CYCLIN E/CDK 2, AND CYCLIN D1/CDK 4 ENZYME ACTIVITIES
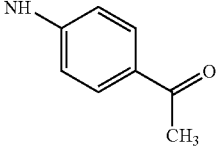
| Compound No. | Z | $R_a$ | $R_2$ | CDK1 $IC_{50}$, nM | CDK2 $IC_{50}$, nM | CDK4 $IC_{50}$, nM |
|---|---|---|---|---|---|---|
| 188 | —C(O)— | 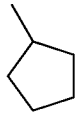 | 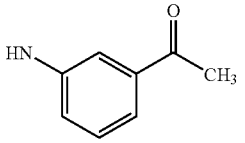 | 14 | 31 | 170 |
| 189 | —C(O)— | 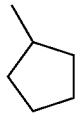 | 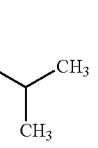 | 20 | 28 | 66 |
| 190 | —C(O)— | 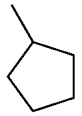 | 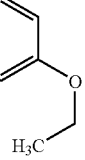 | 23 | 40 | 357 |
| 191 | —C(O)— | 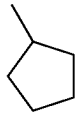 | 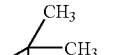 | 23 | 36 | 297 |
| 192 | —C(O)— | 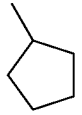 | 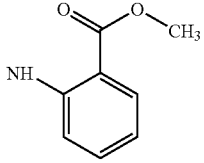 | 1000 | 237 | 400 |
| 193 | —C(O)— | 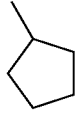 | | 26 | 8 | 507 |

TABLE 2-continued
INHIBITION OF CYCLIN B/CDK 1, CYCLIN E/CDK 2, AND
CYCLIN D1/CDK 4 ENZYME ACTIVITIES
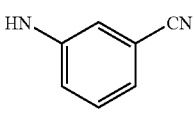
| Compound No. | Z | R$_a$ | R$_2$ | CDK1 IC$_{50}$, nM | CDK2 IC$_{50}$, nM | CDK4 IC$_{50}$, nM |
|---|---|---|---|---|---|---|
| 194 | —C(O)— | 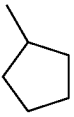 | 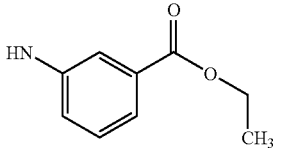 | 40 | 15 | 88 |
| 195 | —C(O)— | 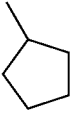 | 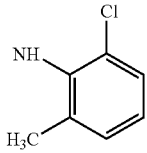 | 50 | 28 | 6 |
| 196 | —C(O)— | 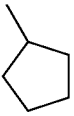 | 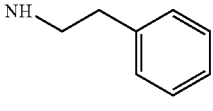 | 350 | 2 | 6 |
| 197 | —C(O)— | 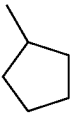 | 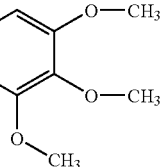 | 200 | 8 | 381 |
| 198 | —C(O)— | 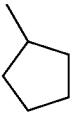 | 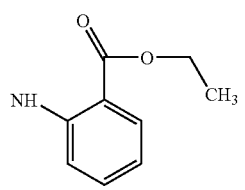 | 40 | 20 | 7 |
| 199 | —C(O)— | 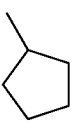 | | 70 | 20 | 670 |

TABLE 2-continued
INHIBITION OF CYCLIN B/CDK 1, CYCLIN E/CDK 2, AND
CYCLIN D1/CDK 4 ENZYME ACTIVITIES
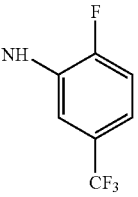
| Compound No. | Z | $R_a$ | $R_2$ | CDK1 $IC_{50}$, nM | CDK2 $IC_{50}$, nM | CDK4 $IC_{50}$, nM |
|---|---|---|---|---|---|---|
| 200 | —C(O)— | 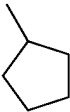 | 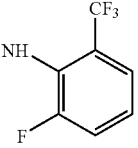 | 10 | 23 | 597 |
| 201 | —C(O)— | 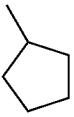 | 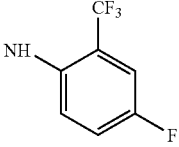 | 170 | 41 | 986 |
| 202 | —C(O)— | 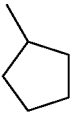 | 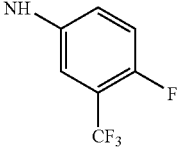 | 137 | 48 | 673 |
| 203 | —C(O)— | 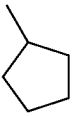 | 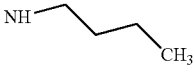 | 10 | 51 | 733 |
| 204 | —C(O)— | 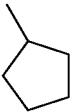 | 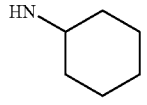 | 200 | 51 | 39 |
| 205 | —C(O)— |  |  | 290 | 232 | 3249 |

TABLE 2-continued

INHIBITION OF CYCLIN B/CDK 1, CYCLIN E/CDK 2, AND CYCLIN D1/CDK 4 ENZYME ACTIVITIES

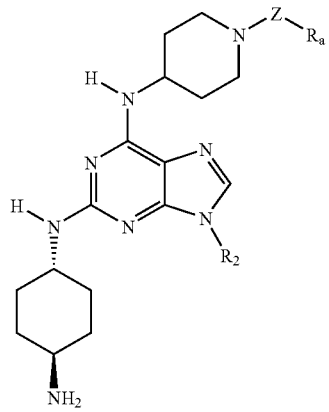

| Compound No. | Z | $R_a$ | $R_2$ | CDK1 $IC_{50}$, nM | CDK2 $IC_{50}$, nM | CDK4 $IC_{50}$, nM |
|---|---|---|---|---|---|---|
| 206 | —C(O)— | NH-CH₂CH₂-CH₃ | cyclopentyl | 210 | 7 | 85 |
| 207 | —C(O)— | NH-(2-F-phenyl) | cyclopentyl | 50 | 46 | 44 |
| 208 | —C(O)— | NH-(2-CH₃-phenyl) | cyclopentyl | 180 | 8 | 73 |
| 209 | —C(O)— | NH-(3,4-diCl-phenyl) | cyclopentyl | 13 | 34 | 50 |
| 210 | —C(O)— | NH-(3-CH₃-phenyl) | cyclopentyl | 20 | 28 | 74 |
| 211 | —C(O)— | NH-(4-OCF₃-phenyl) | CH(CH₃)₂ | 197 | 612 | 7000 |
| | | Flavopiridol | | 13.0 (4.1, n = 6) | 85 (17.8, n = 5) | 50.8 (23.5, n = 5) |

Example 3

In Vitro Tumor Inhibition

In Vitro Proliferation Assay:

The proliferation of tumor cells can be measured using a tetrazolium salt-based assay known as the MTT (3-[4,5-Dimethylthiazol-2-yl]-2,5-diphenyltetrazolium bromide) assay. The proliferation test is performed essentially as described by Carmichael et al., *Cancer Res.* 47: 936-942, 1987. For the assay, the cell lines are plated onto 96 well plates at 1000 to 2500 cells/well (depending on the properties of the individual cell lines), left to attach and recover overnight. (Leukemia cell lines grow in suspension and do not attach to the tissue culture plastic, however, the time frame for drug addition after seeding plates is the same.) Compounds are added as DMSO stocks (10 mM) to cover a concentration range of 0.023 to 50 µM. After 3 days, the cells are incubated with MTT dye (3-[4,5-Dimethylthiazol-2-yl]-2,5-diphenyltetrazolium bromide, Sigma # M5655, 10 mg/ml in Hank's Buffered Saline) to estimate the amount of live cells remaining vs. concentration for the test compounds. Specifically, MTT solution is added to a final concentration of xx mM and the plates incubated at 37 C for 2 to 4 hr. The MTT and culture medium is then removed from the cultures and 200 µl of DMSO is added to solubilize the dye from the cell layer. The absorbance at 570 nm is determined for each culture using a Spectramax plate reader (Molecular Devices).

Another method for measuring proliferation of tumor cells in vitro is a sulforhodamine B assay as described in Skehan, P., et al., *J. Natl. Cancer Inst.* 82: 1107-1112, 1990. Tumor cells are harvested with trypsin-EDTA, cells that excluded trypan blue are counted, then added to 96-well plates and incubated overnight at 37° C. Compounds are added to the wells following dilution in culture medium. Three days later, the medium is removed and replenished with medium containing fresh drug and incubated an additional 4 days. The cells are then fixed with 0.1 ml 10% TCA for 60 min at 4° C. The plates were rinsed five times with tap water, air-dried and stained for 30 min with 0.4% sulforhodamine B in 1% acetic acid and air-dried. Bound dye is solubilized with 0.1 ml 10 mM Tris (pH 10.5) for 5 min and the absorbance measured at 490 nm using a plate reader (as in the MTT assay above).

$IC_{50}$s were determined from the raw data from either the MTT or SRB assays. The $IC_{50}$ equals the amount of drug that causes a 50% decrease in absorbance values relative to those measures from cell cultures that received no test compounds.

Cell Lines:

MCF7 is a human breast adenocarcinoma, hormone-dependent (HTB 22);

MDA-MB-231 is a human breast adenocarcinoma, hormone-independent (HTB 26);

MDA-MB-435 is a human breast carcinoma, hormone-independent (HTB 129);

HT-29 is a human colon adenocarcinoma, moderately well-differentiated grade II (HTB 38); HCT-15 is a human colon adenocarcinoma (CCL 225);

A549 is a human non-small cell lung carcinoma (CCL 185);

NCI-H460 is a human non-small cell lung carcinoma (HTB-177);

HL-60 is a human acute promyelocytic leukemia (CCL-240);

Jurkat is a human acute T cell leukemia (TIB-152);

Molt-4 is a human acute lymphoblastic leukemia (CRL-1582);

PC-3 is a human prostate adenocarcinoma, hormone-independent (CRL 1435); and

DU 145 is a human prostate carcinoma, hormone-independent (HTB 81).

All of the cell lines were obtained from American Type Tissue Collection, with the ATCC accession number in parentheticals. MCF-7 and MDA-MB-231 cells were grown in improved minimum essential medium (Biofluids) without phenol red, supplemented with 5% fetal bovine serum, 0.01 mg/ml gentamicin and 3 mM L-glutamine. All of the other cell lines were grown in RPMI 1640 medium (Life Technologies) supplemented with 5% fetal bovine serum, 0.01 mg/ml gentamicin and 3 mM L-glutamine

TABLE 3

ANTIPROLIFERATIVE DATA
MTT Assays

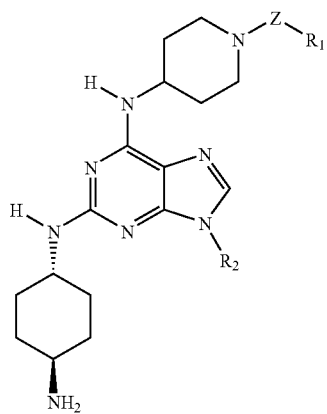

| Compound No. | Z | $R_1$ | $R_2$ | MB-435 Breast ($IC_{50}$ µM) | PC-3 Prostate ($IC_{50}$ µM) | Colo-205 Colon ($IC_{50}$ µM) | H-460 Lung ($IC_{50}$ µM) | HL-60 Leuk. ($IC_{50}$ µM) | Jurkat Leuk. ($IC_{50}$ µM) |
|---|---|---|---|---|---|---|---|---|---|
| 1 | —C(O)— | 4-F-phenyl-methyl | cyclopentyl | 0.69 (0.39, n = 4) | 0.78 (0.33, n = 4) | >50 | >50 | | |

TABLE 3-continued
ANTIPROLIFERATIVE DATA
MTT Assays
| Compound No. | Z | R₁ | R₂ | MB-435 Breast (IC₅₀ μM) | PC-3 Prostate (IC₅₀ μM) | Colo-205 Colon (IC₅₀ μM) | H-460 Lung (IC₅₀ μM) | HL-60 Leuk. (IC₅₀ μM) | Jurkat Leuk. (IC₅₀ μM) |
|---|---|---|---|---|---|---|---|---|---|
| 2 | —C(O)— | 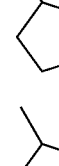 |  | 0.26 (0.08, n = 2) | 1.17 (0.83, n = 2) | <0.02 | 0.15 | | |
| 3 | —C(O)— | 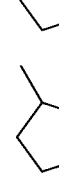 |  | 0.25 (0.08, n = 3) | 0.66 (0.72, n = 3) | | | 0.13 | 0.22 |
| 4 | —C(O)— | 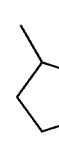 |  | 0.7 (0.28, n = 2) | 0.72 (0.02, n = 2) | 0.16 | 0.33 | | |
| 5 | —C(O)— | 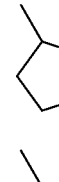 |  | 0.43 (0.06, n = 2) | 0.66 (0.05, n = 2) | <0.02 | 0.27 | | |
| 6 | —C(O)— |  |  | 0.44 (0.22, n = 2) | 1.2 (0.22, n = 2) | <0.02 | 0.24 | | |
| 7 | —C(O)— |  |  | 1.34 (0.22, n = 3) | 2.26 (0.66, n = 2) | <0.02 | 1.11 | | |
| 8 | —C(O)— |  | | 0.75 | 0.86 (0.20, n = 2) | 0.06 | 0.18 | | |

TABLE 3-continued

ANTIPROLIFERATIVE DATA
MTT Assays

| Compound No. | Z | R₁ | R₂ | MB-435 Breast (IC$_{50}$ μM) | PC-3 Prostate (IC$_{50}$ μM) | Colo-205 Colon (IC$_{50}$ μM) | H-460 Lung (IC$_{50}$ μM) | HL-60 Leuk. (IC$_{50}$ μM) | Jurkat Leuk. (IC$_{50}$ μM) |
|---|---|---|---|---|---|---|---|---|---|
| 9 | —C(O)— | phenyl (methyl) | cyclopentyl | 0.58 (0.16, n = 2) | 1.45 (0.85, n = 2) | | | | |
| 10 | —C(O)— | 2-methylthiophene | cyclopentyl | 0.8 | 1.24 | <0.02 | 0.14 | | |
| 11 | —C(O)— | methyl 4-methylbenzoate | cyclopentyl | 0.57 (0.45, n = 2) | 0.72 (0.14, n = 2) | 0.27 | 0.39 | | |
| 12 | —C(O)— | 2-F, 3-CF₃ methylphenyl | cyclopentyl | 0.28 (0.22, n = 2) | 0.48 (0.15, n = 2) | 0.21 | 0.38 | 0.16 (0.06, n = 2) | 0.48 (0.08, n = 2) |
| 13 | —C(O)— | 2-Br methylphenyl | cyclopentyl | 2.89 | 2.55 | | | | |
| 14 | —C(O)— | 2,6-diCl methylphenyl | cyclopentyl | 2.98 | 2.99 | | | | |
| 15 | —C(O)— | 3,4-diCl methylphenyl | cyclopentyl | 0.67 | 0.74 | | | | |

TABLE 3-continued

ANTIPROLIFERATIVE DATA
MTT Assays

| Compound No. | Z | R₁ | R₂ | MB-435 Breast (IC$_{50}$ μM) | PC-3 Prostate (IC$_{50}$ μM) | Colo-205 Colon (IC$_{50}$ μM) | H-460 Lung (IC$_{50}$ μM) | HL-60 Leuk. (IC$_{50}$ μM) | Jurkat Leuk. (IC$_{50}$ μM) |
|---|---|---|---|---|---|---|---|---|---|
| 16 | —C(O)— | 3,4,5-trimethoxyphenyl | cyclopentyl | 8.52 | 7.91 | | | | |
| 17 | —C(O)— | 3,5-dimethoxyphenyl | cyclopentyl | 2.22 | 1.82 | | | | |
| 18 | —C(O)— | 4-O(CH₂)₃CH₃-phenyl | cyclopentyl | 2.76 | 3.43 | | | | |
| 19 | —C(O)— | 4-O(CH₂)₆CH₃-phenyl | cyclopentyl | 0.58 | 0.96 | | | | |
| 20 | —C(O)— | 4-t-Bu-phenyl | cyclopentyl | 2.25 | 1.96 | | | | |
| 21 | —C(O)— | 4-(CH₂)₃CH₃-phenyl | cyclopentyl | 1.43 | 1.45 | | | | |
| 22 | —C(O)— | 4-(CH₂)₄CH₃-phenyl | cyclopentyl | 1.61 | 1.86 | | | | |

TABLE 3-continued
ANTIPROLIFERATIVE DATA
MTT Assays
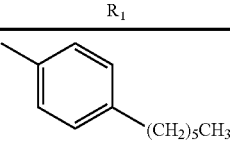
| Compound No. | Z | R₁ | R₂ | MB-435 Breast (IC$_{50}$ μM) | PC-3 Prostate (IC$_{50}$ μM) | Colo-205 Colon (IC$_{50}$ μM) | H-460 Lung (IC$_{50}$ μM) | HL-60 Leuk. (IC$_{50}$ μM) | Jurkat Leuk. (IC$_{50}$ μM) |
|---|---|---|---|---|---|---|---|---|---|
| 23 | —C(O)— | 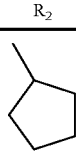 | 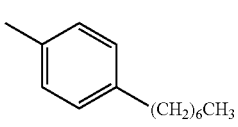 | 1.08 | 2.27 | | | | |
| 24 | —C(O)— |  | 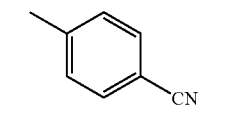 | 2.18 | 3.97 | | | | |
| 25 | —C(O)— | 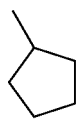 | 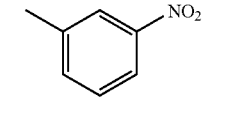 | 3.76 | 2.72 | | | | |
| 26 | —C(O)— |  | 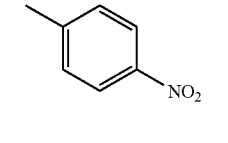 | 2.18 | 1.67 | | | | |
| 27 | —C(O)— |  | 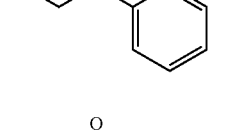 | 1.73 | 2.00 | | | | |
| 28 | —C(O)— | 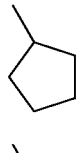 | 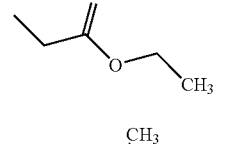 | 0.21 | 0.22 | 0.09 | 0.21 | | |
| 29 | —C(O)— | 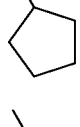 | 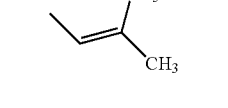 | 3.00 | 2.40 | | | | |
| 30 | —C(O)— |  | | 0.75 | 0.8 | | | | |

TABLE 3-continued
ANTIPROLIFERATIVE DATA
MTT Assays
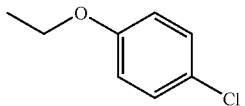
| Compound No. | Z | R₁ | R₂ | MB-435 Breast (IC$_{50}$ μM) | PC-3 Prostate (IC$_{50}$ μM) | Colo-205 Colon (IC$_{50}$ μM) | H-460 Lung (IC$_{50}$ μM) | HL-60 Leuk. (IC$_{50}$ μM) | Jurkat Leuk. (IC$_{50}$ μM) |
|---|---|---|---|---|---|---|---|---|---|
| 31 | —C(O)— | 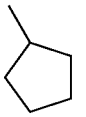 | 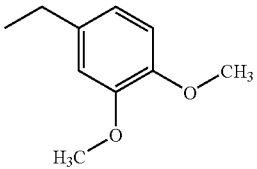 | 0.17 | 0.16 | 0.04 | 0.19 | | |
| 32 | —C(O)— | 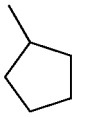 | 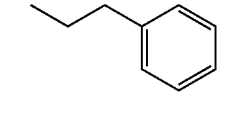 | 5.46 | 4.84 | | | | |
| 33 | —C(O)— | 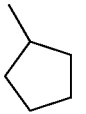 | 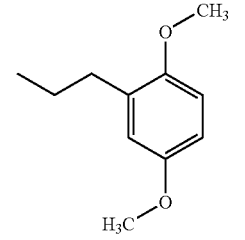 | 0.26 | 0.33 | 0.07 | 0.24 | | |
| 34 | —C(O)— | 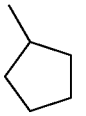 | 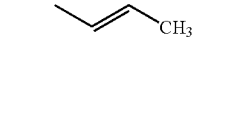 | 0.69 | 0.67 | | | | |
| 35 | —C(O)— | 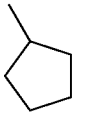 | | 1.38 | 0.98 | | | | |
| 36 | —C(O)— | 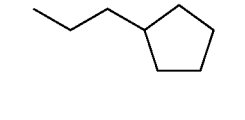 | 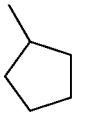 | 0.39 | 0.39 | | | | |

TABLE 3-continued

ANTIPROLIFERATIVE DATA
MTT Assays

| Compound No. | Z | R₁ | R₂ | MB-435 Breast (IC₅₀ μM) | PC-3 Prostate (IC₅₀ μM) | Colo-205 Colon (IC₅₀ μM) | H-460 Lung (IC₅₀ μM) | HL-60 Leuk. (IC₅₀ μM) | Jurkat Leuk. (IC₅₀ μM) |
|---|---|---|---|---|---|---|---|---|---|
| 37 | —C(O)— | benzyloxyethyl | cyclopentyl | 0.26 | 0.20 | <0.02 | 0.23 | | |
| 38 | —C(O)— | 3-methoxyphenylethyl | cyclopentyl | 1.28 | 1.83 | | | | |
| 39 | —C(O)— | cyclopentyl | cyclopentyl | 0.51 | 0.61 | | | | |
| 40 | —C(O)— | diphenylmethyl | cyclopentyl | 0.22 | 0.27 | | | | |
| 41 | —C(O)— | 1-phenylpropyl | cyclopentyl | 0.30 | 0.38 | 0.11 | 0.31 | | |
| 42 | —C(O)— | 4-methoxyphenylethyl | cyclopentyl | 1.10 | 1.06 | | | | |

TABLE 3-continued

ANTIPROLIFERATIVE DATA
MTT Assays

| Compound No. | Z | R₁ | R₂ | MB-435 Breast (IC$_{50}$ μM) | PC-3 Prostate (IC$_{50}$ μM) | Colo-205 Colon (IC$_{50}$ μM) | H-460 Lung (IC$_{50}$ μM) | HL-60 Leuk. (IC$_{50}$ μM) | Jurkat Leuk. (IC$_{50}$ μM) |
|---|---|---|---|---|---|---|---|---|---|
| 43 | —C(O)— | phenylcyclopropyl | cyclopentyl | 0.47 | 0.59 | | | | |
| 44 | —C(O)— | (E)-3-(trifluoromethyl)styryl | cyclopentyl | 0.22 | 0.29 | 0.03 | 0.53 | | |
| 45 | —C(O)— | branched alkyl | cyclopentyl | 0.31 | 0.45 | <0.02 | 0.28 | | |
| 46 | —C(O)— | (phenylthio)ethyl | cyclopentyl | 0.17 | 0.19 | 0.06 | 0.17 | | |
| 47 | —C(O)— | CH(OH)CH₃ | cyclopentyl | 1.99 | 1.8 | | | | |
| 48 | —C(O)— | 4-fluorobenzyl-ethyl | cyclopentyl | 0.75 | 0.84 | | | | |
| 49 | —C(O)— | but-3-enyl | cyclopentyl | 1.23 | 0.92 | | | | |

TABLE 3-continued
ANTIPROLIFERATIVE DATA
MTT Assays
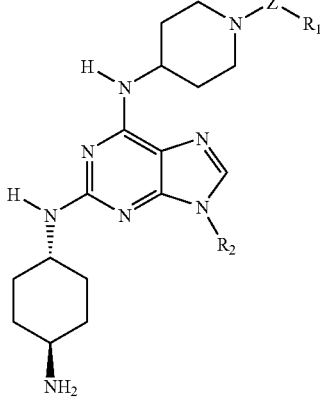
| Compound No. | Z | R₁ | R₂ | MB-435 Breast (IC₅₀ μM) | PC-3 Prostate (IC₅₀ μM) | Colo-205 Colon (IC₅₀ μM) | H-460 Lung (IC₅₀ μM) | HL-60 Leuk. (IC₅₀ μM) | Jurkat Leuk. (IC₅₀ μM) |
|---|---|---|---|---|---|---|---|---|---|
| 50 | —C(O)— |  | 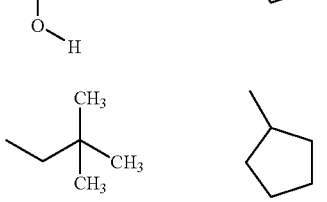 | 1.67 | 1.58 | | | | |
| 51 | —C(O)— | 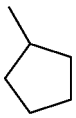 | 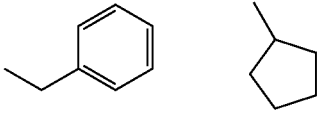 | 0.42 | 0.50 | | | | |
| 52 | —C(O)— |  | 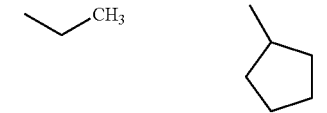 | 0.87 | 0.69 | | | | |
| 53 | —C(O)— |  | 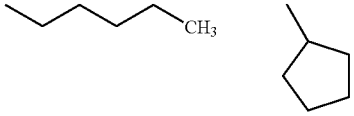 | 1.17 | 0.88 | | | | |
| 54 | —C(O)— |  | 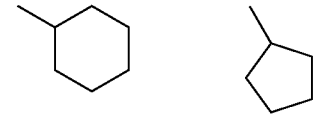 | 0.60 | 0.59 | | | | |
| 55 | —C(O)— |  | 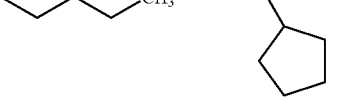 | 0.41 | 0.57 | | | | |
| 56 | —C(O)— |  | | 0.61 | 0.69 | | | | |

TABLE 3-continued

ANTIPROLIFERATIVE DATA
MTT Assays

| Compound No. | Z | R₁ | R₂ | MB-435 Breast (IC₅₀ μM) | PC-3 Prostate (IC₅₀ μM) | Colo-205 Colon (IC₅₀ μM) | H-460 Lung (IC₅₀ μM) | HL-60 Leuk. (IC₅₀ μM) | Jurkat Leuk. (IC₅₀ μM) |
|---|---|---|---|---|---|---|---|---|---|
| 57 | —C(O)— | 3-methylhexyl | cyclopentyl | 0.96 | 1.13 | | | | |
| 58 | —C(O)— | n-butyl | cyclopentyl | 1.01 | 0.94 | | | | |
| 59 | —C(O)— | isobutyl | cyclopentyl | 0.62 | 0.96 | | | | |
| 60 | —C(O)— | sec-butyl | cyclopentyl | 0.69 | 0.65 | | | | |
| 61 | —C(O)— | 2-thienylmethyl | cyclopentyl | 0.61 | 0.58 | | | | |
| 62 | —C(O)— | cinnamyl | cyclopentyl | | | | | | |
| 63 | —C(O)— | cyclobutyl | cyclopentyl | 0.17 | 0.21 | 0.16 | 0.24 | | |
| 64 | —C(O)— | cyclopropyl | cyclopentyl | 1.13 | 1.03 | | | | |

TABLE 3-continued
ANTIPROLIFERATIVE DATA
MTT Assays
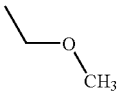
| Compound No. | Z | R₁ | R₂ | MB-435 Breast (IC$_{50}$ μM) | PC-3 Prostate (IC$_{50}$ μM) | Colo-205 Colon (IC$_{50}$ μM) | H-460 Lung (IC$_{50}$ μM) | HL-60 Leuk. (IC$_{50}$ μM) | Jurkat Leuk. (IC$_{50}$ μM) |
|---|---|---|---|---|---|---|---|---|---|
| 65 | —C(O)— | 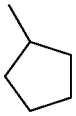 | 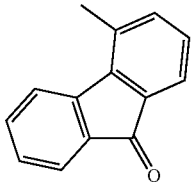 | 3.09 | 3.29 | | | | |
| 66 | —C(O)— |  | 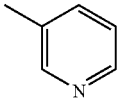 | 1.66 | 1.93 | | | | |
| 67 | —C(O)— |  | 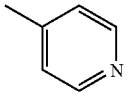 | 50 | 38 | | | | |
| 68 | —C(O)— |  | 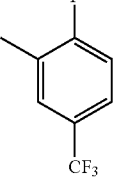 | 21 | 16 | | | | |
| 69 | —C(O)— |  | 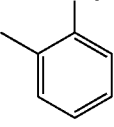 | 0.48 | 0.35 | | | | |
| 70 | —C(O)— |  | | 4.6 | 4.4 | | | | |

TABLE 3-continued
ANTIPROLIFERATIVE DATA
MTT Assays
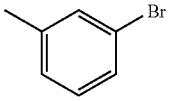
| Compound No. | Z | R₁ | R₂ | MB-435 Breast (IC$_{50}$ μM) | PC-3 Prostate (IC$_{50}$ μM) | Colo-205 Colon (IC$_{50}$ μM) | H-460 Lung (IC$_{50}$ μM) | HL-60 Leuk. (IC$_{50}$ μM) | Jurkat Leuk. (IC$_{50}$ μM) |
|---|---|---|---|---|---|---|---|---|---|
| 71 | —C(O)— | 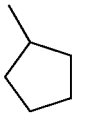 | 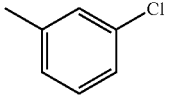 | 0.64 | 0.61 | | | | |
| 72 | —C(O)— | 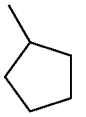 | 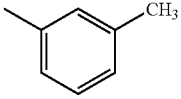 | 0.03 | 0.03 | | | | |
| 73 | —C(O)— | 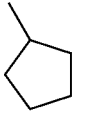 | 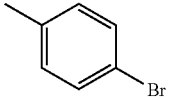 | 1.31 | 1.35 | | | | |
| 74 | —C(O)— |  | 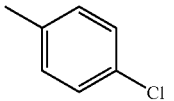 | 1.07 | 1.25 | | | | |
| 75 | —C(O)— |  | 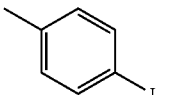 | 1.38 | 1.70 | | | | |
| 76 | —C(O)— |  | 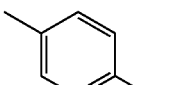 | 1.47 | 1.04 | | | | |
| 77 | —C(O)— |  | | 1.03 | 1.19 | | | | |

TABLE 3-continued
ANTIPROLIFERATIVE DATA
MTT Assays
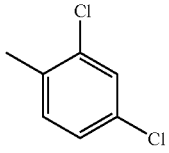
| Compound No. | Z | R$_1$ | R$_2$ | MB-435 Breast (IC$_{50}$ μM) | PC-3 Prostate (IC$_{50}$ μM) | Colo-205 Colon (IC$_{50}$ μM) | H-460 Lung (IC$_{50}$ μM) | HL-60 Leuk. (IC$_{50}$ μM) | Jurkat Leuk. (IC$_{50}$ μM) |
|---|---|---|---|---|---|---|---|---|---|
| 78 | —C(O)— | 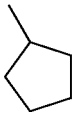 | 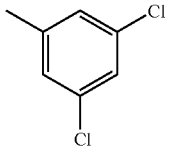 | 1.56 | 1.53 | | | | |
| 79 | —C(O)— |  | 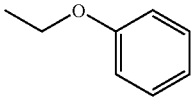 | 0.25 | 0.27 | | | | |
| 80 | —C(O)— |  | 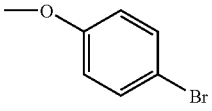 | >50 | >50 | | | | |
| 81 | —C(O)— |  | 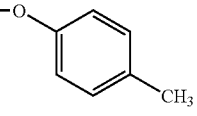 | 0.10 (0.01, n = 2) | 0.12 (0.01, n = 2) | 0.03 | 0.07 | 0.02 | 0.10 |
| 82 | —C(O)— |  | 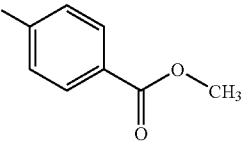 | 0.06 (0.05, n = 2) | 0.12 (0.01, n = 2) | 0.06 | 0.08 | 0.04 | |
| 83 | —C(O)— |  | 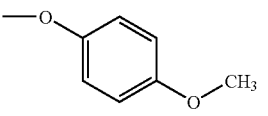 | 0.17 (0.02, n = 2) | 0.15 (0.02, n = 2) | 0.07 | 0.07 | 0.06 | 0.14 |
| 84 | —C(O)— |  | | 0.10 (0.02, n = 2) | 0.12 (0.01, n = 2) | 0.03 | 0.07 | 0.04 | 0.12 |

TABLE 3-continued

ANTIPROLIFERATIVE DATA
MTT Assays

| Compound No. | Z | R₁ | R₂ | MB-435 Breast (IC₅₀ μM) | PC-3 Prostate (IC₅₀ μM) | Colo-205 Colon (IC₅₀ μM) | H-460 Lung (IC₅₀ μM) | HL-60 Leuk. (IC₅₀ μM) | Jurkat Leuk. (IC₅₀ μM) |
|---|---|---|---|---|---|---|---|---|---|
| 85 | —C(O)— | —O-phenyl | cyclopentyl | 0.03 (0.00, n = 2) | 0.06 (0.04, n = 2) | 0.03 | 0.06 | | |
| 86 | —C(O)— | —O-menthyl (O, CH₃, isopropyl substituted cyclohexyl) | cyclopentyl | 0.52 (0.08, n = 2) | 0.69 (0.38, n = 3) | 0.29 | 0.40 | | |
| 87 | —C(O)— | —O-(4-fluorophenyl) | cyclopentyl | 0.11 (0.01, n = 2) | 0.16, (0.15, n = 3) | 0.16 | 0.08 | 0.05 | 0.20 |
| 88 | —C(O)— | —O-(4-chlorophenyl) | cyclopentyl | 0.02 | 0.10 (0.05, n = 2) | 0.04 | 0.06 | 0.07 | 0.02 |
| 89 | —C(O)— | —O-(4-nitrophenyl) | cyclopentyl | 0.06 | 0.06 | 0.01 | 0.03 | 0.02 (0.01, n = 2) | 0.07 |
| 90 | —C(O)— | —O-CH₂-phenyl | cyclopentyl | 0.38 | 0.58 | | | | |
| 91 | —C(O)— | —O-CH₂-CH(CH₃)-CH₃ | cyclopentyl | 0.36 | 0.37 | | | | |
| 92 | —C(O)— | —O-(CH₂)₃-CH₃ | cyclopentyl | 0.33 | 0.20 | 0.2 | 0.2 | 0.07 | 0.25 |

TABLE 3-continued

ANTIPROLIFERATIVE DATA
MTT Assays

| Compound No. | Z | R₁ | R₂ | MB-435 Breast (IC₅₀ μM) | PC-3 Prostate (IC₅₀ μM) | Colo-205 Colon (IC₅₀ μM) | H-460 Lung (IC₅₀ μM) | HL-60 Leuk. (IC₅₀ μM) | Jurkat Leuk. (IC₅₀ μM) |
|---|---|---|---|---|---|---|---|---|---|
| 93 | —C(O)— | CH₃OCH₂CH₂— | cyclopentyl | 0.25 (0.01, n = 2) | 0.26 (0.05, n = 2) | 0.18 | 0.20 | 0.07 | 0.16 |
| 94 | —C(O)— | CH₃O-CH₂-(4-NO₂-C₆H₄) | cyclopentyl | 0.14 (0.02, n = 2) | 0.13 (0.00, n = 2) | 0.07 | 0.14 | 0.06 | 0.18 |
| 95 | —C(O)— | CH₃O-CH₂-CH=CH₂ | cyclopentyl | 0.24 (0.03, n = 2) | 0.21 (0.00, n = 2) | 0.10 | 0.20 | 0.06 | 0.18 |
| 96 | —C(O)— | CH₃O-CH₂CH₂-CH₃ | cyclopentyl | 0.35 | 0.35 | | | | |
| 97 | —C(O)— | CH₃O-CH(CH₂CH₃)-CH₂CH₂CH₂CH₃ | cyclopentyl | 1.52 | 1.65 | | | | |
| 98 | —C(O)— | CH₃O-(CH₂)₅-CH₃ | cyclopentyl | 0.66 | 0.82 | | | | |
| 99 | —C(O)— | —O-(2-NO₂-C₆H₄) | cyclopentyl | 0.12 (0.01, n = 2) | 0.20 (0.11, n = 2) | 0.05 | 0.16 | <0.02 | 0.11 |

TABLE 3-continued
ANTIPROLIFERATIVE DATA
MTT Assays
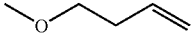
| Compound No. | Z | R₁ | R₂ | MB-435 Breast (IC$_{50}$ μM) | PC-3 Prostate (IC$_{50}$ μM) | Colo-205 Colon (IC$_{50}$ μM) | H-460 Lung (IC$_{50}$ μM) | HL-60 Leuk. (IC$_{50}$ μM) | Jurkat Leuk. (IC$_{50}$ μM) |
|---|---|---|---|---|---|---|---|---|---|
| 100 | —C(O)— |  | 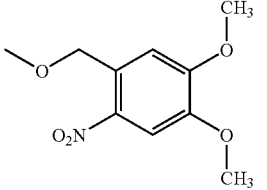 | 0.25 (0.02, n = 2) | 0.22 (0.03, n = 2) | 0.11 | 0.17 | 0.05 | 0.19 |
| 101 | —C(O)— | 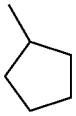 | 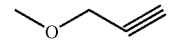 | 0.24 | 0.27 | | | | |
| 102 | —C(O)— |  | 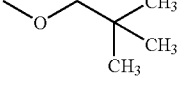 | 0.19 (0.02, n = 2) | 0.14 (0.07, n = 2) | 0.14 | 0.20 | <0.02 | 0.11 |
| 103 | —C(O)— |  | 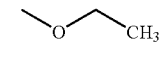 | 0.51 | 0.44 | | | | |
| 104 | —C(O)— |  | 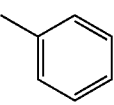 | 2.27 | 1.21 | | | | |
| 105 | —S(O)₂— |  | 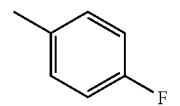 | 0.18 (0.06, n = 2) | 0.50 (0.17, n = 2) | 0.21 | 0.29 | | |
| 106 | —S(O)₂— |  | 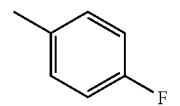 | 0.12 (0.02, n = 2) | 0.82 (0.48, n = 2) | 0.13 | 0.22 | 0.10 (0.02, n = 2) | 0.19 (0.17, n = 2) |

TABLE 3-continued

ANTIPROLIFERATIVE DATA
MTT Assays

| Compound No. | Z | R₁ | R₂ | MB-435 Breast (IC₅₀ μM) | PC-3 Prostate (IC₅₀ μM) | Colo-205 Colon (IC₅₀ μM) | H-460 Lung (IC₅₀ μM) | HL-60 Leuk. (IC₅₀ μM) | Jurkat Leuk. (IC₅₀ μM) |
|---|---|---|---|---|---|---|---|---|---|
| 107 | —S(O)₂— | camphor-ethyl ketone | cyclopentyl | 0.11 (0.01, n = 2) | 0.41 (0.08, n = 2) | 0.18 | 0.29 | | |
| 108 | —S(O)₂— | 4-Cl-phenyl | cyclopentyl | 0.14 (0.03, n = 2) | 0.43 (0.08, n = 2) | 0.18 | 0.29 | | |
| 109 | —S(O)₂— | 4-CN-phenyl | cyclopentyl | 0.11 (0.01, n = 2) | 0.32 (0.07, n = 2) | 0.18 | 0.25 | 0.12 (0.01, n = 2) | 0.44 (0.09, n = 2) |
| 110 | —S(O)₂— | 3,4-dimethyl-5-methyl-isoxazole | cyclopentyl | 0.44 (0.05, n = 2) | 0.76 (0.09, n = 2) | 0.25 | 0.65 | | |
| 111 | —S(O)₂— | 2-methyl-methylbenzoate | cyclopentyl | 0.43 (0.04, n = 2) | 0.76 (0.29, n = 2) | 0.09 | 0.28 | 0.38 (0.08, n = 2) | 1.05 (0.24, n = 2) |
| 112 | —S(O)₂— | 3-CF₃-phenyl | cyclopentyl | 0.87 (0.25, n = 3) | 0.16 (0.17, n = 3) | <0.02 | 0.07 | 0.18 | 0.11 |
| 113 | —S(O)₂— | 4,5-dimethylthiazol-2-yl-acetamide | cyclopentyl | 6.54 | 5.89 | | | | |

TABLE 3-continued
ANTIPROLIFERATIVE DATA
MTT Assays
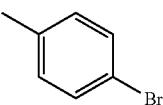
| Compound No. | Z | R₁ | R₂ | MB-435 Breast (IC$_{50}$ μM) | PC-3 Prostate (IC$_{50}$ μM) | Colo-205 Colon (IC$_{50}$ μM) | H-460 Lung (IC$_{50}$ μM) | HL-60 Leuk. (IC$_{50}$ μM) | Jurkat Leuk. (IC$_{50}$ μM) |
|---|---|---|---|---|---|---|---|---|---|
| 114 | —S(O)₂— | 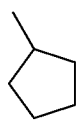 | 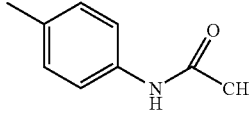 | 0.33 | 0.48 | | | | |
| 115 | —S(O)₂— | 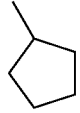 | 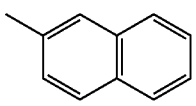 | 4.24 (1.04, n = 2) | 5.10 (0.03, n = 2) | | | | |
| 116 | —S(O)₂— | 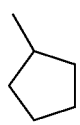 | 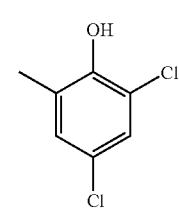 | 0.64 | 1.15 | | | | |
| 117 | —S(O)₂— | 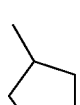 | 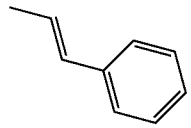 | 38.96 | 34.13 | | | 24.21 | 43.62 |
| 118 | —S(O)₂— | 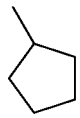 | | 0.28 | 0.38 | | | | |
| 119 | —S(O)₂— | 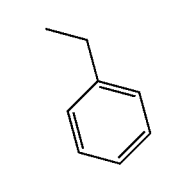 | 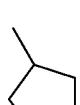 | 0.40 | 0.52 | | | | |
| 120 | —S(O)₂— | 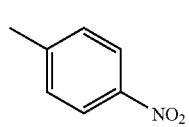 | 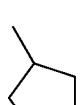 | 0.20 (0.01, n = 2) | 0.22 (0.08, n = 2) | 0.10 | 0.27 | <0.02 | 0.19 |

TABLE 3-continued
ANTIPROLIFERATIVE DATA
MTT Assays
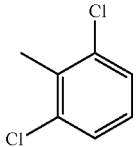
| Compound No. | Z | R₁ | R₂ | MB-435 Breast (IC$_{50}$ μM) | PC-3 Prostate (IC$_{50}$ μM) | Colo-205 Colon (IC$_{50}$ μM) | H-460 Lung (IC$_{50}$ μM) | HL-60 Leuk. (IC$_{50}$ μM) | Jurkat Leuk. (IC$_{50}$ μM) |
|---|---|---|---|---|---|---|---|---|---|
| 121 | —S(O)$_2$— | 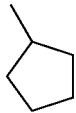 | 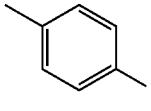 | 0.66 | 0.82 | | | | |
| 122 | —S(O)$_2$— | 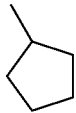 | 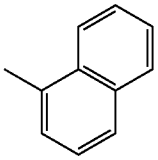 | 0.48 | 0.65 | | | | |
| 123 | —S(O)$_2$— | 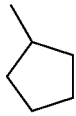 | 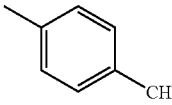 | 0.26 (0.06, n = 2) | 0.20 (0.10, n = 2) | 0.07 | 0.29 | 0.15 | 0.22 |
| 124 | —S(O)$_2$— | 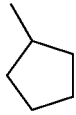 | 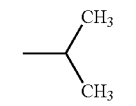 | 0.44 | 0.56 | | | | |
| 125 | —S(O)$_2$— |  | 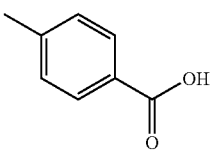 | 1.03 | 1.29 | | | | |
| 126 | —S(O)$_2$— | 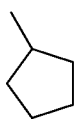 | 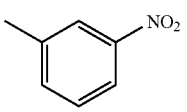 | 19.67 | 16.83 | | | | |
| 127 | —S(O)$_2$— | 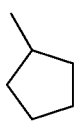 | | 0.61 | 0.62 | | | | |

TABLE 3-continued

ANTIPROLIFERATIVE DATA
MTT Assays

| Compound No. | Z | R₁ | R₂ | MB-435 Breast (IC₅₀ μM) | PC-3 Prostate (IC₅₀ μM) | Colo-205 Colon (IC₅₀ μM) | H-460 Lung (IC₅₀ μM) | HL-60 Leuk. (IC₅₀ μM) | Jurkat Leuk. (IC₅₀ μM) |
|---|---|---|---|---|---|---|---|---|---|
| 128 | —S(O)₂— | 2-methylthiophene | cyclopentyl | 0.49 | 0.57 | | | | |
| 129 | —S(O)₂— | n-pentyl | cyclopentyl | 0.46 | 0.64 | | | | |
| 130 | —S(O)₂— | 4-tert-butylphenyl | cyclopentyl | 0.80 | 2.29 | | | | |
| 131 | —S(O)₂— | n-butyl | cyclopentyl | 0.89 | 1.48 | | | | |
| 132 | —S(O)₂— | 4-methyl-3-nitro-trifluoromethylphenyl | cyclopentyl | 0.21 (0.03, n = 2) | 0.15 (0.04, n = 2) | 0.04 | 0.12 | <0.02 | 0.21 |
| 133 | —S(O)₂— | CH₂CH₂CF₃ | cyclopentyl | 9.10 | 8.97 | | | | |
| 134 | —S(O)₂— | 4-(trifluoromethoxy)phenyl | cyclopentyl | 0.46 | 0.76 | | | | |

TABLE 3-continued
ANTIPROLIFERATIVE DATA
MTT Assays
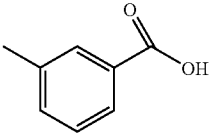
| Compound No. | Z | R₁ | R₂ | MB-435 Breast (IC$_{50}$ μM) | PC-3 Prostate (IC$_{50}$ μM) | Colo-205 Colon (IC$_{50}$ μM) | H-460 Lung (IC$_{50}$ μM) | HL-60 Leuk. (IC$_{50}$ μM) | Jurkat Leuk. (IC$_{50}$ μM) |
|---|---|---|---|---|---|---|---|---|---|
| 135 | —S(O)₂— | 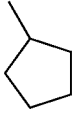 | 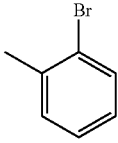 | 3.38 | 4.05 | | | | |
| 136 | —S(O)₂— | 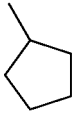 | 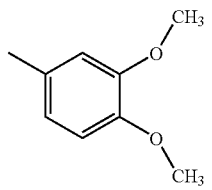 | 0.44 | 0.68 | | | | |
| 137 | —S(O)₂— | 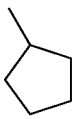 | 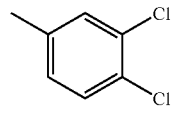 | 0.47 | 1.15 | | | | |
| 138 | —S(O)₂— | 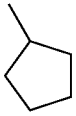 | 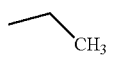 | 0.54 | 1.16 | | | | |
| 139 | —S(O)₂— |  | 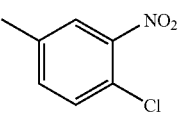 | 1.19 | 1.13 | | | | |
| 140 | —S(O)₂— |  | 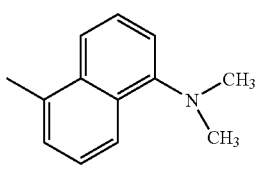 | 2.76 | 4.56 | | | | |
| 141 | —S(O)₂— |  | 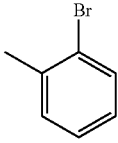 | 0.86 | 1.49 | | | | |

TABLE 3-continued
ANTIPROLIFERATIVE DATA
MTT Assays
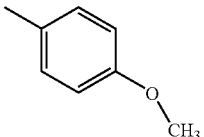
| Compound No. | Z | R$_1$ | R$_2$ | MB-435 Breast (IC$_{50}$ μM) | PC-3 Prostate (IC$_{50}$ μM) | Colo-205 Colon (IC$_{50}$ μM) | H-460 Lung (IC$_{50}$ μM) | HL-60 Leuk. (IC$_{50}$ μM) | Jurkat Leuk. (IC$_{50}$ μM) |
|---|---|---|---|---|---|---|---|---|---|
| 142 | —S(O)$_2$— | 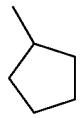 | 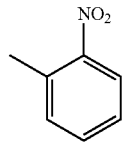 | 0.38 | 0.61 | | | | |
| 143 | —S(O)$_2$— | 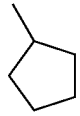 | 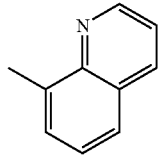 | 0.61 | 0.45 | | | | |
| 144 | —S(O)$_2$— | 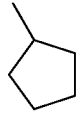 | 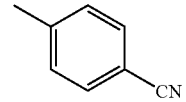 | 0.16 (0.02, n = 2) | 0.18 (0.07, n = 2) | 0.05 | 0.33 | 0.12 | 0.25 |
| 145 | —S(O)$_2$— |  | 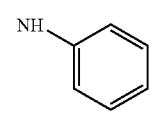 | 4.12 | 6.32 | | | | |
| 146 | —C(O)— | 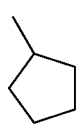 | 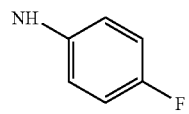 | 0.35 (0.13, n = 3) | 0.34 (0.09, n = 3) | <0.02 | 0.42 | 0.04 | 0.32 |
| 147 | —C(O)— | 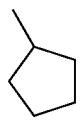 | 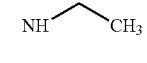 | 0.33 (0.10, n = 3) | 0.36 (0.12, n = 3) | <0.02 | 0.56 | 0.03 | 0.51 |
| 148 | —C(O)— | NH—CH$_3$ | 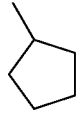 | 4.70 (1.17, n = 2) | 4.79 (1.59, n = 2) | | | | |

TABLE 3-continued
ANTIPROLIFERATIVE DATA
MTT Assays
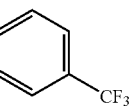
| Compound No. | Z | R₁ | R₂ | MB-435 Breast (IC₅₀ μM) | PC-3 Prostate (IC₅₀ μM) | Colo-205 Colon (IC₅₀ μM) | H-460 Lung (IC₅₀ μM) | HL-60 Leuk. (IC₅₀ μM) | Jurkat Leuk. (IC₅₀ μM) |
|---|---|---|---|---|---|---|---|---|---|
| 149 | —C(O)— | 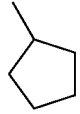 | 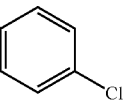 | 0.15 (0.02, n = 3) | 0.26 (0.01, n = 3) | 0.09 | 0.32 | 0.03 | 0.22 |
| 150 | —C(O)— | 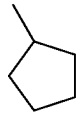 | 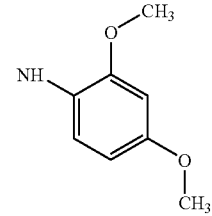 | 0.20 (0.10, n = 3) | 0.25 (0.08, n = 3) | 0.02 | 0.19 | <0.02 | 0.24 |
| 151 | —C(O)— | 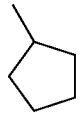 | 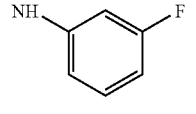 | 0.44 (0.05, n = 2) | 0.50 (0.03, n = 2) | | | | |
| 152 | —C(O)— | 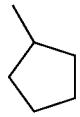 | 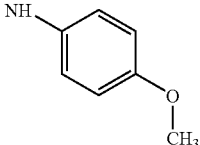 | 0.30 (0.03, n = 2) | 0.38 (0.03, n = 2) | | | | |
| 153 | —C(O)— | 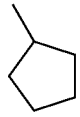 | 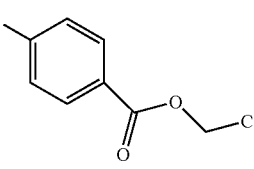 | 0.38 (0.04, n = 3) | 0.45 (0.12, n = 3) | | | | |
| 154 | —C(O)—NH— | 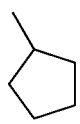 | | 0.21 (0.02, n = 3) | 0.23 (0.01, n = 3) | 0.01 | 0.24 (0.01, n = 2) | 0.06 (0.01, n = 2) | 0.25 (0.02, n = 3) |

TABLE 3-continued
ANTIPROLIFERATIVE DATA
MTT Assays
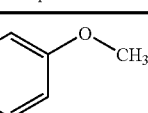
| Compound No. | Z | R₁ | R₂ | MB-435 Breast (IC₅₀ μM) | PC-3 Prostate (IC₅₀ μM) | Colo-205 Colon (IC₅₀ μM) | H-460 Lung (IC₅₀ μM) | HL-60 Leuk. (IC₅₀ μM) | Jurkat Leuk. (IC₅₀ μM) |
|---|---|---|---|---|---|---|---|---|---|
| 155 | —C(O)— | 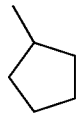 | 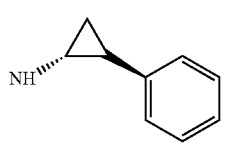 | 0.33 (0.05, n = 3) | 0.44 (0.07, n = 3) | | | | |
| 156 | —C(O)— | 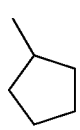 | 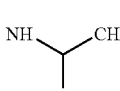 | 0.28 | 0.39 | | | | |
| 157 | —C(O)— | 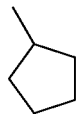 | 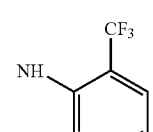 | 2.54 | 3.34 | | | | |
| 158 | —C(O)— | 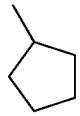 | 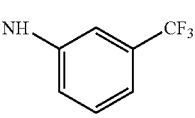 | 0.29 | 0.38 | | | | |
| 159 | —C(O)— | 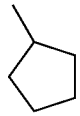 | 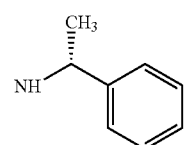 | 0.2 | 0.33 | 0.02 | 0.40 | 0.07 | 0.41 |
| 160 | —C(O)— | 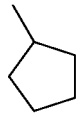 | 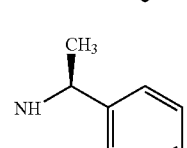 | 1.36 | 1.69 | | | | |
| 161 | —C(O)— | 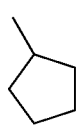 | | 1.01 | 0.96 | | | | |

TABLE 3-continued

ANTIPROLIFERATIVE DATA
MTT Assays

| Compound No. | Z | R₁ | R₂ | MB-435 Breast (IC₅₀ μM) | PC-3 Prostate (IC₅₀ μM) | Colo-205 Colon (IC₅₀ μM) | H-460 Lung (IC₅₀ μM) | HL-60 Leuk. (IC₅₀ μM) | Jurkat Leuk. (IC₅₀ μM) |
|---|---|---|---|---|---|---|---|---|---|
| 162 | —C(O)— | NH-C₆H₄-Br (4-Br) | cyclopentyl | 0.14 | 0.12 | 0.04 | 0.18 | <0.02 | 0.19 |
| 163 | —C(O)— | NH-C₆H₄-OCH₃ (2-OMe) | cyclopentyl | 0.17 | 0.21 | 0.19 | 0.21 | 0.05 | 0.28 |
| 164 | —C(O)— | NH-CH₂-CH=CH₂ | cyclopentyl | 5.03 | 4.99 | | | | |
| 165 | —C(O)— | NH-C₆H₄-Cl (3-Cl) | cyclopentyl | 0.08 | 0.13 | 0.02 | 0.20 | <0.02 | 0.22 |
| 166 | —C(O)— | NH-C₆H₃-2,4-F₂ | cyclopentyl | 0.03 | 0.06 | 0.02 | 0.08 | 0.01 | 0.07 |
| 167 | —C(O)— | NH-C₆H₃-2,4-Cl₂ | cyclopentyl | 0.28 | 0.38 | | | | |
| 168 | —C(O)— | NH-C₆H₄-Br (2-Br) | cyclopentyl | 0.15 | 0.19 | 0.16 | 0.19 | 0.04 | |

TABLE 3-continued
ANTIPROLIFERATIVE DATA
MTT Assays
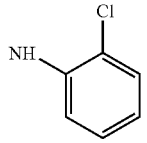
| Compound No. | Z | R₁ | R₂ | MB-435 Breast (IC₅₀ μM) | PC-3 Prostate (IC₅₀ μM) | Colo-205 Colon (IC₅₀ μM) | H-460 Lung (IC₅₀ μM) | HL-60 Leuk. (IC₅₀ μM) | Jurkat Leuk. (IC₅₀ μM) |
|---|---|---|---|---|---|---|---|---|---|
| 169 | —C(O)— | 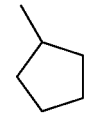 | 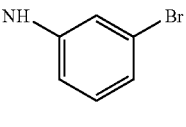 | 0.11 | 0.15 | 0.09 | 0.15 | 0.04 | 0.21 |
| 170 | —C(O)— | 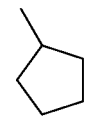 | 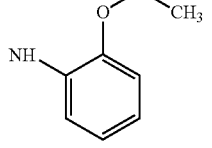 | 0.19 | 0.26 | <0.02 | 0.30 | <0.02 | 0.24 |
| 171 | —C(O)— | 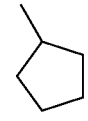 | 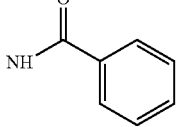 | 0.25 | 0.23 | 0.14 | 0.23 | 0.05 | 0.31 |
| 172 | —C(O)— |  | 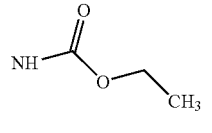 | 1.16 | 1.04 | | | | |
| 173 | —C(O)— | 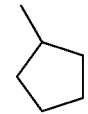 | 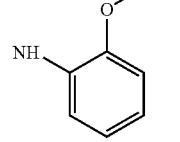 | 2.67 | 2.81 | | | | |
| 174 | —C(O)— | 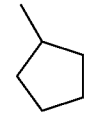 | | 0.31 | 0.27 | | | | |

US 7,429,595 B2
TABLE 3-continued
ANTIPROLIFERATIVE DATA
MTT Assays
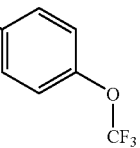
| Compound No. | Z | R₁ | R₂ | MB-435 Breast (IC₅₀ μM) | PC-3 Prostate (IC₅₀ μM) | Colo-205 Colon (IC₅₀ μM) | H-460 Lung (IC₅₀ μM) | HL-60 Leuk. (IC₅₀ μM) | Jurkat Leuk. (IC₅₀ μM) |
|---|---|---|---|---|---|---|---|---|---|
| 175 | —C(O)— | 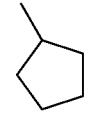 | 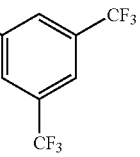 | 0.12 | 0.20 | 0.05 | 0.23 | 0.04 | 0.16 |
| 176 | —C(O)— | 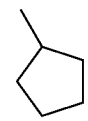 | 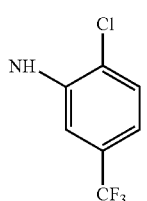 | 0.51 | 0.54 | | | | |
| 177 | —C(O)— | 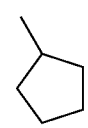 | 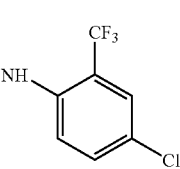 | 0.17 | 0.15 | 0.12 | 0.14 | 0.03 | 0.21 |
| 178 | —C(O)— | 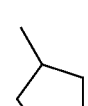 | 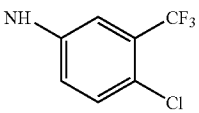 | 0.14 | 0.16 | 0.09 | 0.23 | <0.02 | 0.28 |
| 179 | —C(O)— | 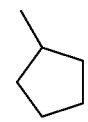 | 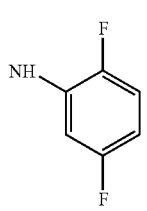 | 0.24 | 0.37 | 0.18 | 0.50 | 0.07 | 0.50 |
| 180 | —C(O)— | 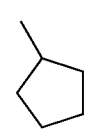 | | 0.10 | 0.09 | 0.04 | 0.12 | <0.02 | 0.20 |

TABLE 3-continued

ANTIPROLIFERATIVE DATA
MTT Assays

| Compound No. | Z | R₁ | R₂ | MB-435 Breast (IC$_{50}$ μM) | PC-3 Prostate (IC$_{50}$ μM) | Colo-205 Colon (IC$_{50}$ μM) | H-460 Lung (IC$_{50}$ μM) | HL-60 Leuk. (IC$_{50}$ μM) | Jurkat Leuk. (IC$_{50}$ μM) |
|---|---|---|---|---|---|---|---|---|---|
| 181 | —C(O)— | adamantyl-NH | cyclopentyl | 0.24 | 0.25 | 0.04 | 0.29 | 0.06 | 0.33 |
| 182 | —C(O)— | 3,5-dichlorophenyl-NH | cyclopentyl | 0.15 | 0.10 | <0.02 | 0.12 | 0.02 | 0.17 |
| 183 | —C(O)— | 4-methylphenyl-NH | cyclopentyl | 0.11 | 0.17 | 0.05 | 0.20 | <0.02 | 0.19 |
| 184 | —C(O)— | NH-(CH₂)₄-CH₃ | cyclopentyl | 0.71 | 0.71 | | | | |
| 185 | —C(O)— | NH-(CH₂)₅-CH₃ | cyclopentyl | 0.29 | 0.41 | | | | |
| 186 | —C(O)— | 4-(methylthio)phenyl-NH | cyclopentyl | 0.09 | 0.16 | 0.03 | 0.28 | <0.02 | 0.21 |

TABLE 3-continued
ANTIPROLIFERATIVE DATA
MTT Assays
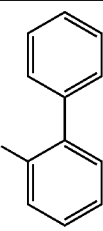
| Compound No. | Z | R₁ | R₂ | MB-435 Breast (IC$_{50}$ μM) | PC-3 Prostate (IC$_{50}$ μM) | Colo-205 Colon (IC$_{50}$ μM) | H-460 Lung (IC$_{50}$ μM) | HL-60 Leuk. (IC$_{50}$ μM) | Jurkat Leuk. (IC$_{50}$ μM) |
|---|---|---|---|---|---|---|---|---|---|
| 187 | —C(O)— | 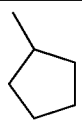 | 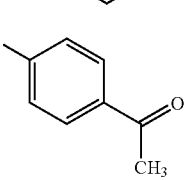 | 0.21 | 0.19 | 0.19 | 0.25 | <0.02 | 0.35 |
| 188 | —C(O)— | 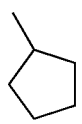 | 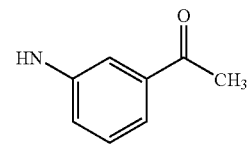 | 0.48 | 0.50 | | | | |
| 189 | —C(O)— | 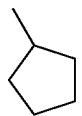 | 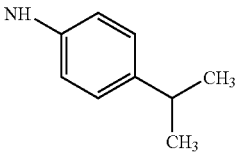 | 1.00 | 1.37 | | | | |
| 190 | —C(O)— | 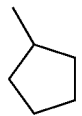 | 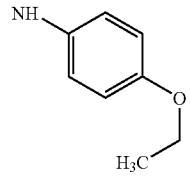 | 0.09 | 0.20 | 0.02 | 0.36 | <0.02 | 0.20 |
| 191 | —C(O)— | 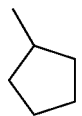 | 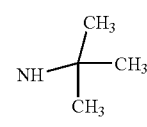 | 0.25 | 0.24 | 0.07 | 0.41 | <0.02 | 0.36 |
| 192 | —C(O)— | 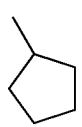 | | 1.49 | 1.89 | | | | |

TABLE 3-continued

ANTIPROLIFERATIVE DATA
MTT Assays

| Compound No. | Z | R₁ | R₂ | MB-435 Breast (IC₅₀ μM) | PC-3 Prostate (IC₅₀ μM) | Colo-205 Colon (IC₅₀ μM) | H-460 Lung (IC₅₀ μM) | HL-60 Leuk. (IC₅₀ μM) | Jurkat Leuk. (IC₅₀ μM) |
|---|---|---|---|---|---|---|---|---|---|
| 193 | —C(O)— | methyl 2-aminobenzoate | cyclopentyl | 0.17 | 0.18 | 0.18 | 0.13 | 0.03 | 0.26 |
| 194 | —C(O)— | 3-cyanoanilino | cyclopentyl | 0.72 | 0.89 | | | | |
| 195 | —C(O)— | ethyl 3-aminobenzoate | cyclopentyl | 0.33 | 0.38 | | | | |
| 196 | —C(O)— | 2-chloro-6-methylanilino | cyclopentyl | 0.50 | 0.59 | | | | |
| 197 | —C(O)— | phenethylamino | cyclopentyl | 0.91 | 1.09 | | | | |
| 198 | —C(O)— | 3,4,5-trimethoxyanilino | cyclopentyl | 2.85 | 31.80 | | | | |

TABLE 3-continued

ANTIPROLIFERATIVE DATA
MTT Assays

| Compound No. | Z | R₁ | R₂ | MB-435 Breast (IC₅₀ μM) | PC-3 Prostate (IC₅₀ μM) | Colo-205 Colon (IC₅₀ μM) | H-460 Lung (IC₅₀ μM) | HL-60 Leuk. (IC₅₀ μM) | Jurkat Leuk. (IC₅₀ μM) |
|---|---|---|---|---|---|---|---|---|---|
| 199 | —C(O)— | ethyl 2-aminobenzoate (NH-C₆H₄-C(O)OCH₂CH₃) | cyclopentyl | 0.26 | 0.26 | 0.06 | 0.18 | 0.06 | 0.34 |
| 200 | —C(O)— | NH-(2-F,5-CF₃-C₆H₃) | cyclopentyl | 0.09 | 0.16 | 0.06 | 0.19 | <0.02 | 0.21 |
| 201 | —C(O)— | NH-(2-CF₃,6-F-C₆H₃) | cyclopentyl | 1.53 | 1.90 | | | | |
| 202 | —C(O)— | NH-(2-CF₃,4-F-C₆H₃) | cyclopentyl | 0.22 | 0.23 | 0.20 | 0.33 | <0.02 | 0.53 |
| 203 | —C(O)— | NH-(4-F,3-CF₃-C₆H₃) | cyclopentyl | 0.22 | 0.30 | 0.17 | 0.54 | <0.02 | 0.50 |
| 204 | —C(O)— | NH-CH₂CH₂CH₂CH₃ | cyclopentyl | 2.53 | 2.64 | | | | |

TABLE 3-continued
ANTIPROLIFERATIVE DATA
MTT Assays
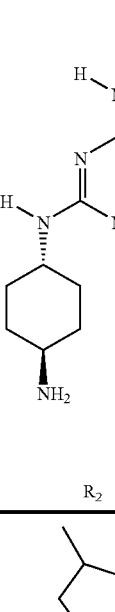
| Compound No. | Z | R₁ | R₂ | MB-435 Breast (IC$_{50}$ μM) | PC-3 Prostate (IC$_{50}$ μM) | Colo-205 Colon (IC$_{50}$ μM) | H-460 Lung (IC$_{50}$ μM) | HL-60 Leuk. (IC$_{50}$ μM) | Jurkat Leuk. (IC$_{50}$ μM) |
|---|---|---|---|---|---|---|---|---|---|
| 205 | —C(O)— | 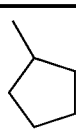 | 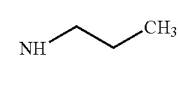 | 1.84 | 1.63 | | | | |
| 206 | —C(O)— | 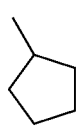 |  | 2.68 | 2.89 | | | | |
| 207 | —C(O)— | 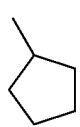 | 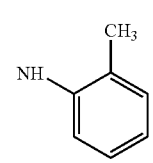 | 0.11 | 0.13 | 0.03 | 0.14 | 0.02 | 0.13 |
| 208 | —C(O)— | 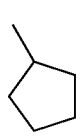 | 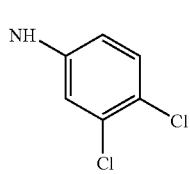 | 0.47 | 0.68 | | | | |
| 209 | —C(O)— | 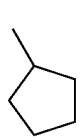 | 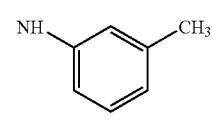 | 0.17 | 0.26 | 0.05 | 0.29 | <0.02 | 0.13 |
| 210 | —C(O)— | 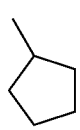 | | | | | | | |

TABLE 3-continued

ANTIPROLIFERATIVE DATA
MTT Assays

| Compound No. | Z | R₁ | R₂ | MB-435 Breast (IC$_{50}$ µM) | PC-3 Prostate (IC$_{50}$ µM) | Colo-205 Colon (IC$_{50}$ µM) | H-460 Lung (IC$_{50}$ µM) | HL-60 Leuk. (IC$_{50}$ µM) | Jurkat Leuk. (IC$_{50}$ µM) |
|---|---|---|---|---|---|---|---|---|---|
| 211 | —C(O)— | NH-C₆H₄-OCF₃ | CH(CH₃)₂ | 0.69 | 0.56 | | | | |
| Flavopiridol | | | | 0.09 (0.02, n = 72) | 0.08 (0.02, n = 72) | 0.03 (0.02, n = 23) | 0.07 (0.01, n = 23) | 0.02 (0.01, n = 12) | 0.08 (0.01, n = 9) |

In Vivo Assays

Example 4

Method for In Vivo Treatment of HL-60 Human Leukemia and PC-3 Human Prostate Tumors in Nude Mice Antitumor efficacy is assessed using two subcutaneous human tumor xenograft models. The studies are performed using conventional assay techniques. Briefly, HL-60 (leukemia, 5×10⁵ cells) and PC-3 (prostate, 5×10⁶ cells) tumor cells are injected subcuateously into nude mice (Crl-CD1-Br-nu, Charles River Laboratory, Wilmington, Mass.). Dosing with compounds began when tumors reached 50 to 100 mm³. The dose route/schedule for the test compounds is ip/q1d (5×/wk). The test doses are set based on the maximum tolerated dose (MTD). The MTD is defined as the level of compound that did not cause more than 20% decrease in body weight or result in death following five daily doses (ip) in non-tumored CD1 mice. The test doses for the efficacy studies are set at ⅓rd the MTD (low dose) and the MTD (high dose). The results are shown in Tables 4 and 5 (HL-60, leukemia) (PC-3, prostate cancer). The length of the treatment phase is dependent on the tumor growth rate for the two models. This treatment phase is typically about 3 weeks for the HL-60 model and about 5 weeks for the PC-3 model. Flavopiridol (3.5 mg/kg/day) is used as a reference compound for these studies. Dosing with flavopiridol is for the same time frame as for the experimental compounds in both xenograft models. Tumor volume (twice weekly) and body weights (once weekly) are monitored throughout the course of the treatment phase of the experiment. Tumor sizes are measured by external caliper measurements of protruding tumor. Volumes are calculated using the following formula: volume=½(a×b2), where b is the smaller of two perpendicular diameters.

The results are provided below in Tables 4 and 5, below.

TABLE 4

Effect of Chemical Group A on Growth of Human Tumor Xenografts

| Compound No | Dose - mg/kg | PC-3 Mean Vol. ± SD | PC-3 P-value vs. Control | HL60 Mean Vol. ± SD | HL60 P-value vs. Control |
|---|---|---|---|---|---|
| | NA | 2698 ± 1815 | NA | 6275 ± 1990 | NA |
| 87 | 1 | 3271 ± 2262 | 0.585 | 3718 ± 2715 | 0.051 |
| 87 | 3 | 1396 ± 958 | 0.105 | 7096 ± 3079 | 0.538 |
| 88 | 1 | 1601 ± 1348 | 0.193 | 4415 ± 2740 | 0.145 |
| 88 | 3 | 2278 ± 2110 | 0.676 | 2624 ± 2108 | 0.003 |
| 89 | 1 | 2572 ± 1052 | 0.867 | 2444 ± 2291 | 0.003 |
| 89 | 3 | 866 ± 384 | 0.025 | 4278 ± 2801 | 0.125 |
| 149 | 1 | 1084 ± 929 | 0.048 | 4010 ± 2371 | 0.058 |
| 149 | 3 | 2089 ± 1382 | 0.464 | 2505 ± 2104 | 0.002 |
| 154 | 3 | 1385 ± 873 | 0.095 | 2641 ± 3024 | 0.033 |
| 154 | 10 | 1707 ± 721 | 0.184 | 2950 ± 1929 | 0.004 |
| 106 | 1 | 1860 ± 741 | 0.256 | 4271 ± 3851 | 0.219 |
| 106 | 3 | 1482 ± 906 | 0.120 | 7368 ± 2592 | 0.361 |
| 109 | 3 | 1807 ± 1388 | 0.290 | 2597 ± 2240 | 0.006 |
| 109 | 10 | 979 ± 734 | 0.034 | 3466 ± 3730 | 0.088 |
| 111 | 3 | 1083 ± 704 | 0.043 | 3798 ± 2431 | 0.043 |
| 111 | 10 | 2114 ± 1320 | 0.475 | 2387 ± 1282 | 0.001 |
| 112 | 0.3 | 1302 ± 869 | 0.078 | 5413 ± 2845 | 0.495 |
| 112 | 1 | 1155 ± 872 | 0.055 | 4170 ± 3111 | 0.156 |

TABLE 5

Effect of Chemical Group A on Growth of Human Tumor Xenografts

| Compound No | Dose - mg/kg | PC-3 Mean Vol. ± SD | PC-3 P-value vs. Control | HL60 Mean Vol. ± SD | HL60 P-value vs. Control |
|---|---|---|---|---|---|
|  | NA | 1308 ± 852 | NA | 8341 ± 5355 | NA |
| 81 | 1 | 1258 ± 523 | 0.890 | 5802 ± 2996 | 0.295 |
| 81 | 3 | 1007 ± 1120 | 0.556 | 5104 ± 4014 | 0.217 |
| 82 | 1 | 810 ± 600 | 0.200 | 5164 ± 5516 | 0.279 |
| 82 | 3 | 967 ± 407 | 0.330 | 2841 ± 1845 | 0.035 |
| 83 | 3 | 899 ± 593 | 0.286 | 5906 ± 2948 | 0.867 |
| 83 | 10 | 1426 ± 1131 | 0.817 | 4057 ± 2599 | 0.200 |
| 84 | 1 | 770 ± 567 | 0.162 | 4790 ± 6912 | 0.284 |
| 84 | 3 | 1386 ± 752 | 0.850 | 4886 ± 3467 | 0.175 |
| 85 | 1 | 912 ± 755 | 0.342 | 3590 ± 2674 | 0.064 |
| 85 | 3 | 1208 ± 1247 | 0.855 | 5215 ± 4068 | 0.258 |
| 3 | 1 | 671 ± 672 | 0.120 | 6370 ± 4655 | 0.465 |
| 3 | 3 | 785 ± 473 | 0.158 | 6092 ± 4278 | 0.392 |
| 12 | 3 | 1063 ± 693 | 0.538 | 4948 ± 2803 | 0.172 |
| 12 | 10 | 1107 ± 606 | 0.595 | 2624 ± 2108 | 0.107 |

Example 5

Red Blood Cell Binding

Compounds, including one positive control, are assessed for red blood cell (RBC) uptake, using a modified procedure based on the protocol reported in Sun, J. X. S., et al. High-performance liquid chromatographic analysis, plasma protein binding and red blood cell partitioning of phenprobamate. *Biopharmaceutics and Drug Disposition*, 8 (1987) 341-351.

Briefly, RBC uptake is evaluated by comparison of the levels in spiked plasma (n=3) and plasma isolated from spiked whole blood (n=3). Compounds are incubated with human and mouse whole blood, respectively, for 30 minutes at 37° C. using a nominal concentration of 500 ng/ml. Following centrifugation, the plasma is removed and submitted for analysis. Each compound is also spiked into blank plasma at a nominal concentration of 500 ng/ml, and submitted for analysis. Levels in the two plasma samples (Cp' and Cp in the equation below) and the blood hematocrit are used to determine the red blood cell to plasma ratio (Crbc/Cp).

$$\frac{Crbc}{Cp} = \frac{Cp'}{Cp \cdot H} - \frac{(1-H)}{H} \qquad (1)$$

In equation 1, Cp' is the level of drug in the spiked "blank" plasma, Cp is the level of drug in the plasma of spiked whole blood, and H is the hematocrit. The hematocrit values are determined as 0.4 for human whole blood and 0.41 for mouse whole blood. The samples are analyzed with ESI LC/MS, using positive ion detection with an internal standard. The results are summarized below and in tables 6-16, following.

The red blood cell to plasma ratio is determined for each compound using equation 1. Tables 6 and 7 summarize the respective mean Crbc/Cp values and standard deviations for mouse and human whole blood, respectively, in descending order based on the red blood cell to plasma ratio, where "*".denotes Positive Control, and "ND" denotes Not Determined. MDL 108552 is included as a positive control for red blood cell uptake.

TABLE 6

Red Blood Cell to Plasma Ratio for compounds in mouse whole blood

| Compound No. | Mean Red Blood Cell to Plasma Ratio | Standard Deviation |
|---|---|---|
| 83 | 112.2 | 19.2 |
| 154 | 17.8 | 3.1 |
| 85 | 6.1 | 0.4 |
| 89 | 4.7 | 0.7 |
| 81 | 4.5 | 0.6 |
| 88 | 3.5 | 0.4 |
| 84 | 3.5 | 0.3 |
| 87 | 3.4 | 0.5 |
| 149 | 3.4 | 0.4 |
| 81 | 3.3 | 0.1 |
| 106 | 3.0 | 0.3 |
| 112 | 2.4 | 0.3 |
| 109 | 2.4 | 0.3 |
| 111 | 2.2 | 0.6 |
| 3 | 2.1 | 0.2 |
| 12 | 1.9 | 0.6 |

TABLE 7

Red Blood Cell to Plasma Ratio for compounds in human whole blood

| Compound No. | Mean Red Blood Cell to Plasma Ratio | Standard Deviation |
|---|---|---|
| 87 | 8.4 | 1.6 |
| 85 | 7.1 | 1.1 |
| 3 | 7.0 | 0.5 |
| 82 | 5.8 | 0.4 |
| 81 | 5.3 | 1.3 |
| 109 | 5.0 | 1.0 |
| 89 | 4.2 | 0.6 |
| 154 | 4.1 | 0.7 |
| 83 | 4.1 | 0.7 |
| 106 | 3.9 | 0.8 |
| 112 | 3.7 | 1.0 |
| 12 | 3.6 | 1.1 |
| 149 | 2.8 | 0.7 |
| 88 | 2.6 | 0.8 |
| 84 | 2.0 | 0.6 |
| 111 | 1.2 | 0.6 |

Example 6

Bioavailability Experiment in Mice Given Single Intravenous Cassette Doses of CDK Inhibitor Compounds Male mice are given single intravenous cassette doses of CDK inhibitor compounds. Each cassette contained 4-5 test compounds and a CDK reference standard, MDL 107167. Groups of mice (n=3/timepoint) are euthanized at specified intervals from 0-24 h after dosing and concentrations of the administered compounds in plasma are quantitated by an assay based on LC/MS. The key results are:

Cassette #1[a]

Compound 83
Compound 12
Compound 85
Compound 109
Compound 111
Reference Compound                    MDL 107167DA-004

-continued

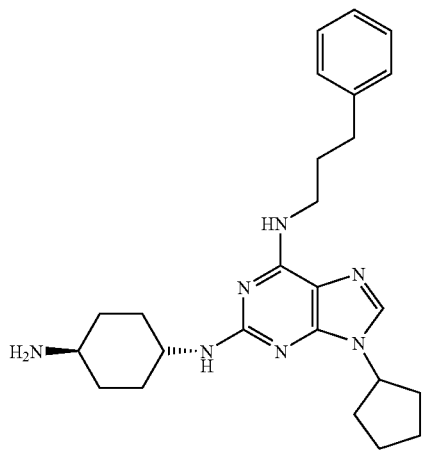

MDL 107167DA

Cassette #2[a]

Compound 3
Compound 81
Compound 84
Compound 154
Compound 819
Reference Compound  MDL 107167DA-004

Cassette #3[a]

Compound 87
Compound 149
Compound 112
Compound 88
Reference Compound  MDL 107167DA-004

Cassette #4[a]

Compound 818
Compound 82
Compound 89
Compound 106
Reference Compound  MDL 107167DA-004

[a]DA = dihydrochloride salt; and TA = trihydrochloride salt

Doses are adjusted for the weight of the individual dihydrochloride and trihydrochloride salts. The compounds are stored desiccated within a closed cabinet at room temperature before use. Dose levels are prepared on the morning of each study.

A single intravenous cassette dose (18 or 15 mg/kg free base) is administered. For each compound, this is equivalent to a dose of approx. 3 mg/kg free base. The compounds are dissolved in 5% Dextrose in Water (D5W) at a nominal concentration of 0.3 mg/ml of each compound (1.8 or 1.5 mg/ml total). The dose is administered at a volume of 10 ml/kg (total volume of approximately 0.25 ml/animal).

Animals:

Male mice (Hsd:ICR(CD-1® SD®), Harlan), each weighing approximately 20-30 g at the start of the study. The mice are fasted overnight (approx. 16 h) before dosing. Food (Certified Rodent Diet #5002, PMI Feeds, Inc.) is returned approx. two hours after dose administration. Water is available ad libitum throughout the study.

Dose Administration and Sample Collection:

A single cassette dose of 5-6 compounds is administered by bolus injection into the tail vein over a 10-15-second period. Groups of mice (n=3/timepoint) are anesthetized with isoflurane at 0.083, 0.25, 0.5, 1, 3, 6, 8, and 24 h after dosing to draw the blood sample. Whole blood (approximately 0.6 ml/sample) is obtained by cardiac puncture and transferred to 3 ml glass tubes containing 45 U sodium heparin.

The doses are administered in the morning.

Sample Processing Plasma: Whole blood is centrifuged at approximately 3,200 rpm for 10 min at approximately 5° C. and the plasma (approx. 0.3 ml/sample) is transferred to chilled plastic vials and stored at approx. −70° C. until bioanalysis.

Sample Analysis Concentrations of each test article in plasma are quantitated by a non-validated method based on LC/MS using the following protocol.

Detailed Bioanalytical Methods Summary

Samples are removed from the freezer, allowed to thaw at room temperature, and vortexed to insure complete homogenization prior to sample manipulation. Samples are then prepared according to the following scheme:
1. transfer 48 µL of plasma (blank mouse sample) into a 12×75 mm test tube.
2. add 12 µL of working standard to the blank plasma for standard curve preparation.
3. Add 60 µl of plasma sample to appropriately labeled 12×75 mm test tubes.
4. add 60 µL of 2% glacial acetic acid in acetonitrile containing internal standard(a similar solution containing no internal standard is used for predose time points and the zero level standard).
5. vortex for 3 minutes and let sit for 15 minutes.
6. centrifuge for 15 minutes at approximately 4500 rpm.
7. transfer the supernatant to injection vials, cap, and re-centrifuge for 5 minutes.
8. Inject 25 µL on LC/MS.

| Chromatographic Conditions: | |
|---|---|
| Column: | 2 × 50 mm, 3µ, C8 Luna manufactured by Phenomenex. |
| Temperature: | heat to 40° C. |
| Mobile Phase: | gradient<br>Mobile phase A: 95% DI water and 5% acetonitrile.<br>Mobile phase B: 95% acetonitrile and 5% DI water.<br>Buffer and pH are adjusted by adding 250 µL of glacial acetic acid and 100 µL of concentrated ammonium hydroxide to both A and B mobile phase. |
| Flow rate: | 0.2 ml/min |
| Injection volume: | 25 µL |
| Retention time: | approximately 4.0 minutes |
| Switching valve: | Zero to 3.5 minutes is diverted to iste;<br>3.5 to 4.5 minutes switch to MS |

| Mass Spectrometry - Finnigan TSQ-700/SIM | |
|---|---|
| Ionization mode | Positive Electrospray |
| Manifold pressure | $2 \times 10^{-6}$ torr |
| ESI spray voltage | 4.5 kV |
| ESI spray current | ~10 uA |
| Capillary temp | 225° C. |
| Electron multiplier | 1600 V |

Data Analysis Concentrations of Compounds in plasma of individual animals are determined by bioanalytics. Where appropriate, concentration values in the text and in the pharmacokinetic summary tables, provided below, have been rounded to the nearest whole number. The lower limit of quantitation was approximately 1 ng/ml plasma for the test compounds. Statistical analyses are limited to simple expressions of variation (mean and standard deviation). The plasma AUC (area-under-curve) is determined by the linear trapezoidal rule. Absolute bioavailability (F %) is calculated from the ratio of the dose-normalized AUC(0-∞) achieved after intravenous administration. All PK parameters are determined by noncompartmental methods using WinNonlin version 3.0 (Pharsight Corp). Plasma vs. time profiles are prepared by Sigma Plot (SPSS, Inc.).

Antemortem Observations No apparent adverse effects occurred after any of the four cassette doses.

Bioanalytical Results Plasma concentration-time profiles are determined for all of the CDK compounds.

Plasma Concentrations are provided in Tables 8-16.

Intravenous Dose Concentrations of Compounds in plasma could be quantitated for up to 8 h postdose. Peak measured concentrations of each compound in the plasma occurred at 0.083 h (the earliest sampling time) postdose.

In the CDK compounds, the mean plasma AUC(0-∞) ranged from 366-2550 ng·h/ml. The mean terminal elimination half-life of the Compounds in plasma ranged from 0.7-5.1 h

TABLE 8

Individual and Mean Concentrations of Compounds in Plasma of Mice Given Single 18 mg/kg Intravenous Cassette Doses (Cassette #1).

| Time (h) | | 83 Conc. (ng/ml) | 12 Conc. (ng/ml) | 85 Conc. (ng/ml) | 109 Conc. (ng/ml) | 111 Conc. (ng/ml) | MDL 107167 Conc. (ng/ml) |
|---|---|---|---|---|---|---|---|
| 0.083 | Mean ± | 1515.7 ± | 4109.0 ± | 843.3 ± | 1693.2 ± | 2454.1 ± | 512.0 ± |
|  | SD | 611.8 | 753.5 | 124.5 | 224.3 | 286.7 | 97.1 |
| 0.25 | Mean ± | 217.9 ± | 2363.5 ± | 341.6 ± | 914.8 ± | 1085.7 ± | 360.0 ± |
|  | SD | 92.8 | 124.3 | 45.1 | 15.2 | 129.0 | 127.8 |
| 0.5 | Mean ± | 61.3 ± | 1094.7 ± | 163.8 ± | 514.3 ± | 587.7 ± | 297.2 ± |
|  | SD | 32.9 | 36.1 | 15.7 | 45.2 | 29.3 | 4.4 |
| 1 | Mean ± | 14.1[a] | 465.3 ± | 89.0 ± | 238.1 ± | 334.9 ± | 146.1 ± |
|  | SD |  | 34.6 | 21.5 | 38.7 | 81.3 | 12.3 |
| 3 | Mean ± | 4.1[a] | 74.7 ± | 14.3 ± | 30.1 ± | 33.8 ± | 20.7 ± |
|  | SD |  | 17.4 | 7.1 | 8.5 | 6.8 | 6.4 |
| 6 | Mean ± | 1.6[a] | 27.0 ± | 5.2 ± | 9.5 ± | 10.9 ± | 4.5 ± |
|  | SD |  | 2.7 | 1.9 | 1.8 | 3.0 | 0.7 |
| 8 | Mean ± | 6.3[a] | 16.9 ± | 3.2 ± | 5.5 ± | 6.0 ± | 2.9 ± |
|  | SD |  | 1.4 | 0.8 | 0.9 | 2.0 | 0.6 |
| 24 | Mean ± SD | BLQ | BLQ | BLQ | BLQ | BLQ | BLQ |

[a]BLQ = below assay quantification limit; BLQ values represented by a numerical zero in mean calculations; standard deviations were not calculated.

TABLE 9

Individual and Mean Concentrations of Compounds in Plasma of Mice Given Single 18 mg/kg Intravenous Cassette Doses (Cassette #2).

| Time (h) | Animal No. | 3 Conc. (ng/ml) | 81 Conc. (ng/ml) | 84 Conc. (ng/ml) | 154 Conc. (ng/ml) | MDL 819 Conc. (ng/ml) | MDL 107167 Conc. (ng/ml) |
|---|---|---|---|---|---|---|---|
| 0.083 | Mean ± | 3254.9 ± | 1772.7 ± | 1505.7 ± | 4854.1 ± | 2774.5 ± | 471.7 ± |
|  | SD | 1046.2 | 383.6 | 376.6 | 794.1 | 545.8 | 239.2 |
| 0.25 | Mean ± | 1136.0 ± | 394.3 ± | 882.7 ± | 1126.5 ± | 624.5 ± | 316.7 ± |
|  | SD | 250.2 | 141.9 | 140.2 | 243.1 | 110.5 | 42.3 |
| 0.5 | Mean ± | 516.3 ± | 163.5 ± | 446.1 ± | 377.4 ± | 227.6 ± | 266.0 ± |
|  | SD | 80.0 | 47.2 | 79.0 | 73.2 | 68.4 | 42.7 |
| 1 | Mean ± | 234.3 ± | 65.3 ± | 201.5 ± | 126.4 ± | 100.6 ± | 132.7 ± |
|  | SD | 63.5 | 10.0 | 37.3 | 12.3 | 11.5 | 21.4 |
| 3 | Mean ± | 36.9 ± | 12.7 ± | 27.0 ± | 8.4 ± | 24.4 ± | 16.1 ± |
|  | SD | 8.3 | 3.4 | 2.4 | 3.1 | 6.7 | 1.4 |
| 6 | Mean ± | 9.5 ± | 5.4 ± | 6.1 ± | 2.3 ± | 15.3 ± | 2.8 ± |
|  | SD | 3.2 | 1.5 | 0.8 | 1.6 | 2.7 | 0.4 |
| 8 | Mean ± | 5.2 ± | 3.5 ± | 2.9 ± | BLQ[a] | 12.4 ± | 1.6 ± |
|  | SD | 1.0 | 0.9 | 0.2 |  | 1.9 | 0.2 |
| 24 | Mean ± SD | BLQ[a] | BLQ | BLQ | BLQ[a] | BLQ | BLQ |

[a]BLQ = below assay quantification limit; BLQ values represented by a numerical zero in mean calculations; standard deviations were not calculated.

TABLE 10

Individual and Mean Concentrations of Compounds in Plasma of Mice Given Single 15 mg/kg Intravenous Cassette Doses (Cassette #3).

| Time (h) | Animal No. | 87 Conc. (ng/ml) | 149 Conc. (ng/ml) | 112 Conc. (ng/ml) | 88 Conc. (ng/ml) | MDL 107167 Conc. (ng/ml) |
|---|---|---|---|---|---|---|
| 0.083 | Mean ± SD | 1171.4 ± 153.4 | 3114.5 ± 702.6 | 2808.0 ± 271.9 | 1483.3 ± 272.5 | 520.1 ± 69.3 |
| 0.25 | Mean ± SD | 371.9 ± 35.9 | 419.0 ± 69.8 | 1696.2 ± 311.7 | 420.9 ± 49.9 | 323.6 ± 32.3 |
| 0.5 | Mean ± SD | 141.4 ± 9.5 | 133.3 ± 10.2 | 435.0 ± 48.0 | 150.2 ± 5.9 | 209.2 ± 24.1 |
| 1 | Mean ± SD | 65.0 ± 14.0 | 59.8 ± 17.3 | 175.3 ± 42.4 | 74.6 ± 16.1 | 107.8 ± 29.3 |
| 3 | Mean ± SD | 19.2 ± 6.0 | 15.5 ± 4.8 | 45.0 ± 7.2 | 24.8 ± 7.4 | 23.5 ± 6.4 |
| 6 | Mean ± SD | 4.3 ± 0.7 | 4.1 ± 2.1 | 17.7 ± 1.7 | 8.9 ± 1.6 | 5.0 ± 0.5 |
| 8 | Mean ± SD | 3.2 ± 1.6 | 5.4 ± 0.5 | 13.6 ± 3.7 | 5.4 ± 2.0 | 2.4 ± 1.7 |
| 24 | Mean ± SD | BLQ[a] | BLQ | BLQ | BLQ | BLQ |

[a]BLQ = below assay quantification limit.

TABLE 11

Individual and Mean Concentrations of Compounds in Plasma of Mice Given Single 15 mg/kg Intravenous Cassette Doses (Cassette #4).

| Time (h) | Animal No. | MDL 818 Conc. (ng/ml) | 82 Conc. (ng/ml) | 89 Conc. (ng/ml) | 106 Conc. (ng/ml) | MDL 107167 Conc. (ng/ml) |
|---|---|---|---|---|---|---|
| 0.083 | Mean ± SD | 482.0 ± 65.5 | 1458.0 ± 77.4 | 642.0 ± 49.5 | 764.8 ± 64.3 | 567.3 ± 43.5 |
| 0.25 | Mean ± SD | 444.9 ± 7.1 | 875.3 ± 96.7 | 303.3 ± 34.3 | 396.7 ± 59.2 | 491.3 ± 32.3 |
| 0.5 | Mean ± SD | 360.6 ± 15.7 | 369.6 ± 40.0 | 142.4 ± 2.7 | 184.8 ± 13.0 | 325.3 ± 13.6 |
| 1 | Mean ± SD | 146.9 ± 16.7 | 133.7 ± 16.3 | 52.4 ± 4.2 | 63.3 ± 0.5 | 145.1 ± 9.5 |
| 3 | Mean ± SD | 28.5 ± 4.4 | 37.5 ± 10.7 | 17.0 ± 4.7 | 21.8 ± 6.1 | 35.3 ± 8.3 |
| 6 | Mean ± SD | 6.1 ± 0.5 | 14.5 ± 3.4 | 3.7 ± 1.0 | 4.3 ± 0.8 | 10.1 ± 3.0 |
| 8 | Mean ± SD | 1.9 ± 0.4 | 12.3 ± 2.2 | 3.8 ± 0.5 | BLQ[a] | 3.7 ± 0.7 |
| 24 | Mean ± SD | BLQ | BLQ | BLQ | BLQ | BLQ |

[a]BLQ = below assay quantification limit; BLQ values represented by a numerical zero in mean calculations; standard deviations were not calculated.

The following information is based on a graph of the semi-log of the plasma concentration in ng/ml versus collection time in hours.

"Cmax" represents the maximum plasma concentration.
"$t_{1/2}$" represents the half-life of the compound.
"$AUC_{0-\infty}$" represents the calculated area under the curve.
"AUC % Extrap(obs.)" represents the extrapolated area under the curve.
"Cls" is the clearance rate.

TABLE 12

Mean Pharmacokinetic Parameter Values for Compounds in Plasma of Mice Given Single Intravenous Cassette Doses (Cassette #1).

| Parameter (units) | 3 mg/kg/compound (18 mg/kg Total Dose) | | | | | |
|---|---|---|---|---|---|---|
| | 83 | 12 | 85 | 109 | 111 | MDL 107167 |
| Cmax (ng/ml)[a] | 1515.7 | 4109.0 | 843.3 | 1693.2 | 2454.1 | 512.0 |
| $t_{1/2}, \lambda_z$ (h) | 0.7 | 2.3 | 2.3 | 2.0 | 2.0 | 1.7 |
| $AUC_{0-\infty}$ (ng · h/ml) | 449 | 2550 | 467 | 1109 | 1460 | 531 |
| AUC % Extrap(obs.) (ng · h/ml) | 0.96 | 2.2 | 2.27 | 1.44 | 1.18 | 1.36 |
| Cls (ml/min/kg) | 111.4 | 19.6 | 107.1 | 45.1 | 34.2 | 94.1 |

[a]Highest measured value.

TABLE 13

Mean Pharmacokinetic Parameter Values for Compounds in Plasma of Mice Given Single Intravenous Cassette Doses (Cassette #2).

| | 3 mg/kg/compound (18 mg/kg Total Dose) | | | | | |
|---|---|---|---|---|---|---|
| Parameter (units) | 3 | 81 | 84 | 154 | MDL 819 | MDL 107167 |
| Cmax (ng/ml)[a] | 3254.9 | 1772.7 | 1505.7 | 4854.1 | 2774.5 | 471.7 |
| $t_{1/2}, \lambda_z$ (h) | 1.3 | 1.7 | 1.5 | 0.8 | 5.1 | 1.5 |
| $AUC_{0-\infty}$ (ng · h/ml) | 1489 | 660 | 965 | 1584 | 1132 | 467 |
| AUC % Extrap(obs.) (ng · h/ml) | 0.66 | 1.34 | 0.67 | 0.16 | 8.0 | 0.73 |
| Cls (ml/min/kg) | 33.6 | 75.8 | 51.8 | 31.6 | 44.2 | 107.1 |

[a]Highest measured value.

TABLE 14

Mean Pharmacokinetic Parameter Values for Compounds in Plasma of Mice Given Single Intravenous Cassette Doses (Cassette #3).

| | 3 mg/kg/compound (15 mg/kg Total Dose) | | | | |
|---|---|---|---|---|---|
| Parameter (units) | 87 | 149 | 112 | 88 | MDL 107167 |
| Cmax (ng/ml)[a] | 1171.4 | 3114.5 | 2808.0 | 1483.3 | 520.1 |
| $t_{1/2}, \lambda_z$ (h) | 1.6 | 1.6 | 2.8 | 1.9 | 1.5 |
| $AUC_{0-\infty}$ (ng · h/ml) | 513 | 1019 | 1462 | 642 | 452 |
| AUC % Extrap(obs.) (ng · h/ml) | 1.41 | 1.22 | 3.80 | 2.27 | 1.15 |
| Cls (ml/min/kg) | 97.4 | 49.1 | 34.2 | 77.9 | 110.7 |

[a]Highest measured value.

TABLE 15

Mean Pharmacokinetic Parameter Values for Compounds in Plasma of Mice Given Single Intravenous Cassette Doses (Cassette #4).

| | 3 mg/kg/compound (15 mg/kg Total Dose) | | | | |
|---|---|---|---|---|---|
| Parameter (units) | 818 | 82 | 89 | 106 | MDL 107167 |
| Cmax (ng/ml)[a] | 482.0 | 1458.0 | 642.0 | 764.8 | 567.3 |
| $t_{1/2}, \lambda_z$ (h) | 1.3 | 3.0 | 1.8 | 1.3 | 1.5 |
| $AUC_{0-\infty}$ (ng · h/ml) | | 944 | 366 | 440 | 627 |
| AUC % Extrap(obs.) (ng · h/ml) | | 5.66 | 2.62 | 1.82 | 1.32 |
| Cls (ml/min/kg) | | 53.0 | 136.5 | 113.7 | 79.7 |

[a]Highest measured value.

TABLE 16

Mean Pharmacokinetic Parameter Values for MDL 107167 (Reference Standard) in Plasma of Mice Given Single Intravenous Cassette Doses.

| | 3 mg/kg MDL 107167 in Cassette Doses | | | |
|---|---|---|---|---|
| Parameter (units) | Cassette #1 | Cassette #2 | Cassette #3 | Cassette #4 |
| Cmax (ng/ml)[a] | 512.0 | 471.7 | 520.1 | 567.3 |
| $t_{1/2}, \lambda_z$ (h) | 1.7 | 1.5 | 1.5 | 1.5 |
| $AUC_{0-\infty}$ (ng · h/ml) | 532 | 467 | 452 | 627 |
| AUC % Extrap(obs.) (ng · h/ml) | 1.36 | 0.73 | 1.15 | 1.32 |
| Cls (ml/min/kg) | 94.1 | 107.1 | 110.7 | 79.7 |

[a]Highest measured value.

There are no apparent adverse effects after administration of any of the four cassette doses.

Plasma concentration time profiles are determinable for all of the CDK compounds.

After the intravenous dose, the mean plasma AUC(0-∞) ranged from 366-2550 ng·h/ml. Peak measured concentrations of each compound in the plasma occurred at 0.083 h postdose.

What is claimed is:

1. A compound according to the formula (I)

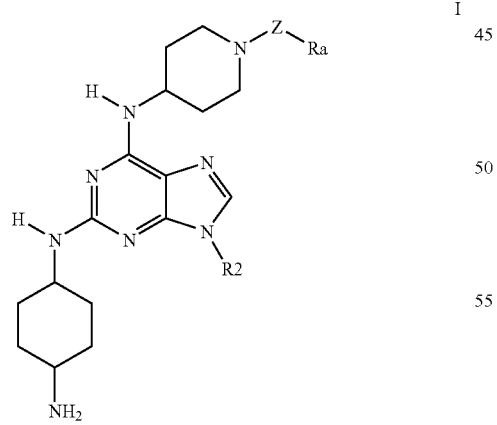

I wherein Z is selected from the group consisting of —S(O)$_2$— and —C(O)—, when Z is —S(O)$_2$—, R$_a$ is selected from the group consisting of: —R1 and —N(R1)(R3), or when Z is —C(O)—, R$_a$ is selected from the group consisting of: —R1, —OR1, —N(R1)(R3) and —SR1, where R1 is selected from the group consisting of:
- —C$_1$-C$_{11}$ alkyl, wherein each carbon may be optionally substituted with one, two or three X substituents,
- —C$_3$-C$_{10}$ cycloalkyl, wherein each carbon may be optionally substituted with one or two X substituents,
- —(CH$_2$)$_n$Q$_p$(CH$_2$)$_n$W, and
- —(CH$_2$)$_n$CHW$_2$;

wherein each carbon of —(CH$_2$)$_n$— may be optionally substituted with one or two X substituents, Q is O, S, or NR3, n is independently an integer 0-6, p is independently an integer 0 or 1, and W is independently selected from the group consisting of hydrogen, C$_3$-C$_{10}$ cycloalkyl, —(C$_3$-C$_{10}$ cycloalkyl)-aromatic, and one of the following aromatic or heteroaromatic rings:

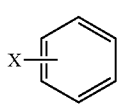 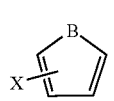 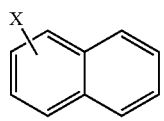

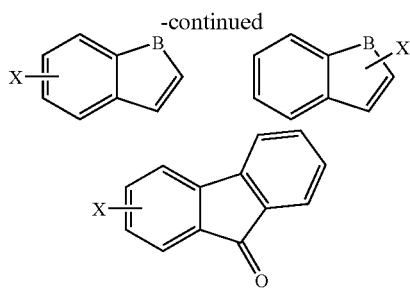

where B is selected from the group consisting of: —O—, —S—, —NR6—; where each carbon of the aromatic or heteroaromatic ring may be independently replaced by a nitrogen atom, and each carbon of the aromatic ring may be independently substituted with an X substituent;

where each X substituent is independently selected from the group consisting of: hydrogen, halogen, methylenedioxy, —$C_1$-$C_8$ saturated or unsaturated, straight or branched chain hydrocarbyl radical of from one to eight carbon atoms, —$C_3$-$C_{10}$ cycloalkyl, substituted or unsubstituted phenyl, —$C_1$-$C_8$ alkoxy, —SR3, —OH, —$CY_3$, —$OCY_3$, —$CO_2$R3, —CN, —CO—NR4R5, —$NO_2$, —COR3, —NR4R5, —NH—C(O)—R3, —NH—C(O)—($C_1$-$C_6$ saturated or unsaturated, straight or branched chain hydrocarbyl radical of from one to six carbon atoms)-aromatic, and —NH—C(O)—($C_1$-$C_6$ saturated or unsaturated, straight or branched chain hydrocarbyl radical of from one to six carbon atoms)-heteroaromatic;

where said phenyl when substituted is substituted with one to five substituents independently selected from the group consisting of hydrogen, halogen, methylenedioxy, —$C_1$-$C_8$ saturated or unsaturated, straight or branched chain hydrocarbyl radical of from one to eight carbon atoms, —$C_3$-$C_{10}$ cycloalkyl, —$C_1$-$C_8$ alkoxy, —OH, —$CY_3$, —$OCY_3$, —$CO_2$R3, —CN, —$NO_2$, —COR3, —SR3, and —NH—C(O)—R3;

where each Y is independently selected from the group consisting of hydrogen and halogen;

where each R3 is independently selected from the group consisting of hydrogen, and $C_1$-$C_8$ saturated or unsaturated, straight or branched chain hydrocarbyl radical of from one to eight carbon atoms, where $C_1$-$C_8$ saturated or unsaturated, straight or branched chain hydrocarbyl radical of from one to eight carbon atoms may be straight or branched, saturated or unsaturated;

where each R4 and R5 is independently selected from the group consisting of hydrogen, and $C_1$-$C_6$ saturated or unsaturated, straight or branched chain hydrocarbyl radical of from one to six carbon atoms, where which each carbon of $C_1$-$C_6$ saturated or unsaturated, straight or branched chain hydrocarbyl radical of from one to six carbon atoms is optionally substituted with a hydrogen, halogen, methylenedioxy, —$C_1$-$C_8$ alkylene, —$C_3$-$C_{10}$ cycloalkyl, substituted or unsubstituted phenyl, —$C_1$-$C_8$ alkoxy, —SR3, —OH, —$CY_3$, —$OCY_3$, —$CO_2$R3, —CN, —$NO_2$, —COR3, —NH—C(O)—R3, —NH—C(O)—($C_1$-$C_6$ saturated or unsaturated, straight or branched chain hydrocarbyl radical of from one to six carbon atoms)-aromatic, or —NH—C(O)—($C_1$-$C_6$ saturated or unsaturated, straight or branched chain hydrocarbyl radical of from one to six carbon atoms)-heteroaromatic, or where said R4 and said R5 taken together with the nitrogen to which they are attached, form a single heterocyclic ring of three to seven atoms including the nitrogen atom as the sole heteroatom;

where —NR6— is selected from the group consisting of an N substituted with—hydrogen, —($C_1$-$C_6$ saturated or unsaturated, straight or branched chain hydrocarbyl radical of from one to six carbon atoms), —$C_3$-$C_{10}$ cycloalkyl, —S(O)$_2$—($C_1$-$C_6$ saturated or unsaturated, straight or branched chain hydrocarbyl radical of from one to six carbon atoms), —S(O)$_2$—($C_3$-$C_{10}$ cycloalkyl), —C(O) R3, —C(O)—($C_1$-$C_6$ saturated or unsaturated, straight or branched chain hydrocarbyl radical of from one to six carbon atoms)-aromatic, —C(O)-aromatic, S(O)$_2$-aromatic and —S(O)$_2$—($C_1$-$C_6$ saturated or unsaturated, straight or branched chain hydrocarbyl radical of from one to six carbon atoms)-aromatic, wherein each carbon of the aromatic ring may be optionally substituted with an X substituent; and R2 is selected from the group consisting of cyclopentyl, cyclopentenyl, and isopropyl;

or a pharmaceutically acceptable salt, optical isomer, solvate or hydrate thereof.

2. A method of inhibiting cyclin-dependent kinases (CDKs) by administering a compound according to claim 1 wherein the CDK is selected from the group consisting of CDK1, CDK2 and CDK4.

3. The method according to claim 2, wherein the CDK is a constituent of a complex selected from the group consisting of CDK1/cyclin B, CDK2/cyclin E, and CDK4/cyclin D wherein the CDK4/cyclin D is selected from the group consisting of CDK4/cyclin D1, CDK4/cyclin D2 and CDK4/cyclin D3 and the complex is inhibited.

4. A compound according to claim 1 of the formula

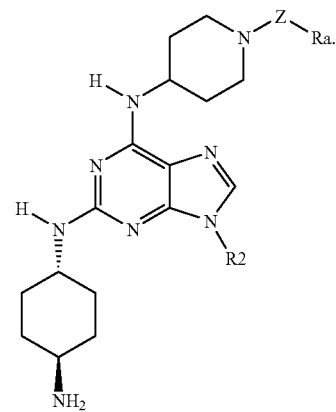

5. A compound according to claim 4 wherein 4 is —C(O)—.

6. A compound according to claim 4 wherein 4 is —S(O)$_2$—.

7. A compound according to claim 5 wherein $R_a$ is selected from the group consisting of: —OR1 and —N(R1)(R3).

8. A compound according to claim 5 wherein $R_a$ is —SR1.

9. A compound according to claim 7 wherein $R_a$ is —OR1.

10. A compound according to claim 7 wherein $R_a$ is —N(R$_1$)(R$_3$).

11. A compound according to claim 1 wherein $R_2$ is cyclopentyl.

12. A compound according to claim 1 wherein R1 is —(CH$_2$)$_n$Q$_p$(CH$_2$)$_n$W.

13. A compound according to claim 10 wherein R1 is —(CH$_2$)$_n$Q$_p$(CH$_2$)$_n$W.

14. A compound according to claim 13 wherein W is selected from the group consisting of:

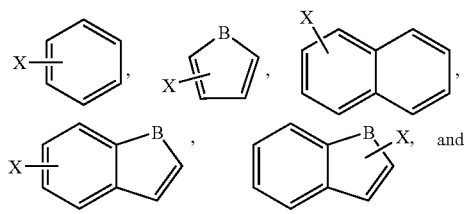

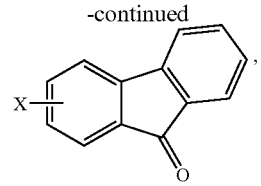

where B is —O—, —S—, —NR6-, where each carbon of the aromatic or heteroaromatic ring may be independently replaced by a nitrogen atom, and each carbon of the aromatic ring may be independently substituted with an X substituent.

15. A compound according to claim 14 wherein W is phenyl, each carbon of which may be independently substituted with an X substituent.

16. The method according to claim 3, wherein the cyclin D is cyclin D1.

* * * * *